United States Patent
Dong et al.

(10) Patent No.: US 9,839,629 B2
(45) Date of Patent: Dec. 12, 2017

(54) INHIBITORS OF THE RENAL OUTER MEDULLARY POTASSIUM CHANNEL

(71) Applicant: Merck Sharp & Dohme Corp., Rahway, NJ (US)

(72) Inventors: Shuzhi Dong, Plainsboro, NJ (US); Alexander Pasternak, Princeton, NJ (US); Xin Gu, Scotch Plains, NJ (US); Qinghong Fu, Plainsboro, NJ (US); Jinlong Jiang, Scotch Plains, NJ (US); Fa-Xiang Ding, Staten Island, NY (US); Haifeng Tang, Metuchen, NJ (US); Reynalda K. DeJesus, East Brunswick, NJ (US); Takao Suzuki, Shanghai (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/101,481

(22) PCT Filed: Dec. 19, 2014

(86) PCT No.: PCT/US2014/071336
§ 371 (c)(1),
(2) Date: Jun. 3, 2016

(87) PCT Pub. No.: WO2015/100147
PCT Pub. Date: Jul. 2, 2015

(65) Prior Publication Data
US 2016/0324833 A1 Nov. 10, 2016

(30) Foreign Application Priority Data

Dec. 24, 2013 (WO) ................ PCT/CN2013/090335

(51) Int. Cl.
| | | |
|---|---|---|
| C07D 471/10 | (2006.01) |
| C07D 498/10 | (2006.01) |
| A61K 31/4545 | (2006.01) |
| A61K 31/537 | (2006.01) |
| A61K 31/4745 | (2006.01) |
| A61K 31/435 | (2006.01) |
| A61K 31/497 | (2006.01) |
| A61K 31/501 | (2006.01) |
| A61K 31/506 | (2006.01) |
| C07D 519/00 | (2006.01) |
| A61K 31/437 | (2006.01) |
| A61K 31/438 | (2006.01) |
| A61K 31/444 | (2006.01) |
| A61K 45/06 | (2006.01) |

(52) U.S. Cl.
CPC .......... *A61K 31/435* (2013.01); *A61K 31/437* (2013.01); *A61K 31/438* (2013.01); *A61K 31/444* (2013.01); *A61K 31/4545* (2013.01); *A61K 31/497* (2013.01); *A61K 31/501* (2013.01); *A61K 31/506* (2013.01); *A61K 31/537* (2013.01); *A61K 45/06* (2013.01); *C07D 471/10* (2013.01); *C07D 498/10* (2013.01); *C07D 519/00* (2013.01)

(58) Field of Classification Search
None
See application file for complete search history.

(56) References Cited

U.S. PATENT DOCUMENTS

| | | |
|---|---|---|
| 4,255,432 A | 3/1981 | Kluge et al. |
| 6,693,109 B2 | 2/2004 | Fisher et al. |
| 9,018,211 B2 | 4/2015 | Pasternak et al. |
| 2012/0122846 A1 | 5/2012 | Calderwood et al. |
| 2014/0142115 A1 | 5/2014 | Pasternak et al. |

FOREIGN PATENT DOCUMENTS

| | | |
|---|---|---|
| CN | 102459216 | 5/2012 |
| WO | WO2012126275 A1 | 9/2012 |
| WO | 2013066718 A2 | 5/2013 |

OTHER PUBLICATIONS

Burger's Medicinal Chemistry, edited by Manfred E. Wolff, 5th Ed. Part 1, pp. 975-977 (1995).*
Banker et al. "Modern Pharmaceutics", 3rd Ed. p. 596 (1996).*
Simplicio et al. Molecules 2008, 13, 519-547.*
Felix et al. Assay and Drug Development Technologies,10(5),pp. 417-431 (2012).*
Bhave,G., Development of a selective small-molecule inhibitor Kir1.1, the renal outer medullary potassium channel, Mol. Pharmacol., 2011, 42-50, 79.
Fringuelli, F. et al., A Simple Procedure for the Synthesis of Labile Aryl Oxiranes by Epoxidation, Organic Preparations and Procedures Int., 1989, p. 757-761, vol. 21, No. 6.
Hebert, S. C. et al., Molecular Diversity and Regulation of Renal Potassium Channels, Physiol Rev., 2005, p. 319-371, vol. 85.

(Continued)

*Primary Examiner* — Emily Bernhardt
(74) *Attorney, Agent, or Firm* — Baerbel R. Brown; Catherine D. Fitch

(57) ABSTRACT

Novel spirocyclic compounds of formula I: and pharmaceutically acceptable salts thereof are disclosed as inhibitors of the ROMK (Kir1.1) channel. The compounds may be used as diuretic and/or natriuretic agents and for the therapy and prophylaxis of medical conditions including cardiovascular diseases such as hypertension, heart failure and chronic kidney disease and conditions associated with excessive salt and water retention. Pharmaceutical compositions and methods of treatment are also included.

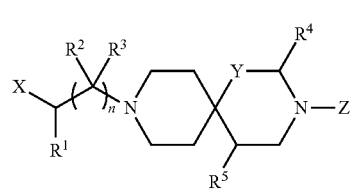

16 Claims, No Drawings

(56) References Cited

OTHER PUBLICATIONS

Ho, K. et al., Cloning and expression of an inwardly rectifying ATP-regulated potassium channel, Nature, 1993, p. 31-38, vol. 362.
International Preliminary Report on Patentability for PCT/US2014/071336 dated Jun. 28, 2016, 5 pages.
International Search Report for PCT/CN2013/090336 dated Sep. 23, 2014, 16 pages.
International Search Report for PCT/US2014/071336 dated Mar. 11, 2015.
Ji, W. et al., Rare independent mutations in renal salt handling genes contribute to blood pressure variation, Nature Genetics, 2008, p. 592-599, vol. 40, No. 5.
Lewis, L M., High-throughput screening reveals a small-molecule inhibitor of the Renal Outer Medullary Potassium Channel and Kir7.1, Mol. Phamcol., 2009, 1094-1103, 76.
Lifton, R. P. et al., Molecular Mechanisms of Human Hypertension, Cell, 2001, p. 545-556, vol. 104.
Lorenz, J. N. et al., Impaired Renal NaCl Absorption inMic Lacking the ROMK Potassium Cannel, a Model for Type II Bartter's Syndrome, The Journal of Biological Chemistry, 2002, p. 37871-37880, vol. 277, No. 40.
Lu, M. et al., Absence of Small Conductance K+ Channel (SK) Activity in Apical Membranes of Thick Ascending Limb and Cortical Collecting Duct in ROMK (Bartter's) Knockout Mice, The Journal of Biological Chemistry, 2002, p. 37881-37887, vol. 277, No. 40.
Molander, G. A. et al., Stereoselective Suzuki-Miyaura Cross-Coupling Reactions of Potassium Alkenyltrifluoroborates with Alkenyl Bromides, J. Org. Chem, 2005, p. 3950-3956, vol. 70.
Molander, G. A. et al., Suzuki-Miyaura Cross-Coupling Reactions of Potassium Vinyltrifluoroborate with Aryl and Heteroaryl Electrophiles, J. Org. Chem, 2006, p. 9861-9686, vol. 71.
Nomura, Y. et al., Synthesis and Structure-Activity Relationships of 2-(4-Benzhydryl-1-piperazinyl)-1-phenylethanols as New Calcium Blockers, Chem. Phar. Bull, 1995, p. 241-246, vol. 43, No. 2.
Qiao, J. X. et al., Copper-Promoted Carbon-Heteroatom Bond Cross-Coupling with Boronic Acids and Derivatives, Synthesis, 2011, p. 829-856, No. 6.
Reinalter, S. C. et al., Pharmacotyping of hypokalaemic salt-losing tubular disorders, Acta Physiol Scand, 2004, p. 513-521, vol. 181.
Shuck, M. E. et al., Cloning and Characterization of Multiple Forms of the Human Kidney ROM-K Potassium channel, The Journal of Biological Chemistry, 1994, p. 24261-24270, Vo. 269, No. 39.
Surry, D. S. et al., Dialkylbiaryl phosphines in Pd-catalyzed amination: a user's guide, Chem. Sci., 2011, p. 27-50, vol. 2.
Tobin, M. D. et al., Common Variants in Genes Underlying Monogenic Hypertension and Hypotension and Blood Pressure in the General Population, Hypertension, 2008, p. 1658-1664, vol. 51. No. 6.
Wang, W. et al., Renal potassium channesl: recent developments, Current Opinion in Nephrology and Hypertension, 2004, p. 549-555, vol. 13, No. 5.
Yin, J. et al., Pd-Catalyzed Intermolecular Amidation of Aryl Halides: The Discovery that Xantphos Can Be Trans-Chelating in a Palladium Complex, J. Am. Chem. Soc., 2002, p. 6043-6048, vol. 124.

\* cited by examiner

INHIBITORS OF THE RENAL OUTER MEDULLARY POTASSIUM CHANNEL

CROSS-REFERENCE TO RELATED APPLICATIONS

This application is a U.S. National Phase application under 35 U.S.C. §371 of PCT Application PCT/US14/071336, filed Dec. 19, 2014, which claims priority from and the benefit of Chinese PCT Application No. PCT/CN13/090335 filed Dec. 24, 2013.

FIELD OF THE INVENTION

The present invention relates to novel spirocyclic compounds and salts thereof useful as renal outer medullary potassium channel inhibitors containing a 6,6-piperidine-piperidine scaffold linked via nitrogen. The present invention further relates to compositions containing such compounds, and methods of use thereof.

BACKGROUND OF THE INVENTION

The Renal Outer Medullary Potassium (ROMK) channel (Kir1.1) (see e.g., H o, K., et al., *Cloning and expression of an inwardly rectifying ATP-regulated potassium channel*, Nature, 1993, 362(6415): p. 31-8.1, 2; and Shuck, M. E., et al., *Cloning and characterization of multiple forms of the human kidney ROM-K potassium channel*, J Biol Chem, 1994, 269(39): p. 24261-70) is a member of the inward rectifier family of potassium channels expressed in two regions of the kidney: thick ascending loop of Henle (TALH) and cortical collecting duct (CCD) (see Hebert, S. C., et al., *Molecular diversity and regulation of renal potassium channels*, Physiol Rev, 2005, 85(1): p. 319-713). At the TALH, ROMK participates in potassium recycling across the luminal membrane which is critical for the function of the $Na^+/K^+/2Cl^-$ co-transporter, the rate-determining step for salt reuptake in this part of the nephron. At the CCD, ROMK provides a pathway for potassium secretion that is tightly coupled to sodium uptake through the amiloride-sensitive sodium channel (see Reinalter, S. C., et al., *Pharmacotyping of hypokalaemic salt-losing tubular disorders*, Acta Physiol Scand, 2004, 181(4): p. 513-21; and Wang, W., *Renal potassium channels: recent developments*, Curr Opin Nephrol Hypertens, 2004, 13(5): p. 549-55). Selective inhibitors of the ROMK channel (also referred to herein as inhibitors of ROMK or ROMK inhibitors) are expected to represent novel diuretics for the treatment of hypertension and other conditions where treatment with a diuretic would be beneficial with potentially reduced liabilities (i.e., hypo- or hyperkalemia, new onset of diabetes, dyslipidemia) over the currently used clinical agents (see Lifton, R. P., A. G. Gharavi, and D. S. Geller, *Molecular mechanisms of human hypertension*, Cell, 2001, 104(4): p. 545-56). Human genetics (Ji, W., et al., *Rare independent mutations in renal salt handling genes contribute to blood pressure variation*, Nat Genet, 2008, 40(5): p. 592-9; and Tobin, M. D., et al., *Common variants in genes underlying monogenic hypertension and hypotension and blood pressure in the general population*, Hypertension, 2008, 51(6): p. 1658-64) and genetic ablation of ROMK in rodents (see Lorenz, J. N., et al., *Impaired renal NaCl absorption in mice lacking the ROMK potassium channel, a model for type II Banter's syndrome*, J Biol Chem, 2002, 277(40): p. 37871-80 and Lu, M., et al., *Absence of small conductance K+ channel (SK) activity in apical membranes of thick ascending limb and cortical collecting duct in ROMK (Bartter's) knockout mice*, J Biol Chem, 2002, 277(40): p. 37881-7) support these expectations. To our knowledge, the first publicly disclosed small molecule selective inhibitors of ROMK, including VU590, were reported from work done at Vanderbilt University as described in Lewis, L. M., et al., *High-Throughput Screening Reveals a Small-Molecule Inhibitor of the Renal Outer Medullary Potassium Channel and Kir7.1*, Mol Pharmacol, 2009, 76(5): p. 1094-1103. The compound VU591 was later reported in Bhave, G. et al., *Development of a Selective Small-Molecule Inhibitor of Kir1.1, the Renal Outer Medullary Potassium Channel*, Mol Pharmacol, 2011, 79(1), p. 42-50, the text of which states that "ROMK (Kir1.1), is a putative drug target for a novel class of loop diuretics that would lower blood pressure without causing hypokalemia."

Since then, numerous ROMK inhibitors have been described.

The continued discovery of selective small molecule inhibitors of ROMK is needed for the development of new treatments for hypertension, heart failure, edematous states and related disorders. The compounds of Formula I and salts thereof of this invention are selective inhibitors of the ROMK channel and could be used for the treatment of hypertension, heart failure and other conditions where treatment with a diuretic or natriuretic would be beneficial.

SUMMARY OF THE INVENTION

The present invention addresses compounds represented by Formula I:

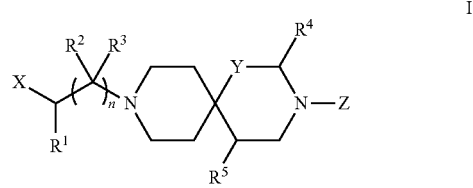

and pharmaceutically acceptable salts thereof. The compounds of Formula I are inhibitors of the ROMK (Kir1.1) channel. As a result, the compounds of Formula I could be used in methods of treatment, inhibition or amelioration of one or more disease states that could benefit from inhibition of ROMK. The compounds of this invention could be used in methods of treatment which comprise administering a therapeutically or prophylactically effective amount of a compound of Formula I to a patient in need of a diuretic and/or natriuretic agent. Therefore, the compounds of Formula I could be valuable pharmaceutically active compounds for the therapy, prophylaxis or both of medical conditions, including, but not limited to, cardiovascular diseases such as hypertension and heart failure as well as chronic kidney disease, and conditions associated with excessive salt and water retention. The compounds of this invention could further be used in combination with other therapeutically effective agents, including but not limited to, other drugs which are useful for the treatment of hypertension, heart failure and conditions associated with excessive salt and water retention. The invention furthermore relates to processes for preparing compounds of Formula I, and pharmaceutical compositions which comprise compounds of Formula I. These and other aspects of the invention will be evident from the description contained herein.

DETAILED DESCRIPTION OF THE INVENTION

The present invention addresses the following compounds, compounds of (1)-(54):

(1) A compound of formula I:

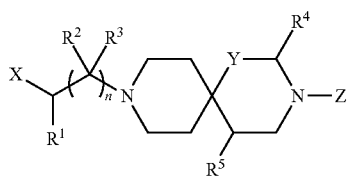

or a pharmaceutically acceptable salt thereof, wherein:
X is

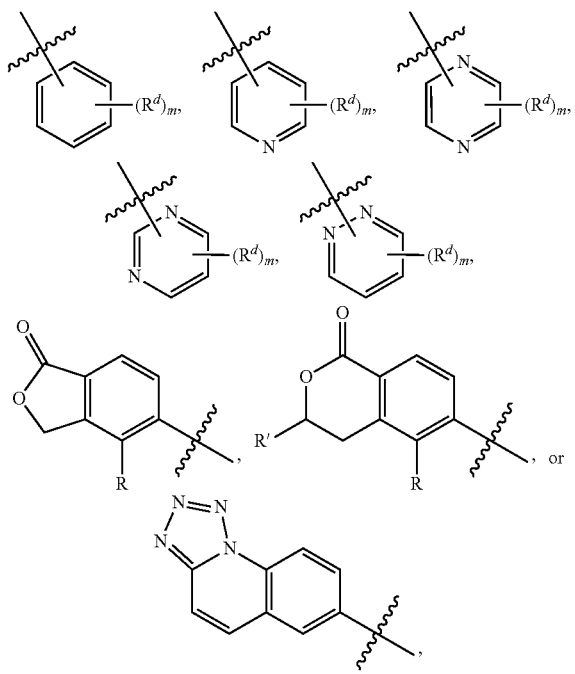

R is H, or $C_{1-6}$alkyl, wherein alkyl substituents are further optionally substituted with 1-4 halogen substituents, R' is H, or $C_{1-6}$alkyl, wherein alkyl substituents are further optionally substituted with 1-4 halogen substituents, $R^1$ is OH, H, $OC_{1-6}$alkyl, $CH_2OH$, or $C_{1-6}$alkyl $OC_{1-6}$alkyl, wherein alkyl substituents are further optionally substituted with 1-4 halogen substituents, or X and $R^1$ together form a bicyclic ring system comprising a saturated carbocyclic ring fused to a heteroaryl ring having 1 N atom, said heteroaryl ring optionally substituted with 1-4 substitutents independently selected from halo, $C_{1-6}$alkyl, 3- to 6-membered cycloalkyl, aryl, heteroaryl, CN, or $OC_{1-6}$ alkyl, wherein alkyl, cycloalkyl, aryl or heteroaryl substituents are further optionally substituted with 1-4 halogen substituents, m is 0, 1, 2, 3, or 4, n is 0, or 1, $R^2$ and $R^3$ are each independently H or $C_{1-6}$alkyl, wherein alkyl substituents are further optionally substituted with 1-4 halogen substituents, or $R^2$ and $R^3$ together form oxo, Y is $CH_2$ or O, $R^4$ is H, $C_{1-6}$alkyl, or oxo, wherein alkyl substituents are further optionally substituted with 1-4 halogen substituents, $R^5$ is H, OH, $C_{1-6}$alkyl, $OC_{1-6}$alkyl, $OC_{1-6}$alkyl $OC_{1-6}$alkyl, or halo, wherein alkyl substituents are further optionally substituted with 1-4 halogen substituents, Z is

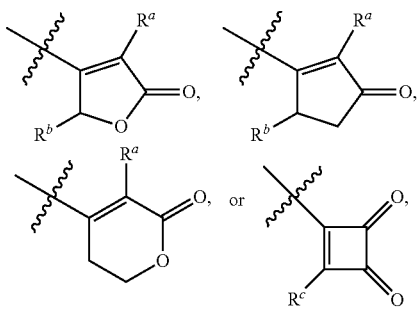

$R^a$ is H, halo, $C_{1-6}$alkyl, 3- to 6-membered cycloalkyl, aryl, or heteroaryl, wherein alkyl, cycloalkyl, aryl or heteroaryl substituents are further optionally substituted with 1-4 halogen substituents, $R^b$ is H, $C_{1-6}$alkyl, or $OC_{1-6}$alkyl, wherein alkyl substituents are further optionally substituted with 1-4 halogen substituents, $R^c$ is $C_{1-6}$alkyl, or 3- to 6-membered cycloalkyl, wherein alkyl or cycloalkyl substituents are further optionally substituted with 1-4 halogen substituents, and each $R^d$ is independently halo, $C_{1-6}$alkyl, 3- to 6-membered cycloalkyl, aryl, heteroaryl, CN, or $OC_{1-6}$ alkyl, wherein alkyl, cycloalkyl, aryl or heteroaryl substituents are further optionally substituted with 1-4 halogen substituents.

(2) The compound of (1) or a pharmaceutically acceptable salt thereof, wherein:

X is

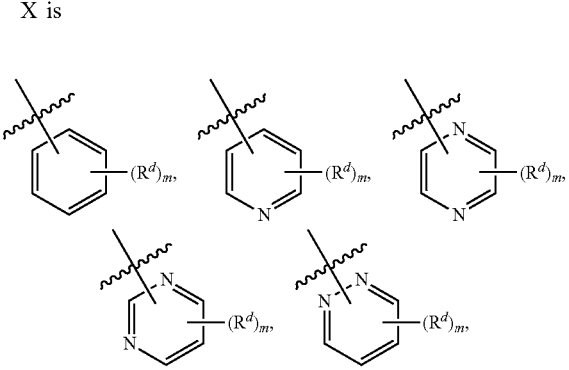

-continued

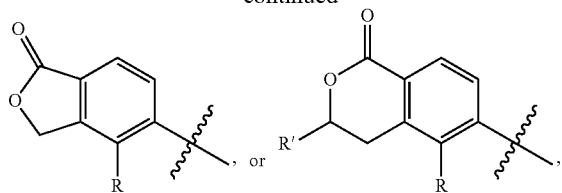

and

R[1] is OH, H, C1-6alkyl, OC$_{1-6}$ alkyl, CH$_2$OH, or C$_{1-6}$alkylOC$_{1-6}$alkyl, wherein alkyl substituents are further optionally substituted with 1-4 halogen substituents, and R[d], m, R and R' are as defined above.

(3) The compound of (1) or (2), or a pharmaceutically acceptable salt thereof, wherein:
X is

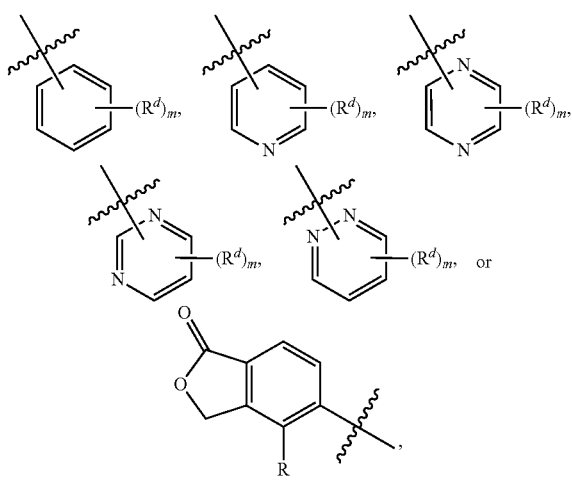

and

R[1] is OH, H, C$_{1-6}$alkyl, OC$_{1-6}$alkyl, CH$_2$OH, or C$_{1-6}$alkylOC$_{1-6}$ alkyl, wherein alkyl substituents are further optionally substituted with 1-4 halogen substituents, and R[d], m R and R' are as defined above.

(4) The compound of any of (1)-(3), or a pharmaceutically acceptable salt thereof, wherein R and R' are independently H or CH$_3$.

(5) The compound of any of (1)-(4), or a pharmaceutically acceptable salt thereof, wherein R and R' are H.

(6) The compound of any of (1)-(5), or a pharmaceutically acceptable salt thereof, wherein:
X is

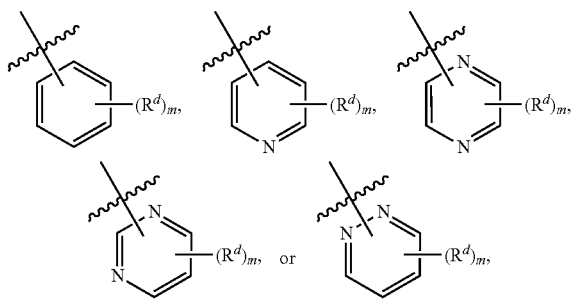

and

R[1] is OH, H, C$_{1-6}$alkyl, OC$_{1-6}$alkyl, CH$_2$OH, or C$_{1-6}$alkyl OC$_{1-6}$ alkyl, wherein alkyl substituents are further optionally substituted with 1-4 halogen substituents, and R[d] and m are as defined above.

(7) The compound of any of (1)-(6), or a pharmaceutically acceptable salt thereof, wherein:
X is

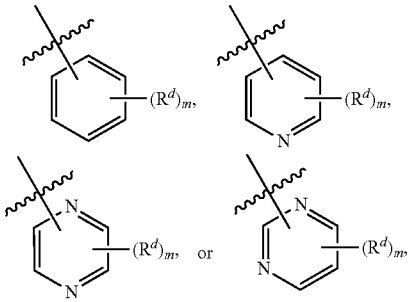

and

R[1] is OH, H, C$_{1-6}$alkyl, OC$_{1-6}$alkyl, CH$_2$OH, or C$_{1-6}$alkylOC$_{1-6}$alkyl, wherein alkyl substituents are further optionally substituted with 1-4 halogen substituents, and R[d] and m are as defined above.

(8) The compound of any of (1)-(7), or a pharmaceutically acceptable salt thereof, wherein:
X is

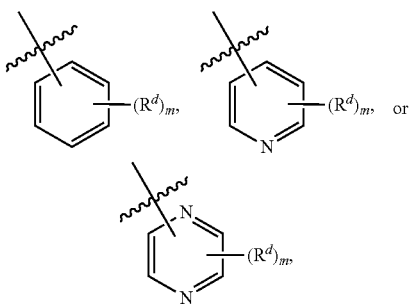

and

R[1] is OH, H, C$_{1-6}$alkyl, OC$_{1-6}$alkyl, CH$_2$OH, or C$_{1-6}$alkylOC$_{1-6}$alkyl, wherein alkyl substituents are further optionally substituted with 1-4 halogen substituents, and R[d] and m are as defined above.

(9) The compound of any of (1)-(8), or a pharmaceutically acceptable salt thereof, wherein:
X is

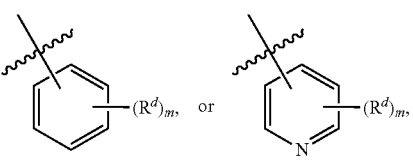

and

R[1] is OH, H, C$_{1-6}$alkyl, OC$_{1-6}$alkyl, CH$_2$OH, or C$_{1-6}$alkylOC$_{1-6}$alkyl, wherein alkyl substituents are further optionally substituted with 1-4 halogen substituents, and R[d] and m are defined above.

(10) The compound of any of (1)-(9), or a pharmaceutically acceptable salt thereof, wherein:

X is

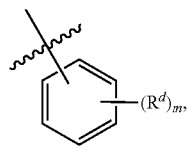

and $R^1$ is OH, H, $C_{1-6}$alkyl, $OC_{1-6}$alkyl, $CH_2OH$, or $C_{1-6}$alkyl$OC_{1-6}$alkyl, wherein alkyl substituents are further optionally substituted with 1-4 halogen substituents, and $R^d$ and m are defined above.

(11) The compound of any of (1)-(10), or a pharmaceutically acceptable salt thereof, wherein $R^1$ is OH, H, $C_{1-6}$alkyl, $OC_{1-6}$alkyl, or $CH_2OH$, wherein alkyl substituents are further optionally substituted with 1-4 halogen substituents.

(12) The compound of any of (1)-(11), or a pharmaceutically acceptable salt thereof, wherein $R^1$ is OH, H, $CH_3$, $CH_2CH_3$, $OCH_3$, or $CH_2OH$.

(13) The compound of any of (1)-(12), or a pharmaceutically acceptable salt thereof, wherein $R^1$ is OH, H, or $OCH_3$.

(14) The compound of any of (1)-(13), or a pharmaceutically acceptable salt thereof, wherein $R^1$ is OH, or H.

(15) The compound of any of (1)-(14), or a pharmaceutically acceptable salt thereof, wherein $R^1$ is OH.

(16) The compound of any of (1)-(15), or a pharmaceutically acceptable salt thereof, wherein m is 0, 1, 2, or 3.

(17) The compound of any of (1)-(16), or a pharmaceutically acceptable salt thereof, wherein m is 0, 1, or 2.

(18) The compound of any of (1)-(17), or a pharmaceutically acceptable salt thereof, wherein m is 0 or 1.

(19) The compound of any of (1)-(18), or a pharmaceutically acceptable salt thereof, wherein m is 1.

(20) The compound of any of (1)-(19), or a pharmaceutically acceptable salt thereof, wherein each $R^d$ is independently halo, $C_{1-6}$alkyl, tetrazolyl, CN, or $OC_{1-6}$alkyl, wherein alkyl substituents are further optionally substituted with 1-4 halogen substituents.

(21) The compound of any of (1)-(20), or a pharmaceutically acceptable salt thereof, wherein each $R^d$ is independently F, Br, $CH_3$, tetrazolyl, CN, or $OCH_3$.

(22) The compound of any of (1)-(21), or a pharmaceutically acceptable salt thereof, wherein each $R^d$ is independently F, $CH_3$, or tetrazolyl.

(23) The compound of any of (1)-(22), or a pharmaceutically acceptable salt thereof, wherein m=1 and $R^d$ is tetrazolyl.

(24) The compound of (1), or a pharmaceutically acceptable salt thereof, wherein:

X and $R^1$ together form

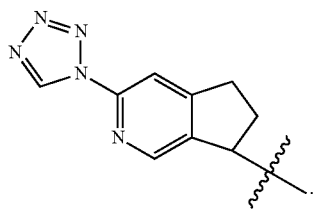 [SMILES: *C1CCc2cc(-n3cnnn3)ncc21]

(25) The compound of any of (1)-(24), or a pharmaceutically acceptable salt thereof, wherein n is 0 or 1.

(26) The compound of any of (1)-(25), or a pharmaceutically acceptable salt thereof, wherein n is 1.

(27) The compound of any of (1)-(26), or a pharmaceutically acceptable salt thereof, wherein $R^2$ and $R^3$ are each H, or $R^2$ and $R^3$ together form oxo.

(28) The compound of any of (1)-(27), or a pharmaceutically acceptable salt thereof, wherein $R^2$ and $R^3$ are each H.

(29) The compound of any of (1)-(27), or a pharmaceutically acceptable salt thereof, wherein $R^2$ and $R^3$ together form oxo.

(30) The compound of any of (1)-(29), or a pharmaceutically acceptable salt thereof, wherein Y is $CH_2$.

(31) The compound of any of (1)-(30), or a pharmaceutically acceptable salt thereof, wherein $R^4$ is H, $CH_3$, or oxo.

(32) The compound of any of (1)-(31), or a pharmaceutically acceptable salt thereof, wherein $R^4$ is H, or $CH_3$.

(33) The compound of any of (1)-(32), or a pharmaceutically acceptable salt thereof, wherein $R^4$ is H.

(34) The compound of any of (1)-(33), or a pharmaceutically acceptable salt thereof, wherein $R^5$ is H, OH, $CH_3$, $CH_2CH_3$, $OCH_3$, $OCH_2OCH_3$, or F.

(35) The compound of any of (1)-(34), or a pharmaceutically acceptable salt thereof, wherein $R^5$ is H, OH, $OCH_3$, or $OCH_2OCH_3$.

(36) The compound of any of (1)-(35), or a pharmaceutically acceptable salt thereof, wherein $R^5$ is H, OH, or $OCH_3$.

(37) The compound of any of (1)-(36), or a pharmaceutically acceptable salt thereof, wherein $R^5$ is H, or OH.

(38) The compound of any of (1)-(37), or a pharmaceutically acceptable salt thereof, wherein $R^5$ is H.

(39) The compound of any of (1)-(38), or a pharmaceutically acceptable salt thereof, wherein $R^c$ is $CH_3$, $CH_2CH_3$, or cyclopropyl.

(40) The compound of any of (1)-(39), or a pharmaceutically acceptable salt thereof, wherein $R^c$ is $CH_3$, or $CH_2CH_3$.

(41) The compound of any of (1)-(40), or a pharmaceutically acceptable salt thereof, wherein $R^c$ is $CH_3$.

(42) The compound of any of (1)-(41), or a pharmaceutically acceptable salt thereof, wherein:

Z is

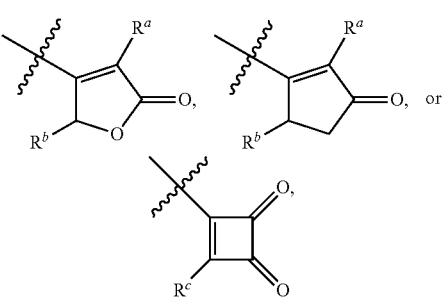

$R^a$, $R^b$ and $R^c$ are as defined above.

(43) The compound of any of (1)-(42), or a pharmaceutically acceptable salt thereof, wherein:
Z is

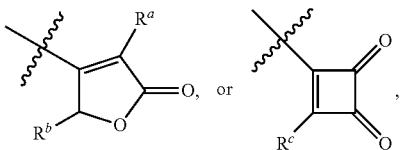

$R^a$, $R^b$ and $R^c$ are as defined above.

(44) The compound of any of (1)-(43), or a pharmaceutically acceptable salt thereof, wherein:
Z is

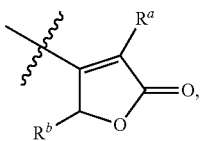

$R^a$ and $R^b$ are as defined above.

(45) The compound of any of (1)-(44), or a pharmaceutically acceptable salt thereof, wherein $R^a$ is H, F, Cl, $CH_3$, cyclopropyl, phenyl, or pyridyl, wherein $CH_3$, cyclopropyl, phenyl, or pyridyl substituents are further optionally substituted with 1-3 halogen substituents.

(46) The compound of any of (1)-(45), or a pharmaceutically acceptable salt thereof, wherein $R^a$ is H, F, Cl, $CH_3$, cyclopropyl, phenyl, or pyridyl.

(47) The compound of any of (1)-(46), or a pharmaceutically acceptable salt thereof, wherein $R^a$ is H, F, Cl, or $CH_3$.

(48) The compound of any of (1)-(47), or a pharmaceutically acceptable salt thereof, wherein $R^a$ is H, or $CH_3$.

(49) The compound of any of (1)-(48), or a pharmaceutically acceptable salt thereof, wherein $R^a$ is H.

(50) The compound of any of (1)-(49), or a pharmaceutically acceptable salt thereof, wherein $R^b$ is H, $CH_3$, or $OCH_2CH_3$.

(51) The compound of any of (1)-(50), or a pharmaceutically acceptable salt thereof, wherein $R^b$ is H, or $CH_3$.

(52) The compound of any of (1)-(51), or a pharmaceutically acceptable salt thereof, wherein $R^b$ is H.

(53) The compound of any of (1)-(3), (6)-(23), (25-28) and (30)-(52), or a pharmaceutically acceptable salt thereof, wherein:
m is 1,
n is 1,
$R^1$ is OH,
$R^2$, $R^3$, $R^4$, and $R^5$ are each H,
$R^d$ is tetrazolyl, and
Y is $CH_2$.

(54) A compound of formula I which is elsewhere disclosed herein or is:
5-{2-[9-(5-oxo-2,5-dihydrofuran-3-yl)-3,9-diazaspiro[5.5]undec-3-yl]ethyl}-2-benzofuran-1(3H)-one;
4-methyl-5-{2-[9-(5-oxo-2,5-dihydrofuran-3-yl)-3,9-diazaspiro[5.5]undec-3-yl]ethyl}-2-benzofuran-1(3H)-one;
3-methyl-4-(9-(2-(4-methyl-1-oxo-1,3-dihydroisobenzofuran-5-yl)ethyl)-3,9-diazaspiro[5.5]undecan-3-yl)cyclobut-3-ene-1,2-dione;
(R)-3-(9-(2-methoxy-2-(4-methyl-1-oxo-1,3-dihydroisobenzofuran-5-yl)ethyl)-3,9-diazaspiro[5.5]undecan-3-yl)-4-methylcyclobut-3-ene-1,2-dione;
5-{(1S)-1-hydroxy-2-[9-(5-oxo-2,5-dihydrofuran-3-yl)-3,9-diazaspiro[5.5]undec-3-yl]ethyl}-4-methyl-2-benzofuran-1(3H)-one;
4-(9-{(2S)-2-hydroxy-2-[6-(1H-tetrazol-1-yl)pyridin-2-yl]ethyl}-3,9-diazaspiro[5.5]undec-3-yl)-3-methylfuran-2(5H)-one;
4-(9-{(2R)-2-hydroxy-2-[6-(1H-tetrazol-1-yl)pyridin-2-yl]ethyl}-3,9-diazaspiro[5.5]undec-3-yl)-3-methylfuran-2(5H)-one;
5-{(1R)-1-hydroxy-2-[9-(4-methyl-5-oxo-2,5-dihydrofuran-3-yl)-3,9-diazaspiro[5.5]undec-3-yl]ethyl}-4-methyl-2-benzofuran-1(3H)-one;
5-{(1R)-1-hydroxy-2-[9-(5-oxo-2,5-dihydrofuran-3-yl)-3,9-diazaspiro[5.5]undec-3-yl]ethyl}-4-methyl-2-benzofuran-1(3H)-one;
6-{(1S)-1-hydroxy-2-[9-(5-oxo-2,5-dihydrofuran-3-yl)-3,9-diazaspiro[5.5]undec-3-yl]ethyl}-4-methoxypyridine-3-carbonitrile;
(3R)-6-{1-hydroxy-2-[9-(5-oxo-2,5-dihydrofuran-3-yl)-3,9-diazaspiro[5.5]undec-3-yl]ethyl}-3-methyl-3,4-dihydro-1H-isochromen-1-one;
(3S)-6-{(1R)-1-hydroxy-2-[9-(5-oxo-2,5-dihydrofuran-3-yl)-3,9-diazaspiro[5.5]undec-3-yl]ethyl}-3-methyl-3,4-dihydro-1H-isochromen-1-one;
(3S)-6-{(1S)-1-hydroxy-2-[9-(5-oxo-2,5-dihydrofuran-3-yl)-3,9-diazaspiro[5.5]undec-3-yl]ethyl}-3-methyl-3,4-dihydro-1H-isochromen-1-one;
4-(9-{(2R)-2-hydroxy-2-[2-methyl-6-(1H-tetrazol-1-yl)pyridin-3-yl]ethyl}-3,9-diazaspiro[5.5]undec-3-yl)furan-2(5H)-one;
4-(9-{(2S)-2-hydroxy-2-[2-methyl-6-(1H-tetrazol-1-yl)pyridin-3-yl]ethyl}-3,9-diazaspiro[5.5]undec-3-yl)furan-2(5H)-one;
4-(9-{2-hydroxy-2-[2-(1H-tetrazol-1-yl)pyrimidin-5-yl]ethyl}-3,9-diazaspiro[5.5]undec-3-yl)furan-2(5H)-one;
4-(9-{(2S)-2-hydroxy-2-[6-(1H-tetrazol-1-yl)pyridazin-3-yl]ethyl}-3,9-diazaspiro[5.5]undec-3-yl)furan-2(5H)-one;
4-(9-{(2R)-2-hydroxy-2-[6-(1H-tetrazol-1-yl)pyridazin-3-yl]ethyl}-3,9-diazaspiro[5.5]undec-3-yl)furan-2(5H)-one;
4-(9-{(2R)-2-hydroxy-2-[6-(1H-tetrazol-1-yl)pyridin-3-yl]ethyl}-3,9-diazaspiro[5.5]undec-3-yl)furan-2(5H)-one;
4-(9-{(2S)-2-hydroxy-2-[6-(1H-tetrazol-1-yl)pyridin-3-yl]ethyl}-3,9-diazaspiro[5.5]undec-3-yl)furan-2(5H)-one;
4-(9-{(2S)-2-hydroxy-2-[3-methyl-5-(1H-tetrazol-1-yl)pyridin-2-yl]ethyl}-3,9-diazaspiro[5.5]undec-3-yl)furan-2(5H)-one;
4-(9-{(2R)-2-hydroxy-2-[3-methyl-5-(1H-tetrazol-1-yl)pyridin-2-yl]ethyl}-3,9-diazaspiro[5.5]undec-3-yl)furan-2(5H)-one;
4-(9-{(2R)-2-[2-fluoro-4-(1H-tetrazol-1-yl)phenyl]-2-hydroxyethyl}-3,9-diazaspiro[5.5]undec-3-yl)furan-2(5H)-one;
4-(9-{(2S)-2-[2-fluoro-4-(1H-tetrazol-1-yl)phenyl]-2-hydroxyethyl}-3,9-diazaspiro[5.5]undec-3-yl)furan-2(5H)-one;
4-(9-{(2R)-2-hydroxy-2-[2-methyl-4-(1H-tetrazol-1-yl)phenyl]ethyl}-3,9-diazaspiro[5.5]undec-3-yl)furan-2(5H)-one;
4-(9-{(2S)-2-hydroxy-2-[2-methyl-4-(1H-tetrazol-1-yl)phenyl]ethyl}-3,9-diazaspiro[5.5]undec-3-yl)furan-2(5H)-one;

9-{(2R)-2-hydroxy-2-[2-methyl-6-(1H-tetrazol-1-yl)pyridin-3-yl]ethyl}-3-(5-oxo-2,5-dihydrofuran-3-yl)-3,9-diazaspiro[5.5]undecan-2-one;

9-[(2R)-2-hydroxy-2-(4-methyl-1-oxo-1,3-dihydro-2-benzofuran-5-yl)ethyl]-3-(5-oxo-2,5-dihydrofuran-3-yl)-3,9-diazaspiro[5.5]undecan-2-one;

9-[(2R)-2-hydroxy-2-(4-methyl-1-oxo-1,3-dihydro-2-benzofuran-5-yl)ethyl]-3-(4-methyl-5-oxo-2,5-dihydrofuran-3-yl)-3,9-diazaspiro[5.5]undecan-2-one;

9-{(2R)-2-hydroxy-2-[2-methyl-6-(1H-tetrazol-1-yl)pyridin-3-yl]ethyl}-3-(4-methyl-5-oxo-2,5-dihydrofuran-3-yl)-3,9-diazaspiro[5.5]undecan-2-one;

(R)-9-(2-(6-(1H-tetrazol-1-yl)pyridin-3-yl)-2-hydroxyethyl)-3-(5-oxo-2,5-dihydrofuran-3-yl)-1-oxa-3,9-diazaspiro[5.5]undecan-2-one;

(R)-9-(2-hydroxy-2-(2-methyl-6-(1H-tetrazol-1-yl)pyridin-3-yl)ethyl)-3-(5-oxo-2,5-dihydrofuran-3-yl)-1-oxa-3,9-diazaspiro[5.5]undecan-2-one;

5-{(1R)-1-hydroxy-2-[8-methyl-9-(5-oxo-2,5-dihydrofuran-3-yl)-3,9-diazaspiro[5.5]undec-3-yl]ethyl}-4-methyl-2-benzofuran-1(3H)-one;

5-{(1R)-1-hydroxy-2-[8-methyl-9-(5-oxo-2,5-dihydrofuran-3-yl)-3,9-diazaspiro[5.5]undec-3-yl]ethyl}-4-methyl-2-benzofuran-1(3H)-one;

5-{(1R)-2-[(7R)-7-fluoro-9-(4-methyl-5-oxo-2,5-dihydrofuran-3-yl)-3,9-diazaspiro[5.5]undec-3-yl]-1-hydroxyethyl}-4-methyl-2-benzofuran-1(3H)-one;

5-{(1R)-2-[(7S)-7-fluoro-9-(4-methyl-5-oxo-2,5-dihydrofuran-3-yl)-3,9-diazaspiro[5.5]undec-3-yl]-1-hydroxyethyl}-4-methyl-2-benzofuran-1(3H)-one;

4-{9-[2-(4-bromophenyl)-2-hydroxyethyl]-3,9-diazaspiro[5.5]undec-3-yl}-3-methylfuran-2(5H)-one;

5-{(1R)-1-hydroxy-2-[9-(2-methyl-5-oxo-2,5-dihydrofuran-3-yl)-3,9-diazaspiro[5.5]undec-3-yl]ethyl}-4-methyl-2-benzofuran-1(3H)-one;

5-{(1R)-2-[9-(4-fluoro-5-oxo-2,5-dihydrofuran-3-yl)-3,9-diazaspiro[5.5]undec-3-yl]-1-hydroxyethyl}-4-methyl-2-benzofuran-1(3H)-one;

3-fluoro-4-(9-{(2R)-2-hydroxy-2-[2-methyl-6-(1H-tetrazol-1-yl)pyridin-3-yl]ethyl}-3,9-diazaspiro[5.5]undec-3-yl)furan-2(5H)-one;

5-{(1R)-2-[9-(4-chloro-5-oxo-2,5-dihydrofuran-3-yl)-3,9-diazaspiro[5.5]undec-3-yl]-1-hydroxyethyl}-4-methyl-2-benzofuran-1(3H)-one;

5-{(1R)-1-hydroxy-2-[9-(5-oxo-4-phenyl-2,5-dihydrofuran-3-yl)-3,9-diazaspiro[5.5]undec-3-yl]ethyl}-4-methyl-2-benzofuran-1(3H)-one;

5-{(1R)-1-hydroxy-2-[9-(5-oxo-4-pyridin-4-yl-2,5-dihydrofuran-3-yl)-3,9-diazaspiro[5.5]undec-3-yl]ethyl}-4-methyl-2-benzofuran-1(3H)-one;

3-cyclopropyl-4-(9-{2-hydroxy-2-[2-methyl-6-(1H-tetrazol-1-yl)pyridin-3-yl]ethyl}-3,9-diazaspiro[5.5]undec-3-yl)furan-2(5H)-one;

5-{(1R)-2-[9-(4-cyclopropyl-5-oxo-2,5-dihydrofuran-3-yl)-3,9-diazaspiro[5.5]undec-3-yl]-1-hydroxyethyl}-4-methyl-2-benzofuran-1(3H)-one;

4-(9-{(2R)-2-hydroxy-2-[2-methyl-6-(1H-tetrazol-1-yl)pyridin-3-yl]ethyl}-3,9-diazaspiro[5.5]undec-3-yl)-3-methylfuran-2(5H)-one;

4-(9-{(2S)-2-hydroxy-2-[2-methyl-6-(1H-tetrazol-1-yl)pyridin-3-yl]ethyl}-3,9-diazaspiro[5.5]undec-3-yl)-3-methylfuran-2(5H)-one;

4-(9-{(2R)-2-hydroxy-2-[6-(1H-tetrazol-1-yl)pyridin-3-yl]ethyl}-3,9-diazaspiro[5.5]undec-3-yl)-3-methylfuran-2(5H)-one;

4-(9-{(2S)-2-hydroxy-2-[6-(1H-tetrazol-1-yl)pyridin-3-yl]ethyl}-3,9-diazaspiro[5.5]undec-3-yl)-3-methylfuran-2(5H)-one;

4-(9-{(2R)-2-hydroxy-2-[4-(1H-tetrazol-1-yl)phenyl]ethyl}-3,9-diazaspiro[5.5]undec-3-yl)-3-methylfuran-2(5H)-one;

4-(9-{(2S)-2-hydroxy-2-[4-(1H-tetrazol-1-yl)phenyl]ethyl}-3,9-diazaspiro[5.5]undec-3-yl)-3-methylfuran-2(5H)-one;

4-(9-{(2S)-2-hydroxy-2-[5-(1H-tetrazol-1-yl)pyridin-2-yl]ethyl}-3,9-diazaspiro[5.5]undec-3-yl)-3-methylfuran-2(5H)-one;

4-(9-{(2R)-2-hydroxy-2-[5-(1H-tetrazol-1-yl)pyridin-2-yl]ethyl}-3,9-diazaspiro[5.5]undec-3-yl)-3-methylfuran-2(5H)-one;

4-(9-{2-[2-fluoro-4-(1H-tetrazol-1-yl)phenyl]-2-hydroxyethyl}-3,9-diazaspiro[5.5]undec-3-yl)-3-methylfuran-2(5H)-one;

4-(9-{2-[2-fluoro-4-(1H-tetrazol-1-yl)phenyl]-2-hydroxyethyl}-3,9-diazaspiro[5.5]undec-3-yl)-3-methylfuran-2(5H)-one;

4-(9-{2-hydroxy-2-[2-methyl-4-(1H-tetrazol-1-yl)phenyl]ethyl}-3,9-diazaspiro[5.5]undec-3-yl)-3-methylfuran-2(5H)-one;

4-(9-{2-hydroxy-2-[2-methyl-4-(1H-tetrazol-1-yl)phenyl]ethyl}-3,9-diazaspiro[5.5]undec-3-yl)-3-methylfuran-2(5H)-one;

4-(9-{2-hydroxy-1-[2-methyl-4-(1H-tetrazol-1-yl)phenyl]ethyl}-3,9-diazaspiro[5.5]undec-3-yl)-3-methylfuran-2(5H)-one;

4-(9-{2-hydroxy-1-[2-methyl-4-(1H-tetrazol-1-yl)phenyl]ethyl}-3,9-diazaspiro[5.5]undec-3-yl)-3-methylfuran-2(5H)-one;

4-(9-{(2R)-2-hydroxy-2-[3-(1H-tetrazol-1-yl)phenyl]ethyl}-3,9-diazaspiro[5.5]undec-3-yl)-3-methylfuran-2(5H)-one;

4-(9-{(2S)-2-hydroxy-2-[3-(1H-tetrazol-1-yl)phenyl]ethyl}-3,9-diazaspiro[5.5]undec-3-yl)-3-methylfuran-2(5H)-one;

4-(9-{(2R)-2-hydroxy-2-[2-(1H-tetrazol-1-yl)pyridin-4-yl]ethyl}-3,9-diazaspiro[5.5]undec-3-yl)-3-methylfuran-2(5H)-one;

4-(9-{(2S)-2-hydroxy-2-[2-(1H-tetrazol-1-yl)pyridin-4-yl]ethyl}-3,9-diazaspiro[5.5]undec-3-yl)-3-methylfuran-2(5H)-one;

4-(9-{(2R)-2-hydroxy-2-[5-(1H-tetrazol-1-yl)pyridin-3-yl]ethyl}-3,9-diazaspiro[5.5]undec-3-yl)-3-methylfuran-2(5H)-one;

4-(9-{(2S)-2-hydroxy-2-[5-(1H-tetrazol-1-yl)pyridin-3-yl]ethyl}-3,9-diazaspiro[5.5]undec-3-yl)-3-methylfuran-2(5H)-one;

4-(9-{(2S)-2-hydroxy-2-[6-(1H-tetrazol-1-yl)pyrazin-2-yl]ethyl}-3,9-diazaspiro[5.5]undec-3-yl)-3-methylfuran-2(5H)-one;

4-(9-{(2R)-2-hydroxy-2-[6-(1H-tetrazol-1-yl)pyrazin-2-yl]ethyl}-3,9-diazaspiro[5.5]undec-3-yl)-3-methylfuran-2(5H)-one;

4-(9-{(2S)-2-hydroxy-2-[4-(1H-tetrazol-1-yl)pyridin-2-yl]ethyl}-3,9-diazaspiro[5.5]undec-3-yl)-3-methylfuran-2(5H)-one;

4-(9-{(2R)-2-hydroxy-2-[4-(1H-tetrazol-1-yl)pyridin-2-yl]ethyl}-3,9-diazaspiro[5.5]undec-3-yl)-3-methylfuran-2(5H)-one;

4-(9-{(2S)-2-hydroxy-2-[2-(1H-tetrazol-1-yl)phenyl]ethyl}-3,9-diazaspiro[5.5]undec-3-yl)-3-methylfuran-2(5H)-one;

3-(9-{(2R)-2-hydroxy-2-[2-methyl-6-(1H-tetrazol-1-yl)pyridin-3-yl]ethyl}-3,9-diazaspiro[5.5]undec-3-yl)cyclopent-2-en-1-one;

3-(9-{(2S)-2-hydroxy-2-[2-methyl-6-(1H-tetrazol-1-yl)pyridin-3-yl]ethyl}-3,9-diazaspiro[5.5]undec-3-yl)cyclopent-2-en-1-one;

5-{(1R)-1-hydroxy-2-[9-(3-oxocyclopent-1-en-1-yl)-3,9-diazaspiro[5.5]undec-3-yl]ethyl}-4-methyl-2-benzofuran-1(3H)-one;

3-(9-{2-hydroxy-2-[2-methyl-4-(1H-tetrazol-1-yl)phenyl]ethyl}-3,9-diazaspiro[5.5]undec-3-yl)cyclopent-2-en-1-one;

3-(9-{(2R)-2-hydroxy-2-[2-methyl-6-(1H-tetrazol-1-yl)pyridin-3-yl]ethyl}-3,9-diazaspiro[5.5]undec-3-yl)-2-methylcyclopent-2-en-1-one;

3-(9-{(2S)-2-hydroxy-2-[2-methyl-6-(1H-tetrazol-1-yl)pyridin-3-yl]ethyl}-3,9-diazaspiro[5.5]undec-3-yl)-2-methylcyclopent-2-en-1-one;

5-{(1R)-1-hydroxy-2-[9-(2-methyl-3-oxocyclopent-1-en-1-yl)-3,9-diazaspiro[5.5]undec-3-yl]ethyl}-4-methyl-2-benzofuran-1(3H)-one;

3-(9-{(2R)-2-hydroxy-2-[2-methyl-4-(1H-tetrazol-1-yl)phenyl]ethyl}-3,9-diazaspiro[5.5]undec-3-yl)-2-methylcyclopent-2-en-1-one;

3-{9-[(2R)-2-hydroxy-2-(4-methyl-1-oxo-1,3-dihydro-2-benzofuran-5-yl)ethyl]-3,9-diazaspiro[5.5]undec-3-yl}-4-methylcyclobut-3-ene-1,2-dione;

(R)-3-ethyl-4-(9-(2-hydroxy-2-(4-methyl-1-oxo-1,3-dihydroisobenzofuran-5-yl)ethyl)-3,9-diazaspiro[5.5]undecan-3-yl)cyclobut-3-ene-1,2-dione;

(R)-3-cyclopropyl-4-(9-(2-hydroxy-2-(4-methyl-1-oxo-1,3-dihydroisobenzofuran-5-yl)ethyl)-3,9-diazaspiro[5.5]undecan-3-yl)cyclobut-3-ene-1,2-dione;

(R)-3-(9-(2-(6-(1H-tetrazol-1-yl)pyridin-3-yl)-2-hydroxyethyl)-3,9-diazaspiro[5.5]undecan-3-yl)-4-methylcyclobut-3-ene-1,2-dione;

(S)-3-(9-(2-(6-(1H-tetrazol-1-yl)pyridin-3-yl)-2-hydroxyethyl)-3,9-diazaspiro[5.5]undecan-3-yl)-4-methylcyclobut-3-ene-1,2-dione;

(S)-3-(9-(2-(6-(1H-tetrazol-1-yl)pyridazin-3-yl)-2-hydroxyethyl)-3,9-diazaspiro[5.5]undecan-3-yl)-4-methylcyclobut-3-ene-1,2-dione;

(R)-3-(9-(2-(6-(1H-tetrazol-1-yl)pyridazin-3-yl)-2-hydroxyethyl)-3,9-diazaspiro[5.5]undecan-3-yl)-4-methylcyclobut-3-ene-1,2-dione;

(S)-3-(9-(2-(5-(1H-tetrazol-1-yl)pyrazin-2-yl)-2-hydroxyethyl)-3,9-diazaspiro[5.5]undecan-3-yl)-4-methylcyclobut-3-ene-1,2-dione;

(R)-3-(9-(2-(5-(1H-tetrazol-1-yl)pyrazin-2-yl)-2-hydroxyethyl)-3,9-diazaspiro[5.5]undecan-3-yl)-4-methylcyclobut-3-ene-1,2-dione;

(S)-3-(9-(2-(5-(1H-tetrazol-1-yl)pyridin-2-yl)-2-hydroxyethyl)-3,9-diazaspiro[5.5]undecan-3-yl)-4-methylcyclobut-3-ene-1,2-dione;

(R)-3-(9-(2-hydroxy-2-(tetrazolo[1,5-a]quinolin-7-yl)ethyl)-3,9-diazaspiro[5.5]undecan-3-yl)-4-methylcyclobut-3-ene-1,2-dione;

(S)-3-(9-(2-hydroxy-2-(tetrazolo[1,5-a]quinolin-7-yl)ethyl)-3,9-diazaspiro[5.5]undecan-3-yl)-4-methylcyclobut-3-ene-1,2-dione;

5-{(1S)-1-methoxy-2-[9-(5-oxo-2,5-dihydrofuran-3-yl)-3,9-diazaspiro[5.5]undec-3-yl]ethyl}-4-methyl-2-benzofuran-1(3H)-one;

5-{(1R)-1-methoxy-2-[9-(5-oxo-2,5-dihydrofuran-3-yl)-3,9-diazaspiro[5.5]undec-3-yl]ethyl}-4-methyl-2-benzofuran-1(3H)-one;

5-{(1R)-2-[9-(2-ethoxy-5-oxo-2,5-dihydrofuran-3-yl)-3,9-diazaspiro[5.5]undec-3-yl]-1-hydroxyethyl}-4-methyl-2-benzofuran-1(3H)-one;

5-{(1R)-1-hydroxy-2-[9-(6-oxo-3,6-dihydro-2H-pyran-4-yl)-3,9-diazaspiro[5.5]undec-3-yl]ethyl}-4-methyl-2-benzofuran-1(3H)-one;

5-{(1R)-1-hydroxy-2-[(7R)-7-hydroxy-9-(4-methyl-5-oxo-2,5-dihydrofuran-3-yl)-3,9-diazaspiro[5.5]undec-3-yl]ethyl}-4-methyl-2-benzofuran-1(3H)-one;

5-{(1R)-1-hydroxy-2-[(7R)-7-(methoxymethoxy)-9-(4-methyl-5-oxo-2,5-dihydrofuran-3-yl)-3,9-diazaspiro[5.5]undec-3-yl]ethyl}-4-methyl-2-benzofuran-1(3H)-one;

5-{(1R)-1-hydroxy-2-[(7S)-7-(methoxymethoxy)-9-(4-methyl-5-oxo-2,5-dihydrofuran-3-yl)-3,9-diazaspiro[5.5]undec-3-yl]ethyl}-4-methyl-2-benzofuran-1(3H)-one;

5-{(1R)-1-hydroxy-2-[(7R)-7-methoxy-9-(4-methyl-5-oxo-2,5-dihydrofuran-3-yl)-3,9-diazaspiro[5.5]undec-3-yl]ethyl}-4-methyl-2-benzofuran-1(3H)-one;

5-{(1R)-1-hydroxy-2-[(7S)-7-methoxy-9-(4-methyl-5-oxo-2,5-dihydrofuran-3-yl)-3,9-diazaspiro[5.5]undec-3-yl]ethyl}-4-methyl-2-benzofuran-1(3H)-one;

4-(9-{[6-(1H-tetrazol-1-yl)pyridin-3-yl]acetyl}-3,9-diazaspiro[5.5]undec-3-yl)furan-2(5H)-one;

4-(9-{[2,6-difluoro-4-(1H-tetrazol-1-yl)phenyl]acetyl}-3,9-diazaspiro[5.5]undec-3-yl)furan-2(5H)-one;

4-(9-{[5-fluoro-6-(1H-tetrazol-1-yl)pyridin-3-yl]acetyl}-3,9-diazaspiro[5.5]undec-3-yl)furan-2(5H)-one;

4-(9-{[4-(1H-tetrazol-1-yl)phenyl]acetyl}-3,9-diazaspiro[5.5]undec-3-yl)furan-2(5H)-one;

4-(9-{[3-(1H-tetrazol-1-yl)-6,7-dihydro-5H-cyclopenta[c]pyridin-7-yl]carbonyl}-3,9-diazaspiro[5.5]undec-3-yl)furan-2(5H)-one;

4-(9-{[2,5-difluoro-4-(1H-tetrazol-1-yl)phenyl]acetyl}-3,9-diazaspiro[5.5]undec-3-yl)furan-2(5H)-one;

4-methyl-5-{2-oxo-2-[9-(5-oxo-2,5-dihydrofuran-3-yl)-3,9-diazaspiro[5.5]undec-3-yl]ethyl}-2-benzofuran-1(3H)-one; or 4-(9-{[5-(1H-tetrazol-1-yl)pyrazin-2-yl]acetyl}-3,9-diazaspiro[5.5]undec-3-yl)furan-2(5H)-one;

or a pharmaceutically acceptable salt thereof.

The compounds of the present invention are further described herein using the terms defined below unless otherwise specified.

"Alkyl", as well as other groups having the prefix "alk", such as alkoxy, and the like, means carbon chains which may be linear or branched, or combinations thereof, containing the indicated number of carbon atoms. Examples of alkyl groups include methyl, ethyl, propyl, isopropyl, butyl, sec- and tert-butyl, pentyl, hexyl, heptyl, octyl, nonyl and the like. In specific embodiments, alkyl means a linear or branched $C_{1-6}$ or $C_{1-3}$ alkyl.

"Alkoxy" refers to an alkyl group linked to oxygen. In specific embodiments, alkoxy means a linear or branched $C_{1-6}$ or $C_{1-3}$ in which the point of attachment is at oxygen.

"Aryl" relates to a phenyl, naphthyl, indanyl group, or a phenyl ring fused to a cycloalkyl or a heterocycle group in which the point of attachment is on the aromatic portion. In specific embodiments, aryl means phenyl.

"Cycloalkyl" means a saturated cyclic hydrocarbon radical having the number of carbon atoms designated. "Cycloalkyl" also includes a monocyclic ring fused to an aryl or heteroaryl group in which the point of attachment is on the non-aromatic portion. A non-limiting example of a monocyclic non-aromatic ring fused to a heteroaryl group is tetrazolo[1,5-a]quinolone. Examples of cycloalkyl include cyclopropyl, cyclobutyl, cyclopentyl, cyclohexyl, cycloheptyl, tetrahydronaphthyl, decahydronaphthyl, indanyl and the like. In specific embodiments, cycloalkyl means a $C_{3-8}$ or $C_{3-6}$cycloalkyl. In particular embodiments, cycloalkyl means $C_3$cycloalkyl.

"Heteroaryl" means an aromatic or partially aromatic cyclic ring structure in which one or more atoms in the ring, the heteroatom(s), is an element other than carbon and wherein the point of attachment is on the aromatic portion. Heteroatoms are typcially oxygen ("O"), sulfur ("S") or nitrogen ("N") atoms. Examples of heteroaryl groups include: pyrrolyl or pyrrole, isoxazolyl or isoxazole, isothiazolyl or isothiazole, pyrazolyl or pyrazole, pyridyl, oxazolyl or oxazole, oxadiazolyl or oxadiazole, thiadiazolyl or thiadiazole, thiazolyl or thiazole, imidazolyl or imidazole, triazolyl or triazole, tetrazolyl or tetrazole, furyl, triazinyl, thienyl, pyrimidyl, benzisoxazolyl or benzisoxazole, benzoxazolyl or benzoazole, benzothiazolyl or benzothiazole, benzothiadiazolyl or benzothiadiazole, dihydrobenzofuranyl or dihydrobenzofurane, indolinyl or indoline, pyridazinyl or pyridazine, indazolyl or indazole, isoindolyl or isoindole, dihydrobenzothienyl, indolizinyl or indolizine, cinnolinyl or cinnoline, phthalazinyl or phthalazine, quinazolinyl or quinazoline, naphthyridinyl or naphthyridine, carbazolyl or carbazole, benzodioxolyl or benzodioxole, quinoxalinyl or quinoxaline, purinyl or purine, furazanyl or furazane, isobenzylfuranyl or isobenzylfurane, benzimidazolyl or benzimidazole, benzofuranyl or benzofurane, benzothienyl or benzothiene, quinolyl or quinoline, oxo-dihydroqunoline, indolyl or indole, oxindole, isoquinolyl or isoquinoline, dibenzofuranyl or dibenzofurane, and the like.

"Heterocycle" or "heterocyclic" refers to a saturated cyclic ring structure in which one or more atoms in the ring, the heteroatom(s), is an element other than carbon. Heteroatoms are typcially oxygen ("O"), sulfur ("S") or nitrogen ("N") atoms. "Heterocycle" or "heterocyclic" also includes a monoheterocyclic ring fused to an aryl or heteroaryl group in which the point of attachment is on the non-aromatic portion.

"Halogen" includes fluorine, chlorine, bromine and iodine.

Unless expressly depicted or described otherwise, variables depicted in a structural formula with a "floating" bond, such as substituent —$(R^d)_m$, are permitted on any available carbon atom in the ring to which each is attached.

Substitution, where applicable, may be on any available carbon atom that results in a stable structure. Furthermore, where language indicates that certain groups or substituents (e.g., alkyl groups or substituents) are further optionally substituted, that language includes all groups or substituents having that particular group or substituent as a component thereof. For example, use of the language "wherein alkyl substituents are further optionally substituted" indicates that any substituents possessing an alkyl component(s) can be substituted in the alkyl group(s) thereof.

Also, number ranges where provided (e.g., 1-6) expressly include each and every number in that range as a discrete embodiment.

Atoms of the compounds described herein may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of any of (1)-(54). For example, different isotopic forms of hydrogen (H) include protium ($^1H$) and deuterium ($^2H$). Protium is the predominant hydrogen isotope found in nature. Enriching for deuterium may yield certain therapeutic advantages, such as increasing in vivo half-life or reducing dosage requirements, or may provide a compound useful as a standard for characterization of biological samples. Isotopically-enriched compounds of any of (1)-(54) described herein can be prepared without undue experimentation by conventional techniques well known to those skilled in the art or by processes analogous to those described in the Examples herein using appropriate isotopically-enriched reagents and/or intermediates.

Individual tautomers of the compounds of any of (1)-(54), as well as mixtures thereof, are encompassed herein. Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers.

Compounds described herein may contain an asymmetric center and may thus exist as enantiomers. Where the compounds according to the invention possess two or more asymmetric centers, they may additionally exist as diastereomers. When bonds to the chiral carbon are depicted as straight lines in the formulas of the invention, it is understood that both the (R) and (S) configurations of the chiral carbon, and hence both enantiomers and mixtures thereof, are embraced. The present invention includes all such possible stereoisomers as substantially pure resolved enantiomers, racemic mixtures thereof, as well as mixtures of diastereomers. Except where otherwise specified, the formulae encompassing compounds of the present invention are shown without a definitive stereochemistry at certain positions. The present invention therefore may be understood to include all stereoisomers of compounds of any of (1)-(54) and pharmaceutically acceptable salts thereof.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of any of (1)-(54) may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Solvates, and in particular, the hydrates of the compounds of any of (1)-(54) are also included in the present invention.

The term "pharmaceutically acceptable salt" refers to a salt prepared from pharmaceutically acceptable non-toxic bases or acids including inorganic bases or acids and organic bases or acids.

Salts of basic compounds encompassed within the term "pharmaceutically acceptable salt" refer to non-toxic salts of the compounds described herein which are generally prepared by reacting the free base with a suitable organic or inorganic acid. Representative salts of basic compounds described herein include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, formate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, palmitate, pamoate (embonate), pantothenate, phosphate/diphosphate, polygalacturonate, salicylate, stearate, sulfate, subacetate, succinate, tannate, tartrate, teoclate, tosylate, triethiodide and valerate. Furthermore, where the compounds described herein carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. In particular embodiments, the salt is selected from ammonium, calcium, magnesium, potassium, or sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO⁻ depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$ alkyl esters and —$C_{1-6}$ alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The compounds of Formula I according to the invention are inhibitors of ROMK, and therefore could be used as diuretic and/or natriuretic agents. ROMK inhibitors may be used to help to increase urination and increase urine volume and also to prevent or reduce reabsorption of sodium in the kidneys leading to increased excretion of sodium and water. Therefore, the compounds could be used for treatment or prophylaxis or both of disorders that benefit from increased excretion of water and sodium from the body. Accordingly, the compounds of this invention could be used in a method for inhibiting ROMK comprising administering a compound of Formula I in a ROMK-inhibitory effective amount to a patient in need thereof. This also encompasses the use of the compounds for inhibiting ROMK in a patient comprising administering a compound of claim 1 in a therapeutically effective amount to a patient in need of diueresis, natriuresis or both. The inhibition of ROMK by the compounds of Formula I can be examined, for example, in the Thallium Flux Assay described below. Moreover, this invention also relates to the use of the compounds of Formula I or salts thereof to validate in vitro assays, for example but not limited to the Thallium Flux Assay described herein.

The compounds of this invention could be used in a method for causing diuresis, natriuresis or both, comprising administering a compound of Formula I in a therapeutically effective amount to a patient in need thereof. Therefore, the compounds of Formula I of this invention could be used in methods for treatment of, prevention of or reduction of risk for developing medical conditions that benefit from increased excretion of water and sodium, such as but not limited to one or more of hypertension, such as essential hypertension (also known as primary or idiopathic hypertension) which is a form of hypertension for which no cause can be found, heart failure (which includes both acute heart failure and chronic heart failure, the latter also known as congestive heart failure) and/or other conditions associated with excessive salt and water retention. The compounds could also be used to treat hypertension which is associated with any of several primary diseases, such as renal, pulmonary, endocrine, and vascular diseases, including treatment of patients with medical conditions such as heart failure and/or chronic kidney disease. Furthermore, the compounds of Formula I could be used in methods for treatment of, prevention of or reduction of risk for developing one or more disorders such as pulmonary hypertension, particularly pulmonary arterial hypertension (PAH), cardiovascular disease, edematous states, diabetes mellitus, diabetes insipidus, post-operative volume overload, endothelial dysfunction, diastolic dysfunction, systolic dysfunction, stable and unstable angina pectoris, thromboses, restenosis, myocardial infarction, stroke, cardiac insufficiency, pulmonary hypertonia, atherosclerosis, hepatic cirrhosis, ascitis, pre-eclampsia, cerebral edema, nephropathy, glomerulonephritis, nephrotic syndrome, acute kidney insufficiency, chronic kidney insufficiency (also referred to as chronic kidney disease, or more generally as renal impairment), acute tubular necrosis, hypercalcemia, idiopathic edema, Dent's disease, Meniere's disease, glaucoma, benign intracranial hypertension, and other conditions for which a diuretic or natriuretic or both would have therapeutic or prophylactic benefit. The compounds of the invention may be administered to a patient having, or at risk of having, one or more conditions for which a diuretic or natriuretic or both would have therapeutic or prophylactic benefit such as those described herein.

The compounds of Formula I may potentially have reduced liabilities (for example, hypo- or hyperkalemia, new onset of diabetes, dyslipidemia, etc.) over currently used clinical agents. Also the compounds may have reduced risk for diuretic tolerance, which can be a problem with long-term use of loop diuretics.

In general, compounds that are ROMK inhibitors can be identified as those compounds which, when tested, have an $IC_{50}$ of 5 µM or less, preferably 1 µM or less, and more preferably 0.25 µM or less, in the Thallium Flux Assay, described in more detail further below.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 100 mg/kg, preferably 0.001 to 30 mg/kg, in particular 0.001 to 10 mg/kg (in each case mg per kg of bodyweight) is appropriate for administration to an adult weighing approximately 75 kg in order to obtain the desired results. The daily dose is preferably administered in a single dose or can be divided into several, for example two, three or four individual doses, and may be, for example but not limited to, 0.1 mg, 0.25 mg, 0.5 mg, 0.75 mg, 1 mg, 1.25 mg, 2 mg, 2.5 mg, 5 mg, 10 mg, 20 mg, 40 mg, 50 mg, 75 mg, 100 mg, 125 mg, 150 mg, 175 mg, 200 mg, etc., on a daily basis. In some cases, depending on the potency of the compound or the individual response, it may be necessary to deviate upwards or downwards from the given daily dose. Furthermore, the compound may be formulated for immediate or modified release such as extended or controlled release.

The term "patient" includes animals, preferably mammals and especially humans, who use the instant active agents for the prophylaxis or treatment of a medical condition. Administering of the drug to the patient includes both self-administration and administration to the patient by another person. The patient may be in need of treatment for an existing disease or medical condition, or may desire prophylactic treatment to prevent or reduce the risk for developing said disease or medical condition or developing long-term complications from a disease or medical condition.

The term therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The terms "preventing," "prevention," "prophylactic" and derivatives of these terms as used herein refer to administering a compound to a patient before the onset of clinical symptoms of a condition not yet present in the patient. It is understood that a specific daily dosage amount can simultaneously be both a therapeutically effective amount, e.g., for treatment of hypertension, and a prophylactically effective amount, e.g., for prevention or reduction of risk of myocardial infarction or prevention or reduction of risk for complications related to hypertension.

In the methods of treatment of this invention, the ROMK inhibitors may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous (IV), intramuscular, intrasternal injection or infusion techniques. Oral formulations are preferred for treatment of chronic indications such as hypertension or chronic heart failure, particularly solid oral dosage units such as pills, tablets or capsules, and more particularly tablets. IV dosing is preferred for acute treatment, for example for the treatment of acute heart failure.

This invention also provides pharmaceutical compositions comprised of a compound of Formula I and a pharmaceutically acceptable carrier which is comprised of one or more excipients or additives. An excipient or additive is an inert substance used to formulate the active drug ingredient. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Tablets contain the active ingredient in admixture with non-toxic pharmaceutically acceptable excipients which are suitable for the manufacture of tablets. The excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Pharmaceutical compositions may also contain other customary additives, for example but not limited to, wetting agents, stabilizers, emulsifiers, dispersants, preservatives, sweeteners, colorants, flavorings, aromatizers, thickeners, buffer substances, solvents, solubilizers, agents for achieving a depot effect, salts for altering the osmotic pressure, coating agents or antioxidants. Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. Furthermore, a therapeutically effective amount of a compound of this invention can be used for the preparation of a medicament useful for inhibiting ROMK, for causing diuresis and/or natriuresis, and/or for treating, preventing or reducing the risk for any of the medical conditions described herein, in dosage amounts described herein.

The amount of active compound of Formula I and/or its pharmaceutically acceptable salts in the pharmaceutical composition may be, for example but not limited to, from about 0.1 mg to 1 g, particularly 0.1 mg to about 200 mg, more particularly from about 0.1 mg to about 100 mg, and even more particularly from about 0.1 to about 50 mg, per dose on a free acid/free base weight basis, but depending on the type of the pharmaceutical composition, potency of the active ingredient and/or the medical condition being treated, it could also be lower or higher. Pharmaceutical compositions usually comprise about 0.5 to about 90 percent by weight of the active compound on a free acid/free base weight basis.

The compounds of Formula I inhibit ROMK. Due to this property, apart from use as pharmaceutically active compounds in human medicine and veterinary medicine, they can also be employed as a scientific tool or as aid for biochemical investigations in which such an effect on ROMK is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents may be administered in combination with a compound of Formula I. The additional active agent (or agents) is intended to mean a medicinal compound that is different from the compound of Formula I, and which is a pharmaceutically active agent (or agents) that is active in the body, including pro-drugs, for example esterified forms, that convert to pharmaceutically active form after administration, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of the one or more additional active agents which may be employed include but are not limited to thiazide-like diuretics, e.g., hydrochlorothiazide (HCTZ or HCT); angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists, also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®, etc.); potassium sparing diuretics such as amiloride HCl, spironolactone, epleranone, triamterene, each with or without HCTZ; carbonic anhydrase inhibitors, such as acetazolamide; neutral endopeptidase inhibitors (e.g., thiorphan and phosphoramidon); aldosterone antagonists; aldosterone synthase inhibitors; renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643); enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxy-propoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine, bepridil, nisoldipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); nitrates or nitric oxide donating compounds, e.g. isosorbide mononitrate; lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; phosphodiesterase-5 (PDE5) inhibitors such as sildenafil (Revatio, Viagra), tadalafil (Cialis, Adcirca) vardenafil HCl (Levitra); or with other drugs beneficial for the prevention or the treatment of the above-mentioned diseases including but not limited to diazoxide; and including the free-acid, free-base, and pharmaceutically acceptable salt forms, pro-drug forms (including but not limited to esters), and salts of pro-drugs of the above medicinal agents where chemically possible. Trademark names of pharmaceutical drugs noted above are provided for exemplification of the marketed form of the active agent(s); such pharmaceutical drugs could be used in a separate dosage form for concurrent or sequential administration with a compound of Formula I, or the active agent(s) therein could be used in a fixed dose drug combination including a compound of Formula I.

EXAMPLES

Several methods for preparing the compounds of this invention are described in the examples. Starting materials and intermediates are purchased, made from known procedures, or as otherwise illustrated. Some frequently applied routes to the compounds of Formula I are also described by the Schemes as follows. In some cases the order of carrying out the the steps of reaction schemes may be varied to facilitate the reaction or to avoid unwanted reaction products. The "R" substituents in the Schemes correspond to the substituents defined in Formula I at the same positions on the structures.

Compound IA, which is substituted at the benzylic position with an OH group, can be prepared following the sequence detailed in Scheme 1. Coupling of epoxide 1 to spirocyclic amines 2 at elevated temperatures leads to the formation of alcohols IA and IA' as the major and minor products, respectively (Nomura, Y. et al. Chemical & Pharmaceutical Bulletin, 1995, 43(2), 241-6). The reaction can be carried out with conventional heating, or by heating using a microwave apparatus. A number of solvents can be used in this reaction, for example, ethanol and 2-propanol. Spirocyclic amines may be free bases, or they may be salts, in which case a base such as triethylamine or N,N'-diisopropylethylamine may be added. Note that when enantiopure chiral epoxides are employed (such as (R)-1 in Scheme 1) epoxide opening occurs with retention of stereochemistry in the benzylic position and individual isomers (R)-IA and (S)-IA' may be obtained as the major and minor products, respectively (and if the (S)-epoxide is employed the alcohol produced will have the opposite stereochemistry to that shown). Alternatively, chiral HPLC separation of enantiomers or diastereomers of IA may be performed to provide single enantiomers or diastereomers.

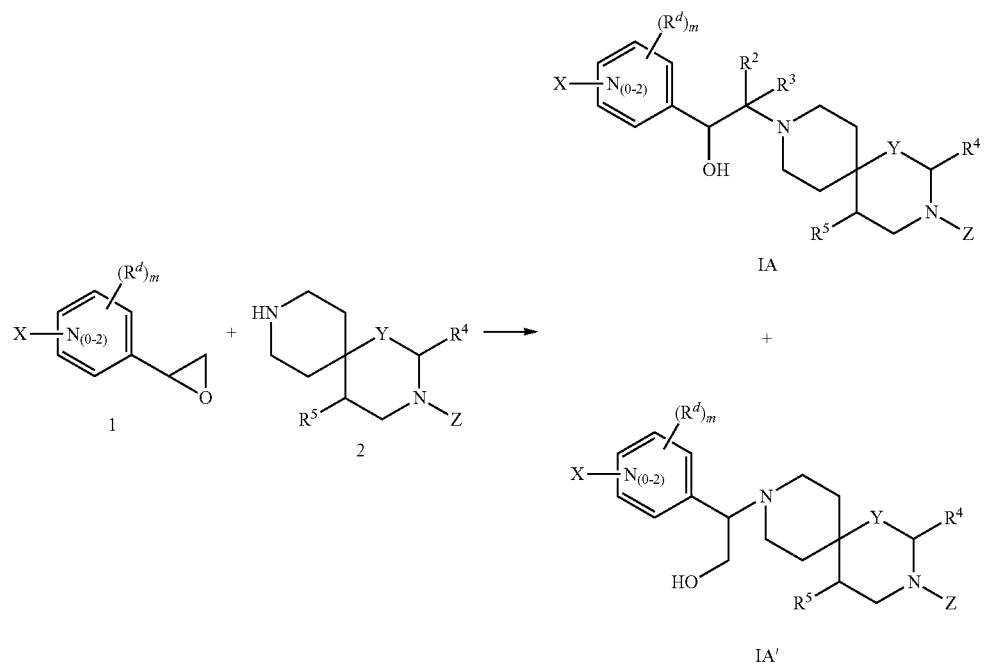

SCHEME 1

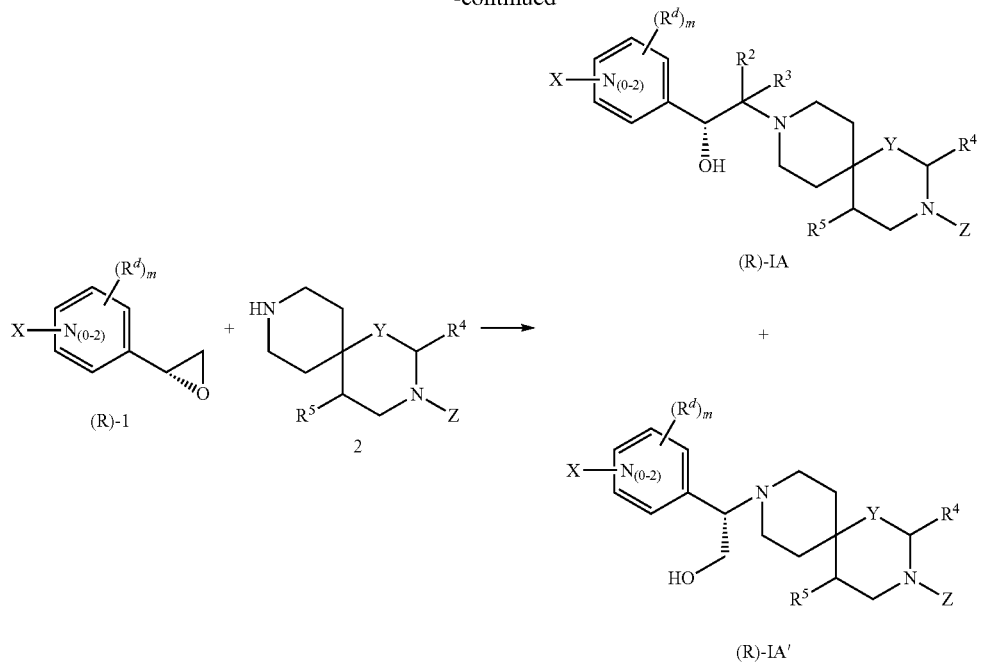

(R)-1 + 2 → (R)-IA + (R)-IA'

Compounds of formula IB can be prepared by the sequence detailed in Scheme 2. Alhehydes or aldehyde 3 may be used in reductive alkylation reactions of spirocyclic amines 2 to afford ROMK inhibitors of the formula IB by using various reductive amination conditions (for example using sodium cyanoborohydride, sodium triacetoxy borohydride, or titanium tetra-isopropoxide, followed by sodium borohydride or sodium cyanoborohydride).

Alternatively, compounds of the formula IC may be prepared by coupling of the NH in spirocycles 4 to an aromatic or heterocyclic coupling partner (where A represents chloride, bromide, iodide, fluoride, boronic acid). This coupling reaction may be accomplished in a variety of ways, depending upon the nature of of 4 and the coupling partner (A-Z). For example in some cases this coupling can be achieved by thermal or microwave heating in one of a variety of potential solvents, such as DMF or dioxane, in the presence or absence of a base such as triethylamine or potassium carbonate, or cesium carbonate. Or the coupling can be accomplished using a catalyst-ligand system, for example heating with XantPhos and $Pd_2(dba)_3$ in the presence of a base such as cesium carbonate in a solvent such as dioxane (Buchwald, S. L.; Yin, J. *J. Am. Chem. Soc.* 2002, 124, 6043). Numerous other C—N coupling conditions, known from the literature such as Pd-catalyzed (Review: Buchwald, S. L. *Chem. Sci.* 2011, 2, 27) and Cu(II)-catalyzed Chan-Lam reactions (Review: Qiao, Lam et al. *Synthesis* 2011, 829), may be applied.

SCHEME 2

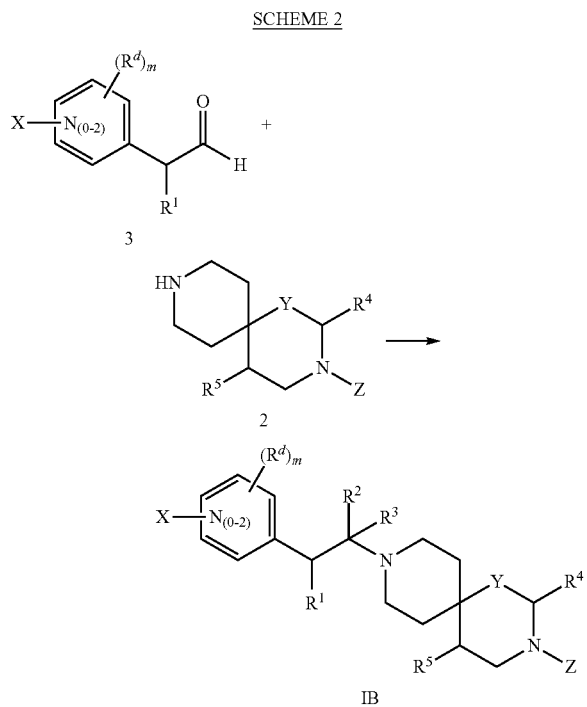

SCHEME 3

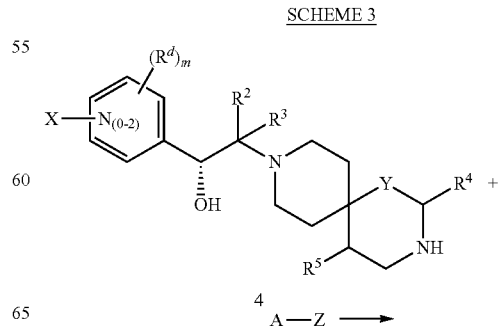

-continued

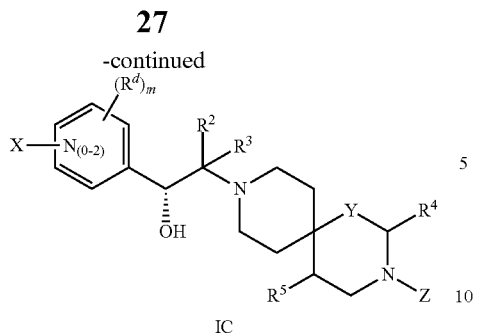

IC

A=chloride, bromide, iodide, fluoride, boronic acid

Compounds of formula ID can be prepared by amide formation conditions between acids 5 and amines 2 using suitable coupling reagents (for example HATU and DIPEA), as shown in Scheme 4. Synthesis of acids 5 are described in the experimental section below.

SCHEME 4

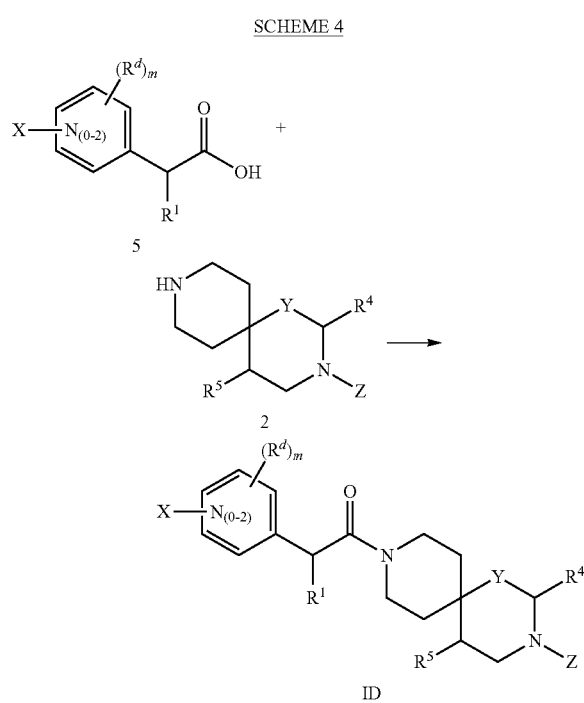

ID

The epoxides 1 (and single enatiomers (R)-1 and (S)-1) can be prepared following the method detailed in Scheme 5. Treatment of 6 (where halide is chloride, bromide, iodide, or trifluoromethane sulfonate) with commercially available potassium vinyl trifluoroborate (Molander, G.; Luciana, A. *Journal of Organic Chemistry*, 2005, 70, 3950-3956) under palladium catalyzed coupling conditions with an appropriate phosphine ligand gives rise to styrene 7 (Molander, G.; Brown, A. *Journal of Organic Chemistry*, 2006, 71, 9681-9686). Alternatively, other methods may be employed, for example, using vinylstannane reagents and palladium catalysis. The resulting styrenes 7 can be converted to the corresponding epoxides 1 under various epoxidation conditions, for example, with mCPBA (Fringuelli, F. et al. *Organic Preparations and Procedures International*, 1989, 21, 757-761). The racemic epoxide 1 can be resolved under chiral HPLC chromatography conditions to afford its enantiomers, which can be used in place of 1 according to Scheme 1.

SCHEME 5

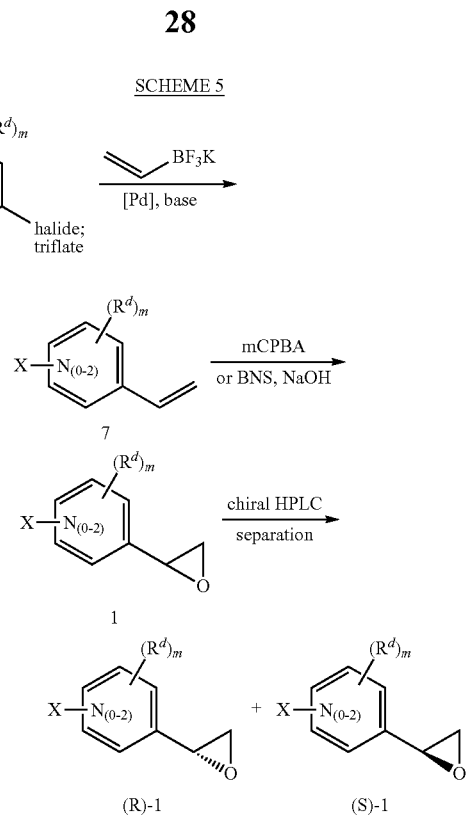

Alternatively, enantiopure epoxides (R)-1 or (S)-1 can be prepared as shown in Scheme 6. Treatment of 6 (where halide is bromide, iodide, or trifluoromethane sulfonate) with commercial available vinyl butylether 8 under palladium catalyzed conditions with a suitable ligand and base (for example Pd(OAc)$_2$, DPPP, Et$_3$N) can provide the enol ethers 9. Enol ethers may be prepared using other methods known to the chemist. Treatment of the resulting enol ethers 9 with NBS or other similar reagents affords the corresponding bromomethyl ketones 10. These can be subjected to a variety of asymmetric ketone reduction conditions, for example with an enzyme that can affect such a transformation with high enantioselectivity. Subsequent treatment with a base such as triethylamine leads to cyclization, affording the enantioenriched epoxides (R)-1 or (S)-1 (depending upon the asymmetric reducing agent).

SCHEME 6

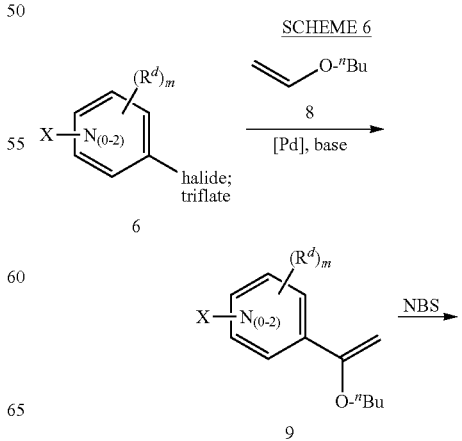

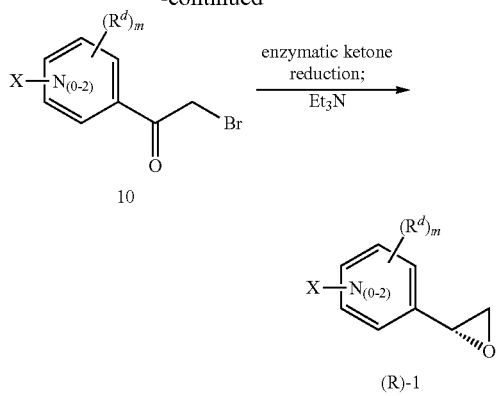

Aldehydes 3A may be prepared in numerous ways, with two approaches described in Scheme 7. Treatment of 6 (where halide is bromide, iodide, or trifluoromethane sulfonate) with bromo(1,3-dioxolan-2-ylmethyl)zinc in the presence of an appropriate palladium catalyst and ligand, such as palladium(II) acetate and tri-t-butylphosphine-BF$_4$ complex, provides the corresponding aryl 1,3-dioxolan-2-ylmethyl derivative 11. Then the aldehydes 3A may be obtained by treatment with HCl in the presence of water and an organic solvent. Alternatively, reaction of 6 (where halide is bromide, iodide, or trifluoromethane sulfonate) with allyltributylstannane in the presence of palladium catalyst affords the allyl product 12. Oxidation, for example with ozone, followed by dimethyl sulfide, provides aldehydes 3A.

SCHEME 7

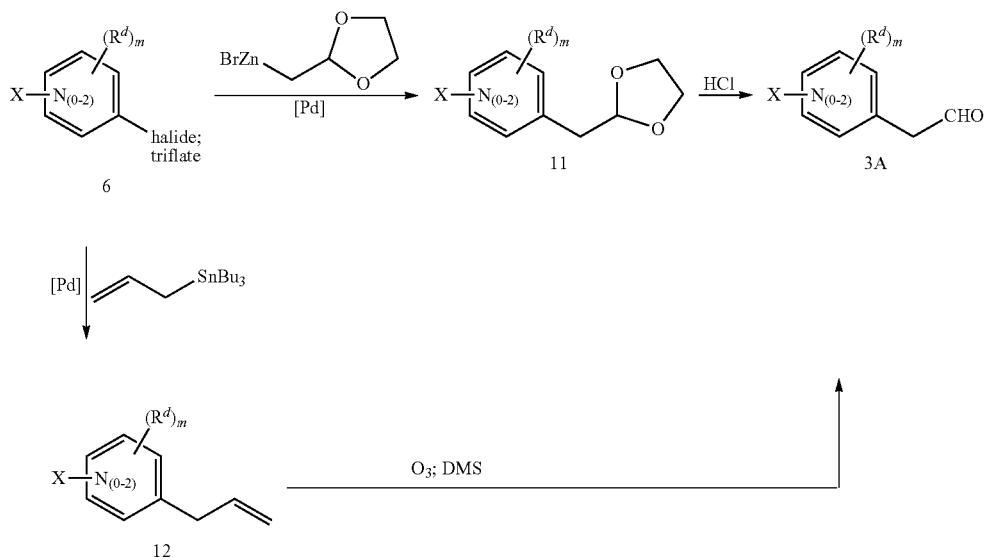

Alternatively aldehydes 3A and 3B can be prepared in pathways described in Scheme 8. Aldehyde 3A can be prepared by hydrogenation of intermediate epoxides (1, from Scheme 5) followed by oxidation with Dess-Martine periodinane. Aldehydes 3B with alkoxy substituted at the benzylic position may be synthesized by PTSA-catalyzed addition of alcohols to the epoxides (1, from Scheme 5), and subsequent oxidation of alcohols 14.

SCHEME 8

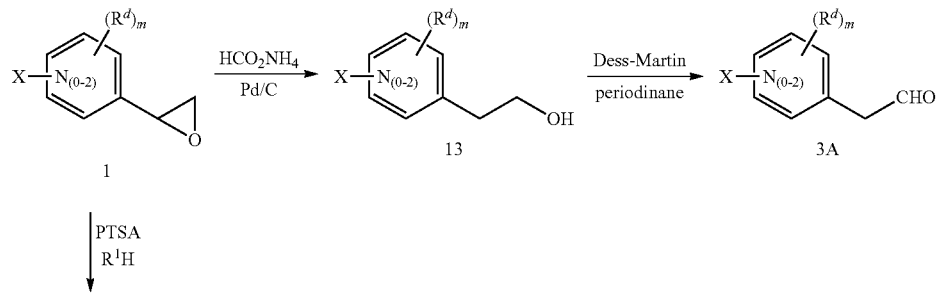

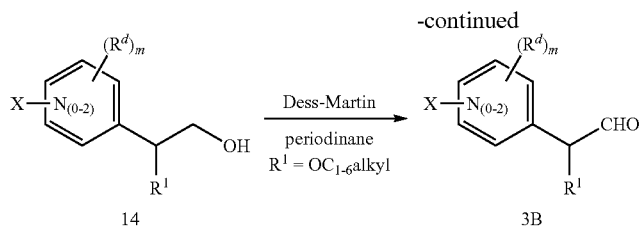

or Amine 4 can be prepared in sequences described in Scheme 9. Treatment of epoxide (R)-1 with commercially available or unavailable amines 15 (commercially unavailable amines 15 are prepared as described in the experimental section below) under conventional microwave heating conditions leads to 16, which was then deprotected by TFA or HCl to give free amine 4 after treatment with ion-exchange column.

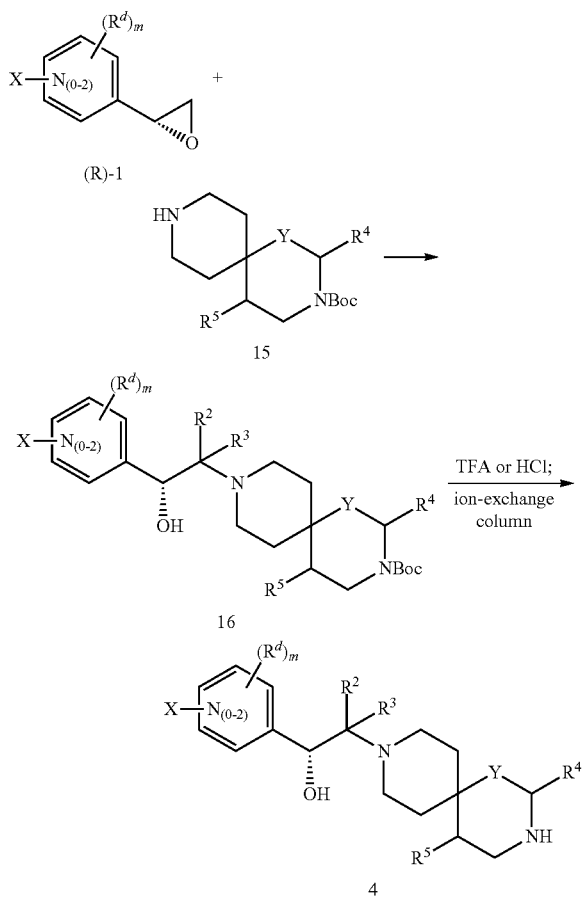

Spirocyclic amines 2 can be prepared as described in Scheme 10. Spirocyclic diamines or amino lactams 17, protected as appropriate (Greene, T.; Wuts, P. G. M. *protective Groups in Organic Synthesis*, John Wiley and Sons, Inc., New York, N.Y. 1991), can be coupled to electrofiles 18 (where A represents OH, Br or OTf) in a variety of ways, depending upon the nature of 18. For example, in some cases this coupling can be achieved by thermal or microwave heating in the presence or absence of an acid, such as AcOH, or a base, such as DIPEA. Sometimes the coupling can be achieved using a catalyst-ligand system, for example palladium(II) acetate and 4,5-bis(diphenylphosphino)-9,9-dimethylxanthene. Some spirocyclic diamines or amino lactams 17 described herein are commercially available; others can prepared as described in the experimental section below. 4-Bromofuran-2(5H)-one is commercially available; some furanones and squarates 18 can be prepared as described in the examples below. Intermediate 19 is converted to spirocyclic amines 2 by removal of the protective group, for example, tert-butoxycarbonyl can be removed with TFA or HCl.

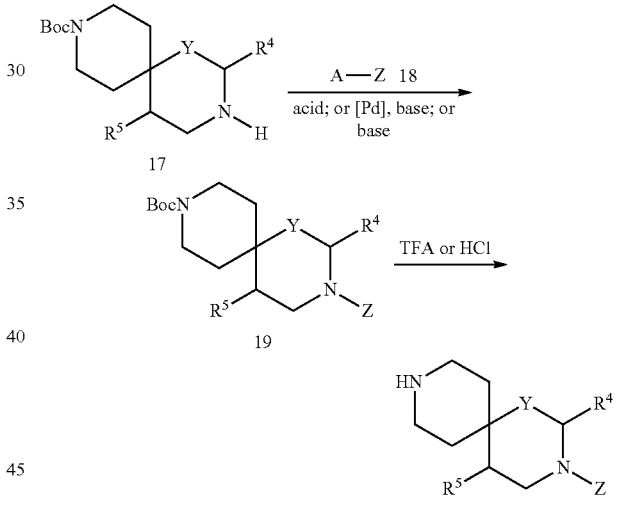

A = OH, Br, OTf

The compounds of the invention can be prepared using the representative experimental procedures described herein as well as any of several alternate methods which will be apparent to a chemist skilled in the art. Starting materials and intermediates are purchased, made from known procedures, or as otherwise illustrated.

The independent synthesis of diastereomers and enantiomers or their chromatographic separations may be achieved as known in the art by appropriate modification of the methodology disclosed herein. Their absolute stereochemistry may be determined by x-ray crystallography of crystalline products or crystalline intermediates which are derivatized, if necessary, with a reagent containing an asymmetric center of known absolute stereochemistry, or by vibrational circular dichroism (VCD) spectroscopy.

Reactions sensitive to moisture or air were performed under nitrogen or argon using anhydrous solvents and reagents. The progress of reactions was determined by either analytical thin layer chromatography (TLC) usually performed with E. Merck pre-coated TLC plates, silica gel 60F-254, layer thickness 0.25 mm or liquid chromatography-mass spectrometry (LC-MS).

Typically the analytical LC-MS system used consisted of a Waters ZQ platform with electrospray ionization in positive ion detection mode with an Agilent 1100 series HPLC with autosampler. The column was usually a Water XTERRA MS C18, 3.0×50 mm, 5 μm. The flow rate was 1 mL/min, and the injection volume was 10 μL. UV detection was in the range of 210-400 nm. The mobile phase consisted of solvent A (water plus 0.06% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 min.

Preparative HPLC purifications were usually performed using a mass spectrometry directed system. Usually they were performed on a Waters Chromatography Workstation configured with LC-MS System Consisting of: Waters ZQ single quad MS system with Electrospray Ionization, Waters 2525 Gradient Pump, Waters 2767 Injector/Collector, Waters 996 PDA Detector, the MS Conditions of: 150-750 amu, Positive Electrospray, Collection Triggered by MS, and a Waters Sunfire C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 μL, and the UV detection range was 210-400 nm. Mobile phase gradients were optimized for the individual compounds.

Reactions performed using microwave irradiation were normally carried out using an Emrys Optimizer manufactured by Personal Chemistry, or an Initiator manufactured by BIOTAGE (Uppsala, Sweden).

Concentration of solutions was carried out on a rotary evaporator under reduced pressure. Flash chromatography was usually performed using a BIOTAGE Flash Chromatography apparatus (Dyax Corp.) on silica gel (32-63 mM, 60 Å pore size) in pre-packed cartridges of the size noted. $^1$H NMR spectra were acquired at 500 MHz spectrometers in CDCl$_3$ solutions unless otherwise noted. Chemical shifts were reported in parts per million (ppm). Tetramethylsilane (TMS) was used as an internal reference in CD$_3$Cl solutions, and residual CH$_3$OH peak or TMS was used as internal reference in CD$_3$OD solutions. Coupling constants (J) were reported in hertz (Hz).

Chiral analytical chromatography was usually performed on one of CHIRALPAK AS, CHIRALPAK AD, CHIRALCEL OD, CHIRALCEL IA, or CHIRALCEL OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was sometimes conducted on one of CHIRALPAK AS, CHIRALPAK AD, CHIRALCEL OD, CHIRALCEL IA, or CHIRALCEL OJ columns (20×250 mm) (Daicel Chemical Industries, Ltd.) with desired isocratic solvent systems identified on chiral analytical chromatography or by supercritical fluid (SFC) conditions. Alternatively, chiral preparative chromatography was by supercritical fluid (SFC) conditions using one of CHIRALPAK AS, CHIRALPAK AD-H, CHIRALCEL OD-H, CHIRALPAK IC, or CHIRALCEL OJ-H columns (250×21.2 mm) (Daicel Chemical Industries, Ltd.). Where retention times (or order of elution) are provided in the Examples and Tables, they are not intended to be a definitive characteristic of a particular compound since, as known to those skilled in the art, retention times will vary and the timing and/or order of peak elution may change depending on the chromatographic conditions, such as the column used, the condition of the column, and the solvent system and instruments used. Concentration of solutions was generally carried out on a rotary evaporator under reduced pressure. Crystallization or recrystallization techniques are intended to describe a purification procedure that was used, but do not imply that the resulting product obtained from the procedure is crystalline.

Abbreviations and acronyms that may be used herein include: —C(O)CH$_3$ (Ac); —OC(O)CH$_3$ (OAc); acetic acid (AcOH; HOAc); 1-chloroethylchloroformate (ACE-Cl); 2,2'-bis(diphenylphosphino)-1,1'-binaphthyl (BINAP); benzyl (Bn); t-butyloxycarbonyl (Boc or BOC); di-t-butyl dicarbonate ((BOC)$_2$O, Boc$_2$O); benzyloxycarbonyl (Cbz); Cyclopentyl methyl ether (CPME); Carbonyldiimidazole (CDI); deuterium ($^2$H, or D); Diethylaminosulfur trifluoride (DAST); dibenzylideneacetone (dba); 1,8-Diazabicyclo[5.4.0]undec-7-ene (DBU); 1,2-dichloroethane (DCE); dichloromethane (DCM); diethyl amine (DEA); dimethoxyethane (DME); Diisobutylaluminium hydride (DIBAL-H); N,N-diisopropylethylamine (DIEA, DIPEA, Hunig's base); dioxane is 1,4-dioxane; di-isopropylamine (DIPA); 1,1'-bis(diphenylphosphino)ferrocene (dppf, DPPF); Dess-Martin Periodinane (DMP; 1,1,1-Triacetoxy-1,1-dihydro-1,2-benziodoxol-3(1H)-one); dimethylsulfide (DMS); dimethylsulfoxide (DMSO); N;N-dimethylformamide (DMF); 4-dimethylaminopyridine (DMAP); dimethylacetamide (DMA; DMAC); 1,3-Bis(diphenylphosphino)propane (DPPP); (Oxydi-2,1-phenylene)bis(diphenylphosphine) (DPEPhos); ethyl acetate (EtOAc or EA); diethyl ether (ether or Et$_2$O); 1-ethyl-3-(3-dimethylaminopropyl)carbodiimide (EDC, EDAC or EDCI); ethylmagnesium chloride (EtMgCl); 2-(7-Aza-1H-benzotriazole-1-yl)-1,1,3,3-tetramethyluronium hexafluorophosphate (HATU); O-(Benzotriazol-1-yl)-N,N,N',N'-tetramethyluronium hexafluorophosphate, also known as N-[(1H-benzotriazol-1-yloxy)(dimethylamino)methylidene]-N-methylmethanaminium hexafluorophosphate (HBTU); hexane (Hex); hexamethylphosphoramide (HMPA); 1-Hydroxybenzotriazole hydrate (HOBt); isopropanol (IPA); isopropyl acetate (IPAc); lithium aluminum hydride (LAH); lithium diisopropylamide (LDA); 3-chloroperoxybenzoic acid (mCPBA); methanol (MeOH); CH$_3$SO$_2$— (mesyl or Ms); methane sulfonyl chloride or mesyl chloride (MsCl); methanesulfonic acid (MsOH); methyl tert-butyl ether (MTBE); nicotinamide adenine dinucleotide phosphate (NADP); N-bromo succinimide (NBS); N-chlorosuccinimide (NCS); N-iodosuccinimide (NIS); N-methylmorpholine-N-oxide (NMO); N-methyl morpholine (NMP); sodium hexamethyldisilazide (NaHMDS); sodium triacetoxyborohydride (NaBH(OAc)$_3$); Pyridinium chlorochromate (PCC); phenyl (Ph); petroleum ether (PE or petrol ether); tetrakis(triphenylphosphine)palladium (Pd(PPh$_3$)$_4$); tris(dibenzylidineacetone)dipalladium (Pd$_2$(dba)$_3$); Pd(dppf)Cl$_2$ or PdCl$_2$(dppf) is 1,1'-Bis(diphenylphosphino)ferrocene]dichloropalladium(II) which may be complexed with CH$_2$Cl$_2$; tetra-n-butylammonium fluoride (TBAF); tert-Butyl methyl ether (TBME); tert-butyldimethylsilyl chloride (TBS-Cl); triethylamine (TEA, Et$_3$N); trifluoroacetic acid (TFA); trifluoroacetic anhydride (TFAA); —SO$_2$CF$_3$ (TO; trifluoromethanesulfonic acid (triflic acid, TfOH); trifluoromethanesulfonic anhydride (triflic anhydride, (Tf)$_2$O); 2-tetrahydrofuran (THF); N,N,N',N'-Tetramethylethylenediamine (TMEDA); trimethylsilyl azide (TMSA); trimethylsilyl trifluoroacetate (TMSTFA); p-toluenesulfonic acid (TsOH or PTSA); Dicyclohexylphosphino-2',4',6'-triisopropylbiphenyl (X-Phos); Diethylaminodifluorosulfinium tetrafluoroborate (XtalFluor-E®); 4,5-Bis(diphenylphosphino)-9,9-dimethylxanthene (Xantphos). Additional abbreviations and acronyms are: racemic or racemate (rac.); starting material (SM); round-bottom flask (RB or RBF); aqueous (aq); saturated aqueous (sat'd); saturated aqueous sodium chloride solution (brine); medium pressure liquid chromatography (MPLC); high pressure liquid chromatography (HPLC); ultra-performance liquid chromatography (UPLC); preparative HPLC (prep-HPLC); flash chromatography (FC); liquid chromatography (LC); super-critical fluid chromatography (SFC); thin layer chromatography (TLC); preparative TLC (prep-TLC); mass spectrum (ms or MS); liquid chromatography-mass spectrometry (LC-MS, LCMS or LC/MS); column volume (CV); room temperature (rt, r.t. or RT); hour(s) (h or hr); minute(s) (min); retention time ($R_t$); gram(s) (g); milligram(s) (mg); milliliter(s) (mL); microliter(s) (L); millimole (mmol); volume:volume (V/V). CELITE® is a trademark name for diatomaceous earth, and SOLKA FLOC® is a trademark name for powdered cellulose. X or x may be used to express the number of times an action was repeated (e.g., washed with 2×200 mL 1N HCl), or to convey a dimension (e.g., the dimension of a column is 30×250 mm)

The following are representative procedures for the preparation of intermediates used to prepare the final products described in the Examples that follow thereafter. These examples are provided for the purpose of further illustration only and are not intended to be limitations on the disclosed invention.

It is understood that a chiral center in a compound may exist in the "S" or "R" stereo-configurations, or as a mixture of both. In many of the examples for intermediate compounds and final compounds, such compounds having a racemic chiral center were separated into individual stereoisomers, for example, referred to as isomer A (or enantiomer A or the like), which generally refers to the observed faster eluting isomer unless stated otherwise, and isomer B (or enantiomer B or the like), which refers to the observed slower eluting isomer unless stated otherwise, and each such isomer may be noted in the example as either the fast or slow eluting isomer. When a single "A" or "B" isomer intermediate is used to prepare a downstream compound, the downstream compound will take the "A" or "B" designation that corresponds to the previously used intermediate. Any Intermediates described below may be referred to herein by their number preceded by "I—." For illustration, in the example titled "Intermediate 4," the racemic parent title compound would be referred to as Intermediate 4 (or I-4), and the separated stereoisomers are noted as Intermediates 4A and 4B (or I-4A and I-4B). Except for a defined chiral center that may be present in a parent isomer mixture, absolute stereochemistry (R or S) of each of the separated isomers was not determined, unless specifically described otherwise. An asterisk (*) may be used in a chemical structure drawing that indicates the location of a chiral center.

Intermediate 1

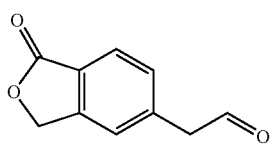 [SMILES: O=CCc1ccc2c(c1)COC2=O]

(1-Oxo-1,3-dihydro-2-benzofuran-5-yl)acetaldehyde

Step A: 5-(1,3-Dioxolan-2-ylmethyl)-2-benzofuran-1(3H)-one

A three-neck 5 L round bottomed flask equipped with a stir bar, firestone valve, thermocouple, condenser and heating mantle was charged with tri-t-butyl phosphonium tetrafluoroborate (500 mg, 1.72 mmol), palladium (II) acetate (250 mg, 1.1 mmol) and 5-bromo-2-benzofuran-1(3H)-one (100 g, 470 mmol). DMF (1.88 L) was added to the flask, and the mixture was degassed three times by alternating vacuum and nitrogen purge. Commercially available bromo (1,3-dioxolan-2-ylmethyl)zinc solution (1.03 L, 516 mmol) was added via canula and the mixture was again degassed three times. The mixture was then heated at 85° C. for 10 h. The mixture was then allowed to return to room temperature for overnight. 2-methylTHF (2 L) and brine were added, and the mixture was stirred for 5 min. The layers were separated and the aqueous layer was extracted again with 2-methyl-THF. The organic layers were combined, washed three times with brine (4 L each), dried over MgSO₄, filtered, and concentrated. The crude product was purified by flash chromatography (1.5 kg silica cartridge), eluting with 0-20% ethyl acetate in dichloromethane to afford 5-(1,3-dioxolan-2-ylmethyl)-2-benzofuran-1(3H)-one.

Step B: (1-Oxo-1,3-dihydro-2-benzofuran-5-yl)acetaldehyde 5-(1,3-Dioxolan-2-ylmethyl)-2-benzofuran-1(3H)-one (61 g, 280 mmol) was combined with water (2.2 L) in a 5 L round bottomed flask equipped with a Claisen adapter, thermocouple, stir bar and nitrogen bubbler. Aqueous HCl solution (2M, 1.14 L, 2.29 mol) was added and the resulting mixture was heated at 40° C. for 8 h. Then the mixture was stirred overnight at room temperature. The mixture was extracted three times with 2 L of ethyl acetate. The combined organic layers were concentrated to give (1-oxo-1,3-dihydro-2-benzofuran-5-yl)acetaldehyde.

Intermediate 2

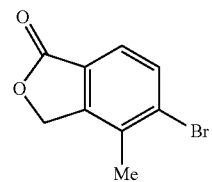 [SMILES: Cc1c(Br)ccc2c1COC2=O]

5-bromo-4-methyl-2-benzofuran-1(3H)-one

Step A: (3-bromo-2-methylphenyl)methanol

To a solution of 3-bromo-2-methyl benzoic acid (35 g, 163 mmol) in THF (200 mL) was added Borane THF Complex (1.0 M, 212 mL, 212 mmol). The mixture was allowed to stir for 24 h. The reaction was quenched with water. The solvent THF was removed under reduced pressure. The resulting solid was dissolved in ethyl acetate (500 mL), washed with 1N HCl, sodium carbonate, and brine.

The organic layer was dried over sodium sulfate and concentrated to afford (3-bromo-2-methylphenyl)methanol.

Step B: 5-bromo-4-methyl-2-benzofuran-1(3H)-one

To a flask charged with (3-bromo-2-methylphenyl)methanol (6.0 g, 30 mmol) was added a 1M TFA solution of Thallium Trifluoroacetate (16.2 g, 29.8 mmol). The mixture was stirred at RT overnight. The solvent was removed under vacuum, and the residue was pumped under high vacuum for 30 min to ensure complete removal of TFA. To the residue was then added Palladium(II) Chloride (529 mg, 2.98 mmol), Lithium Chloride (2.53 g, 59.7 mmol), Magnesium Oxide (2.41 g, 59.7 mmol), and MeOH (150 mL). The reaction was flushed with CO twice, and kept under CO at room temperature. After two hours, to this solution was added ethyl acetate to precipitate the salts. The black solution was filtered through a CELITE® pad, washed with EtOAc, adsorbed onto silica and purified by silica gel chromatography to afford title compound.

Intermediate 3

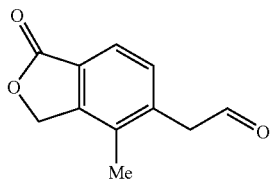 [SMILES: Cc1c(CC=O)ccc2c1COC2=O]

(4-Methyl-1-oxo-1,3-dihydro-2-benzofuran-5-yl)acetaldehyde

Step A: 4-Methyl-5-prop-2-en-1-yl-2-benzofuran-1(3H)-one

To a flask charged with 5-bromo-4-methyl-2-benzofuran-1(3H)-one (320 mg, 1.409 mmol) and a stir bar was added allyl tri-n-butyltin (0.655 mL, 2.11 mmol), Pd(PPh$_3$)$_4$ (244 mg, 0.211 mmol), lithium chloride (179 mg, 4.23 mmol), and toluene (15 mL). The reaction was purged with nitrogen 2 times then was heated at reflux for 4 hours. The product was separated by silica gel chromatography to give 4-methyl-5-prop-2-en-1-yl-2-benzofuran-1(3H)-one.

Step B: (4-Methyl-1-oxo-1,3-dihydro-2-benzofuran-5-yl)acetaldehyde

A solution of the above olefin (220 mg, 1.2 mmol) in MeOH (20 mL) was cooled to −78° C. To this solution was bubbled ozone until the reaction turned blue. Nitrogen was bubbled through the reaction to drive off excess ozone, followed by addition of DMS (0.870 mL, 11.7 mmol). The reaction was allowed to warm up to RT. The crude product was purified by flash chromatography to afford the title compound.

Intermediate 4

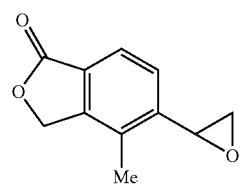 [SMILES: Cc1c(C2CO2)ccc2c1COC2=O]

4-methyl-5-oxiran-2-yl-2-benzofuran-1(3H)-one

Step A: 5-ethenyl-4-methyl-2-benzofuran-1(3H)-one

5-Bromo-4-methyl-2-benzofuran-1(3H)-one (598 mg, 4.47 mmol), potassium vinyl trifluoroborate (507 mg, 2.23 mmmol), PdCl$_2$(dppf)-CH$_2$Cl$_2$ adduct (182 mg, 0.223 mmmol), and TEA (0.622 mL, 4.47 mmol) were added to 10 mL ethanol in a 20 mL microwave tube. The tube was sealed and degassed, then heated to 140° C. for 20 min. The reaction mixture was diluted with ethyl acetate, washed with brine twice, dried and evaporated to dryness. The crude product was purified by MPLC chromatography using a 120 g Redi-sep column and 0-80% EtOAC/Hexane solvent system to yield 5-ethenyl-4-methyl-2-benzofuran-1(3H)-one.

Step B: 4-methyl-5-oxiran-2-yl-2-benzofuran-1(3H)-one 5-ethenyl-4-methyl-2-benzofuran-1(3H)-one (1.46 g, 8.38 mmol) was added to DCM (25 mL) at 0° C., then mCPBA (2.89 g, 16.8 mmol) was added and the mixture was stirred at RT overnight. The reaction mixture was washed once each with saturated aqueous Na$_2$S$_2$O$_3$, NaHCO$_3$, and brine. The organic layer was dried over Na$_2$SO$_4$, filtered, and evaporated to dryness. The crude material was purified by MPLC chromatography through 120 g Redi-sep column eluting with 0-80% EtOAc/hexane solvent system to yield target 4-methyl-5-oxiran-2-yl-2-benzofuran-1(3H)-one.

Intermediates 4A and 4B (Method 1)

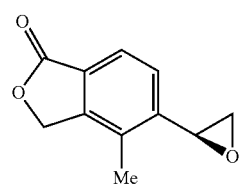

4A

Slow eluting

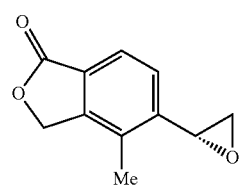

4B

Fast eluting

4A: 4-methyl-5-[(2S)-oxiran-2-yl]-2-benzofuran-1(3H)-one

4B: 4-methyl-5-[(2R)-oxiran-2-yl]-2-benzofuran-1(3H)-one

Racemic 4-methyl-5-oxiran-2-yl-2-benzofuran-1(3H)-one was resolved on a ChiralPak® AD-H column (5×25 cm) under supercritical fluid chromatography (SFC) conditions on a Berger MGIII preparative SFC instrument. The racemate was diluted to 50 mg/mL in 1:1 DCM:MeOH. The separation was accomplished using 10% EtOH/CO$_2$, flow rate 200 mL/min, 100 bar, 25° C. 500 µl Injections were spaced every 2.12 mins. The fast epoxide (4-methyl-5-[(2R)-oxiran-2-yl]-2-benzofuran-1(3H)-one, 4B) eluted first, and the slow epoxide (4-methyl-5-[(2S)-oxiran-2-yl]-2-benzofuran-1(3H)-one, 4A) eluted second.

Alternatively, the resolution could also be achieved using a mobile phase of 8% MeOH/98% CO$_2$ with a flow rate of 100 mL/min. In that case the sample was prepared by dissolving in methanol, 20 mg/mL, and using a 1 mL volume per injection. After separation, the fractions were dried off via rotary evaporator at bath temperature 40° C.

The absolute stereochemistry of each enantiomer was inferred based on the X-ray crystal structure determination of a final compound made with 4B and by Mosher ester and Trost ester $^1$H NMR analysis of esters made starting from 4B.

Intermediate 4B (Method 2)

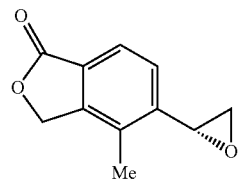 [SMILES: Cc1c([C@@H]2CO2)ccc2c1COC2=O]

4-methyl-5-[(2R)-oxiran-2-yl]-2-benzofuran-1(3H)-one

Step A: 3-hydroxymethyl-2-methyl phenol

To a 5 L 3 neck RB equipped with overhead stirrer was charged NaBH$_4$ (87.0 g, 2.30 mol) and THF (3.0 L) and the resulting slurry was cooled to 10° C. To the slurry was then added 3-hydroxy-2-methyl benzoic acid (175 g, 1.15 mol) portionwise over 20 min (Tmax 17° C.). A stirrable slurry formed, and was aged for an additional 45 min at 10-15° C. after which BF$_3$—OEt$_2$ (321 mL, 2.53 mol) was added slowly over 1.5 hours. The slurry was aged at 10° C.-15° C. for 2 h, then the slurry was cooled to <10° C. and quenched with 931 mL of MeOH slowly over 1.5 h (gas evolution). The resulting slurry was aged overnight at RT. The batch was cooled to <10° C. then quenched with 1 N HCl (1.5 L) to get a homogeneous solution (pH solution ~1), which was aged for 30 min and then the organic solvents were removed by rotary evaporation to approximately 1.8 L of total reaction volume. The slurry was held at 45° C. for 30 min then cooled slowly to 15° C. The solids were filtered and washed with cold (15° C.) water (2×300 mL), providing 3-hydroxymethyl-2-methyl phenol.

Step B: 4-Bromo-3-hydroxymethyl-2-methyl phenol

3-Hydroxymethyl-2-methyl phenol (113.9 g, 824.0 mmol) was dissolved in a mixture of acetonitrile (850 mL) and trifluoroacetic acid (750.0 mL, 9,735 mmol) in a 3-neck 5-L flask under nitrogen. The reaction mixture was cooled to −33° C. N-bromosuccinimide (141 g, 791 mmol) was added over 15 minutes, with the temperature during addition in the range of −35 to −33° C. The reaction mixture was allowed to stir for an additional 15 min during which time the temperature decreased to −40° C. The cooling bath was removed, and potassium carbonate (741.0 g, 5,358 mmol) diluted with water to a total of 1.0 L was added. Off-gassing was observed, and the temperature increased to 25° C. MTBE (1.5 L) was added, and the reaction mixture was transferred to a separatory funnel. The layers were separated. The aqueous layer was diluted with water (500 mL) and extracted with MTBE (1 L) with EtOAc (500 mL), and then MTBE (500 mL) with EtOAc (250 mL). The combined organic layers were washed with water (240 mL) and dried over sodium sulfate. The sodium sulfate was removed by filtration, washed with additional MTBE and concentrated under reduced pressure. MTBE (684 mL, 2 volumes) was added, and the suspension was heated to 40° C. to produce a homogeneous solution. The solution was allowed to cool to room temperature. Six volumes of heptane were added, and the suspension was stirred overnight. The suspension was filtered, and the crystals were washed with 4:1 heptane:MTBE (500 mL), followed by heptane (500 mL). The solid was dried under vacuum, providing 4-bromo-3-hydroxymethyl-2-methyl phenol.

Step C: 5-Hydroxy-4-methyl-3H-isobenzofuran-1-one

To a 2 L 3 neck flask equipped with overhead stirrer, N$_2$ inlet, and condenser were charged 4-bromo-3-hydroxymethyl-2-methyl phenol (100 g, 461 mmol), CuCN (83.0 g, 921 mmol), and DMF (500 mL). The solution was sparged with N$_2$ for 15 min then heated to 145° C. to obtain a homogeneous solution. The solution was aged at 145° C. for 2 h, then the reaction mixture was cooled to 95° C. 41.5 mL of water was added (sparged with N$_2$), and the reaction was aged for 20 h. The reaction was cooled to RT then the solids filtered through SOLKA FLOC® and the cake washed with 50 mL DMF. To a 3 L flask containing 1 L EtOAc was added the DMF filtrate. A precipitate coating formed in bottom of flask. The DMF/EtOAc suspension was filtered through SOLKA FLOC® and the cake was washed with 250 mL EtOAc. The resulting filtrate was washed with 5% brine solution (3×500 mL). The aqueous layers were extracted with 500 mL EtOAc and the combined organics were dried over MgSO$_4$, filtered and evaporated. The solids were slurried in 250 mL MTBE at RT then filtered and washed with 100 mL MTBE. The solids were dried under vaccum at RT, providing 5-hydroxy-4-methyl-3H-isobenzofuran-1-one.

Step D: 4-methyl-1-oxo-1,3-dihydroisobenzofuran-5-yl trifluoromethanesulfonate

5-Hydroxy-4-methyl-3H-isobenzofuran-1-one (46.8 g, 285 mmol) was suspended in dichloromethane (935 mL) in 2-L roundbottom flask equipped with overhead stirrer under nitrogen. Triethylamine (59.5 mL, 427 mmol) was added, and the reaction mixture was cooled in an ice bath to 3.8° C. Trifluoromethanesulfonic anhydride (67.4 mL, 399 mmol)

was added via addition funnel over 50 min, keeping the temperature <10° C. After stirring the recation mixture for an additional 15 min, the reaction mixture was quenched with water (200 mL), then stirred with DARCO® KB (activated carbon, 25 g) for 15 min. The biphasic mixture was filtered over SOLKA FLOC®, washing with additional dichloromethane, and transferred to a separatory funnel, whereupon it was diluted with additional water (300 mL). The layers were separated, and the organic layer was washed with water (500 mL) and 10% brine (200 mL). The dichloromethane solution was dried over sodium sulfate, filtered and evaporated. The orange-red solid was adsorbed onto silica gel (27.5 g) and eluted through a pad of silica gel (271 g) with 25% ethyl acetate/hexanes. The resulting solution was concentrated under vacuum with the product crystallizing during concentration. The suspension was filtered, the solid washed with heptane and dried under vacuum and nitrogen, providing trifluoromethanesulfonic acid 4-methyl-1-oxo-1,3-dihydro-isobenzofuran-5-yl ester.

Step E: 5-(1-Butoxy-vinyl)-4-methyl-3H-isobenzofuran-1-one

To a 1 L 3-neck was charged trifluoromethanesulfonic acid 4-methyl-1-oxo-1,3-dihydro-isobenzofuran-5-yl ester (63.0 g, 213 mmol), DMF (315 mL), butyl vinyl ether (138 mL, 1063 mmol)) and Et$_3$N (35.6 mL, 255 mmol). The solution was sparged with N$_2$ for 20 min. To the solution was added Pd(OAc)$_2$ (1.19 g., 5.32 mmol) and DPPP (2.41 g., 5.85 mmol) and sparged for an additional 10 min then heated to 80° C. After a 1 hr age, the solution was cooled to <10° C. then quenched with 630 mL of EtOAc and washed with 5% NH$_4$Cl (2×315 mL), 10% brine (2×315 mL), dried over MgSO$_4$, filtered, concentrated by rotary evaporation and flushed with EtOAc (3×100 mL) to remove excess butyl vinyl ether, providing crude 5-(1-butoxy-vinyl)-4-methyl-3H-isobenzofuran-1-one.

Step F: 5-(2-Bromo-acetyl)-4-methyl-3H-isobenzofuran-1-one

To a 1 L 3-neck flask equipped with overhead stirrer was added crude 5-(1-butoxy-vinyl)-4-methyl-3H-isobenzofuran-1-one (55.8 g) and THF (315 mL). The solution was cooled to <5° C. after which water (79 mL) was added and the solution was maintained at <5° C. NBS (41.6 g) was then added portion-wise while maintaining <19° C. The solution was then warmed to RT for 30 minutes. HBr (48%, 0.241 mL) was added and the reaction was aged at RT for approximately 1 h after which 236 mL of water was then added to the batch. A water bath is used to maintain temp at 20° C. Another 315 mL of water was added (solvent composition 1:2 THF:water) and the slurry was cooled to 15° C. The resulting solids were filtered and washed with cold 1:2 THF:water (15° C.): 150 mL of displacement wash followed by 100 mL of slurry wash. The solids were dried under vacuum at RT to provide 5-(2-bromo-acetyl)-4-methyl-3H-isobenzofuran-1-one.

Step G: 4-methyl-5-[(2R)-oxiran-2-yl]-2-benzofuran-1(3H)-one 5-(2-Bromo-acetyl)-4-methyl-3H-isobenzofuran-1-one (48.8 g., 181 mmol) was charged to a 5 L 3 neck round bottom equipped with overhead stirrer, thermocouple, and heating mantle. 2-Propanol (1.22 L) was added, followed by 610 mL of pH 7 0.1M potassium phosphate buffer. Buffer solution (610 mL) was charged to a 1.0 L erlenmeyer, and 2.44 g of NADP was added to the erlenmeyer and swirled to dissolve. A reducing enzyme, KRED MIF-20 (2.44 g) (available from Codexis, Inc., 200 Penobscot Drive, Redwood City, Calif. 94063, www.codexis.com, tel. 1-650-421-8100) was added to the erlenmeyer flask and the mixture was swirled to dissolve the solids. The resulting solution was added to the 5 L round bottom, which was then heated to 28° C. and aged for 6 hours, at which point the reaction was cooled to RT and triethylamine (50.2 mL, 360 mmol) was added. The resulting solution was aged at 40° C. for 1 h. The light slurry solution was cooled to RT, after which 122 g NaCl was added. The solution was aged at RT then extracted with 1.22 L of isopropyl acetate (IPAc). The aqueous layer was re-extracted with 400 mL IPAc and the combined organics were washed with 400 mL 20% brine solution, dried over MgSO$_4$, filtered and concentrated by rotary evaporation. The resulting solids were diluted in 100 mL IPAc (thick slurry). Hexanes were added (400 mL) and the suspension aged at RT then filtered and washed w/ 5:1 Hexanes:IPAc solution (150 mL). The crystalline solids were dried under vacuum at RT to provide 4-methyl-5-[(2R)-oxiran-2-yl]-2-benzofuran-1(3H)-one.

Intermediate 5A

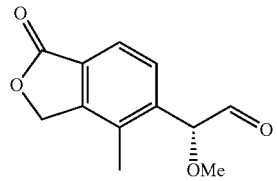 [SMILES: CO[C@@H](C=O)c1ccc2c(c1C)COC2=O]

(R)-2-Methoxy-2-(4-methyl-1-oxo-1,3-dihydroisobenzofuran-5-yl)acetaldehyde

Step A: (R)-5-(2-Hydroxy-1-methoxyethyl)-4-methylisobenzofuran-1(3H)-one

To a solution of (S)-4-methyl-5-(oxiran-2-yl)isobenzofuran-1(3H)-one (INTERMEDIATE 4A; 2.00 g, 10.5 mmol) in MeOH (20 mL) was added p-toluenesulfonic acid monohydrate (0.100 g, 0.526 mmol). After heating at 80° C. for 48 h, the reaction mixture was cooled to RT and then concentrated. The crude product was purified by column chromatography eluting with 0-45% EtOAc/Hexane.

Step B: (R)-2-Methoxy-2-(4-methyl-1-oxo-1,3-dihydroisobenzofuran-5-yl)acetaldehyde (R)-5-(2-Hydroxy-1-methoxyethyl)-4-methylisobenzofuran-1(3H)-one (500 mg, 2.25 mmol) was dissolved in DCM (10 mL) and treated with Dess-Martin periodinane (954 mg, 2.25 mmol). The reaction mixture was stirred at room temperature under nitrogen overnight. The crude product was used directly.

Intermediate 5B

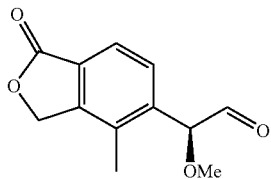 [SMILES: CO[C@H](C=O)c1ccc2c(c1C)COC2=O]

(S)-2-Methoxy-2-(4-methyl-1-oxo-1,3-dihydroisobenzofuran-5-yl)acetaldehyde

The title compound was prepared in an analogous fashion to that described for the synthesis of (R)-2-Methoxy-2-(4-methyl-1-oxo-1,3-dihydroisobenzofuran-5-yl)acetaldehyde except starting from (R)-4-methyl-5-(oxiran-2-yl)isobenzofuran-1(3H)-one (INTERMEDIATE 4B).

Intermediate 6A

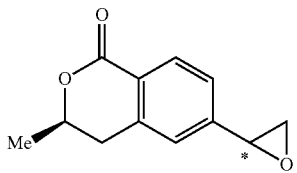 [SMILES: C[C@@H]1Cc2cc(C3CO3)ccc2C(=O)O1]

(3R)-3-methyl-6-(oxiran-2-yl)-3,4-dihydro-1H-isochromen-1-one

Step A: (3R)-6-ethenyl-3-methyl-3,4-dihydro-1H-isochromen-1-one

A solution of (3R)-6-bromo-3-methyl-3,4-dihydro-1H-isochromen-1-one (2.4 g, 9.96 mmol) and triethylamine (2.78 ml, 19.91 mmol) in EtOH (39.8 ml) was added to a microwave vial containing PdCl$_2$(dppf)$_2$-DCM (0.406 g, 0.498 mmol) and potassium vinyltrifluoroborate (2.000 g, 14.93 mmol). The contents of the vial were heated to 100° C. for 1 hour after which the mixture was cooled, diluted with chloroform (50 mL) and washed with aqueous ammonium chloride (25 mL). The organic layer was then dried over magnesium sulfate, filtered and the solvent was evaporated under reduced pressure. MPLC purification (15-60% EtOAc/Hex) gave title compound.

Step B: (3R)-3-methyl-6-(oxiran-2-yl)-3,4-dihydro-1H-isochromen-1-one

A solution of 6-ethenyl-3-methyl-3,4-dihydro-1H-isochromen-1-one (1.69 g, 8.98 mmol) in DCM (60 mL) was treated with m-CPBA (3.10 g, 17.96 mmol) overnight at room temperature. The reaction was then diluted with water (50 mL) and DCM (50 mL). The organic layer was further washed successively with saturated aqueous sodium bicarbonate (30 mL), water (30 mL), and brine (30 mL). The organic layer was then dried over magnesium sulfate, filtered and concentrated. The residue was purified via MPLC (15-40% EtOAc/Hex) to give title compound.

Intermediate 6B

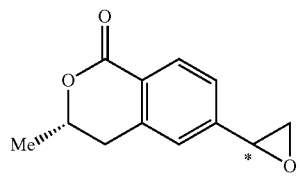 [SMILES: C[C@H]1Cc2cc(C3CO3)ccc2C(=O)O1]

(3S)-3-methyl-6-(oxiran-2-yl)-3,4-dihydro-1H-isochromen-1-one

The title compound was prepared in an analogous fashion to that described for the synthesis of (3R)-3-methyl-6-(oxiran-2-yl)-3,4-dihydro-1H-isochromen-1-one except starting from (3S)-6-bromo-3-methyl-3,4-dihydro-1H-isochromen-1-one.

Intermediate 7

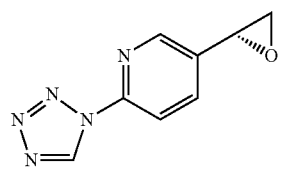

Fast eluting

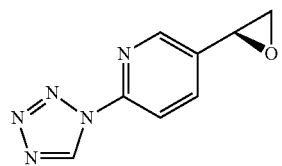

Slow eluting

7A: (S)-5-(oxiran-2-yl)-2-(1H-tetrazol-1-yl)pyridine

7B: (R)-5-(oxiran-2-yl)-2-(1H-tetrazol-1-yl)pyridine

Step A: 5-Bromo-2-(1H-tetrazol-1-yl)pyridine

To a solution of 5-bromopyridin-2-amine (5.0 g, 28.9 mmol) in acetic acid (40 ml, 699 mmol) was added (diethoxymethoxy) ethane (7.70 ml, 46.2 mmol), followed by sodium azide (2.82 g, 43.3 mmol). The mixture was heated at 80° C. for 1 h, cooled to room temperature and diluted with water. Precipitate was collected by filtration and dried under high vacuum to provide the title compound.

Step B: 5-Ethenyl-2-(1H-tetrazol-1-yl)pyridine

To a stirring solution of 5-bromo-2-(1H-tetrazol-1-yl)pyridine (1.0 g, 4.42 mmol), in EtOH (70 mL) were added bis[(diphenylphosphino)ferrocene]dichloropalladium(II) complex with dichloromethane (0.361 g, 0.442 mmol), potassium vinyl trifluoroborate (1.18 g, 8.85 mmol, 2 equiv.), triethylamine (1.23 mL, 8.85 mmol, 2 equiv), and water (0.5 mL). The reaction mixture was heated at reflux (90° C., oil bath) under N₂. Upon completion (1-2 h), the mixture was cooled to room temperature, and diluted with water. The organic layer was separated, and the aqueous was extracted with EtOAc. The combined organic layers were washed with brine, dried over MgSO₄, and concentrated. The crude material was chromatographed over a column of SiO₂ (0-20% EtOAc in hexane as eluent). Evaporation of the solvent yielded the title compound Step C: 5-(Oxiran-2-yl)-2-(1H-tetrazol-1-yl)pyridine To a solution of 5-ethenyl-2-(1H-tetrazol-1-yl)pyridine (0.664 g, 3.83 mmol) in a 2:1 ratio of H₂O: t-BuOH (30 mL) was added N-bromosuccinimide (0.751 g, 4.22 mmol) in portions over 5 min. The mixture was heated at 40° C. for 1 h, cooled to 5° C., made basic with sodium hydroxide aqueous solution (0.46 g in 5 mL of H₂O, 11.50 mmol), stirred for another 1 h at the same temperature, and poured into H₂O (10 mL). The product was precipitated out as white solid. The solid was collected by filtration, washed with water, and dried in vacuum. Further chiral separation (AD-H 30×250 mm, 50% MeOH/CO₂, 70 mL/min, 100 bar, 46 mg in MeOH/DCM) afforded fast eluted 7A (S)-5-(oxiran-2-yl)-2-1H-tetrazol-1-yl)pyridine and slow eluted 7B (R)-5-(oxiran-2-yl)-2-(1H-tetrazol-1-yl)pyridine Intermediate 8

8A

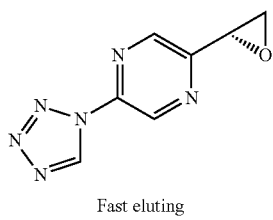

Fast eluting

8B

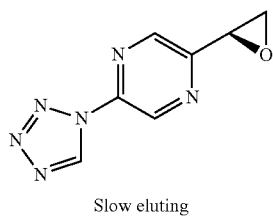

Slow eluting

8A: (S)-2-(oxiran-2-yl)-5-(1H-tetrazol-1-yl)pyrazine

8B: (R)-2-(oxiran-2-yl)-5-(1H-tetrazol-1-yl)pyrazine

Step A: 2-Bromo-5-(1H-tetrazol-1-yl)pyrazine

To a solution of 5-bromopyrazin-2-amine (10.75 g, 57.5 mmol) in ethyl acetate (150 ml) was added trimethylsilyl 2,2,2-trifluoroacetate (16.88 ml, 98 mmol). After the mixture was stirred for 5 min, triethoxymethane (17.21 ml, 103 mmol) was added. The resulting mixture was stirred for another five min, and this was followed by addition of azidotrimethylsilane (12.09 ml, 92 mmol). Stirring continued at rt for 2 days, and the mixture was concentrated under reduced pressure. Recrystallization of the residue from ethyl acetate afforded 2-bromo-5-(1H-tetrazol-1-yl)pyrazine.

Step B: 2-(1H-tetrazol-1-yl)-5-vinylpyrazine

A solution of 2-bromo-5-(1H-tetrazol-1-yl)pyrazine (11.2 g, 49.3 mmol), potassium vinyltrifluoroborate (13.22 g, 99.0 mmol), 1,1'-bis(diphenylphosphino)ferrocene-palladium(ii) dichloride dichloromethane complex (2.01 g, 2.47 mmol), and TEA (13.75 ml, 99.0 mmol) in ethanol (150 ml) was heated at reflux at 82° C. for 4 h. The reaction mixture was cooled to rt, and the precipitation was filtered off. The filtrate was concentrated, and the residue was purified by flash chromatography (SiO₂, ethyl acetate in hexane: 35 to 45%) affording 2-(1H-tetrazol-1-yl)-5-vinylpyrazine. The filter cake was stirred in DCM (50 mL), and the solid was filtered off. The filtrate was concentrated to afford more 2-(1H-tetrazol-1-yl)-5-vinylpyrazine.

Step C: 2-(oxiran-2-yl)-5-(1H-tetrazol-1-yl)pyrazine

To a suspension of 2-(1H-tetrazol-1-yl)-5-vinylpyrazine (6.7 g, 38.5 mmol) in ᵗBuOH:water (96 ml: 190 ml) was added N-bromosuccinimide (7.53 g, 42.3 mmol) in portion at rt. The mixture was heated at 50° C. for 1 h, and cooled to 0° C. in an ice bath. NaOH (4.61 g in 30 mL water, 115 mmol) was added dropwise, and the resulting mixture was stirred at the same temperature for 20 min. The white solid product was collected by filtration, washed with water, and dried under vacuum to give 2-(1H-tetrazol-1-yl)-5-vinylpyrazine. Chiral separation (AD-H 30×250 mm, 50% MeOH/CO₂, 70 mL/min, 100 bar, MeOH/DCM) afforded fast eluted isomer 8A (S)-2-(oxiran-2-yl)-5-(1H-tetrazol-1-yl)pyrazine and slow eluted isomer 8B (R)-2-(oxiran-2-yl)-5-(1H-tetrazol-1-yl)pyrazine.

TABLE 1 epoxides prepared according to the method described for INTERMEDIATE 7 or 8

| INTERMEDIATE # | Starting material and method | Structure A | Structure B | LC-MS [M + 1]⁺ or [M + 1-28]⁺ |
| --- | --- | --- | --- | --- |
| 9 | NH₂-pyridine-Br  Method for Int. 7 | Fast eluted 9A (S)-2-(oxiran-2-yl)-5-(1H-tetrazol-1-yl)pyridine | Slow eluted 9B (R)-2-(oxiran-2-yl)-5-(1H-tetrazol-1-yl)pyridine | 190.10 |

TABLE 1-continued epoxides prepared according to the method described for INTERMEDIATE 7 or 8

| INTERMEDIATE # | Starting material and method | Structure A | Structure B | LC-MS [M + 1]+ or [M + 1-28]+ |
|---|---|---|---|---|
| 10 | 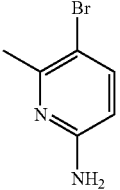<br>Method for Int. 7 | 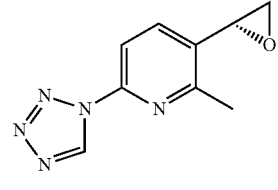<br>Fast eluted 10A<br>(S)-2-methyl-3-(oxiran-2-yl)-6-(1H-tetrazol-1-yl)pyridine | 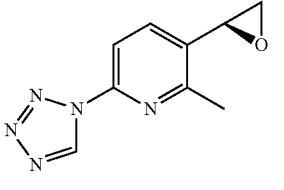<br>Slow eluted 10B<br>(R)-2-methyl-3-(oxiran-2-yl)-6-(1H-tetrazol-1-yl)pyridine | 188.10 |
| 11 | 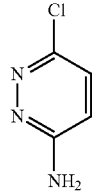<br>Method for Int. 8 | 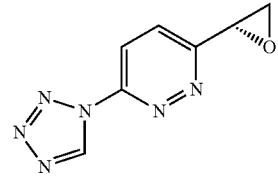<br>Fast eluted 11A<br>(S)-3-(oxiran-2-yl)-6-(1H-tetrazol-1-yl)pyridazine | 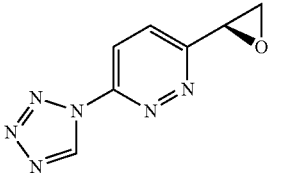 [SMILES: c1cc(-n2cnnn2)nnc1[C@@H]1CO1]<br>Slow eluted 11B<br>(R)-3-(oxiran-2-yl)-6-(1H-tetrazol-1-yl)pyridazine | 191.16 |
| 12 | 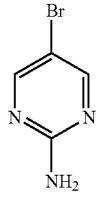<br>Method for Int. 8 | 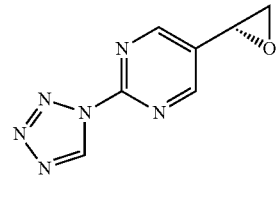 [SMILES: c1nc(-n2cnnn2)ncc1[C@H]1CO1]<br>Fast eluted 12A<br>(S)-5-(oxiran-2-yl)-2-(1H-tetrazol-1-yl)pyrimidine | 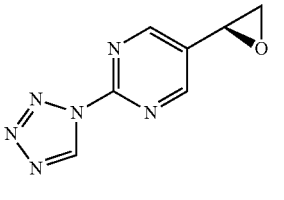<br>Slow eluted 12B<br>(R)-5-(oxiran-2-yl)-2-(1H-tetrazol-1-yl)pyrimidine | 191.07 |
| 13 | 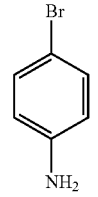<br>Method for Int. 8 | 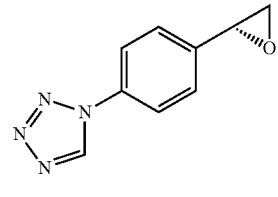 [SMILES: c1cc(-n2cnnn2)ccc1[C@H]1CO1]<br>Fast eluted 13A<br>(S)-1-(4-(oxiran-2-yl)phenyl)-1H-tetrazole | 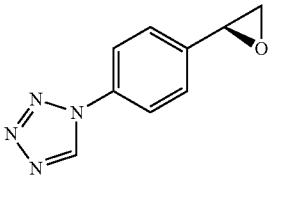 [SMILES: c1cc(-n2cnnn2)ccc1[C@@H]1CO1]<br>Slow eluted 13B<br>(R)-1-(4-(oxiran-2-yl)phenyl)-1H-tetrazole | 189.13 |
| 14 | 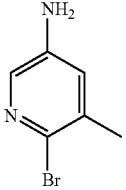<br>Method for Int. 8 | 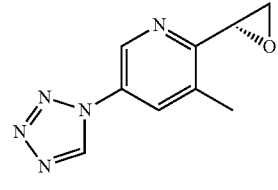<br>Fast eluted 14A<br>(S)-3-methyl-2-(oxiran-2-yl)-5-(1H-tetrazol-1-yl)pyridine | 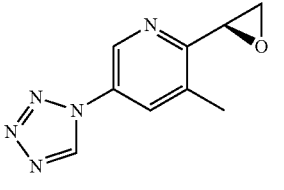<br>Slow eluted 14B<br>(R)-3-methyl-2-(oxiran-2-yl)-5-(1H-tetrazol-1-yl)pyridine | 204.12 |

TABLE 1-continued epoxides prepared according to the method described for INTERMEDIATE 7 or 8

| INTERMEDIATE # | Starting material and method | Structure A | Structure B | LC-MS [M + 1]+ or [M + 1-28]+ |
|---|---|---|---|---|
| 15 | 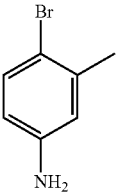<br>Method for Int. 8 | 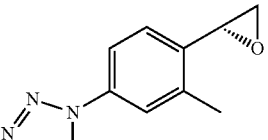<br>Fast eluted 15A<br>(S)-1-(3-methyl-4-(oxiran-2-yl)phenyl)-1H-tetrazole | 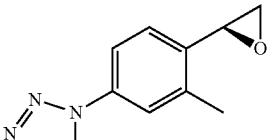<br>Slow eluted 15B<br>(R)-1-(3-methyl-4-(oxiran-2-yl)phenyl)-1H-tetrazole | |
| 16 | 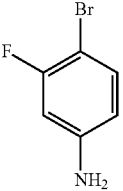<br>Method for Int. 8 | 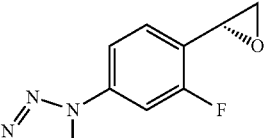<br>Fast eluted 16A<br>(S)-1-(3-fluoro-4-(oxidant-2-yl)phenyl)-1H-tetrazole | 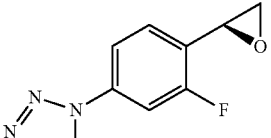<br>Slow eluted 16B<br>(R)-1-(3-fluoro-4-(oxidant-2-yl)phenyl)-1H-tetrazole | 207.1 |
| 17 | 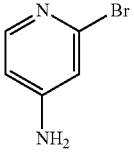<br>Method for Int. 7 | 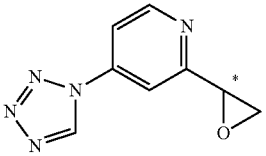 [SMILES: c1cc(-n2cnnn2)cc(C2CO2)n1]<br>2-(oxiran-2-yl)-4-(1H-tetrazol-1-yl)pyridine | No chiral separation at this stage | 190 |
| 18 | 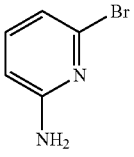<br>Method for Int. 7 | 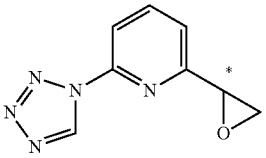 [SMILES: c1cc(C2CO2)nc(-n2cnnn2)c1]<br>2-(oxiran-2-yl)-6-(1H-tetrazol-1-yl)pyridine | No chiral separation at this stage | 162 |
| 19 | 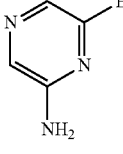<br>Method for Int. 7 | 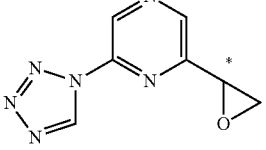<br>2-(oxiran-2-yl)-6-(1H-tetrazol-1-yl)pyridine | No chiral separation at this stage | 191 |
| 20 | 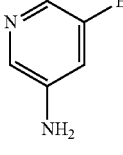<br>Method for Int. 7 | 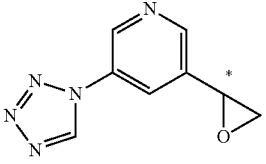 [SMILES: c1ncc(-n2cnnn2)cc1C1CO1]<br>3-(oxiran-2-yl)-5-(1H-tetrazol-1-yl)pyridine | No chiral separation at this stage | 190 |

TABLE 1-continued epoxides prepared according to the method described for INTERMEDIATE 7 or 8

| INTERMEDIATE # | Starting material and method | Structure A | Structure B | LC-MS [M + 1]+ or [M + 1-28]+ |
|---|---|---|---|---|
| 21 | <br>Method for Int. 7 | 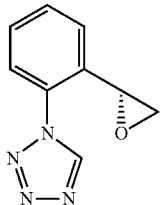 [SMILES: c1ccc(-n2cnnn2)c([C@H]2CO2)c1]<br>(S)-1-(2-(oxiran-2-yl)phenyl)-1H-tetrazole fast eluting isomer from chiral SFC separation using AD-3 column | 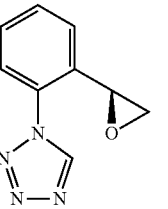<br>(R)-1-(2-(oxiran-2-yl)phenyl)-1H-tetrazole slow eluting isomer from chiral SFC separation using AD-3 column | 189 |

Intermediate 22

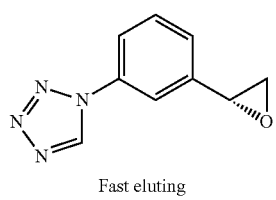

Fast eluting

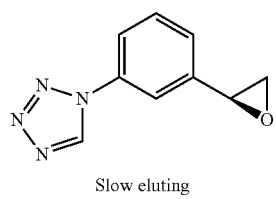

Slow eluting

22A: (S)-1-(3-(oxiran-2-yl)phenyl)-1H-tetrazole

22B: (R)-1-(3-(oxiran-2-yl)phenyl)-1H-tetrazole

Step A: 1-(3-bromophenyl)-1H-tetrazole

A 10-20 mL BIOTAGE Initiator microwave reactor vessel equipped with magnetic stir bars and septum cap was charged with 3-bromoaniline (0.633 mL, 5.81 mmol), AcOH (10 mL), triethyl orthoformate (2.90 mL, 17.44 mmol) and NaN$_3$ (1.134 g, 17.44 mmol). The reaction mixture was placed into a pre-heated 80° C. metal reaction block and stirred for 3 h. The reaction mixture was cooled to room temperature and diluted with deionized H$_2$O. The aqueous medium was extracted with EtOAc. The organic layer was separated and washed with saturated aq. NaCl—dried (Na$_2$SO$_4$), filtered, concentrated under reduced pressure and dried in vacuo to afford the title compound.

Step B: 1-(3-vinylphenyl)-1H-tetrazole

To a flask was charged 1-(3-bromophenyl)-1H-tetrazole (640 mg, 2.84 mmol), potassium vinyltrifluoroborate (571 mg, 4.27 mmol), and PdCl$_2$(dppf) (104 mg, 0.142 mmol). The flask was sealed, degassed, and filled with EtOH (14 mL) and Et$_3$N (1.19 mL, 8.53 mmol). The reaction mixture was heated at 85° C. for 3 h, and filtered to give the crude product, which was purified by column chromatography (0-100% EtOAc/hexanes) to give the title compound.

Step C: (S)-1-(3-(oxiran-2-yl)phenyl)-1H-tetrazole and (R)-1-(3-(oxiran-2-yl)phenyl)-1H-tetrazole To 1-(3-vinylphenyl)-1H-tetrazole (444 mg, 2.58 mmol) in DCM (25 mL) was added mCPBA (1335 mg, 7.74 mmol). The reaction mixture was stirred at rt overnight, washed with NaHCO$_3$, and brine, dried and evaporated to give the crude product, which was purified by column chromatography (0-100% EtOAc/hexanes) to afford the racemic compound. The racemate was subjected to SFC chiral separation with CHIRALPAK IC, 20% (2:1 MeOH:MeCN)/CO$_2$ to give the Fast and Slow eluting enantiomers.

Intermediate 23

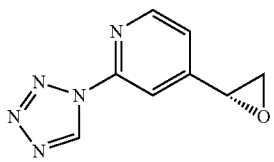

Fast eluting

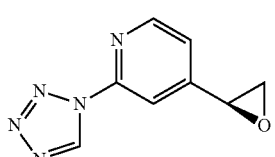

Slow eluting

23A: (S)-4-(oxiran-2-yl)-2-(1H-tetrazol-1-yl)pyridine

23B: (R)-4-(oxiran-2-yl)-2-(1H-tetrazol-1-yl)pyridine

Step A: 4-bromo-2-(1H-tetrazol-1-yl)pyridine

To 4-bromopyridin-2-amine (1000 mg, 5.78 mmol) in ethyl acetate (17 mL) was added trimethylsilyl trifluoroacetate (1.7 mL, 9.83 mmol). After 5 min, triethyl orthoformate (1.7 mL, 10.23 mmol) was added, followed by azidotrimethylsilane (1.2 mL, 9.25 mmol) after another 5 min. The reaction mixture was stirred at rt overnight, and concentrated to give the crude product, which was purified by column chromatography (0-10% EtOAc/hexanes) to afford the title compound.

Step B: 2-(1H-tetrazol-1-yl)-4-vinylpyridine

To a flask was charged 4-bromo-2-(1H-tetrazol-1-yl)pyridine (1162 mg, 5.14 mmol), potassium vinyltrifluoroborate (1033 mg, 7.71 mmol), and PdCl$_2$(dppf) (188 mg, 0.257 mmol). The flask was sealed, degassed, and filled with EtOH (26 mL) and triethylamine (2.2 mL, 15.42 mmol). The reaction mixture was heated at 85° C. for 3 h, and filtered to give the crude product, which was purified by column chromatography (0-10% EtOAc/hexanes) to afford the title compound.

Step C: (S)-4-(oxiran-2-yl)-2-(1H-tetrazol-1-yl)pyridine and (R)-4-(oxiran-2-yl)-2-(1H-tetrazol-1-yl)pyridine To 2-(1H-tetrazol-1-yl)-4-vinylpyridine (400 mg, 2.31 mmol) in DCM (23 mL) was added mCPBA (1196 mg, 6.93 mmol). The reaction mixture was stirred at rt overnight, washed with NaHCO$_3$ and brine, dried and evaporated to give the crude product, which was purified by column chromatography (0-100% EtOAc/hexanes) to afford the racemic compound. The racemate was submitted for SFC chiral separation with method CHIRALPAK IC, 20% (2:1 MeOH:MeCN)/CO$_2$ to give the Fast and Slow eluting enantiomers.

Intermediate 24

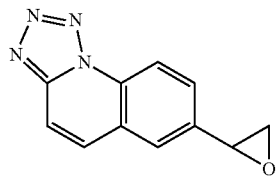 [SMILES: c1cc2c(ccc3nnnn32)cc1C1CO1]

7-(oxiran-2-yl)tetrazolo[1,5-a]quinoline

Step A: 6-bromo-2-chloroquinoline 6-bromoquinolin-2(1H)-one (3.40 g, 0.15 mol) in POCl$_3$ (12 mL) was heated under reflux for 1 h. The mixture cooled, concentrated, dissolved in chloroform (20 mL) and poured onto crushed ice (50 g). The mixture was neutralized with ammonia. The phases were separated and the aqueous phase was extracted with chloroform (2×15 mL). The combined organic layers were dried over magnesium sulfate, filtered and concentrated. The residue was purified by flash chromatography (petroleum ether: EtOAc from 50:1 to 5:1) to afford the title compound.

Step B: 7-bromotetrazolo[1,5-a]quinoline

A mixture of 6-bromo-2-chloroquinoline (1.10 g, 4.5 mmol) and NaN$_3$ (0.88 g, 13.5 mmol) in DMF (15 mL) was stirred at 120° C. for 3 h and then cooled, and poured into water. The precipitate was filtered off, washed with water, dried, and purified by flash chromatography (DCM/MeOH from 50:1 to 15:1) to afford the title compound.

Step C: 7-vinyltetrazolo[1,5-d]quinoline

To a mixture of 7-bromotetrazolo[1,5-a]quinoline (490 mg, 1.98 mmol), potassium vinyltrifluoroborate (530 mg, 3.95 mmol), and PdCl$_2$(dppf) (49 mg, 10%) in EtOH (10 mL) was added Et$_3$N (120 mg, 1.95 mmol). The resulting mixture was heated to 80° C. and stirred for 2 hours. The mixture was concentrated and purified by flash chromatography (petroleum ether/EtOAc from 10/1 to 3/1) to afford the title compound.

Step D: 7-(oxiran-2-yl)tetrazolo[1,5-a]quinoline

The mixture of 7-vinyltetrazolo[1,5-c]quinoline (300 mg, 1.53 mmol) and NBS (298 mg, 1.68 mmol) in a solution of t-butanol (5 mL) and water (10 mL) was heated to 40° C. It was stirred until the solid was mostly dissolved, then stirred for another 2 hours. It was added to a solution of NaOH (184 mg, 4.59 mmol) in water (2 mL) slowly, cooled to 0° C., then stirred for 1 hour. It was concentrated, and the residue was purified by Pre-TLC (petroleum ether/EtOAc=1/1) to afford the title compound.

Intermediate 25

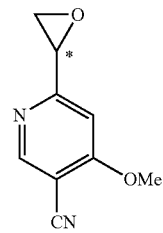

4-Methoxy-6-(oxiran-2-yl)pyridine-3-carbonitrile

Step A: 5-Bromo-2-chloro-4-methoxypyridine

To a solution of 2-chloro-4-methoxypyridine (10.0 g, 69.7 mmol) in 50 mL of sulfuric acid at 0° C. was added NBS. The reaction mixture was allowed to stir and warm up to room temperature for 2 hours and then heated at 60° C. for 5 h. Then it was cooled to room temperature and neutralized with 1 N NaOH (pH ~7), diluted with water (50 mL) and the aqueous layer was extracted with ethyl acetate (2×100 mL). The organic layers were washed with water (2×50 mL), saturated NaHCO$_3$, and brine, dried over Mg$_2$SO$_4$, and concentrated to provide a crude, which was chromatographed. On elution with 0-25% EtOAc/hexanes, the final product was obtained.

Step B: 6-Chloro-4-methoxypyridine-3-carbonitrile

A solution of 5-bromo-2-chloro-4-methoxypyridine (5.0 g, 22.48 mmol) in DMF (80 mL) was purged with nitrogen for 15 min. At this point, Zn(CN)$_2$ (3.96 g, 33.7 mmol) and Pd(Ph$_3$P)$_4$ (2.60 g, 2.25 mmol) were added successively. The resulting suspension was stirred at 95° C. for 12 h under nitrogen. The reaction mixture was cooled to ambient temperature, and filtered to remove inorganic solid. The solvent (DMF) was evaporated to provide the crude residue, which was purified on silica gel and eluted with 0-30% ethyl acetate/hexanes to afford the product.

Step C: 6-Ethenyl-4-methoxypyridine-3-carbonitrile

A 20 mL microwave tube was charged with 6-chloro-4-methoxypyridine-3-carbonitrile (200.0 mg, 1.2 mmol), bis(diphenylphosphino)ferrocene]dichloropalladium(II) complex with dichloromethane (97.0 mg, 0.12 mmol), potassium vinyl trifluoroborate (318.0 mg, 2.37 mmol), triethylamine (0.33 mL, 2.37 mmol), and EtOH (6 mL). The microwave tube was evacuated, filled with nitrogen (two times), and heated to 140° C. After 1 h, the reaction mixture was diluted with water and extracted with EtOAc. The combined organic layers were washed with brine and dried over Na$_2$SO$_4$. The extracts were concentrated and chromatographed over a column of SiO$_2$ (0-30% EtOAc/hexanes as eluent). Evaporation of the solvent yielded the title compound.

Step D: 6-(2-Bromo-1-hydroxyethyl)-4-methoxypyridine-3-carbonitrile

A solution of 6-ethenyl-4-methoxypyridine-3-carbonitrile (80.0 mg, 0.499 mmol) in 1, 4-dioxane (8 mL) and H$_2$O (4 mL) was treated with N-bromosuccinimide (89.0 mg, 0.499 mmol, 1.0 equiv). The reaction mixture was allowed to stir at room temperature overnight. The reaction mixture was poured into H$_2$O (8 mL) and extracted with EtOAc (3×30 mL). The combined organic layers were washed with saturated aqueous NaCl (1×30 mL), and dried over Na$_2$SO$_4$. Evaporation of the solvent gave a crude that was purified over SiO$_2$ (0-30% EtOAc/hexanes as eluent) yielding 6-(2-bromo-1-hydroxyethyl)-4-methoxypyridine-3-carbonitrile.

Step E: 4-Methoxy-6-(oxiran-2-yl)pyridine-3-carbonitrile

A solution of 6-(2-bromo-1-hydroxyethyl)-4-methoxypyridine-3-carbonitrile (74.0 mg, 0.288 mmol) in anhydrous methanol (7 mL) was treated with sodium carbonate (61.0 mg, 0.576 mmol, 2.0 equiv), and allowed to stir at room temperature overnight. The solvent was evaporated. The residue was diluted in EtOAc (30 mL) and washed with water and brine. After drying over Na$_2$SO$_4$, the solvent was removed and the residue was purified over SiO$_2$ (10-45% EtOAc/hexanes as eluent) to yield 4-methoxy-6-(oxiran-2-yl)pyridine-3-carbonitrile. Resolution of the epoxides was carried out (prep SFC, 160 mL/min., 10% MeOH in SC CO$_2$, AD-H) to provide:
Fast Eluting Isomer A: (M+1)$^+$=177.
Slow Eluting Isomer B: (M+1)$^+$=177.

Intermediate 26

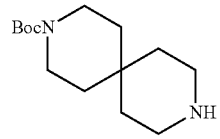

tert-butyl 3,9-diazaspiro[5.5]undecane-3-carboxylate

Step A: 9-benzyl-2,4-dioxo-3,9-diazaspiro[5.5]undecane-1,5-dicarbonitrile

A mixture of 1-benzylpiperidin-4-one (1 kg) and ethyl cyanoacetate (1.195 kg) in a saturated ethanolic ammonia solution (3 L) was stirred for 12 h at 0~2° C. The reaction mixture was filtered and the solid was dried in vacuo to afford the title compound which was used for next step directly without further purification.

Step B: diethyl 2,2'-(1-benzylpiperidine-4,4-diyl)diacetate

The crude 9-benzyl-2,4-dioxo-3,9-diazaspiro[5.5]undecane-1,5-dicarbonitrile in concentrated H$_2$SO$_4$ (1.2 L) and water (1 L) was refluxed for 3 days. The reaction mixture was neutralized by sodium carbonate (1.9 kg) and extracted with ethyl acetate. The combined organic layer was washed with brine, dried and concentrated in vacuo to afford the title compound.

Step C: diethyl 2,2'-(1-(tert-butoxycarbonyl)piperidine-4,4-diyl)diacetate

A mixture of diethyl 2,2'-(1-benzylpiperidine-4,4-diyl)diacetate (500 g, 1.44 mol), Boc$_2$O (380 g) and Pd(OH)$_2$/C (50 g) in methanol (500 mL) under H$_2$ atmosphere (50 psi) was stirred for 24 hours at RT. The mixture was filtered and the filtrate was concentrated in vacuo to afford the title compound.

Step D: tert-butyl 4,4-bis(2-hydroxyethyl)piperidine-1-carboxylate

To a suspension of LiAlH$_4$ (81.9 g, 2.15 mol) in dry THF (6 L) at −40° C. was added a solution of diethyl 2,2'-(1-(tert-butoxycarbonyl)piperidine-4,4-diyl)diacetate (478 g, 1.34 mol) in dry THF (2 L) for 2 hours. The reaction mixture was stirred for 0.5 h at this same temperature and warmed to RT slowly. Then the mixture was cooled to 0° C., and water (85.8 mL), 1N sodium hydroxide solution (171.6 mL) and water (195 ml) was added slowly. The mixture was stirred for 0.5 h, filtered, and washed with THF (150 mL×3). The filtrated was concentrated in vacuo to afford the title compound.

Step E: tert-butyl 4,4-bis(2-((methylsulfonyl)oxy)ethyl)piperidine-1-carboxylate To a solution of tert-butyl 4,4-bis(2-hydroxyethyl)piperidine-1-carboxylate (329 g, 1.21 mol) in dry DCM (3.5 L) at −25° C. was added TEA (505 mL, 3.62 mol) followed by addition of DMAP (32.9 g, 0.27 mol) and MsCl (310 g). The reaction mixture was stirred for 0.5 h at the same temperature. Then a solution of 10% citric acid was added, the organic layer was separated and the aqueous layer was extracted with ethyl acetate. The combined organic layer was washed with brine, dried and concentrated in vacuo to afford the title compound.

Step F: tert-butyl 9-benzyl-3,9-diazaspiro[5.5]undecane-3-carboxylate

A mixture of tert-butyl 4,4-bis(2-((methylsulfonyl)oxy)ethyl)piperidine-1-carboxylate (500 g, 1.17 mol) and BnNH₂ (508 g, 4.75 mol) in ethanol (5 L) was refluxed for 20 h. The solvent was removed in vacuo, the residue was diluted with ethyl acetate and filtered to remove the salt. The filtrate was concentrated in vacuo and purified by column chromatography on silica gel (PE/EA=10/1) to afford the title compound.

Step G: tert-butyl 3,9-diazaspiro[5.5]undecane-3-carboxylate

A mixture of tert-butyl 9-benzyl-3,9-diazaspiro[5.5]undecane-3-carboxylate (240 g, 0.7 mol) and Pd(OH)₂/C (24 g) in methanol (1.5 L) under hydrogen atmosphere (60 psi) was stirred at 40° C. for 24 h. The mixture was filtered and the filtrate was concentrated in vacuo. The residue was treated with 1N HCl/methanol and filtered to afford compound the title compound as a HCl salt.

Intermediate 27

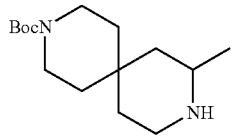 [SMILES: CC1CC2(CCN1)CCN(C(=O)OC(C)(C)C)CC2]

tert-Butyl 8-methyl-9-(5-oxo-2,5-dihydrofuran-3-yl)-3,9-diazaspiro[5.5]undecane-3-carboxylate Step A: tert-Butyl 9-benzyl-8-oxo-3,9-diazaspiro[5.5]undecane-3-carboxylate tert-Butyl 8-oxo-3,9-diazaspiro[5.5]undecane-3-carboxylate (400 mg, 1.491 mmol) was dissolved in THF (13 ml) and cooled to 0° C. NaH (119 mg, 2.98 mmol) was added. After the mixture was stirred at 0° C. under nitrogen for 0.5 hour and then at room temperature for 0.5 hour, benzyl bromide (443 μl, 3.73 mmol) was added and the reaction was stirred overnight. The reaction was diluted with EtOAc (20 ml) and washed with saturated NaHCO₃ aqueous solution (10 ml), brine, dried (Na₂SO₄), filtered and concentrated. The residue was purified by column chromatography eluting with 0-100% EtOAc/hexane to give the title compound.

Step B: tert-Butyl 9-benzyl-8-methyl-3,9-diazaspiro[5.5]undecane-3-carboxylate

Under nitrogen, tert-butyl 9-benzyl-8-oxo-3,9-diazaspiro[5.5]undecane-3-carboxylate (543 mg, 1.515 mmol) in anhydrous THF (7.6 ml) was treated with a solution of methylmagnesium chloride (2.52 ml, 7.57 mmol) dropwise.

After heating at 65° C. under nitrogen for 18 hours, the reaction mixture was cooled to 0° C., and acetic acid (3.37 ml, 58.9 mmol) and NaBH₄ (115 mg, 3.03 mmol) were added subsequently. The mixture was allowed to warm up to room temperature and stirred overnight. The reaction mixture was concentrated to remove excess of the reagent and the solvent, and 2 ml of THF and 2 ml of saturated aqueous NaHCO₃ solution were added. A small amount of solid Na₂CO₃ was also added to neutralize acetic acid. BOC₂O (0.703 ml, 3.03 mmol) was then added. The mixture was stirred at room temperature for 2 hours and then extracted with EtOAc (20 mL). The extracts were washed with brine (10 ml), and the organic layer was dried over sodium sulfate, filtered and concentrated. The residue was purified by column chromatography eluting with 0-7% MeOH/EtOAc to give the title compound.

Step C: tert-Butyl 8-methyl-3,9-diazaspiro[5.5]undecane-3-carboxylate tert-Butyl 9-benzyl-8-methyl-3,9-diazaspiro[5.5]undecane-3-carboxylate (214 mg, 0.597 mmol) was dissolved in EtOH (2 ml) and treated with Pd(OH)₂ (120 mg, 0.171 mmol) and ammonium formate (376 mg, 5.97 mmol). The mixture was heated at 80° C. for 2 hours. The mixture was then filtered and the filtrates were concentrated to give the title compound.

Intermediate 28

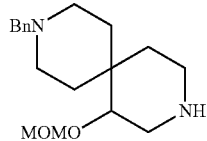

9-benzyl-1-(methoxymethoxy)-3,9-diazaspiro[5.5]undecane

Step A: ethyl 2-(1-benzylpiperidin-4-ylidene)-2-cyanoacetate

To a solution of 1-benzylpiperidin-4-one (50.00 g, 0.264 mol) and DIPEA (50.00 g, 0.317 mol) in DCM (500 mL) was added ethyl 2-cyanoacetate (29.90 g, 0.264 mol). The reaction mixture was stirred at room temperature overnight. The reaction solution was washed with brine, dried over anhydrous Na₂SO₄ and concentrated. The residue was purified by column chromatography (petroleum ether:EtOAc=20:1 to 3:1) to afford the title compound.

Step B: ethyl 2-(1-benzyl-4-(1-cyano-2-ethoxy-2-oxoethyl)piperidin-4-yl)-2-(methoxymethoxy)acetate n-BuLi (84.4 mL, 0.211 mol) was added to a solution of diisopropylamine (21.40 g, 0.211 mol) in dry THF (500 mL) cooled at −78° C. The mixture was stirred at −78° C. for 30 min, and ethyl 2-(methoxymethoxy)acetate (26.10 g, 0.176 mol) was added. The mixture was stirred at 0° C. for 30 min, and ethyl 2-(1-benzylpiperidin-4-ylidene)-2-cyanoacetate (50.00 g, 0.176 mol) was added. The reaction mixture was stirred at room temperature overnight. The mixture was quenched by saturated NH₄Cl, then extracted by ethyl acetate, washed by brine, dried over anhydrous Na$_2$SO$_4$, filtered and concentrated. The residue was purified by column chromatography (petroleum ether: EtOAc=10:1 to 2:1) to afford the title compound.

Step C: ethyl 2-(1-benzyl-4-(cyanomethyl)piperidin-4-yl)-2-(methoxymethoxy)acetate A mixture of ethyl 2-(1-benzyl-4-(1-cyano-2-ethoxy-2-oxoethyl)piperidin-4-yl)-2-(methoxymethoxy)acetate (2.00 g, 4.62 mmol), and LiCl (588 mg, 13.9 mmol) in DMSO (5 mL) and water (5 mL) was heated at 150° C. for 2 h by microwave radiation. The mixture was diluted with ethyl acetate, washed by brine, dried over anhydrous Na$_2$SO$_4$, filtered and concentrated. The residue was purified by column chromatography (petroleum ether: EtOAc=10:1 to 1:1) to afford the title compound.

Step D: 9-benzyl-1-(methoxymethoxy)-3,9-diazaspiro[5.5]undecan-2-one

To a solution of ethyl 2-(1-benzyl-4-(cyanomethyl)piperidin-4-yl)-2-(methoxymethoxy)acetate (40.00 g, 0.111 mol) in MeOH (500 mL) was added CoCl$_2$.6H$_2$O (18.80 g, 0.111 mol). Then NaBH$_4$ (21.00 g, 0.555 mol) was slowly added, and the reaction mixture was heated to reflux and stirred overnight. The mixture was concentrated under reduced pressure. The residue was dissolved in H$_2$O, then extracted by DCM, washed by brine, dried over anhydrous Na$_2$SO$_4$, filtered and concentrated. The residue which was purified by column chromatography (DCM: MeOH=50:1 to 10:1) to afford the title compound.

Step E: 9-benzyl-1-(methoxymethoxy)-3,9-diazaspiro[5.5]undecane

LAH (11.90 g, 0.314 mol) was added to a solution of 9-benzyl-1-(methoxymethoxy)-3,9-diazaspiro[5.5]undecan-2-one (20.00 g, 62.8 mmol) in dry THF cooled at 0° C. The mixture was heated to reflux and stirred for 2 h. The reaction mixture was cooled to 0° C., then water (12 mL), 15% NaOH aq. (12 mL) and H$_2$O (36 mL) was added in turn. The mixture was stirred for 30 min, then dried over anhydrous MgSO$_4$, filtered and concentrated to afford the title compound.

Intermediate 29

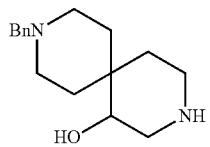

9-benzyl-3,9-diazaspiro[5.5]undecan-1-ol

To a solution of 9-benzyl-1-(methoxymethoxy)-3,9-diazaspiro[5.5]undecane (INTERMEDIATE 28; 5.00 g, 16.4 mmol) in EtOH (50 mL) was added conc. HCl (2 mL), then the reaction mixture was heated to reflux and stirred overnight. The reaction mixture was concentrated under reduced pressure to afford the title compound.

Intermediate 30

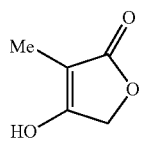

4-hydroxy-3-methylfuran-2(5H)-one

Step A: ethyl 4-bromo-2-methyl-3-oxobutanoate

To a solution of ethyl 2-methyl-3-oxobutanoate (5.05 g, 35.0 mmol) in water (10 mL) at 0° C. was added bromine (1.805 mL, 35.0 mmol) dropwise over 2 h. The resulting solution was stirred at rt for 16 h. The reaction mixture was extracted with ethyl acetate, and the organic phase was dried over sodium sulfate, and concentrated to give ethyl 4-bromo-2-methyl-3-oxobutanoate.

Step B: 4-hydroxy-3-methylfuran-2(5H)-one

Ethyl 4-bromo-2-methyl-3-oxobutanoate (7.81 g, 35 mmol) was treated with hydrogen bromide (0.040 mL, 48%, 0.35 mmol) and the mixture was heated at 100° C. for 6 h. The precipitate was collected by filtration followed by washing with ethyl acetate to give 4-hydroxy-3-methylfuran-2(5H)-one.

Intermediate 31

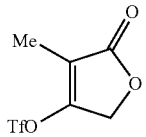

4-methyl-5-oxo-2,5-dihydrofuran-3-yl trifluoromethanesulfonate

To a solution of 4-hydroxy-3-methylfuran-2(5H)-one (INTERMEDIATE 30; 400 mg, 3.51 mmol) in dichloromethane (10 mL) at −78° C. was added 2,6-lutidine (0.612 mL, 5.26 mmol) and triflic anhydride (0.711 mL, 4.21 mmol) dropwise. The reaction temperature was maintained at −78° C. for 0.5 h before warmed to rt for 1 h. The mixture was diluted with DCM (100 mL), washed with 1 N hydrogen chloride (3 times 100 mL), diluted sodium bicarbonate solution, dried over sodium sulfate, and concentrated to give 4-methyl-5-oxo-2,5-dihydrofuran-3-yl trifluoromethanesulfonate.

Intermediate 32

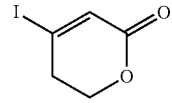

4-iodo-5,6-dihydro-2H-pyran-2-one

Step A: ethyl 2-cyclopropylideneacetate (1-Ethoxycyclopropoxy)trimethylsilane (1700 mg, 9.75 mmol) was dissolved in MeOH (4.3 mL) and the mixture was stirred for 17 h at room temperature. The solvent was removed under reduced pressure. The residue was dissolved in benzene (16.0 mL) and benzoic acid (232 mg, 1.9 mmol) was added. This flask was brought to gentle reflux. To the refluxing solution was added ethyl 2-(triphenylphosphoranylidene)acetate (3.0 g, 8.6 mmol) in benzene(16.0 mL) at a rate so as to maintain reflux. After completion of the addition the mixture was allowed to reflux for 2 h. After cooling to room temperature, benzene was removed under reduced pressure and the residue was purified by flash column chromatography (n-hexane/EtOAc=3:1) to afford the title compound.

Step B: 4-iodo-5,6-dihydro-2H-pyran-2-one

A solution of ethyl 2-cyclopropylideneacetate (300 mg, 2.378 mmol) with iodine (2414 mg, 9.51 mmol) and CuI (45.3 mg, 0.238 mmol) in MeCN (38 mL) and water (9.5 mL) was stirred at 85° C. for 10 h. The mixture was then diluted with 100 mL of saturated Na₂S₂O₃ and extracted three times with diethyl ether. The ether phases were combined and dried over MgSO₄. After evaporation, the residues were purified via chromatography on silica gel with n-hexane/diether ether (2:1) as the eluent to afford the title compound.

Intermediate 33

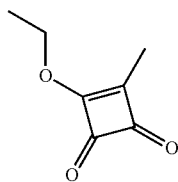

3-ethoxy-4-methylcyclobut-3-ene-1,2-dione

CH₃Li (1.0 Min THF, 60 mL) was added dropwise to a solution of 3,4-diethoxycyclobut-3-ene-1,2-dione (5.00 g, 29.4 mmol) in THF (100 mL) cooled at −78° C. The resulting mixture was stirred at −78° C. for 2 h and then TFAA (56 mL, 87 mmol) was added dropwise at −78° C. The mixture was warmed to r.t. After 30 min, the reaction was quenched by the addition of saturated aqueous NH₄Cl. The mixture was extracted with EtOAc, and washed with water. The combined organic layer was dried over Na₂SO₄ and concentrated to afford the title compound.

Intermediate 34

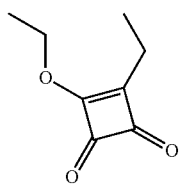

3-ethoxy-4-ethylcyclobut-3-ene-1,2-dione

EtMgCl (3.0 Min THF, 0.8 mL, 2.4 mmol) was added dropwise to a solution of 3,4-diethoxycyclobut-3-ene-1,2-dione (200 mg, 1.17 mmol) in THF (5 mL) cooled at −78° C. The reaction mixture was warmed to 0° C. slowly and then treated with TFAA (0.25 mL, 1.7 mmol) at 0° C. The mixture was then stirred overnight. Water was added to the mixture and the pH adjusted to 7 using NaHCO₃. The mixture was extracted with DCM, washed with water, dried and concentrated to afford the title compound.

Intermediate 35

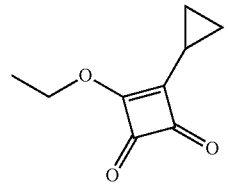

3-cyclopropyl-4-ethoxycyclobut-3-ene-1,2-dione

Cyclopropylmagnesium chloride (2.0 M in THF, 1.5 mL, 3.0 mmol) was added dropwise to a solution of 3,4-diethoxycyclobut-3-ene-1,2-dione (200 mg, 1.17 mmol) in anhydrous THF (10 mL) cooled at −78° C. After the reaction mixture was allowed to warm to 0° C., TFAA (0.25 mL, 1.7 mmol) was added dropwise over a period of 2 min. After an additional 10 min at 0° C., the solution was cooled to −78° C. and poured into water (10 mL). The mixture was extracted with TBME. The combined organic phase was washed with brine (15 mL), dried over Na₂SO₄, filtered and concentrated to afford the title compound.

Intermediate 36

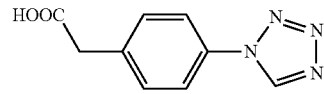 [SMILES: O=C(O)Cc1ccc(-n2cnnn2)cc1]

2-(4-(1H-tetrazol-1-yl)phenyl)acetic acid

To 2-(4-aminophenyl)acetic acid (10 g, 66.2 mmol) and triethyl orthoformate (17.7 mL, 107 mmol) in acetic acid (300 mL) was added NaN₃ (6.5 g, 99 mmol). The reaction mixture was warmed to reflux and stirred for 4 h, then stirred at rt overnight. The mixture was poured into ice water (~300 mL) and added 10 mL of concentrated HCl and extracted with EtOAc (2×). The organic layer was washed with water twice and brine, dried (MgSO4), filtered, and concentrated to give the title compound.

Intermediate 37

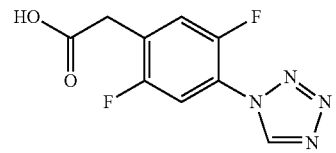 [SMILES: O=C(O)Cc1cc(F)c(-n2cnnn2)cc1F]

[2,5-difluoro-4-(1H-tetrazol-1-yl)phenyl]acetic acid

Step A: diethyl (2,5-difluoro-4-nitrophenyl)propanedioate

To an ice-cooled slurry of NaH (475 mg, 11.8 mmol, 60%) in dry DMF (10 mL) was added CH$_2$(COOEt)$_2$ dropwise under an N$_2$ atmosphere. After 20 minutes, 1,2,4-trifluoro-5-nitrobenzene (1 g, 5.6 mmol) was added dropwise over 10 minutes and the mixture was stirred at −6° C. overnight. After the reaction was completed, the mixture was diluted with water and extracted with EtOAc. The organic layer was washed with brine, dried over anhydrous Na$_2$SO$_4$ and concentrated. The residue was purified by chromatography to give diethyl (2,5-difluoro-4-nitrophenyl) propanedioate.

Step B: (2,5-difluoro-4-nitrophenyl)acetic acid

A mixture of diethyl (2,5-difluoro-4-nitrophenyl)propanedioate (700 mg, 2.2 mmol) with HOAc (10 mL) and HCl (6 N, 10 mL) was heated under N$_2$ at 120° C. for 2.5 hours, allowed to cool and stirred overnight. Most of the solvent was removed by evaporation and then water was added. The mixture was extracted with EtOAc. The organic layer was washed with brine, dried over anhydrous Na$_2$SO$_4$ and concentrated to give (2,5-difluoro-4-nitrophenyl)acetic acid.

Step C: (4-amino-2,5-difluorophenyl)acetic acid

To a solution of (2,5-difluoro-4-nitrophenyl)acetic acid (440 mg, 2.03 mmol) in 20 ml of EtOAc was added HOAc (121 mg, 2.03 mmol) and 200 mg of Pd/C. The mixture was stirred at room temperature under H$_2$ atmosphere for 3 hours. The reaction mixture was filtrated and concentrated to give (4-amino-2,5-difluorophenyl)acetic acid.

Step D: [2,5-difluoro-4-(1H-tetrazol-1-yl)phenyl]acetic acid

A solution of (4-amino-2,5-difluorophenyl)acetic acid (380 mg, 2.0 mmol) and triethyl orthoformate (902 mg, 6.1 mmol) in HOAc (10 mL) was added sodium azide (158 mg, 2.44 mmol) and the mixture was heated to 100° C. for 3 hours. After the reaction was completed, the reaction mixture was cooled to ambient temperature. The solvent was removed under vacuum. The residue was dissolved in EtOAc, washed with water, dried over anhydrous sodium sulfate, and concentrated to give the title compound.

Intermediate 38

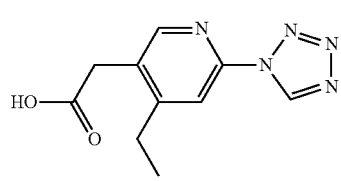 [SMILES: CCc1cc(-n2cnnn2)ncc1CC(=O)O]

[4-ethyl-6-(1H-tetrazol-1-yl)pyridin-3-yl]acetic acid

Step A: 4-ethyl-5-iodopyridin-2-amine

1-Iodopyrrolidine-2,5-dione (NIS, 3.87 g, 17.2 mmol) was added in portions to 4-ethylpyridin-2-amine (2.00 g, 16.4 mmol) in AcOH (60 m) during 30 min at 65° C. The mixture was heated at 65° C. for 36 hours, and was concentrated. The residue was purified by silica gel column chromatography (ethyl acetate/hexane 25 to 40%) to provide 4-ethyl-5-iodopyridin-2-amine Step B: tert-butyl (6-amino-4-ethylpyridin-3-yl)acetate To a solution of 4-ethyl-5-iodopyridin-2-amine (400 mg, 1.612 mmol) in THF are added Pd$_2$(dba)$_3$ (118 mg, 0.129 mmol), and X-PHOS (92 mg, 0.19 mmol). The reaction mixture was degassed, filled with nitrogen, and followed by the addition of 2-(tert-butoxy)-2-oxoethylzink chloride (8.06 ml, 4.03 mmol). The reaction mixture was heated at 60° C. overnight, cooled to RT, quenched with saturated NH$_4$Cl, and extracted with EtOAc. The organic layer was washed with brine, dried over Na$_2$SO$_4$, and concentrated. The residue was purified with preparative TLC (1500 uM, hex/EA=2/1) to give tert-butyl (6-amino-4-ethylpyridin-3-yl)acetate.

Step C: tert-butyl [4-ethyl-6-(1H-tetrazol-1-yl)pyridin-3-yl]acetate

To a solution of tert-butyl (6-amino-4-ethylpyridin-3-yl) acetate (198 mg, 0.838 mmol) in EtOAc (4 mL) was added trimethylsilyl trifluoroacetate (0.246 ml, 1.424 mmol) at room temperature. After stirring for 5 min, triethyl orthoformate (0.251 ml, 1.508 mmol) was added. After stirring for another 5 min, azidotrimethylsilane (0.176 ml, 1.34 mmol) was added. The reaction mixture was stirred at room temperature for two days, and was then concentrated. The residue was purified by prep TLC (hex/EA=1/1) to give tert-butyl [4-ethyl-6-(1H-tetrazol-1-yl)pyridin-3-yl]acetate.

Step D: [4-ethyl-6-(1H-tetrazol-1-yl)pyridin-3-yl]acetic acid

To a solution of tert-butyl [4-ethyl-6-(1H-tetrazol-1-yl) pyridin-3-yl]acetate (165 mg, 0.570 mmol) in DCM containing thioanisole (0.405 ml, 3.42 mmol) was added TFA (0.879 ml, 11.41 mmol) at 0° C. The mixture was stirred at RT overnight, and concentrated. The residue was triturated with ether:hexane (1:1) to give [4-ethyl-6-(1H-tetrazol-1-yl) pyridin-3-yl]acetic acid.

Intermediate 39

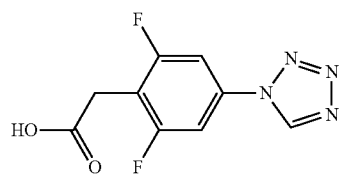 [SMILES: O=C(O)Cc1c(F)cc(-n2cnnn2)cc1F]

[2,6-Difluoro-4-(1H-tetrazol-1-yl)phenyl]acetic acid

[2,6-Difluoro-4-(1H-tetrazol-1-yl)phenyl]acetic acid was prepared according to the method described for the preparation of [4-ethyl-6-(1H-tetrazol-1-yl)pyridin-3-yl]acetic acid (INTERMEDIATE 38, Steps B-D) starting from 4-bromo-3,5-difluoroaniline.

Intermediate 40 (Method 1)

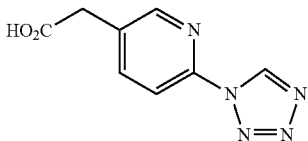 [SMILES: O=C(O)Cc1ccc(-n2cnnn2)nc1]

[6-(1H-tetrazol-1-yl)pyridin-3-yl]acetic acid

Step A: 5-chloro-2-nitropyridine

To concentrated H₂SO₄ (50 mL) was added 30% H₂O₂ (25 mL) at 0° C. and a solution of 5-chloropyridin-2-amine (5.0 g, 39 mmol) in concentrated H₂SO₄ (20 mL) at 0° C. The mixture was stirred for 20 hours at room temperature. The mixture was poured into ice water under vigorous stirring and the resulting solid was filtered. The solid was recrystallized from ethanol to give 5-chloro-2-nitropyridine.

Step B: tert-butyl ethyl (6-nitropyridin-3-yl)propanedioate

To a suspension of NaH (60% in oil, 0.650 g, 16.4 mmol) in DMF (40 mL) was added tert-butyl ethyl propanedioate (2.8 g, 15.1 mmol) at room temperature. The mixture was stirred for 30 min. A solution of 5-chloro-2-nitropyridine (2.00 g, 12.6 mmol) in DMF (10 mL) was added. The mixture was heated to 80° C. and stirred for 4 hours. The solvent was removed under reduce pressure. Water was added and the mixture was extracted with EtOAc. The combined organic layer was washed with brine, dried over anhydrous Na₂SO₄, concentrated and the residue was purified by column chromatography with silca gel to give tert-butyl ethyl (6-nitropyridin-3-yl)propanedioate.

Step C: ethyl (6-nitropyridin-3-yl)acetate

A mixture of tert-butyl ethyl (6-nitropyridin-3-yl)propanedioate (1.4 g, 4.5 mmol) in a mixed solution of TFA/DCM (10 mL/10 mL) was stirred for 5 hours at room temperature. The mixture was concentrated under reduce pressure. The residue was dissolved with DCM, washed with saturated NaHCO₃, dried over anhydrous Na₂SO₄ and concentrated to give ethyl (6-nitropyridin-3-yl)acetate.

Step D: ethyl (6-aminopyridin-3-yl)acetate

A mixture of ethyl (6-nitropyridin-3-yl)acetate (0.9 g, 4.28 mmol), and Pd/C (10%, 0.1 g) in MeOH (50 mL) was stirred for 2 hours under H₂ atmosphere at room temperature. The mixture was filtered and concentrated to give ethyl (6-aminopyridin-3-yl)acetate.

Step E: ethyl [6-(1H-tetrazol-1-yl)pyridin-3-yl]acetate

To a mixture of ethyl (6-aminopyridin-3-yl)acetate (0.55 g, 3.05 mmol), and CH(OEt)₃ (1.35 g, 9.15 mmol) in AcOH (20 mL) was added NaN₃ (0.24 g, 3.7 mmol) at room temperature. The mixture was heated to 80° C. and stirred for 3 hours. The mixture was concentrated under reduced pressure. Water was added, and the mixture was extracted with EtOAc. The combined organic layer was washed with brine, dried over anhydrous Na₂SO₄, concentrated and the residue was purified by column chromatography via silica gel to give ethyl [6-(1H-tetrazol-1-yl)pyridin-3-yl]acetate.

Step F: [6-(1H-tetrazol-1-yl)pyridin-3-yl]acetic acid

To a mixture of ethyl [6-(1H-tetrazol-1-yl)pyridin-3-yl] acetate (0.42 g, 1.8 mmol) in THF (3 mL) was added 1.4 M LiOH (aq.) (5 mL) at room temperature. The mixture was stirred for 3 hours at room temperature. The reaction was acidified with citric acid until pH of about 3-4. The mixture was extracted with EtOAc. The combined organic layer was washed with brine, dried over anhydrous Na₂SO₄, and concentrated to give [6-(1H-tetrazol-1-yl)pyridin-3-yl]acetic acid.

Intermediate 40 (Method 2)

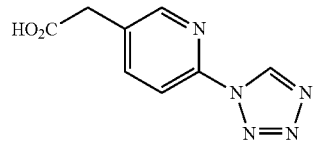 [SMILES: O=C(O)Cc1ccc(-n2cnnn2)nc1]

[6-(1H-tetrazol-1-yl)pyridin-3-yl]acetic acid

Step A: ethyl (6-nitropyridin-3-yl)acetate

To a suspension of NaH (60% in mineral oil, 13.8 g, 345 mmol) in 250 mL DMF in a 1 L flask with a magnetic stir bar was added tert-butyl ethyl propanedioate (65.3 mL, 345 mmol) maintaining the temperature below +12° C. in an ice bath over ~20 min (gas evolution). After 20 min, the ice bath was removed, and the mixture was allowed to warm to rt over 30 min. Commercially available 5-bromo-2-nitropyridine (50 g, 246 mmol) was added. A red suspension was formed immediately. After 15 min, the reaction flask was placed in a 60° C. oil bath. After 1 h, the heating was turned off. The red-black slurry was allowed to stir overnight while cooling down. After 15 h at rt, the mixture was cooled in an ice bath. An additional 0.7 equiv NaH (60% in mineral oil, 6.90 g, 172 mmol) was added in ~10 portions below +10° C. (internal) to control foam. After 30 min, an additional 100 mL DMF (2 volumes) was added to facilitate stirring. The rest of NaH was added over 10 min. The ice bath was stirred for an additional 10 min. The cooling bath was removed and the mixture was stirred to rt for 1 h. The reaction mixture was heated to 60° C. over 30 min, then heated for a total of 3.5 h at 60° C. whereupon ~95% of the bromide had been consumed. The flask was then cooled in an ice bath. After 20 min in the ice bath, 100 mL MTBE was added followed by 300 mL of 1 M aqueous H₃PO₄ below +15° C. (pH=5). The red-black color of the reaction mixture sharply turned to light brown. The mixture was combined with 750 mL EtOAc, and washed with 4×1 L water. The organic phase was concentrated and the crude was carried directly into the next step.

The resulting crude tert-butyl ethyl (6-nitropyridin-3-yl) propanedioate was dissolved in 153 mL of DCM, and TFA (95 mL, 1230 mmol) was added. The mixture was stirred at 25° C. for 2 h, then was heated at 35° C. for 2 h, (80% conversion). An additional 2 equiv of TFA (39 mL, 492 mmol) was added. The mixture was heated at 35° C. for 1 h, then was kept at rt overnight (>95% conversion). The reaction was quenched with 1.0 L of 1 M aq K₃PO₄ in an ice bath below +20° C. to pH=6. The layers were separated, and the aqueous phase was extracted with an additional 200 mL of DCM. The organic phase was dried (MgSO₄), filtered, and concentrated. The residue was dissolved in 200 mL MTBE and the solution was filtered through 20 g of silica gel to remove tar. The silica plug was eluted with additional 750 mL of MTBE. The filtrate was concentrated, and the oily residue was suspended in ~100 mL of 3:1 Hexane/EtOAc. Crystallization occurred upon stirring/seeding. The suspension was filtered, and the filter cake was washed with 100 mL of 5:1 hexane/EtOAc to provide the desired product. The mother liquors were concentrated, and purified by flash chromatography on 7.5×18 cm silica (Hexane:EtOAc 3:1 to 3:2). The purest fractions were collected, concentrated to an oil, and treated with ~100 mL hexane to crystallize additional product. The slurry was stirred at rt for 1 h, and filtered. The filter cake was washed with hexane to afford additional ethyl (6-nitropyridin-3-yl)acetate.

Step B: ethyl (6-aminopyridin-3-yl)acetate

A suspension of 10% Pd on carbon (9.21 g, 8.66 mmol) in a solution of the ethyl (6-nitropyridin-3-yl)acetate (36.4 g, 173 mmol) in EtOH (364 mL) was hydrogenated at 20 psi and 25° C. for 2 h. The suspension was filtered through SOLKA FLOC® eluting with 200 mL EtOH. The filtrate was concentrated and solvent was switched with EtOAc, and then concentrated to afford the title compound.

Step C: ethyl [6-(1H-tetrazol-1-yl)pyridin-3-yl]acetate

A 1 L 3-neck flask was purged with nitrogen and charged with a solution of ethyl (6-aminopyridin-3-yl)acetate (31.7 g, 176 mmol) in EtOAc (317 mL) at +22° C. Then 30 mL of TMSTFA was added (1.0 equiv) while cooling in a water bath. A mild exotherm to +25° C. and partial crystallization was observed. After 5 min, triethylorthoformate was added (44.0 mL, 264 mmol) followed by TMSA (28.0 mL, 211 mmol). The resulting suspension was stirred at +23° C. After 15 min, an additional 10 mL of TMSTFA was added (0.30 equiv). A clear solution was formed after ~10 min. The mixture was stirred for 3 days at +20° C. whereupon a thin, light yellow suspension had formed. The mixture was cooled in an ice bath, and 200 mL of 1M aq K₃PO₄ was added while maintaining the temperature below +20° C. Then 465 mL of EtOAc was added to solubilize the product. The layers were separated (pH of aq~8), then the organic phase was washed with 2×250 mL of water, and concentrated to a thick slurry. Then 400 mL of n-heptane was added to the concentrated organic phase over 20 min. After 30 min, the suspension was filtered to afford the title tetrazole product.

Step D: [6-(1H-tetrazol-1-yl)pyridin-3-yl]acetic acid

To a suspension of ethyl [6-(1H-tetrazol-1-yl)pyridin-3-yl]acetate (30.0 g, 129 mmol) in 150 mL of water was added 28 mL of 5M aq NaOH (141 mmol) over 5 min while cooling in a water bath. A very mild exotherm to +22° C. was observed. The mixture was stirred for 40 min at rt whereupon 106 mL of 2M aq H₃PO₄ was added over 30 min at rt. The resulting suspension was filtered, and the filter cake was washed with 2×50 mL of water and dried on the frit under a stream of nitrogen overnight to afford [6-(1H-tetrazol-1-yl)pyridin-3-yl]acetic acid.

Intermediate 41

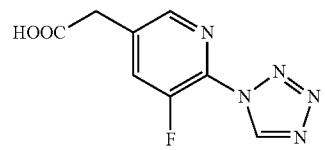 [SMILES: O=C(O)Cc1cnc(-n2cnnn2)c(F)c1]

2-(5-fluoro-6-(1H-tetrazol-1-yl)pyridin-3-yl)acetic acid

Step A: tert-butyl 2-(6-amino-5-fluoropyridin-3-yl)acetate

To 5-bromo-3-fluoropyridin-2-amine (300 mg, 2.0 mmol) in THF (10 mL) was added Pd₂(dba)₃ (94 mg, 0.10 mmol) and X-PHOS (98 mg, 0.20 mmol), followed by 2-(tert-butoxy)-2-oxoethylzinc chloride solution (10.6 mL, 0.5 M, 5.3 mmol). The reaction mixture was heated at 65° C. over night. The reaction mixture was quenched with NH₄Cl, and the aqueous layer was extracted with EtOAc. The organic extracts were washed with brine, dried, and evaporated to give the crude product, which was purified by column chromatography (0-100% EtOAc/hexanes) to give tert-butyl 2-(6-amino-5-fluoropyridin-3-yl)acetate.

Step B: tert-butyl 2-(5-fluoro-6-(1H-tetrazol-1-yl)pyridin-3-yl)acetate

To tert-butyl 2-(6-amino-5-fluoropyridin-3-yl)acetate (120 mg, 0.53 mmol) in EtOAc (2.6 mL) was added trimethylsilyl trifluoroacetate (156 µL, 0.90 mmol), triethyl orthoformate (156 µl, 0.94 mmol), and azidotrimethylsilane (112 µL, 0.85 mmol). The reaction mixture was stirred at rt overnight. The reaction mixture was concentrated to give the crude product, which was purified by column chromatography (0-100% EtOAc/hexanes) to give tert-butyl 2-(5-fluoro-6-(1H-tetrazol-1-yl)pyridin-3-yl)acetate.

Step C: 2-(5-fluoro-6-(1H-tetrazol-1-yl)pyridin-3-yl)acetic acid

To tert-butyl 2-(5-fluoro-6-(1H-tetrazol-1-yl)pyridin-3-yl)acetate (70 mg, 0.25 mmol) in DCM (0.50 mL) was added thioanisole (163 µl, 1.38 mmol) and TFA (241 µl, 3.13 mmol) at 0° C. The reaction mixture was stirred at rt for 5 h. The reaction mixture was concentrated to give the crude product, which was used in the next step without further purification.

Intermediate 42

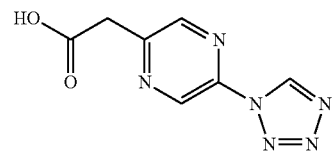

[5-(1H-tetrazol-1-yl)pyrazin-2-yl]acetic acid

Step A: 5-bromopyrazin-2-amine

To a solution of pyrazin-2-amine (20 g, 210 mmol) in 1.5 L of DCM was added NBS (37.4 g, 210 mmol) at 0° C. The resulting mixture was stirred for 3 hours at 0° C. then filtered through CELITE®. The filtrate was washed with saturated $Na_2CO_3$ and brine, dried over $Na_2SO_4$ and evaporated to afford a solid. The crude material was purified on silica gel (eluting with 20-40 percent ethyl acetate in hexane) to give 5-bromopyrazin-2-amine.

Step B: 2-bromo-5-[(dimethyl-$\lambda^4$-sulfanylidene) amino]pyrazine

To a solution of DMSO (11 g, 138 mmol) in 100 mL of DCM was added $Tf_2O$ (42 g, 149 mmol) at −70° C. The resulting mixture was stirred at −70° C. for 15 minutes then a solution of 5-bromopyrazin-2-amine (20 g, 115 mmol, in 100 mL of DCM and 50 mL of DMSO) was added dropwise. The mixture was stirred at −60° C. for 3 hours and diluted with 500 mL of DCM and washed with water. The water layer was basified to pH=11 with aq. $Na_2CO_3$ and extracted with DCM twice. The combined DCM layer was washed with brine, dried over $Na_2SO_4$ and evaporated to afford 2-bromo-5-[(dimethyl-$\lambda^4$-sulfanylidene)amino]pyrazine.

Step C: 2-bromo-5-nitropyrazine

To a solution of mCPBA (85%, 37.4 g, 184.2 mmol) in 1 L of DCM was added a solution of 2-bromo-5-[(dimethyl-$\lambda^4$-sulfanylidene)amino]pyrazine (26.7 g, 114 mmol) in 800 mL of DCM at 0° C. The resulting mixture was stirred at 0° C. for 45 minutes and 30 mL of DMSO was added. Ozone was bubbled through the mixture for 45 minutes then diluted with 2 L of DCM, washed subsequently with water, aq. $Na_2CO_3$ and brine, dried over $Na_2SO_4$ and evaporated. The crude material was purified on silica gel (eluting with 20 percent ethyl acetate in hexane) to give 2-bromo-5-nitropyrazine.

Step D: tert-butyl ethyl (5-nitropyrazin-2-yl)propanedioate

A suspension of NaH (60%, 3.0 g, 75 mmol) in 100 mL of DMF was added tert-butyl ethyl propanedioate (14.1 g, 75 mmol) dropwise at 25° C. The mixture was stirred at 40° C. for 30 minutes and 2-bromo-5-nitropyrazine (10.2 g, 50 mmol) in 50 mL of DMF was added dropwise. The resulting suspension was stirred at 50° C. for 2 hours and diluted with 500 mL of EtOAc. The mixture was washed with water (100 mL×3), brine, dried over anhydrous $Na_2SO_4$ and concentrated. The residue was purified by column chromatography (petrol ether:EtOAc=5:1) to afford tert-butyl ethyl (5-nitropyrazin-2-yl)propanedioate.

Step E: ethyl (5-nitropyrazin-2-yl)acetate

A mixture of tert-butyl ethyl (5-nitropyrazin-2-yl)propanedioate (10.7 g, 34.4 mmol) in 30 mL of TFA and 30 mL DCM was stirred at 35° C. for 3 hours and then was concentrated to dryness. The residue was dissolved in 200 mL of EtOAc, washed with water (25 mL) and brine (25 mL), dried over anhydrous $Na_2SO_4$ and concentrated to afford ethyl (5-nitropyrazin-2-yl)acetate.

Step F: ethyl [5-(hydroxyamino)pyrazin-2-yl]acetate

A mixture of ethyl (5-nitropyrazin-2-yl)acetate (6.7 g, 31.7 mmol) and Pd/C (1 g, 10%) in 300 mL of EtOAc was stirred at room temperature under hydrogen balloon for 6 hours before filtration. The filtrate was concentrated to afford ethyl [5-(hydroxyamino)pyrazin-2-yl]acetate.

Step G: ethyl (5-aminopyrazin-2-yl)acetate

A mixture of ethyl [5-(hydroxyamino)pyrazin-2-yl]acetate (2.8 g, 14.2 mmol) and $Pd(OH)_2$ (3 g, 10%) in 150 mL of methanol was stirred at room temperature under 50 psi of $H_2$ for 2 hours before filtration. The filtrate was concentrated to afford ethyl (5-aminopyrazin-2-yl)acetate.

Step H: ethyl [5-(1H-tetrazol-1-yl)pyrazin-2-yl]acetate

A solution of ethyl (5-aminopyrazin-2-yl)acetate (2.0 g, 11.0 mmol) and triethyl orthoformate (4.9 g, 33.1 mmol) in 60 mL of HOAc was added sodium azide (0.9 g, 13.8 mmol) and the mixture was heated to 100° C. for 1 hour. The reaction was completed which was checked by TLC. The reaction mixture was cooled to r.t. The solvent was removed under vacuum. The residue was dissolved in EtOAc, washed with water, dried over anhydrous sodium sulfate, and concentrated. The residue was purified by column chromatography to afford the product ethyl [5-(1H-tetrazol-1-yl) pyrazin-2-yl]acetate.

Step I: [5-(1H-tetrazol-1-yl)pyrazin-2-yl]acetic acid

A mixture of ethyl [5-(1H-tetrazol-1-yl)pyrazin-2-yl]acetate (2.0 g, 8.5 mmol) in 60 mL of THF/MeOH/$H_2O$ (2:2:1) was added $LiOH \cdot H_2O$ (540 mg, 12.8 mmol) portionwise and the mixture was stirred for 30 minutes before diluting with 200 mL of water and washed with ether (30 mL×3). The water layer was acidified to pH=4 with diluted hydrochloric acid and extracted with EtOAc (50 mL×5). The combined organic layer was washed with brine, dried over anhydrous $Na_2SO_4$ and concentrated to afford [5-(1H-tetrazol-1-yl) pyrazin-2-yl]acetic acid.

Intermediate 43

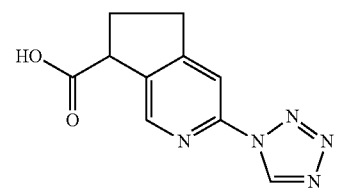 [SMILES: O=C(O)C1CCc2cc(-n3cnnn3)ncc21]

3-(1H-tetrazol-1-yl)-6,7-dihydro-5H-cyclopenta[c] pyridine-7-carboxylic acid

Step A: N-(5-bromo-4-methylpyridin-2-yl)-2,2-dimethylpropanamide

To a solution of 5-bromo-4-methylpyridin-2-amine (20.6 g, 110 mmol) in 80 mL of pyridine was added trimethylacetyl chloride (19.9 g, 165 mmol) dropwise. The reaction mixture was allowed to stir at room temperature for 12 hours. The mixture was diluted with water and extracted with dichloromethane (3×). The organic layers were washed with water (2×) and brine, dried over Na$_2$SO$_4$ and concentrated to provide crude product, which was purified by chromatography. On elution with 2->20% EtOAc/hexanes N-(5-bromo-4-methylpyridin-2-yl)-2,2-dimethylpropanamide was obtained.

Step B: N-[5-bromo-4-(2-hydroxyethyl)pyridin-2-yl]-2,2-dimethylpropanamide

A solution of N-(5-bromo-4-methylpyridin-2-yl)-2,2-dimethylpropanamide (30.0 g, 111 mmol) in THF (80 mL) was cooled in an ice bath and treated dropwise with a solution of lithium diisopropylamine in heptane/tetrahydrofuran/ethylbenzene (2.0 M, 138 mL). After stirring for 1 h, the solution was treated with paraformaldehyde (24.9 g, 277 mmol) and allowed to warm gradually to room temperature while stirring 12 h. The mixture was diluted with saturated sodium bicarbonate solution and extracted with ethyl acetate (3×). The combined organic layers were washed with brine, dried (Na$_2$SO$_4$), filtered and concentrated. Purification by MPLC (eluent 6-50% ethyl acetate/hexanes) afforded N-[5-bromo-4-(2-hydroxyethyl)pyridin-2-yl]-2,2-dimethylpropanamide.

Step C: tert-butyl{6-[(2,2-dimethylpropanoyl)amino]-4-(2-hydroxyethyl)pyridin-3-yl}acetate A 250 mL round bottomed flask was charged with N-[5-bromo-4-(2-hydroxyethyl)pyridin-2-yl]-2,2-dimethylpropanamide (1.9 g, 6.31 mmol), tris(dibenzylideneacetone)dipalladium(0) (0.173 g, 0.189 mmol), and 2-(dicyclohexylphosphino)-2',4',6'-triisopropylbiphenyl (0.180 g, 0.379). The mixture was flushed with nitrogen for 30 min. Tetrahydrofuran was added, followed by a solution of 2-tert-butoxy-2-oxoethylzinc chloride in diethyl ether (0.5 M, 47.9 mL) and the mixture was placed in an oil bath maintained at 45° C. After 12 h, the reaction was recharged with tris(dibenzylideneacetone)dipalladium(0) (0.173 g, 0.189 mmol) and 2-(dicyclohexylphosphino)-2',4',6'-triisopropylbiphenyl (0.180 g, 0.379), and an additional quantity of 2-tert-butoxy-2-oxoethylzinc chloride in diethyl ether (0.5 M, 12.6 mL) was added. After stirring for an additional 2 h in the 45° C. bath, the reaction mixture was diluted with ethyl acetate and 10% ammonium hydroxide solution, and filtered to remove solids. The layers were separated. The organic layer was washed with water and brine, dried (Na$_2$SO$_4$), filtered and concentrated. Purification by MPLC (eluent 9-90% ethyl acetate/hexanes) afforded tert-butyl {6-[(2,2-dimethylpropanoyl)amino]-4-(2-hydroxyethyl)pyridin-3-yl}acetate.

Step D: tert-butyl {4-(2-bromoethyl)-6-[(2,2-dimethylpropanoyl)amino]pyridin-3-yl}acetate A mixture of tert-butyl {6-[(2,2-dimethylpropanoyl)amino]-4-(2-hydroxyethyl)pyridin-3-yl}acetate (2.30 g, 6.84 mmol) with imidazole (0.558 g, 8.20 mmol) in dichloromethane (50 mL) was treated with triphenylphosphine (1.79 g, 6.84 mmol) and carbon tetrabromide (2.72 g, 8.20 mmol). The reaction mixture was allowed to stir at room temperature for 2 h, then was diluted with water and the layers separated. The organic layer was washed successively with 5% hydrochloric acid, saturated sodium bicarbonate solution, and brine, then dried (Na$_2$SO$_4$), filtered and concentrated. The residue was filtered through a short silica plug (20% EtOAc:hexanes eluent) to afford tert-butyl{4-(2-bromoethyl)-6-[(2,2-dimethylpropanoyl)amino]pyridin-3-yl}acetate.

Step E: tert-butyl 3-[(2,2-dimethylpropanoyl)amino]-6,7-dihydro-5H-cyclopenta[c]pyridine-7-carboxylate A solution of tert-butyl {4-(2-bromoethyl)-6-[(2,2-dimethylpropanoyl)amino]pyridin-3-yl}acetate (6.5 g, 16.3 mmol) in tetrahydrofuran (50 mL) cooled in a dry ice-acetone bath was treated with a solution of lithium diisopropylamine in tetrahydrofuran (50 mL) (prepared from diisopropylamine (3.79 g, 34.7 mmol) and n-butyllithium (2.5 M, 13.7 mL) dropwise via addition funnel over 1 h. The reaction was stirred for an additional 1 h, then was quenched with saturated sodium bicarbonate solution and allowed to warm to room temperature. The resulting mixture was diluted with ethyl acetate and water and transferred to a separatory funnel. The layers were separated and the aqueous layer was extracted with ethyl acetate (2×). The combined organics were washed with brine, dried (Na$_2$SO$_4$), filtered and concentrated. Purification of the resulting residue (2->25% EtOAc/hexanes eluent) provided tert-butyl 3-[(2,2-dimethylpropanoyl)amino]-6,7-dihydro-5H-cyclopenta[c]pyridine-7-carboxylate.

Step F: 3-amino-6,7-dihydro-5H-cyclopenta[c]pyridine-7-carboxylic acid

A solution of tert-butyl 3-[(2,2-dimethylpropanoyl)amino]-6,7-dihydro-5H-cyclopenta[c]pyridine-7-carboxylate (0.624 mg, 1.96 mmol) in 6N hydrochloric acid (25 mL) was heated to reflux for 24 h. The solution was cooled and concentrated to provide 3-amino-6,7-dihydro-5H-cyclopenta[c]pyridine-7-carboxylic acid.

Step G: methyl 3-amino-6,7-dihydro-5H-cyclopenta[c]pyridine-7-carboxylate

A solution of 3-amino-6,7-dihydro-5H-cyclopenta[c]pyridine-7-carboxylic acid in methanol (10 mL) was treated dropwise with a solution of trimethylsilyl diazomethane in diethyl ether (2.0 M, 1.96 mL) at 0° C. Then the reaction was warmed to room temperature and stirred 30 min. It was concentrated. The resulting residue was dried under high vacuum to afford methyl 3-amino-6,7-dihydro-5H-cyclopenta[c]pyridine-7-carboxylate.

Step H: methyl 3-(1H-tetrazol-1-yl)-6,7-dihydro-5H-cyclopenta[c]pyridine-7-carboxylate A mixture of methyl 3-amino-6,7-dihydro-5H-cyclopenta[c]pyridine-7-carboxylate (365 mg, 1.90 mmol), triethyl orthoformate (451 mg, 3.04 mmol), and sodium azide (185 mg, 2.85 mmol) in acetic acid (8 mL) was maintained in an oil bath heated at 80° C. for 3 h. After cooling to room temperature, the mixture was diluted with water and ethyl acetate and the layers separated. The aqueous was extracted with ethyl acetate (2×) and the combined organic layers were washed with brine, dried (Na$_2$SO$_4$), filtered and concentrated. Purification of the resulting residue (8->80% EtOAc/hexanes eluent) provided methyl 3-(1H-tetrazol-1-yl)-6,7-dihydro-5H-cyclopenta[c]pyridine-7-carboxylate.

Step I: 3-(1H-tetrazol-1-yl)-6,7-dihydro-5H-cyclopenta[c]pyridine-7-carboxylic acid A solution of 3-(1H-tetrazol-1-yl)-6,7-dihydro-5H-cyclopenta[c]pyridine-7-carboxylate (235 mg, 0.958 mmol) in tetrahydrofuran (5 mL) and water (1.5 mL) at room temperature was treated with lithium hydroxide solution (1 M, 1.44 mL). After 30 min, the solution was concentrated to remove tetrahydrofuran and the resulting aqueous solution was acidified with 1 N hydrochloric acid solution (to Ph ~4) and extracted with ethyl acetate (3×). The combined organics were washed with brine, dried (Na₂SO₄), filtered and concentrated to provide 3-(1H-tetrazol-1-yl)-6,7-dihydro-5H-cyclopenta[c]pyridine-7-carboxylic acid.

Intermediate 44

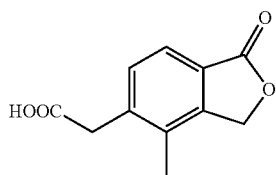

2-(4-methyl-1-oxo-1,3-dihydroisobenzofuran-5-yl) acetic acid

Step A: 3-hydroxymethyl-2-methyl phenol

To a 5 3 neck RB equipped with overhead stirrer was charged NaBH₄ (87.0 g, 2.30 mol) and THF (3.0 L) and the resulting slurry was cooled to 10° C. To the slurry was then added 3-hydroxy-2-methyl benzoic acid (175 g, 1.15 mol) portionwise over 20 min (Tmax 17° C.). A stirrable slurry formed, and was aged for an additional 45 min at 10-15° C. after which BF₃—OEt₂ (321 mL, 2.53 mol) was added slowly over 1.5 hours. The slurry was aged at 10° C.-15° C. for 2 h. The slurry was cooled to <10° C. and quenched with 931 mL of MeOH slowly over 1.5 h (gas evolution). The resulting slurry was aged overnight at RT. The batch was cooled to <10° C. then quenched with 1 N HCl (1.5 L) to get a homogeneous solution (pH solution ~1), which was aged for 30 min and then the organic solvents were removed by rotary evaporation to approximately 1.8 L of total reaction volume (bath temperature was set to 50° C.; internal temp of concentrate after rotary evaporation was 40° C.). The slurry was held at 45° C. for 30 min then cooled slowly to 15° C. The solids were filtered and washed with cold (15° C.) water (2×300 mL), providing 3-hydroxymethyl-2-methyl phenol.

Step B: 4-Bromo-3-hydroxymethyl-2-methyl phenol

3-Hydroxymethyl-2-methyl phenol (113.9 g, 824.0 mmol) was dissolved in a mixture of acetonitrile (850 mL) and trifluoroacetic acid (750.0 mL, 9,735 mmol) in a 3-neck 5-L flask under nitrogen. The reaction mixture was cooled to −33° C. N-bromosuccinimide (141 g, 791 mmol) was added over 15 minutes, with the temperature during addition in the range of −35 to −33° C. The reaction mixture was allowed to stir for an additional 15 min during which time the temperature decreased to −40° C. The cooling bath was removed, and potassium carbonate (741.0 g, 5,358 mmol) diluted with water was added to a total of 1.0 L. Off-gassing was observed, and the temperature increased to 25° C. MTBE (1.5 L) was added, and the reaction mixture was transferred to a separatory funnel. The layers were separated. The aqueous layer was diluted with water (500 mL) and extracted with MTBE and EtOAc (500 mL). The combined organic layers were washed with water (240 mL) and dried over sodium sulfate. The sodium sulfate was removed by filtration, washed with additional MTBE and concentrated under reduced pressure. MTBE (684 mL, 2 volumes) was added, and the suspension was heated to 40° C. to produce a homogeneous solution. The solution was allowed to cool to room temperature. Six volumes of heptane were added, and the suspension was stirred overnight. The suspension was filtered, and the crystals were washed with 4:1 heptane: MTBE (500 mL), followed by heptane (500 mL). The solid was dried under vacuum, providing 4-bromo-3-hydroxymethyl-2-methyl phenol.

Step C:
5-Hydroxy-4-methyl-3H-isobenzofuran-1-one

To a 2 L 3 neck flask equipped with overhead stirrer, N₂ inlet, and condenser were charged 4-bromo-3-hydroxymethyl-2-methyl phenol (100 g, 461 mmol), CuCN (83.0 g, 921 mmol), and DMF (500 mL). The solution was sparged with N₂ for 15 min then heated to 145° C. to obtain a homogeneous solution. The solution was aged at 145° C. for 2 h, then the reaction mixture was cooled to 95° C. 41.5 mL of water was added (sparged with N₂), and the reaction was aged for 20 h. The reaction was cooled to RT then the solid was filtered through SOLKA FLOC® and the cake was washed with 50 mL of DMF. To a 3 L flask containing 1 L of EtOAc was added the DMF filtrate. A precipitate coating was formed in bottom of flask. The DMF/EtOAc suspension was filtered through SOLKA FLOC® and the cake was washed with 250 mL of EtOAc. The resulting filtrate was washed with 5% brine solution (3×500 mL). The aqueous layers were extracted with 500 mL of EtOAc and the combined organics were dried over MgSO4, filtered and evaporated. The solids were slurried in 250 mL of MTBE at RT then filtered and washed with 100 mL of MTBE. The solids were dried under vaccum at RT, providing 5-hydroxy-4-methyl-3H-isobenzofuran-1-one.

Step D:
4-methyl-1-oxo-1,3-dihydroisobenzofuran-5-yl trifluoromethanesulfonate

5-Hydroxy-4-methyl-3H-isobenzofuran-1-one (46.8 g, 285 mmol) was suspended in dichloromethane (935 mL) in 2-L roundbottom flask equipped with overhead stirrer under nitrogen. Triethylamine (59.5 mL, 427 mmol) was added, and the reaction mixture was cooled in an ice bath to 3.8° C. Trifluoromethanesulfonic anhydride (67.4 mL, 399 mmol) was added via addition funnel over 50 min, keeping the temperature <10° C. After stirring for an additional 15 min, the reaction mixture was quenched with water (200 mL), then stirred with DARCO® KB (activated carbon, 25 g) for 15 min. The biphasic mixture was filtered over SOLKA FLOC®, washing with additional dichloromethane, and transferred to a separatory funnel, whereupon it was diluted with additional water (300 mL). The layers were separated, and the organic layer was washed with water (500 mL) and 10% brine (200 mL). The dichloromethane layer was dried over sodium sulfate, filtered and evaporated. The solid was adsorbed onto silica gel (27.5 g) and eluted through a pad of silica gel (271 g) with 25% ethyl acetate/hexanes. The resulting solution was concentrated under vacuum with the product crystallizing during concentration. The suspension was filtered, and the solid was washed with heptane and dried under vacuum and nitrogen, providing the title compound.

Step E: tert-butyl 2-(4-methyl-1-oxo-1,3-dihydroisobenzofuran-5-yl)acetate

To 4-methyl-1-oxo-1,3-dihydroisobenzofuran-5-yl trifluoromethanesulfonate (1 g, 3.38 mmol) in THF (50 ml) was added X-Phos (0.193 g, 0.405 mmol), Pd$_2$(dba)$_3$ (0.185 g, 0.203 mmol) and (2-(tert-butoxy)-2-oxoethyl)zinc(II) chloride (17.55 ml, 0.5 M in THF, 8.78 mmol). The mixture was degased with N$_2$. The reaction mixture was stirred at 60° C. for 2 h, and qenched with saturated aqueous NH$_4$Cl. The organic layer was separated, dried over MgSO$_4$, and concentrated. The crude material was purified with column chromatography (40 g silica gel, 0% to 50% EtOAc in hex) to provide the title compound.

Step F: 2-(4-methyl-1-oxo-1,3-dihydroisobenzofuran-5-yl)acetic acid tert-butyl 2-(4-methyl-1-oxo-1,3-dihydroisobenzofuran-5-yl)acetate (0.5 g, 1.906 mmol) in DCM (10 mL) was stirred with TFA (2 ml, 26.0 mmol) for 3 h. The volatiles were removed under vaccum to provide the title compound.

Intermediate 45

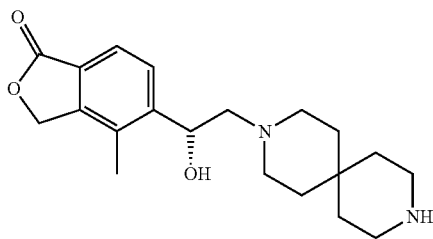

(R)-5-(1-hydroxy-2-(3,9-diazaspiro[5.5]undecan-3-yl)ethyl)-4-methylisobenzofuran-1(3H)-one

Step A: (R)-tert-butyl 9-(2-hydroxy-2-(4-methyl-1-oxo-1,3-dihydroisobenzofuran-5-yl)ethyl)-3,9-diazaspiro[5.5]undecane-3-carboxylate To a solution of tert-butyl 3,9-diazaspiro[5.5]undecane-3-carboxylate hydrochloride (114 g, 0.39 mol) in ethanol (1 L) was added Et$_3$N (60 mL). The mixture was stirred for 2 hours. Then (R)-4-methyl-5-(oxiran-2-yl)isobenzofuran-1(3H)-one (INTERMEDIATE 4B; 75 g, 0.39 mol) was added. The mixture was heated to reflux for 24 h. The mixture was concentrated, washed with brine, dried over Na$_2$SO$_4$ and concentrated to provide the crude product. The crude product was purified by SFC separation to provide the title compound.

Step B: (R)-5-(1-hydroxy-2-(3,9-diazaspiro[5.5]undecan-3-yl)ethyl)-4-methylisobenzofuran-1(3H)-one To a solution of (R)-tert-butyl 9-(2-hydroxy-2-(4-methyl-1-oxo-1,3-dihydroisobenzofuran-5-yl)ethyl)-3,9-diazaspiro[5.5]undecane-3-carboxylate (83 g, 0.19 mol) in CH$_2$Cl$_2$ (1 L) was slowly added a 4 M HCl solution (300 mL). The mixture was stirred for 8 h. The mixture was filtered. The solid was washed with CH$_2$Cl$_2$, and dried to give product as HCl salt. The product was dissolved in methanol, and NaHCO$_3$ was added. The mixture was stirred for 3 h. After filtration, the filtrate was concentrated, and washed with ethyl acetate. The residue was concentrated in vacuo to give the title compound.

Intermediate 46

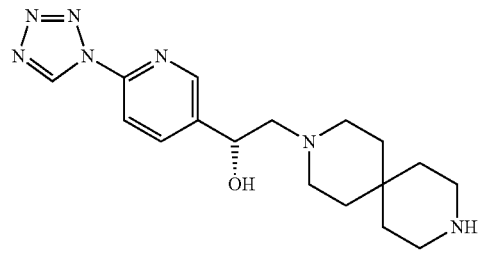

(R)-1-(6-(1H-tetrazol-1-yl)pyridin-3-yl)-2-(3,9-diazaspiro[5.5]undecan-3-yl)ethanol

Step A: (R)-tert-butyl 9-(2-(6-(1H-tetrazol-1-yl)pyridin-3-yl)-2-hydroxyethyl)-3,9-diazaspiro[5.5]undecane-3-carboxylate To a solution of tert-butyl 3,9-diazaspiro[5.5]undecane-3-carboxylate (11.6 g, 0.04 mol) in EtOH (104 mL) was added TEA (6 mL). The mixture was stirred for 3 h at 25° C. (R)-5-(oxiran-2-yl)-2-(1H-tetrazol-1-yl)pyridine (7.56 g, 0.04 mol) was added. The mixture was heated to reflux for 48 h. The mixture was concentrated, washed with brines, dried over Na$_2$SO$_4$, and concentrated to provide the crude product. Further purification by chiral SFC (Column: AD, 250×30 mmI.D.20 um; Mobile phase: A: Supercritical CO$_2$, B: EtOH (0.05% NH$_3$H$_2$O); Flow rate: 80 mL/min; Back pressure: 100 bar; Wavelength: 220 nm; Column temp: 38° C.) afforded the title compound.

Step B: (R)-1-(6-(1H-tetrazol-1-yl)pyridin-3-yl)-2-(3,9-diazaspiro[5.5]undecan-3-yl)ethanol To a solution of (R)-tert-butyl 9-(2-(6-(1H-tetrazol-1-yl)pyridin-3-yl)-2-hydroxyethyl)-3,9-diazaspiro[5.5]undecane-3-carboxylate (15 g, 0.032 mol) in CH$_2$Cl$_2$ (187 mL) was slowly added a 4 M HCl solution (57 mL). The mixture was stirred for 3 h. The mixture was filtered. The solid was washed with CH$_2$Cl$_2$, and dried to give the title compound as a HCl salt.

Intermediate 47

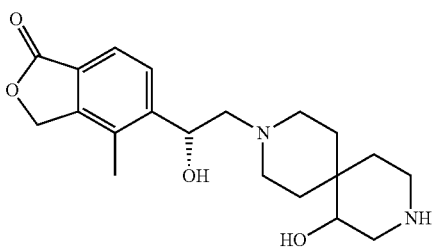

5-((1R)-1-hydroxy-2-(7-hydroxy-3,9-diazaspiro[5.5]undecan-3-yl)ethyl)-4-methylisobenzofuran-1(3H)-one

Step A: tert-butyl 9-benzyl-1-hydroxy-3,9-diazaspiro[5.5]undecane-3-carboxylate To a solution of 9-benzyl-3,9-diazaspiro[5.5]undecan-1-ol (4.00 g, 15.4 mmol) in DCM was added Et$_3$N (1.90 g, 18.4 mmol) and Boc$_2$O (3.70 g, 16.9 mmol). The reaction mixture was stirred at room temperature overnight. The reaction mixture was concentrated and the residue was purified by column chromatography (DCM: MeOH=50:1 to 10:1) to afford the title compound.

Step B: tert-butyl 1-hydroxy-3,9-diazaspiro[5.5]undecane-3-carboxylate

To a solution of tert-butyl 9-benzyl-1-hydroxy-3,9-diazaspiro[5.5]undecane-3-carboxylate (2.00 g, 5.5 mmol) in MeOH was added 10% Pd/C (0.30 g), then the reaction mixture was stirred under H$_2$ atmosphere (30 psi) at room temperature overnight. The reaction mixture was filtered and concentrated to afford the title compound.

Step C: tert-butyl 1-hydroxy-9-((R)-2-hydroxy-2-(4-methyl-1-oxo-1,3-dihydroisobenzofuran-5-yl)ethyl)-3,9-diazaspiro[5.5]undecane-3-carboxylate To a solution of tert-butyl 1-hydroxy-3,9-diazaspiro[5.5]undecane-3-carboxylate (500 mg, 1.9 mmol) in EtOH was added (R)-4-methyl-5-(oxiran-2-yl)isobenzofuran-1(3H)-one (INTERMEDIATE 4B; 422 mg, 2.2 mmol). The reaction mixture was heated to reflux and stirred overnight. The reaction mixture was concentrated and the residue was purified by column chromatography (DCM: MeOH=50:1 to 10:1) to afford the title compound.

Step D: 5-((1R)-1-hydroxy-2-(7-hydroxy-3,9-diazaspiro[5.5]undecan-3-yl)ethyl)-4-methylisobenzofuran-1(3H)-one To a solution of tert-butyl 1-hydroxy-9-((R)-2-hydroxy-2-(4-methyl-1-oxo-1,3-dihydroisobenzofuran-5-yl)ethyl)-3,9-diazaspiro[5.5]undecane-3-carboxylate (150 mg, 0.93 mmol) in DCM was added TFA (180 mg, 1.4 mmol). The reaction mixture was stirred at room temperature for 1 h and then concentrated to afford the title compound.

Intermediate 48

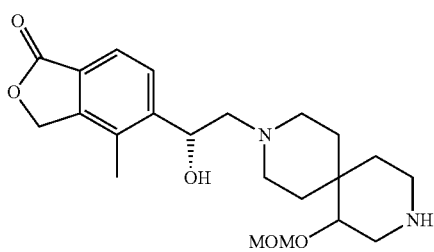

5-((1R)-1-hydroxy-2-(7-(methoxymethoxy)-3,9-diazaspiro[5.5]undecan-3-yl)ethyl)-4-methylisobenzofuran-1(3H)-one 5-((1R)-1-hydroxy-2-(7-(methoxymethoxy)-3,9-diazaspiro[5.5]undecan-3-yl)ethyl)-4-methylisobenzofuran-1(3H)-one was prepared in a similar fashion to that described for the synthesis of INTERMEDIATE 47 starting from 9-benzyl-1-(methoxymethoxy)-3,9-diazaspiro[5.5]undecane (INTERMEDIATE 28).

Intermediate 49

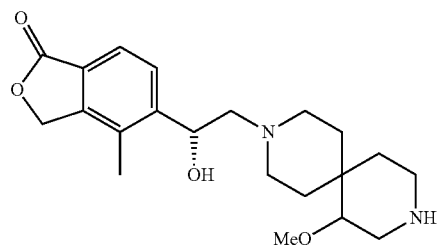

5-((1R)-1-hydroxy-2-(7-methoxy-3,9-diazaspiro[5.5]undecan-3-yl)ethyl)-4-methylisobenzofuran-1(3H)-one

Step A: tert-butyl 9-benzyl-1-hydroxy-3,9-diazaspiro[5.5]undecane-3-carboxylate To a solution of 9-benzyl-3,9-diazaspiro[5.5]undecan-1-ol (4.00 g, 15.4 mmol) in DCM was added Et$_3$N (1.90 g, 18.4 mmol) and Boc$_2$O (3.70 g, 16.9 mmol). The reaction mixture was stirred at room temperature overnight. The reaction mixture was concentrated and the residue was purified by column chromatography (DCM: MeOH=50:1 to 10:1) to afford the title compound.

Step B: tert-butyl 9-benzyl-1-methoxy-3,9-diazaspiro[5.5]undecane-3-carboxylate NaH (266 mg, 6.7 mmol) was added to a solution of tert-butyl 9-benzyl-1-hydroxy-3,9-diazaspiro[5.5]undecane-3-carboxylate (2.00 g, 5.5 mmol) in DMF cooled at 0° C. The mixture was stirred at 0° C. for 30 min, then MeI (945 mg, 6.7 mmol) was added. The mixture was stirred at room temperature for 2 h. The mixture was quenched by saturated NH$_4$Cl, then extracted by ethyl acetate. The organic layer was washed with brine, dried over anhydrous Na$_2$SO$_4$, filtered and concentrated. The residue was purified by column chromatography (petroleum ether: EtOAc=10:1 to 1:1) to afford the title compound.

Steps C-E were conducted in a similar fashion to steps B-D of INTERMEDIATE 47 to prepare 5-((1R)-1-hydroxy-2-(7-methoxy-3,9-diazaspiro[5.5]undecan-3-yl)ethyl)-4-methylisobenzofuran-1(3H)-one.

Intermediate 50

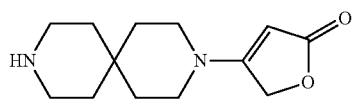

4-(3,9-diazaspiro[5.5]undecan-3-yl)furan-2(5H)-one

Step A: tert-Butyl 9-(5-oxo-2,5-dihydrofuran-3-yl)-3,9-diazaspiro[5.5]undecane-3-carboxylate To a solution of tert-butyl 3,9-diazaspiro[5.5]undecane-3-carboxylate (1.05 g, 4.13 mmol) in MeOH (30 ml) was added 1 mL of acetic acid. The solution was concentrated under vacuum to get the acetic acid salt of tert-butyl 3,9-diazaspiro[5.5]undecane-3-carboxylate. Tetronic acid (0.497 g, 4.96 mmol) and the acetic acid thus obtained 1 (1.3 g, 4.13 mmol) in 30 ml iPrOH was heated in a sealed tube at 120° C. overnight. The mixture was cooled to rt, and concentrated under vaccum. The residue was purified by column (silica gel 80 g, 0-100% EtOAc/hexane then EtOAc) to afford the title compound.

Step B: 4-(3,9-diazaspiro[5.5]undecan-3-yl)furan-2(5H)-one tert-Butyl 9-(5-oxo-2,5-dihydrofuran-3-yl)-3,9-diazaspiro[5.5]undecane-3-carboxylate was dissolved in DCM (20 ml), and the solution was stirred with TFA (5.39 ml, 70.0 mmol) at rt for 1 h. Volatiles were removed under reduced pressure. The residue was dissolved in methanol, and the residue was loaded onto BOND ELUT strong cation exchanger (SCX) column, and eluted out with 1N NH$_3$ in methanol (~30 ml). The solution was concentrated to give a free base of the title compound.

Intermediate 51

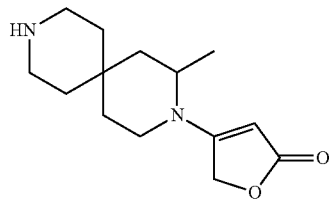 [SMILES: CC1CC2(CCNCC2)CCN1C1=CC(=O)OC1]

4-(2-methyl-3,9-diazaspiro[5.5]undecan-3-yl)furan-2(5H)-one

Step A: tert-Butyl 8-methyl-9-(5-oxo-2,5-dihydrofuran-3-yl)-3,9-diazaspiro[5.5]undecane-3-carboxylate tert-Butyl 8-methyl-3,9-diazaspiro[5.5]undecane-3-carboxylate (INTERMEDIATE 27; 45 mg, 0.168 mmol) and 4-bromofuran-2-one (146.5 mg, 0.899 mmol) were mixed in THF (860 μl). DIEA (100 μl, 0.570 mmol) was then added. The reaction mixture was heated at 80° C. overnight. After cooling to room temperature, the reaction was diluted with THF and filtered to remove the tar formed during the reaction. The filtrates were concentrated and purified by column chromatography eluting with 0-7% MeOH/EtOAc to give the title compound.

Step B: 4-(2-methyl-3,9-diazaspiro[5.5]undecan-3-yl)furan-2(5H)-one

The title compound can be prepared in a similar fashion to that described for 4-(3,9-diazaspiro[5.5]undecan-3-yl)furan-2(5H)-one above using TFA (INTERMEDIATE 50, Step B).

Intermediate 52

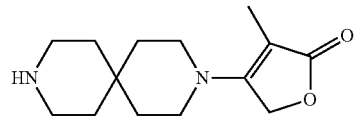 [SMILES: CC1=C(N2CCC3(CCNCC3)CC2)COC1=O]

3-methyl-4-(3,9-diazaspiro[5.5]undecan-3-yl)furan-2(5H)-one

Step A: tert-butyl 9-(4-methyl-5-oxo-2,5-dihydrofuran-3-yl)-3,9-diazaspiro[5.5]undecane-3-carboxylate A solution of tert-Butyl 3,9-diazaspiro[5.5]undecane-3-carboxylate (INTERMEDIATE 26; 397 mg, 1.262 mmol), acetic acid (0.072 mL, 1.262 mmol), and 4-hydroxy-3-methylfuran-2(5H)-one (INTERMEDIATE 30; 160 mg, 1.402 mmol) in 2-propanol (4.14 ml) was heated at 108° C. overnight. After concentration the residue was purified on silica gel using EtOAc/hexane as eluting solvents to give tert-butyl 9-(4-methyl-5-oxo-2,5-dihydrofuran-3-yl)-3,9-diazaspiro[5.5]undecane-3-carboxylate.

Step B: 3-methyl-4-(3,9-diazaspiro[5.5]undecan-3-yl)furan-2(5H)-one

To the solution of tert-butyl 9-(4-methyl-5-oxo-2,5-dihydrofuran-3-yl)-3,9-diazaspiro[5.5]undecane-3-carboxylate (376 mg, 1.073 mmol) in methylene chloride (2 ml) was added trifluoroacetic acid (3.31 ml, 42.9 mmol) and the resulting solution was stirred at rt for 1 h. After removing the volatile, the residue was dissolved in methanol and loaded onto an ion exchange column. After washing with MeOH, the column was eluted with 2N ammonia/methanol to give 3-methyl-4-(3,9-diazaspiro[5.5]undecan-3-yl)furan-2(5H)-one.

Intermediate 53

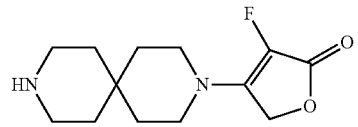

3-fluoro-4-(3,9-diazaspiro[5.5]undecan-3-yl)furan-2(5H)-one

Step A: 3-bromo-4-ethoxy-3-fluoro-4-hydroxydihydrofuran-2(3H)-one

To the solution of 4-hydroxyfuran-2(5H)-one (2.25 g, 22.48 mmol) in ethanol (20 ml) was added NBS (4.00 g, 22.48 mmol). The resulting solution was stirred at rt for 40 min. Then 1-chloromethyl-4-fluoro-1,4-diazoniabicyclo[2.2.2]octane bis(tetrafluoroborate) (7.97 g, 22.48 mmol) was added and the resulting mixture was stirred at rt overnight. After filtration and concentration, the residue was purified on silica gel column using EtOAc/hexane as eluting solvents to give 3-bromo-4-ethoxy-3-fluoro-4-hydroxydihydrofuran-2(3H)-one.

Step B: 3-fluoro-4-hydroxyfuran-2(5H)-one

To the solution of 3-bromo-4-ethoxy-3-fluoro-4-hydroxydihydrofuran-2(3H)-one (4.39 g, 18.06 mmol) in tetrahydrofuran (20 ml) was added tri-n-butyltin hydride (9.39 ml, 35.0 mmol) at 0° C. under $N_2$. The resulting solution was stirred at rt overnight. After removing the volatile, the residue was stirred in 30 mL of 50% acetic acid and 30 mL of hexane at rt for 30 min. The acidic phase was washed with hexane (3×30 mL) before concentration. The residue was dissolved in sodium carbonate (50 mL, 2N), and extracted with 40% EtOAc/hexane (4×50 mL). The alkaline phase was acidified to pH<1 by 1 N hydrogen chloride. The acidic phase was then extracted with ethyl acetate (8×60 mL). The combined organic phase was dried over sodium sulphate, and concentrated to give 3-fluoro-4-hydroxyfuran-2(5H)-one.

Step C: 4-fluoro-2-methyl-5-oxo-2,5-dihydrofuran-3-yl trifluoromethanesulfonate

To the solution of 3-fluoro-4-hydroxyfuran-2(5H)-one (400 mg, 3.39 mmol) in methylene chloride (10 ml) at −78° C. was added 2,6-lutidine (0.592 ml, 5.08 mmol) and triflic anhydride (0.687 ml, 4.07 mmol) dropwise. The reaction temperature was maintained at −78° C. for 1 h before warming to rt for 2 h. The mixture was washed with 1 N hydrogen chloride (3×100 mL), and diluted sodium bicarbonate solution, dried over sodium sulphate, and concentrated to give 4-fluoro-2-methyl-5-oxo-2,5-dihydrofuran-3-yl trifluoromethanesulfonate.

Step D: tert-butyl 9-(4-fluoro-5-oxo-2,5-dihydrofuran-3-yl)-3,9-diazaspiro[5.5]undecane-3-carboxylate The mixture of tert-butyl 3,9-diazaspiro[5.5]undecane-3-carboxylate (INTERMEDIATE 26; 173 mg, 0.680 mmol), 4-fluoro-2-methyl-5-oxo-2,5-dihydrofuran-3-yl trifluoromethanesulfonate (170 mg, 0.680 mmol), potassium phosphate (202 mg, 0.952 mmol), 2-(di-tert-butylphosphino) biphenyl (20.28 mg, 0.068 mmol), and Palladium (II) acetate (7.63 mg, 0.034 mmol) in tetrahydrofuran (10 ml) was heated at 80° C. for overnight. After filtration through CELITE®, the filtrate was concentrated and the residue was purified on silica gel using EtOAc/hexane as eluting solvents to give tert-butyl 9-(4-fluoro-5-oxo-2,5-dihydrofuran-3-yl)-3,9-diazaspiro[5.5]undecane-3-carboxylate.

Step E: 3-fluoro-4-(3,9-diazaspiro[5.5]undecan-3-yl)furan-2(5H)-one

To the solution of tert-butyl 9-(4-fluoro-5-oxo-2,5-dihydrofuran-3-yl)-3,9-diazaspiro[5.5]undecane-3-carboxylate (58 mg, 0.164 mmol) in methylene chloride (91 mL) was added trifluoroacetic acid (2 mL) and the resulting solution was stirred at rt for 1 h. After removing the volatile, the residue was dissolved in methanol and loaded onto an ion exchange column. After washing with methanol, the column was then eluted with 2N ammonia in methanol to give 3-fluoro-4-(3,9-diazaspiro[5.5]undecan-3-yl)furan-2(5H)-one.

Intermediate 54

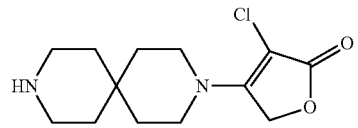 [SMILES: O=C1OCC(N2CCC3(CCNCC3)CC2)=C1F]

3-chloro-4-(3,9-diazaspiro[5.5]undecan-3-yl)furan-2(5H)-one

Step A: tert-butyl 9-(4-chloro-5-oxo-2,5-dihydrofuran-3-yl)-3,9-diazaspiro[5.5]undecane-3-carboxylate To the solution of tert-butyl 9-(5-oxo-2,5-dihydrofuran-3-yl)-3,9-diazaspiro[5.5]undecane-3-carboxylate (title product of Step A for INTERMEDIATE 50; 50 mg, 0.149 mmol) in Ethanol (1 ml) was added NCS (23.82 mg, 0.178 mmol) at rt for 0.5 h. After removing the volatile, the residue was purified on TLC (2000MU) using 80% ethyl acetate/hexane as developing solvents to give tert-butyl 9-(4-chloro-5-oxo-2,5-dihydrofuran-3-yl)-3,9-diazaspiro[5.5]undecane-3-carboxylate.

Step B: 3-chloro-4-(3,9-diazaspiro[5.5]undecan-3-yl)furan-2(5H)-one

To the solution of tert-butyl 9-(4-chloro-5-oxo-2,5-dihydrofuran-3-yl)-3,9-diazaspiro[5.5]undecane-3-carboxylate (46.7 mg, 0.126 mmol) in methylene chloride (2 ml) was added trifluoroacetic acid (2 mL) and the resulting solution was stirred at rt for 1 h before concentration on a rotary evaporator. The residue was dissolved in methanol and loaded onto an ion exchange column. After washing with methanol, the column was then eluted with 2N ammonia in methanol to give 3-chloro-4-(3,9-diazaspiro[5.5]undecan-3-yl)furan-2(5H)-one.

Intermediate 55

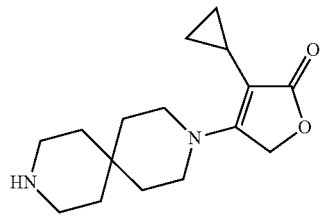 [SMILES: O=C1OCC(N2CCC3(CCNCC3)CC2)=C1C1CC1]

3-cyclopropyl-4-(3,9-diazaspiro[5.5]undecan-3-yl)furan-2(5H)-one

Step A: tert-Butyl 9-(4-bromo-5-oxo-2,5-dihydrofuran-3-yl)-3,9-diazaspiro[5.5]undecane-3-carboxylate tert-Butyl 3,9-diazaspiro[5.5]undecane-3-carboxylate hydrochloride (500 mg, 1.72 mmol) was mixed with DIEA (0.661 mL, 3.78 mmol) in THF (8 mL). 3,4-Dibromofuran- 2(5H)-one (457 mg, 1.891 mmol) was added. The mixture was stirred at 40° C. overnight. Solvent was then removed with a ROTAVAPOR evaporator and the resulting residue was purified with flash chromatography eluting with 0-10% MeOH/DCM on 40 g silica gel column to give the title product.

Step B: tert-Butyl 9-(4-cyclopropyl-5-oxo-2,5-dihydrofuran-3-yl)-3,9-diazaspiro[5.5]undecane-3-carboxylate tert-Butyl 9-(4-bromo-5-oxo-2,5-dihydrofuran-3-yl)-3,9-diazaspiro[5.5]undecane-3-carboxylate (455 mg, 1.096 mmol) was dissolved in toluene (10 mL) and cyclopropyl boronic acid (188 mg, 2.191 mmol) and $K_3PO_4 \cdot 3H_2O$ (292 mg, 1.096 mmol) were added. After degassing with bubling nitrogen for 10 minutes, $Pd(Ph_3P)_4$ (43.6 mg, 0.038 mmol) was added. Then the mixture was stirred at 100° C. for 4 hours. After cooling down to room temperature, the solvent was removed on ROTAVAPOR evaporator. The resulting residue was dissolved in 50 mL of EtOAc, washed with 30 mL of water and 30 mL of brine, then dried over anhydrous sodium sulfate. Removing solvent gave crude product that was purified with flash chromatography eluting with 0-100% EtOAc/Hexane to give the title compound.

Step C: 3-cyclopropyl-4-(3,9-diazaspiro[5.5]undecan-3-yl)furan-2(5H)-one

The title compound can be prepared in a similar fashion to that described for 4-(3,9-diazaspiro[5.5]undecan-3-yl)furan-2(5H)-one above using TFA (INTERMEDIATE 50, Step B).

Intermediate 56

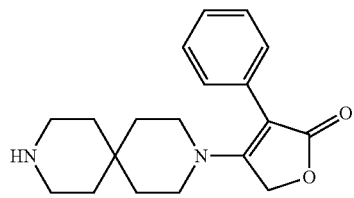 [SMILES: O=C1OCC(N2CCC3(CCNCC3)CC2)=C1c1ccccc1]

3-phenyl-4-(3,9-diazaspiro[5.5]undecan-3-yl)furan-2(5H)-one

Step A: tert-butyl 9-(4-bromo-5-oxo-2,5-dihydrofuran-3-yl)-3,9-diazaspiro[5.5]undecane-3-carboxylate To the solution of tert-butyl 9-(5-oxo-2,5-dihydrofuran-3-yl)-3,9-diazaspiro[5.5]undecane-3-carboxylate (title product of Step A for INTERMEDIATE 50; 270 mg, 0.803 mmol) in Ethanol (5 ml) was added NBS (157 mg, 0.883 mmol) at rt for 0.5 h. After removing the volatile, the residue was purified on TLC (2000MU) using 80% ethyl acetate/hexane as developing solvents to give tert-butyl 9-(4-bromo-5-oxo-2,5-dihydrofuran-3-yl)-3,9-diazaspiro[5.5]undecane-3-carboxylate.

Step B: tert-butyl 9-(5-oxo-4-phenyl-2,5-dihydrofuran-3-yl)-3,9-diazaspiro[5.5]undecane-3-carboxylate To the solution of tert-butyl 9-(4-bromo-5-oxo-2,5-dihydrofuran-3-yl)-3,9-diazaspiro[5.5]undecane-3-carboxylate (57 mg, 0.137 mmol), phenylboronic acid (21.75 mg, 0.178 mmol) in Dioxane (4 ml) was added sodium carbonate (0.412 ml, 0.412 mmol) and tetrakis(triphenylphosphine)palladium(0)(15.86 mg, 0.014 mmol). The resulting solution was heated at microwave at 150° C. for 30 min. After concentration, the residue was purified on silica gel using ethyl acetate/hexane to give tert-butyl 9-(5-oxo-4-phenyl-2,5-dihydrofuran-3-yl)-3,9-diazaspiro[5.5]undecane-3-carboxylate.

Step C: 3-phenyl-4-(3,9-diazaspiro[5.5]undecan-3-yl)furan-2(5H)-one

To the solution of tert-butyl 9-(5-oxo-4-phenyl-2,5-dihydrofuran-3-yl)-3,9-diazaspiro[5.5]undecane-3-carboxylate (30 mg, 0.073 mmol) in methylyene chloride (1 ml) was added trifluoroacetic acid (2 ml) and the resulting solution was stirred at rt for 1 h. After removing the volatile, the residue was dissolved in methanol and loaded onto an ion exchange column. After washing with methanol, the column was eluted with 2N ammonia in methanol to give 3-phenyl-4-(3,9-diazaspiro[5.5]undecan-3-yl)furan-2(5H)-one.

Intermediate 57

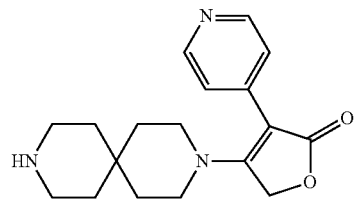 [SMILES: O=C1OCC(N2CCC3(CCNCC3)CC2)=C1c1ccncc1]

3-(pyridin-4-yl)-4-(3,9-diazaspiro[5.5]undecan-3-yl)furan-2(5H)-one

Step A: tert-butyl 9-(5-oxo-4-(pyridin-4-yl)-2,5-dihydrofuran-3-yl)-3,9-diazaspiro[5.5]undecane-3-carboxylate To the solution of tert-butyl 9-(4-bromo-5-oxo-2,5-dihydrofuran-3-yl)-3,9-diazaspiro[5.5]undecane-3-carboxylate (title product of Step A for INTERMEDIATE 55; 50 mg, 0.120 mmol) and pyridin-4-ylboronic acid (19.24 mg, 0.157 mmol) in Dioxane (4 ml) was added sodium carbonate (0.361 ml, 0.361 mmol) and tetrakis(triphenylphosphine)palladium(0) (13.91 mg, 0.012 mmol). The resulting solution was heated in a microwave at 150° C. for 30 min. After concentration, the residue was purified on TLC using EtOAc/hexane as developing solvents to give tert-butyl 9-(5-oxo-4-(pyridin-4-yl)-2,5-dihydrofuran-3-yl)-3,9-diazaspiro[5.5]undecane-3-carboxylate.

Step B: 3-(pyridin-4-yl)-4-(3,9-diazaspiro[5.5]undecan-3-yl)furan-2(5H)-one

To the solution of tert-butyl 9-(5-oxo-4-(pyridin-4-yl)-2,5-dihydrofuran-3-yl)-3,9-diazaspiro[5.5]undecane-3-carboxylate (20 mg, 0.048 mmol) in methylene chloride (1 ml) was added TFA (2 ml) and the resulting solution was stirred at rt for 1 h. After removing the volatile, the residue was dissolved in methanol and loaded onto ion exchange column. After washing with methanol, the column was eluted with 2N ammonia in methanol to give 3-(pyridin-4-yl)-4-(3,9-diazaspiro[5.5]undecan-3-yl)furan-2(5H)-one.

Intermediate 58

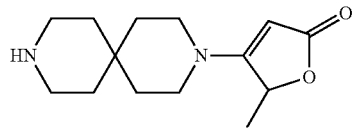 [SMILES: CC1OC(=O)C=C1N1CCC2(CCNCC2)CC1]

5-methyl-4-(3,9-diazaspiro[5.5]undecan-3-yl)furan-2(5H)-one

Step A: ethyl 4-bromo-3-oxopentanoate

To the solution of ethyl 3-oxopentanoate (5.0 g, 34.7 mmol) in chloroform (27 mL) at 0° C. was added bromine (1.787 ml, 34.7 mmol) in chloroform (10 mL) dropwise. The resulting solution was stirred at rt for 16 h. The solution was washed with water, dried over sodium sulphate, concentrated to give ethyl 4-bromo-3-oxopentanoate.

Step B: 4-hydroxy-5-methylfuran-2(5H)-one

Ethyl 4-bromo-3-oxopentanoate (7.49 g, 33.6 mmol) was treated with potassium hydroxide (5.03 g, 90 mmol) in water (36 mL) at 0° C. The resulting mixture was vigorously stirred at 0° C. for 4 h. The reaction mixture was extracted with methylene chloride (2×100 mL). The alkaline phase was acidified to pH<1 by 6 N hydrogen chloride. The acidic phase was extracted with methylene chloride (3×100 mL). The latter combined organic phase was dried over sodium sulphate, and concentrated to give 4-hydroxy-5-methylfuran-2(5H)-one.

Step C: tert-butyl 9-(2-methyl-5-oxo-2,5-dihydrofuran-3-yl)-3,9-diazaspiro[5.5]undecane-3-carboxylate The solution of tert-butyl 3,9-diazaspiro[5.5]undecane-3-carboxylate (INTERMEDIATE 26; 200 mg, 0.636 mmol), 4-hydroxy-5-methylfuran-2(5H)-one (80 mg, 0.700 mmol) and acetic acid (0.036 mL, 0.636 mmol) in 2-Propanol (4.14 ml) was heated at 108° C. overnight. After concentration the residue was purified on reverse phase HPLC using 20-80% acetonitrile (0.1% TFA) to give tert-butyl 9-(2-methyl-5-oxo-2,5-dihydrofuran-3-yl)-3,9-diazaspiro[5.5]undecane-3-carboxylate.

Step D: 5-methyl-4-(3,9-diazaspiro[5.5]undecan-3-yl)furan-2(5H)-one

To the solution of tert-butyl 9-(2-methyl-5-oxo-2,5-dihydrofuran-3-yl)-3,9-diazaspiro[5.5]undecane-3-carboxylate (173 mg, 0.494 mmol) in methylene chloride (1 ml) was added TFA (1.902 ml, 24.68 mmol) and the resulting solution was stirred at rt for 1 h. After concentration, the residue was treated with HCl in diethyl ether(4N, 1 mL) and concentrated to give 5-methyl-4-(3,9-diazaspiro[5.5]undecan-3-yl)furan-2(5H)-one as HCl salt.

Intermediate 59

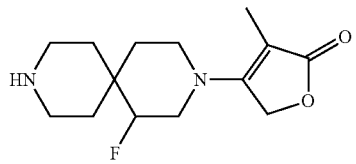 [SMILES: CC1=C(N2CCC3(CCNCC3)C(F)C2)COC1=O]

4-(1-fluoro-3,9-diaza-spiro[5.5]undec-3-yl)-3-methyl-5H-furan-2-one

Step A: 4-(9-benzyl-1-hydroxy-3,9-diazaspiro[5.5]undecan-3-yl)-3-methylfuran-2(5H)-one To a solution of 9-benzyl-3,9-diazaspiro[5.5]undecan-1-ol (INTERMEDIATE 29; 1.00 g, 3.9 mmol) in toluene (15 mL) was added 4-methyl-5-oxo-2,5-dihydrofuran-3-yl trifluoromethanesulfonate (INTERMEDIATE 31; 1.10 g, 4.6 mmol) and Et$_3$N (467 mg, 4.6 mmol). Then the reaction mixture was heated to reflux and stirred overnight. The reaction mixture was concentrated and the residue was purified by column chromatography (DCM: MeOH=50:1 to 10:1) to afford the title compound.

Step B: tert-butyl 7-hydroxy-9-(4-methyl-5-oxo-2,5-dihydrofuran-3-yl)-3,9-diazaspiro[5.5]undecane-3-carboxylate To a solution of 4-(9-benzyl-1-hydroxy-3,9-diazaspiro[5.5]undecan-3-yl)-3-methylfuran-2(5H)-one (800 mg, 2.2 mmol) in MeOH was added 10% Pd/C (150 mg) and Boc$_2$O (540 mg, 2.5 mmol). The reaction mixture was stirred under H$_2$ atmosphere (30 psi) at room temperature overnight. The reaction mixture was filtered and concentrated, and the residue was purified by column chromatography (DCM: MeOH=50:1 to 10:1) to afford the title compound.

Step C: tert-butyl 7-fluoro-9-(4-methyl-5-oxo-2,5-dihydrofuran-3-yl)-3,9-diazaspiro[5.5]undecane-3-carboxylate DAST (396 mg, 2.5 mmol) and triethylamine trihydrofluoride (301 mg, 4.9 mmol) were added to a solution of tert-butyl 7-hydroxy-9-(4-methyl-5-oxo-2,5-dihydrofuran-3-yl)-3,9-diazaspiro[5.5]undecane-3-carboxylate (750 mg, 2.0 mmol) in dry DCM (10 mL) cooled at −78° C. The reaction mixture was stirred at −78° C. for 30 min and then quenched by saturated NaHCO$_3$. The mixture was extracted by DCM, washed by brine, dried over anhydrous Na$_2$SO$_4$, filtered and concentrated. The residue was purified with prep-HPLC to afford the title compound.

Step D: 4-(1-fluoro-3,9-diaza-spiro[5.5]undec-3-yl)-3-methyl-5H-furan-2-one

To a solution of tert-butyl 7-fluoro-9-(4-methyl-5-oxo-2,5-dihydrofuran-3-yl)-3,9-diazaspiro[5.5]undecane-3-carboxylate (50 mg, 0.93 mmol) in DCM (10 mL) was added TFA (1 mL). The reaction mixture was stirred at room temperature for 1 h and then concentrated to afford the title compound.

Intermediate 60

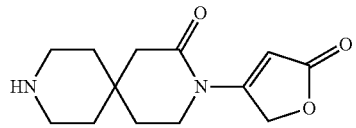 [SMILES: O=C1C=C(N2CCC3(CCNCC3)CC2=O)CO1]

3-(5-oxo-2,5-dihydrofuran-3-yl)-3,9-diazaspiro[5.5]undecan-2-one

Step A: tert-butyl 8-oxo-9-(5-oxo-2,5-dihydrofuran-3-yl)-3,9-diazaspiro[5.5]undecane-3-carboxylate A mixture of 4-bromofuran-2(5H)-one (0.167 g, 1.025 mmol), tert-butyl 8-oxo-3,9-diazaspiro[5.5]undecane-3-carboxylate (0.25 g, 0.932 mmol), Pd(OAc)$_2$ (10.46 mg, 0.047 mmol), Xant-Phos (0.054 g, 0.093 mmol), K$_2$CO$_3$ (0.258 g, 1.863 mmol) and water (0.050 ml, 2.79 mmol) in toluene (150 ml) was heated at 60° C. under N$_2$ for 2 h. The mixture was diluted with EtOAc and filtered, and the filtrate was concentrated. The residue was purified by column (40 g silica gel, 0-100% of EtOAc in hexane, then 100% EtOAc) to afford the title compound.

Step B: 3-(5-oxo-2,5-dihydrofuran-3-yl)-3,9-diazaspiro[5.5]undecan-2-one tert-Butyl 8-oxo-9-(5-oxo-2,5-dihydrofuran-3-yl)-3,9-diazaspiro[5.5]undecane-3-carboxylate (0.14 g, 0.400 mmol) was dissolved in DCM (20 mL). The solution was stirred with TFA (0.616 ml, 7.99 mmol) at rt for 1 h. Volatiles were removed. The residue was dissolved in methanol, and loaded on 5×BOND ELUT SCX column. The column with the desired compound was eluted with methanol to remove TFA (~20 ml methanol each column), and the free base of the desired compound was eluted out with 2N NH$_3$ in methanol (~20 ml each column) The solution was concentrated to give the title compound as a free base.

Intermediate 61

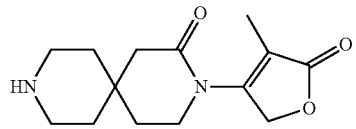 [SMILES: CC1=C(N2CCC3(CCNCC3)CC2=O)COC1=O]

3-(4-methyl-5-oxo-2,5-dihydrofuran-3-yl)-3,9-diazaspiro[5.5]undecan-2-one 3-(4-methyl-5-oxo-2,5-dihydrofuran-3-yl)-3,9-diazaspiro[5.5]undecan-2-one was prepared in a similar fashion to that described for the synthesis of INTERMEDIATE 60 starting from tert-butyl 2-oxo-1-oxa-3,9-diazaspiro[5.5]undecane-9-carboxylate and 4-bromofuran-2(5H)-one.

Intermediate 62

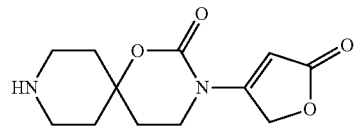 [SMILES: O=C1C=C(N2CCC3(CCNCC3)OC2=O)CO1]

3-(5-oxo-2,5-dihydrofuran-3-yl)-1-oxa-3,9-diazaspiro[5.5]undecan-2-one 3-(5-oxo-2,5-dihydrofuran-3-yl)-1-oxa-3,9-diazaspiro[5.5]undecan-2-one was prepared in a similar fashion to that described for the synthesis of INTERMEDIATE 60 starting from tert-butyl 8-oxo-3,9-diazaspiro[5.5]undecane-3-carboxylate and 4-methyl-5-oxo-2,5-dihydrofuran-3-yl trifluoromethanesulfonate (INTERMEDIATE 31).

Intermediate 63

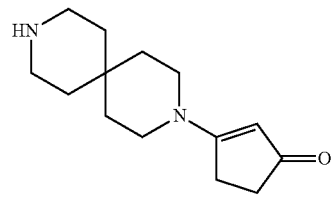 [SMILES: O=C1C=C(N2CCC3(CCNCC3)CC2)CC1]

3-(3,9-diazaspiro[5.5]undecan-3-yl)cyclopent-2-enone

Step A: tert-butyl 9-(3-oxocyclopent-1-en-1-yl)-3,9-diazaspiro[5.5]undecane-3-carboxylate To a solution of tert-butyl 3,9-diazaspiro[5.5]undecane-3-carboxylate (INTERMEDIATE 26; 230 mg, 0.904 mmol) in a microwave tube was added 2-propanol (7 ml) followed by cyclopentadione (115 mg, 1.175 mmol). The tube was sealed and heated at 120° C. for 16 hrs. The reaction was concentrated, diluted with ethyl acetate, and washed with saturated NaHCO$_3$ (1×). Organic layer was dried over Na$_2$SO$_4$, filtered and concentrated to yield tert-butyl 9-(3-oxocyclopent-1-en-1-yl)-3,9-diazaspiro[5.5]undecane-3-carboxylate.

Step B: 3-(3,9-diazaspiro[5.5]undecan-3-yl)cyclopent-2-enone tert-Butyl 9-(3-oxocyclopent-1-en-1-yl)-3,9-diazaspiro[5.5]undecane-3-carboxylate (280 mg, 0.837 mmol) was stirred in TFA (2 ml) for 1 hr. Then it was concentrated and diluted with methanol (1 ml) and passed thru a Varian BOND ELUT SCX column. The column was first washed with methanol (1 CV) then eluted with 1N NH$_3$ in MeOH (4 CV) to yield 3-(3,9-diazaspiro[5.5]undecan-3-yl)cyclopent-2-enone.

Intermediate 64

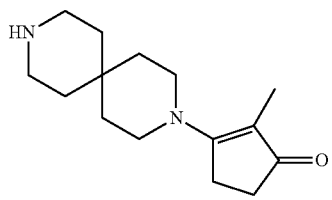 [SMILES: CC1=C(N2CCC3(CCNCC3)CC2)CCC1=O]

2-methyl-3-(3,9-diazaspiro[5.5]undecan-3-yl)cyclopent-2-enone

Step A: tert-butyl 9-(2-methyl-3-oxocyclopent-1-en-1-yl)-3,9-diazaspiro[5.5]undecane-3-carboxylate To a solution of tert-butyl 3,9-diazaspiro[5.5]undecane-3-carboxylate (INTERMEDIATE 26; 119 mg, 0.468 mmol) in a microwave tube was added 2-propanol (7 ml) followed by 2-methyl-1,3-cyclopentadione (62.9 mg, 0.561 mmol). The tube was sealed and heated at 120° C. for 16 hr. The reaction was concentrated, diluted with ethyl acetate, and washed with saturated NaHCO$_3$ (1×). Organic layer was dried over Na$_2$SO$_4$, filtered and concentrated to yield tert-butyl 9-(2-methyl-3-oxocyclopent-1-en-1-yl)-3,9-diazaspiro[5.5] undecane-3-carboxylate.

Step B: 2-methyl-3-(3,9-diazaspiro[5.5]undecan-3-yl)cyclopent-2-enone tert-Butyl 9-(2-methyl-3-oxocyclopent-1-en-1-yl)-3,9-diazaspiro[5.5]undecane-3-carboxylate (275 mg, 0.789 mmol) was stirred in TFA (2 ml) for 1 hr. The mixture was then concentrated. The residue was purified by chromatography, washed with MeOH (1 CV), and then eluted with 10% NH4OH/MeOH(2 CV) to yield 2-methyl-3-(3,9-diazaspiro[5.5]undecan-3-yl)cyclopent-2-enone.

Intermediate 65

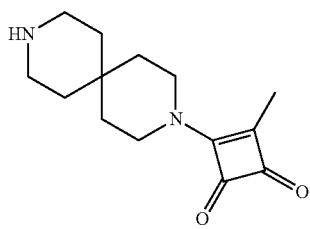 [SMILES: Cc1c(N2CCC3(CCNCC3)CC2)c(=O)c1=O]

3-methyl-4-(3,9-diazaspiro[5.5]undecan-3-yl)cyclobut-3-ene-1,2-dione

Step A: tert-butyl 9-(2-methyl-3,4-dioxocyclobut-1-en-1-yl)-3,9-diazaspiro[5.5]undecane-3-carboxylate The mixture of 3-ethoxy-4-methylcyclobut-3-ene-1,2-dione (INTERMEDIATE 33; 1.40 g, 10.0 mmol), tert-butyl 3,9-diazaspiro[5.5]undecane-3-carboxylate hydrochloride (1.16 g, 4.00 mmol) and NEt$_3$ (1.38 mL, 10.0 mmol) in THF (40 mL) was stirred at 25° C. for 4 hours. The mixture was concentrated and the residue was purified via BIOTAGE (Uppsala, Sweden) column (EtOAc in DCM: 0 to 40%) to afford the title compound.

Step B: 3-methyl-4-(3,9-diazaspiro[5.5]undecan-3-yl)cyclobut-3-ene-1,2-dione

The mixture of tert-butyl 9-(2-methyl-3,4-dioxocyclobut-1-en-1-yl)-3,9-diazaspiro[5.5]undecane-3-carboxylate (760 mg, 2.18 mmol) in HCl/EtOAc (40 mL, ~4 mol/L) was stirred at 25° C. for 2 hrs. The mixture was then concentrated to afford the title compound as HCl salt.

Example 1

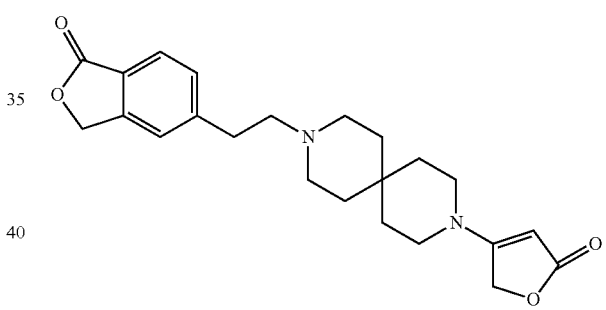

5-(2-(9-(5-oxo-2,5-dihydrofuran-3-yl)-3,9-diazaspiro[5.5]undecan-3-yl)ethyl)isobenzofuran-1(3H)-one A solution of 2-(1-oxo-1,3-dihydroisobenzofuran-5-yl)acetaldehyde (INTERMEDIATE 1, 0.037 g, 0.212 mmol) and 4-(3,9-diazaspiro[5.5]undecan-3-yl)furan-2(5H)-one (INTERMEDIATE 50, 0.05 g, 0.212 mmol) was stirred in DCM (5 ml) with 1 drop of AcOH for 10 min. Sodium triacetoxyborohydride (0.045 g, 0.212 mmol) was added. The suspension was stirred overnight, and concentrated under vacuum. The residue was purified by preparative TLC (30% methanol in EtOAc) to afford the title compound. LC/MS: (M+1)$^+$397.23.

The following compounds were prepared in an analogous fashion to EXAMPLE 1 starting from piperidine and aldehyde intermediates prepared as described above.

| EXAMPLE | INTERMEDIATES | EXAMPLE STRUCTURE/NAME | Characterization, LC/MS |
|---|---|---|---|
| 2 | 3, 50 | 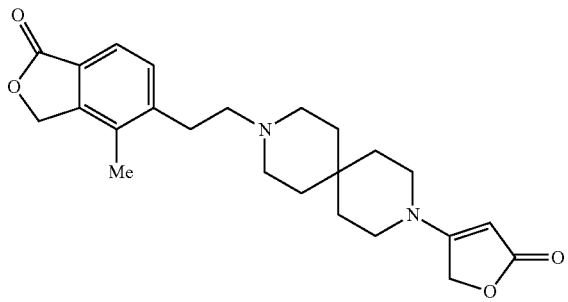 [SMILES: Cc1c(CCN2CCC3(CC2)CCN(C2=CC(=O)OC2)CC3)ccc2c1COC2=O]<br>4-methyl-5-(2-(9-(5-oxo-2,5-dihydrofuran-3-yl)-3,9-diazaspiro[5.5]undecan-3-yl)ethyl)isobenzofuran-1(3H)-one | [M + 1]$^+$: 411.22 |
| 3 | 3, 665 | 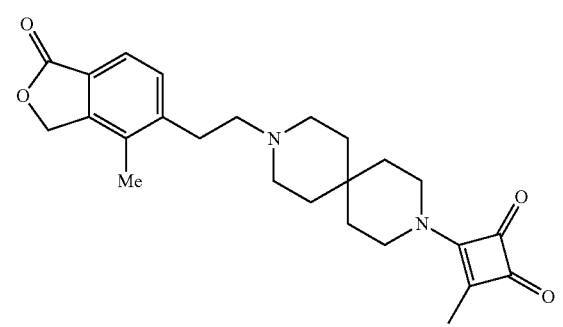 [SMILES: Cc1c(CCN2CCC3(CC2)CCN(c2c(C)c(=O)c2=O)CC3)ccc2c1COC2=O]<br>3-methyl-4-(9-(2-(4-methyl-1-oxo-1,3-dihydroisobenzofuran-5-yl)ethyl)-3,9-diazaspiro[5.5]undecan-3-yl)cyclobut-3-ene-1,2-dione | [M + 1]$^+$: 423 |
| 4 | 5A, 665 | 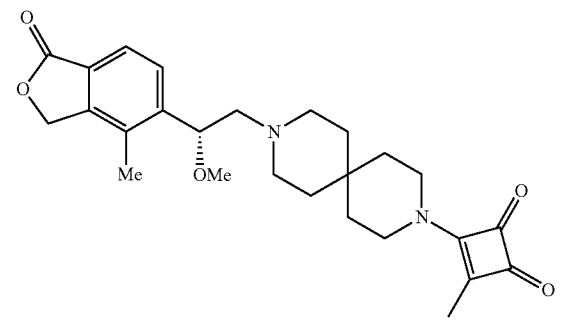<br>(R)-3-(9-(2-methoxy-2-(4-methyl-1-oxo-1,3-dihydroisobenzofuran-5-yl)ethyl)-3,9-diazaspiro[5.5]undecan-3-yl)-4-methylcyclobut-3-ene-1,2-dione | [M + 1]$^+$: 453 |

Example 5

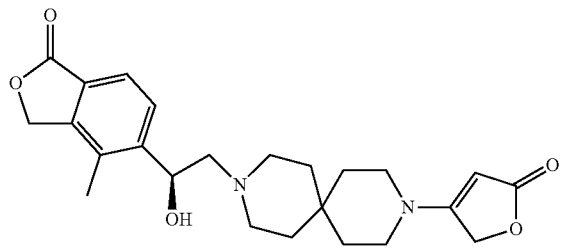 [SMILES: Cc1c([C@H](O)CN2CCC3(CC2)CCN(C2=CC(=O)OC2)CC3)ccc2c1COC2=O]

(S)-5-(1-hydroxy-2-(9-(5-oxo-2,5-dihydrofuran-3-yl)-3,9-diazaspiro[5.5]undecan-3-yl)ethyl)-4-methyl-isobenzofuran-1(3H)-one 4-(3,9-Diazaspiro[5.5]undecan-3-yl)furan-2(5H)-one (INTERMEDIATE 50, 0.22 g, 0.931 mmol) and (S)-4-methyl-5-(oxiran-2-yl)isobenzofuran-1(3H)-one (INTERMEDIATE 4A, 0.212 g, 1.117 mmol) in EtOH (3 mL) was microwaved at 140° C. for 3 h. The solution was cooled to rt, and concentrated. The residue was purified on preparative TLC developed with 20% MeOH/DCM to afford the title compound. LC-MS: 414.13 $[M+1]^+$.

Example 6

6A

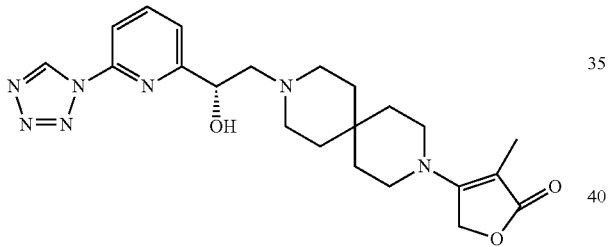

Fast eluting

6B

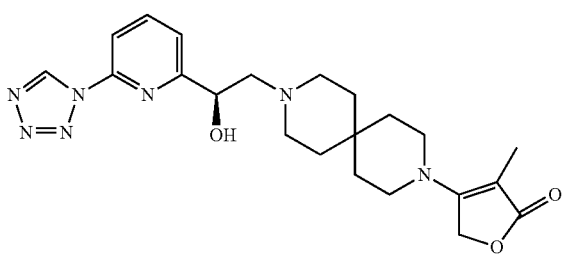

Slow eluting

6A: (S)-4-(9-(2-(6-(1H-tetrazol-1-yl)pyridin-2-yl)-2-hydroxyethyl)-3,9-diazaspiro[5.5]undecan-3-yl)-3-methylfuran-2(5H)-one 6B: (R)-4-(9-(2-(6-(1H-tetrazol-1-yl)pyridin-2-yl)-2-hydroxyethyl)-3,9-diazaspiro[5.5]undecan-3-yl)-3-methylfuran-2(5H)-one The mixture of 2-(oxiran-2-yl)-6-(1H-tetrazol-1-yl)pyridine (INTERMEDIATE 18, 300 mg, 1.59 mmol), TEA (481 mg, 4.76 mmol), 3-methyl-4-(3,9-diazaspiro[5.5]undecan-3-yl)furan-2(5H)-one hydrochloride (INTERMEDIATE 52, 636 mg, 1.75 mmol) in EtOH (5 mL) was stirred at 90° C. for 16 h. The mixture was concentrated and the residue was purified by Prep. HPLC followed by chiral SFC [eluting with 40% MeOH (0.05% DEA)/CO$_2$ on CHIRALPAK AS-H column] to afford the title compounds.

(S)-4-(9-(2-(6-(1H-tetrazol-1-yl)pyridin-2-yl)-2-hydroxyethyl)-3,9-diazaspiro[5.5]undecan-3-yl)-3-methyl-furan-2(5H)-one (fast eluting): LC-MS (ESI, m/z): 440 $[M+1]^+$.

(R)-4-(9-(2-(6-(1H-tetrazol-1-yl)pyridin-2-yl)-2-hydroxyethyl)-3,9-diazaspiro[5.5]undecan-3-yl)-3-methyl-furan-2(5H)-one (slow eluting): LC-MS (ESI, m/z): 440 $[M+1]^+$.

Example 7

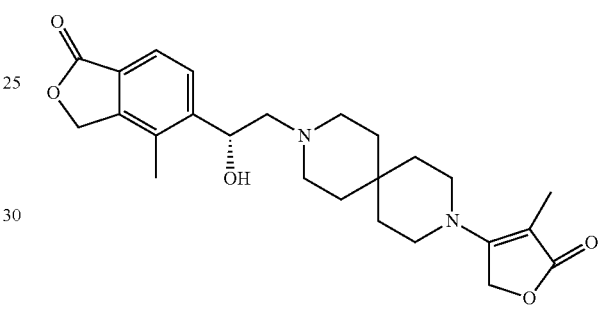

(R)-5-(1-hydroxy-2-(9-(4-methyl-5-oxo-2,5-dihydro-furan-3-yl)-3,9-diazaspiro[5.5]undecan-3-yl)ethyl)-4-methylisobenzofuran-1(3H)-one To the solution of 3-methyl-4-(3,9-diazaspiro[5.5]undecan-3-yl)furan-2(5H)-one (INTERMEDIATE 52, 80 mg, 0.320 mmol) in EtOH (4 ml) was added (R)-4-methyl-5-(oxiran-2-yl)isobenzofuran-1(3H)-one (INTERMEDIATE 4B, 72.9 mg, 0.383 mmol), and the resulting solution was heated at microwave at 140° C. for 3 h. After removing the volatile, the residue was purified on preparative TLC (1000 MU) using 10% MeOH/DCM to give the product, which was repurified on preparative TLC (1000 MU) using 30% MeOH/EtOAc to afford the title compound. LC-MS (ESI, m/z): 441.23 $[M+1]^+$. $^1$H-NMR (500 MHz, CDCl$_3$) δ ppm 7.824 (s, 2H), 5.278 (s, 2H), 5.134-5.118 (m, 1H), 4.596 (s, 2H), 3.417-3.394 (t, J=5.7 Hz, 4H), 2.803 (m, 2H), 2.598-2.418 (m, 4H), 2.309 (s, 3H), 1.968 (s, 3H), 1.689-1.618 (m, 8H).

The following compounds were prepared in an analogous fashion to EXAMPLES 5-7 starting from the indicated piperidine and epoxide intermediates prepared as described above.

| EXAMPLE | INTERMEDIATES | EXAMPLE STRUCTURE/NAME | Characterization, LC/MS |
|---|---|---|---|
| 8 | 4B, 50 | 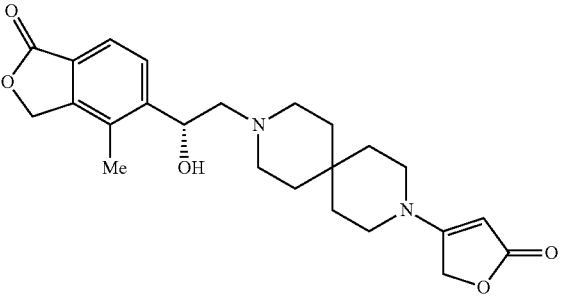 [SMILES: Cc1c([C@@H](O)CN2CCC3(CC2)CCN(C2=CC(=O)OC2)CC3)ccc2c1COC2=O]<br>(R)-5-(1-hydroxy-2-(9-(5-oxo-2,5-dihydrofuran-3-yl)-3,9-diazaspiro[5.5]undecan-3-yl)ethyl)-4-methylisobenzofuran-1(3H)-one | [M + 1]$^+$: 427.21 |
| 9 | 25B, 50 | 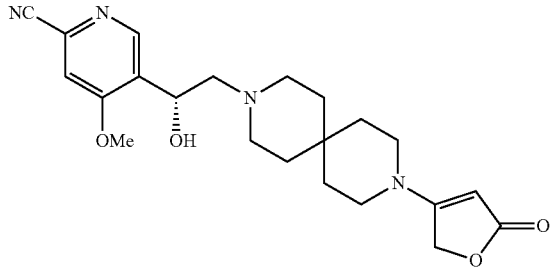 [SMILES: COc1cc(C#N)ncc1[C@@H](O)CN1CCC2(CC1)CCN(C1=CC(=O)OC1)CC2]<br>(R)-5-(1-hydroxy-2-(9-(5-oxo-2,5-dihydrofuran-3-yl)-3,9-diazaspiro[5.5]undecan-3-yl)ethyl)-4-methoxypicolinonitrile | [M + 1]$^+$: 413.13 |
| 10 | 6A, 50 | 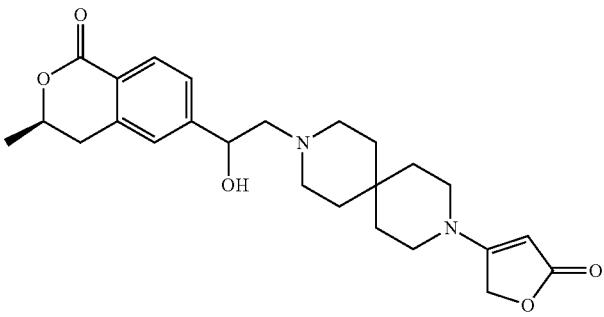 [SMILES: C[C@@H]1Cc2cc(C(O)CN3CCC4(CC3)CCN(C3=CC(=O)OC3)CC4)ccc2C(=O)O1]<br>(3R)-6-(1-hydroxy-2-(9-(5-oxo-2,5-dihydrofuran-3-yl)-3,9-diazaspiro[5.5]undecan-3-yl)ethyl)-3-methylisochroman-1-one | [M + 1]$^+$: 441.18 |
| 11 | 6B, 50 | 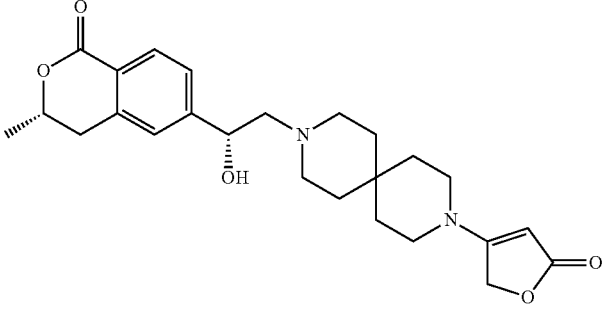 [SMILES: C[C@H]1Cc2cc([C@@H](O)CN3CCC4(CC3)CCN(C3=CC(=O)OC3)CC4)ccc2C(=O)O1]<br>(S)-6-((R)-1-hydroxy-2-(9-(5-oxo-2,5-dihydrofuran-3-yl)-3,9-diazaspiro[5.5]undecan-3-yl)ethyl)-3-methylisochroman-1-one; fast eluting isomer | [M + 1]$^+$: 441.27 |

-continued

| EXAMPLE | INTERMEDIATES | EXAMPLE STRUCTURE/NAME | Characterization, LC/MS |
|---|---|---|---|
| 12 | 6B, 50 | 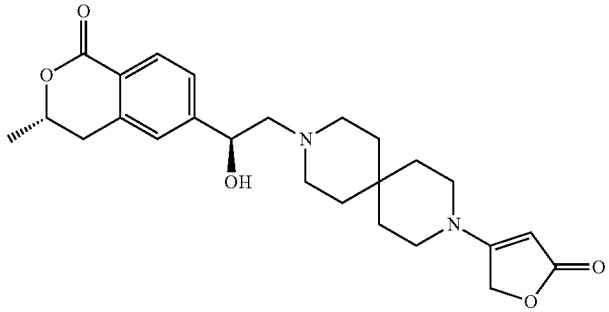 [SMILES: C[C@H]1Cc2cc([C@H](O)CN3CCC4(CC3)CCN(C3=CC(=O)OC3)CC4)ccc2C(=O)O1]<br>(S)-6-((S)-1-hydroxy-2-(9-(5-oxo-2,5-dihydrofuran-3-yl)-3,9-diazaspiro[5.5]undecan-3-yl)ethyl)-3-methylisochroman-1-one; slow eluting isomer | [M + 1]⁺: 441.21 |
| 13 | 10A, 50 | 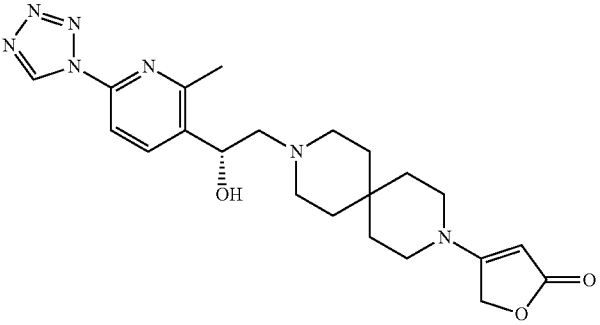<br>(R)-4-(9-(2-hydroxy-2-(2-methyl-6-(1H-tetrazol-1-yl)pyridin-3-yl)ethyl)-3,9-diazaspiro[5.5]undecan-3-yl)furan-2(5H)-one | [M + 1]⁺: 440.22 |
| 14 | 10B, 50 | 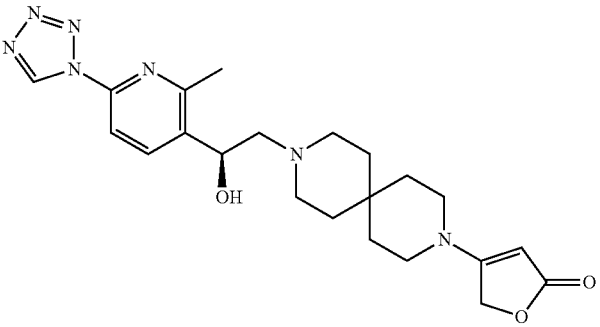 [SMILES: Cc1nc(-n2cnnn2)ccc1[C@H](O)CN1CCC2(CC1)CCN(C1=CC(=O)OC1)CC2]<br>(S)-4-(9-(2-hydroxy-2-(2-methyl-6-(1H-tetrazol-1-yl)pyridin-3-yl)ethyl)-3,9-diazaspiro[5.5]undecan-3-yl)furan-2(5H)-one | [M + 1]⁺: 440.23 |
| 15 | 12, 50 | 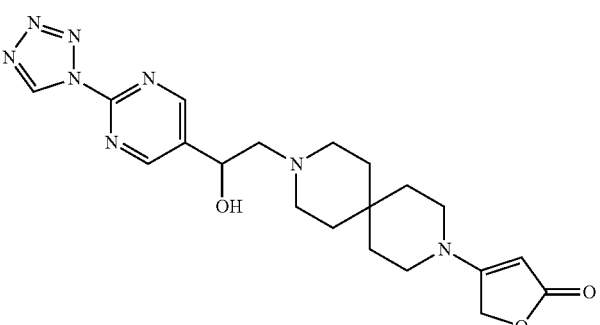<br>4-(9-(2-(2-(1H-tetrazol-1-yl)pyrimidin-5-yl)-2-hydroxyethyl)-3,9-diazaspiro[5.5]undecan-3-yl)furan-2(5H)-one | [M + 23]⁺: 449.22 |

-continued
| EXAMPLE | INTERMEDIATES | EXAMPLE STRUCTURE/NAME | Characterization, LC/MS |
|---|---|---|---|
| 16 | 11A, 50 | 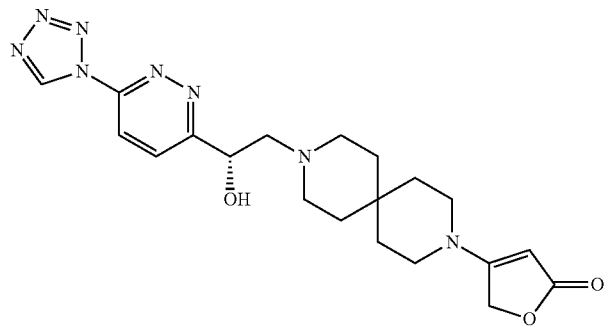 [SMILES: O=C1C=C(N2CCC3(CCN(C[C@H](O)c4ccc(-n5cnnn5)nn4)CC3)CC2)CO1]<br>(S)-4-(9-(2-(6-(1H-tetrazol-1-yl)pyridazin-3-yl)-2-hydroxyethyl)-3,9-diazaspiro[5.5]undecan-3-yl)furan-2(5H)-one | [M + 23]$^+$: 449.20 |
| 17 | 11B, 50 | 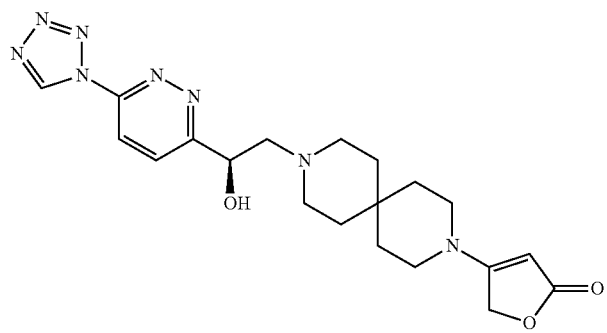 [SMILES: O=C1C=C(N2CCC3(CCN(C[C@@H](O)c4ccc(-n5cnnn5)nn4)CC3)CC2)CO1]<br>(R)-4-(9-(2-(6-(1H-tetrazol-1-yl)pyridazin-3-yl)-2-hydroxyethyl)-3,9-diazaspiro[5.5]undecan-3-yl)furan-2(5H)-one | [M + 23]$^+$: 449.11 |
| 18 | 7A, 50 | 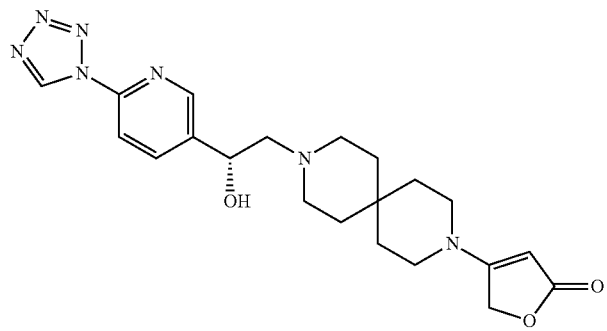 [SMILES: O=C1C=C(N2CCC3(CCN(C[C@H](O)c4ccc(-n5cnnn5)nc4)CC3)CC2)CO1]<br>(R)-4-(9-(2-(6-(1H-tetrazol-1-yl)pyridin-3-yl)-2-hydroxyethyl)-3,9-diazaspiro[5.5]undecan-3-yl)furan-2(5H)-one | [M + 1]$^+$: 426.17 |

| EXAMPLE | INTERMEDIATES | EXAMPLE STRUCTURE/NAME | Characterization, LC/MS |
|---|---|---|---|
| 19 | 7B, 50 | 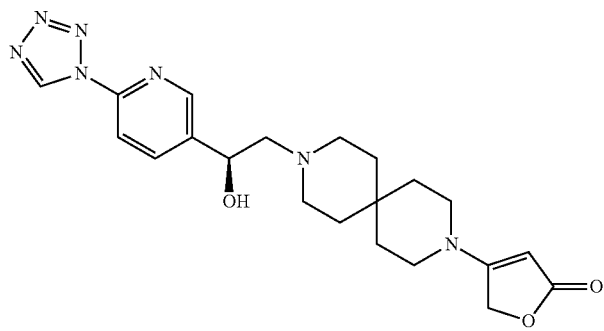 [SMILES: O=C1C=C(N2CCC3(CCN(C[C@@H](O)c4ccc(-n5cnnn5)nc4)CC3)CC2)CO1]<br>(S)-4-(9-(2-(6-(1H-tetrazol-1-yl)pyridin-3-yl)-2-hydroxyethyl)-3,9-diazaspiro[5.5]undecan-3-yl)furan-2(5H)-one | [M + 23]$^+$: 448.18 |
| 20 | 14A, 50 | 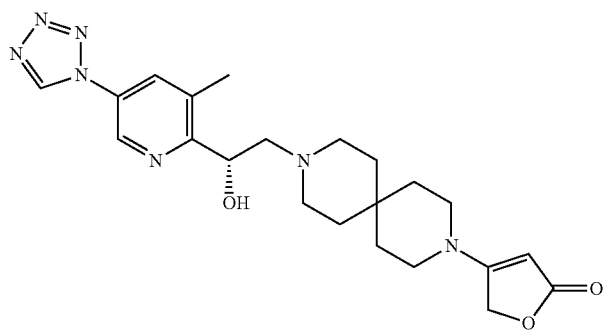<br>(S)-4-(9-(2-hydroxy-2-(3-methyl-5-(1H-tetrazol-1-yl)pyridin-2-yl)ethyl)-3,9-diazaspiro[5.5]undecan-3-yl)furan-2(5H)-one | [M + 1-28]$^+$: 412.19 |
| 21 | 14B, 50 | 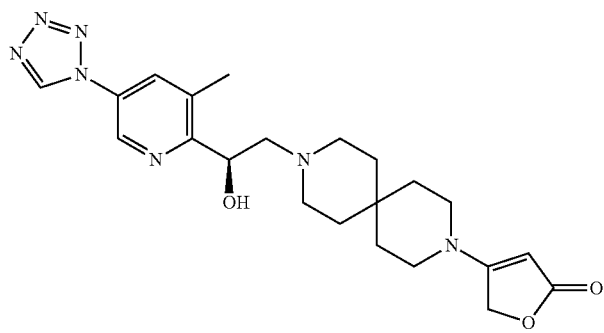 [SMILES: Cc1cc(-n2cnnn2)cnc1[C@H](O)CN1CCC2(CC1)CCN(C1=CC(=O)OC1)CC2]<br>(S)-4-(9-(2-hydroxy-2-(3-methyl-5-(1H-tetrazol-1-yl)pyridin-2-yl)ethyl)-3,9-diazaspiro[5.5]undecan-3-yl)furan-2(5H)-one | [M + 1]$^+$: 440.22 |

-continued

| EXAMPLE | INTERMEDIATES | EXAMPLE STRUCTURE/NAME | Characterization, LC/MS |
|---|---|---|---|
| 22 | 16A, 50 | 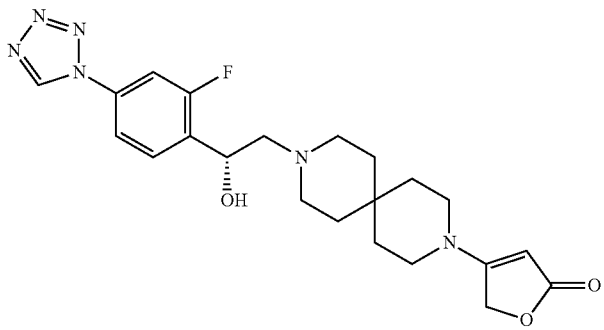 [SMILES: O=C1C=C(N2CCC3(CCN(C[C@H](O)c4ccc(-n5cnnn5)cc4F)CC3)CC2)CO1]<br>(R)-4-(9-(2-(2-fluoro-4-(1H-tetrazol-1-yl)phenyl)-2-hydroxyethyl)-3,9-diazaspiro[5.5]undecan-3-yl)furan-2(5H)-one | [M + 1]$^+$: 443.16 |
| 23 | 16B, 50 | 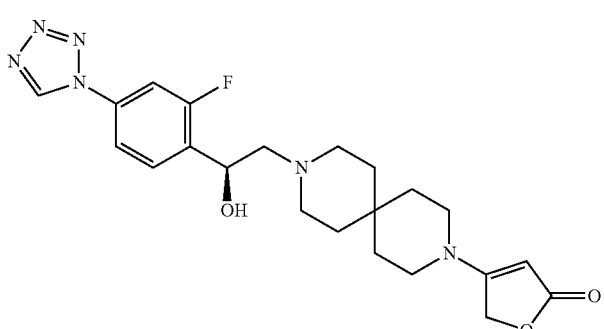<br>(S)-4-(9-(2-(2-fluoro-4-(1H-tetrazol-1-yl)phenyl)-2-hydroxyethyl)-3,9-diazaspiro[5.5]undecan-3-yl)furan-2(5H)-one | [M + 1]$^+$: 443.18 |
| 24 | 15A, 50 | 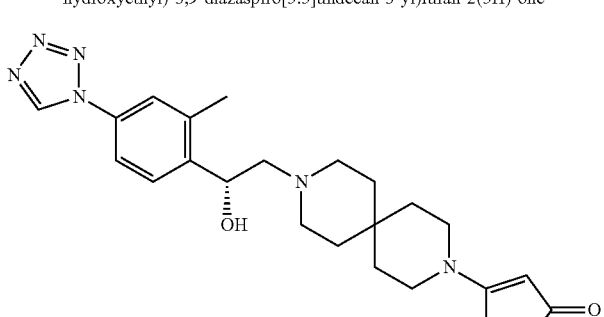<br>(R)-4-(9-(2-hydroxy-2-(2-methyl-4-(1H-tetrazol-1-yl)phenyl)ethyl)-3,9-diazaspiro[5.5]undecan-3-yl)furan-2(5H)-one | [M + 1]$^+$: 439.24 |
| 25 | 15B, 50 | 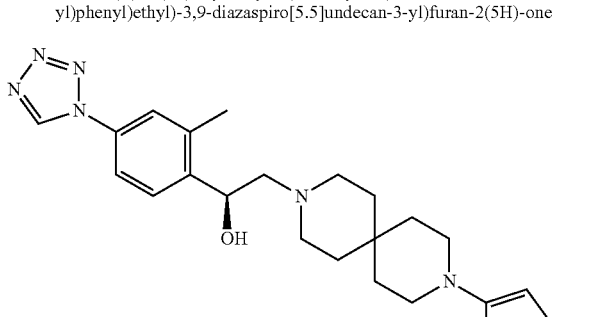<br>(S)-4-(9-(2-hydroxy-2-(2-methyl-4-(1H-tetrazol-1-yl)phenyl)ethyl)-3,9-diazaspiro[5.5]undecan-3-yl)furan-2(5H)-one | [M + 1]$^+$: 439.25 |

| EXAMPLE | INTERMEDIATES | EXAMPLE STRUCTURE/NAME | Characterization, LC/MS |
|---|---|---|---|
| 26 | 10A, 60 | 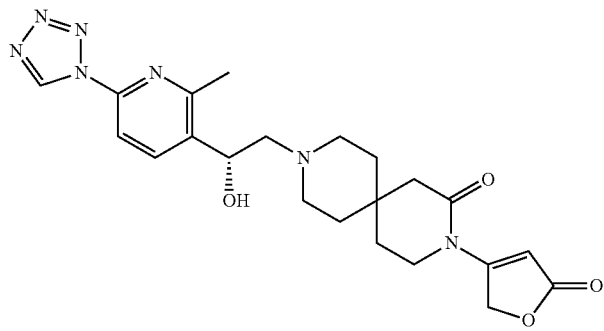<br>(R)-9-(2-hydroxy-2-(2-methyl-6-(1H-tetrazol-1-yl)pyridin-3-yl)ethyl)-3-(5-oxo-2,5-dihydrofuran-3-yl)-3,9-diazaspiro[5.5]undecan-2-one | [M + 23]$^+$: 476.16 |
| 27 | 4B, 60 | 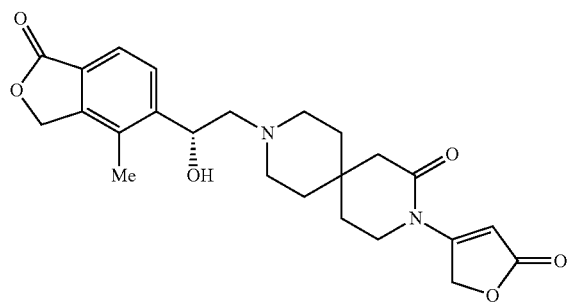 [SMILES: Cc1c([C@@H](O)CN2CCC3(CC2)CCN(C2=CC(=O)OC2)C(=O)C3)ccc2c1COC2=O]<br>(R)-9-(2-hydroxy-2-(4-methyl-1-oxo-1,3-dihydroisobenzofuran-5-yl)ethyl)-3-(5-oxo-2,5-dihydrofuran-3-yl)-3,9-diazaspiro[5.5]undecan-2-one | [M + 1]$^+$: 441.14 |
| 28 | 4B, 61 | 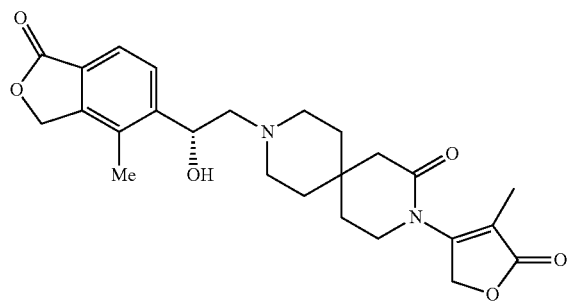 [SMILES: CC1=C(N2CCC3(CCN(C[C@H](O)c4ccc5c(c4C)COC5=O)CC3)CC2=O)COC1=O]<br>(R)-9-(2-hydroxy-2-(4-methyl-1-oxo-1,3-dihydroisobenzofuran-5-yl)ethyl)-3-(4-methyl-5-oxo-2,5-dihydrofuran-3-yl)-3,9-diazaspiro[5.5]undecan-2-one | [M + 1]$^+$: 455.16 |

| EXAMPLE | INTERMEDIATES | EXAMPLE STRUCTURE/NAME | Characterization, LC/MS |
|---|---|---|---|
| 29 | 10A, 61 | 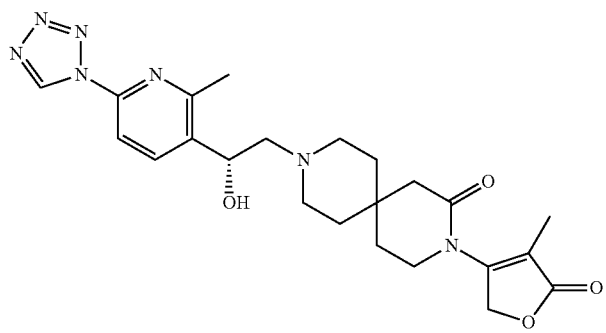 [SMILES: CC1=C(N2CCC3(CCN(C[C@H](O)c4ccc(-n5cnnn5)nc4C)CC3)CC2=O)COC1=O](R)-9-(2-hydroxy-2-(2-methyl-6-(1H-tetrazol-1-yl)pyridin-3-yl)ethyl)-3-(4-methyl-5-oxo-2,5-dihydrofuran-3-yl)-3,9-diazaspiro[5.5]undecan-2-one | [M + 1]+: 468.19 |
| 30 | 7A, 62 | 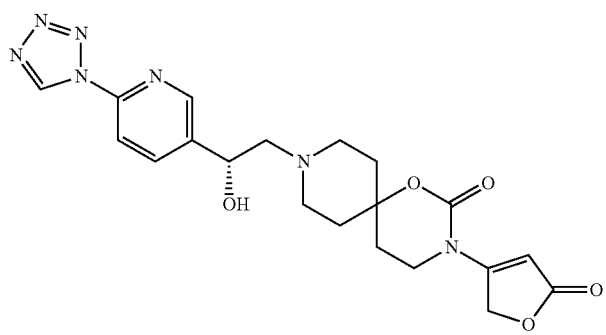 [SMILES: O=C1C=C(N2CCC3(CCN(C[C@H](O)c4ccc(-n5cnnn5)nc4)CC3)OC2=O)CO1](R)-9-(2-(6-(1H-tetrazol-1-yl)pyridin-3-yl)-2-hydroxyethyl)-3-(5-oxo-2,5-dihydrofuran-3-yl)-1-oxa-3,9-diazaspiro[5.5]undecan-2-one | [M + 1]+: 442.33 |
| 31 | 10A, 62 | 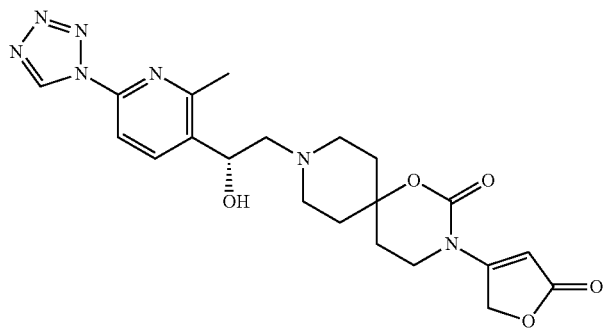(R)-9-(2-hydroxy-2-(2-methyl-6-(1H-tetrazol-1-yl)pyridin-3-yl)ethyl)-3-(5-oxo-2,5-dihydrofuran-3-yl)-1-oxa-3,9-diazaspiro[5.5]undecan-2-one | [M + 1-28-18]+: 410.31 |

| EXAMPLE | INTERMEDIATES | EXAMPLE STRUCTURE/NAME | Characterization, LC/MS |
|---|---|---|---|
| 32 | 4B, 51 | 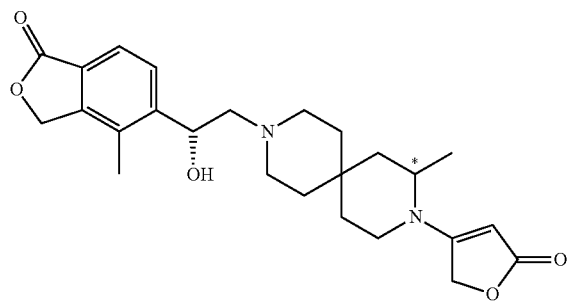<br>5-((1R)-1-hydroxy-2-(8-methyl-9-(5-oxo-2,5-dihydrofuran-3-yl)-3,9-diazaspiro[5.5]undecan-3-yl)ethyl)-4-methylisobenzofuran-1(3H)-one; fast eluting isomer from chiral SFC separation using AS column | [M + 1]⁺: 441 |
| 33 | 4B, 51 | 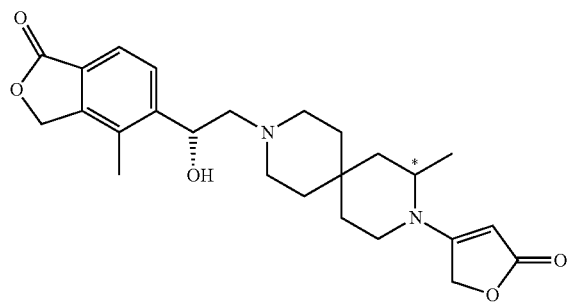<br>5-((1R)-1-hydroxy-2-(8-methyl-9-(5-oxo-2,5-dihydrofuran-3-yl)-3,9-diazaspiro[5.5]undecan-3-yl)ethyl)-4-methylisobenzofuran-1(3H)-one; slow eluting isomer from chiral SFC separation using AS column | [M + 1]⁺: 441 |
| 34 | 4B, 59 | 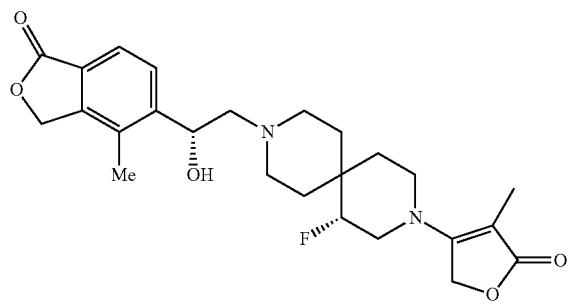 [SMILES: CC1=C(N2CCC3(CCN(C[C@H](O)c4ccc5c(c4C)COC5=O)CC3)[C@@H](F)C2)COC1=O]<br>5-((R)-2-((R)-7-fluoro-9-(4-methyl-5-oxo-2,5-dihydrofuran-3-yl)-3,9-diazaspiro[5.5]undecan-3-yl)-1-hydroxyethyl)-4-methylisobenzofuran-1(3H)-one; fast eluting isomer from chiral SFC separation using CHIRALPAK AS-H column | [M + 1]⁺: 459 |

| EXAMPLE | INTERMEDIATES | EXAMPLE STRUCTURE/NAME | Characterization, LC/MS |
|---|---|---|---|
| 35 | 4B, 59 | 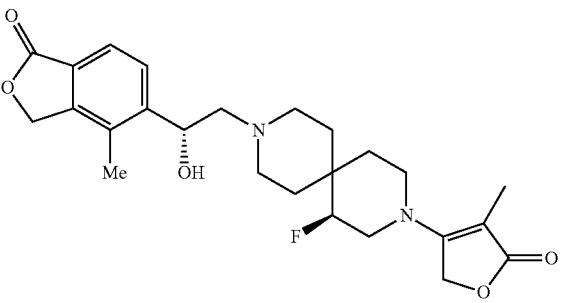 [SMILES: CC1=C(N2CCC3(CCN(C[C@H](O)c4ccc5c(c4C)COC5=O)CC3)[C@H](F)C2)COC1=O]<br>5-((R)-2-((S)-7-fluoro-9-(4-methyl-5-oxo-2,5-dihydrofuran-3-yl)-3,9-diazaspiro[5.5]undecan-3-yl)-1-hydroxyethyl)-4-methylisobenzofuran-1(3H)-one; slow eluting isomer from chiral SFC separation using CHIRALPAK AS-H column | [M + 1]⁺: 459 |
| 36 | 2-(4-bromophenyl)oxirane, 52 | 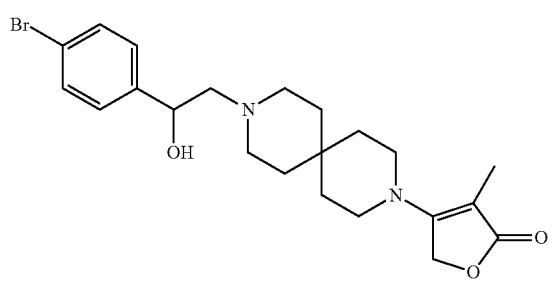 [SMILES: CC1=C(N2CCC3(CCN(CC(O)c4ccc(Br)cc4)CC3)CC2)COC1=O]<br>4-(9-(2-(4-bromophenyl)-2-hydroxyethyl)-3,9-diazaspiro[5.5]undecan-3-yl)-3-methylfuran-2(5H)-one | [M + 1]⁺: 449.01 |
| 37 | 4B, 58 | 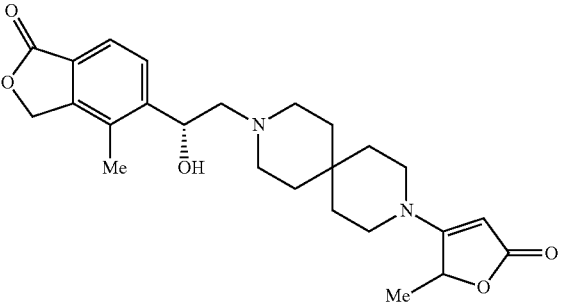 [SMILES: Cc1c([C@@H](O)CN2CCC3(CC2)CCN(C2=CC(=O)OC2C)CC3)ccc2c1COC2=O]<br>5-((1R)-1-hydroxy-2-(9-(2-methyl-5-oxo-2,5-dihydrofuran-3-yl)-3,9-diazaspiro[5.5]undecan-3-yl)ethyl)-4-methylisobenzofuran-1(3H)-one | [M + 1]⁺: 441.25 |
| 38 | 4B, 53 | 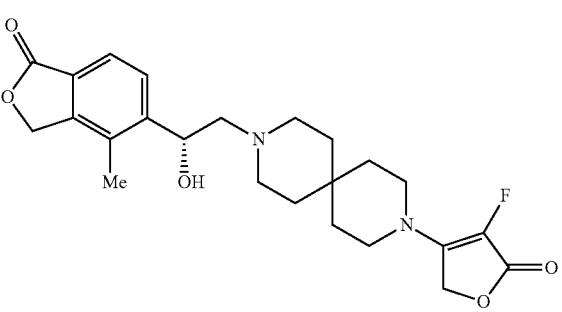 [SMILES: Cc1c([C@@H](O)CN2CCC3(CC2)CCN(C2=C(F)C(=O)OC2)CC3)ccc2c1COC2=O]<br>(R)-5-(2-(9-(4-fluoro-5-oxo-2,5-dihydrofuran-3-yl)-3,9-diazaspiro[5.5]undecan-3-yl)-1-hydroxyethyl)-4-methylisobenzofuran-1(3H)-one | [M + 1]⁺: 445.18 |

-continued

| EXAMPLE | INTERMEDIATES | EXAMPLE STRUCTURE/NAME | Characterization, LC/MS |
|---|---|---|---|
| 39 | 10A, 53 | 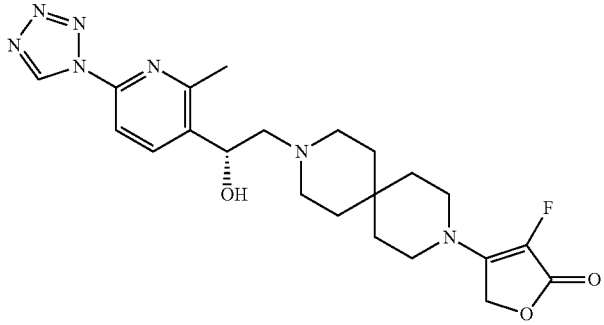 [SMILES: Cc1nc(-n2cnnn2)ccc1[C@@H](O)CN1CCC2(CC1)CCN(C1=C(F)C(=O)OC1)CC2]<br>(R)-3-fluoro-4-(9-(2-hydroxy-2-(2-methyl-6-(1H-tetrazol-1-yl)pyridin-3-yl)ethyl)-3,9-diazaspiro[5.5]undecan-3-yl)furan-2(5H)-one | [M + 1]⁺: 480.19 |
| 40 | 4B, 54 | 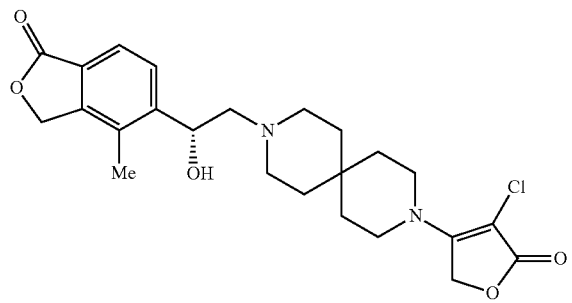 [SMILES: Cc1c([C@@H](O)CN2CCC3(CC2)CCN(C2=C(Cl)C(=O)OC2)CC3)ccc2c1COC2=O]<br>(R)-5-(2-(9-(4-chloro-5-oxo-2,5-dihydrofuran-3-yl)-3,9-diazaspiro[5.5]undecan-3-yl)-1-hydroxyethyl)-4-methylisobenzofuran-1(3H)-one | [M + 1]⁺: 461.11 |
| 41 | 4B, 56 | 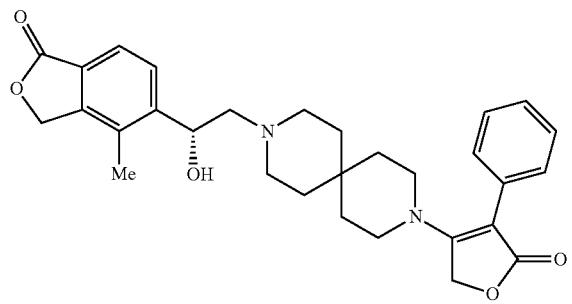 [SMILES: Cc1c([C@@H](O)CN2CCC3(CC2)CCN(C2=C(c4ccccc4)C(=O)OC2)CC3)ccc2c1COC2=O]<br>(R)-5-(1-hydroxy-2-(9-(5-oxo-4-phenyl-2,5-dihydrofuran-3-yl)-3,9-diazaspiro[5.5]undecan-3-yl)ethyl)-4-methylisobenzofuran-1(3H)-one | [M + 1]⁺: 503.27 |
| 42 | 4B, 57 | 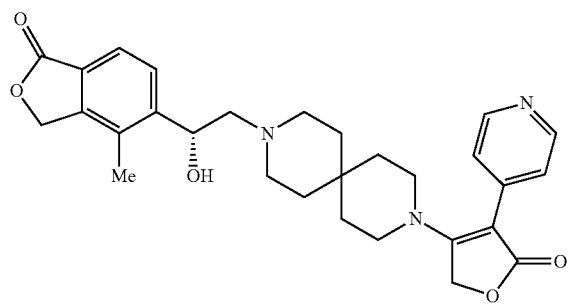 [SMILES: Cc1c([C@@H](O)CN2CCC3(CC2)CCN(C2=C(c4ccncc4)C(=O)OC2)CC3)ccc2c1COC2=O]<br>(R)-5-(1-hydroxy-2-(9-(5-oxo-4-(pyridin-4-yl)-2,5-dihydrofuran-3-yl)-3,9-diazaspiro[5.5]undecan-3-yl)ethyl)-4-methylisobenzofuran-1(3H)-one | [M + 1]⁺: 504.26 |

| EXAMPLE | INTERMEDIATES | EXAMPLE STRUCTURE/NAME | Characterization, LC/MS |
|---|---|---|---|
| 43 | 10A, 55 | 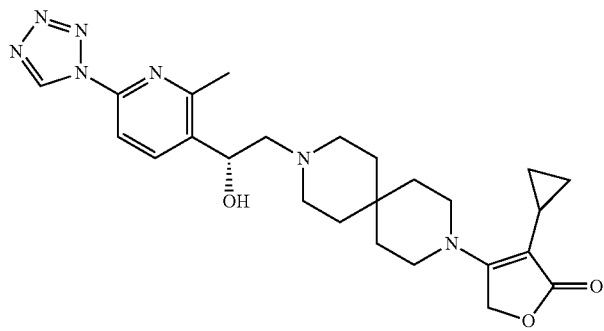 [SMILES: Cc1nc(-n2cnnn2)ccc1[C@@H](O)CN1CCC2(CC1)CCN(C1=C(C3CC3)C(=O)OC1)CC2]<br>3-cyclopropyl-4-(9-(2-hydroxy-2-(2-methyl-6-(1H-tetrazol-1-yl)pyridin-3-yl)ethyl)-3,9-diazaspiro[5.5]undecan-3-yl)furan-2(5H)-one | [M + 23]$^+$: 502 |
| 44 | 4B, 55 | 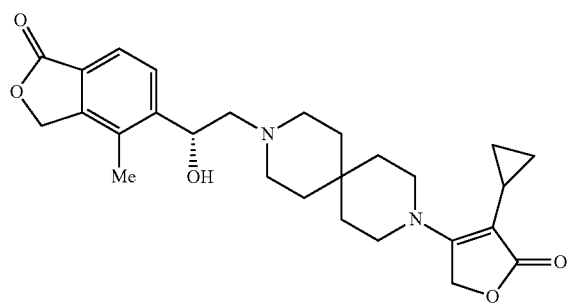 [SMILES: Cc1c([C@@H](O)CN2CCC3(CC2)CCN(C2=C(C4CC4)C(=O)OC2)CC3)ccc2c1COC2=O]<br>(R)-5-(2-(9-(4-cyclopropyl-5-oxo-2,5-dihydrofuran-3-yl)-3,9-diazaspiro[5.5]undecan-3-yl)-1-hydroxyethyl)-4-methylisobenzofuran-1(3H)-one | [M + 1]$^+$: 467 |
| 45 | 10A, 52 | 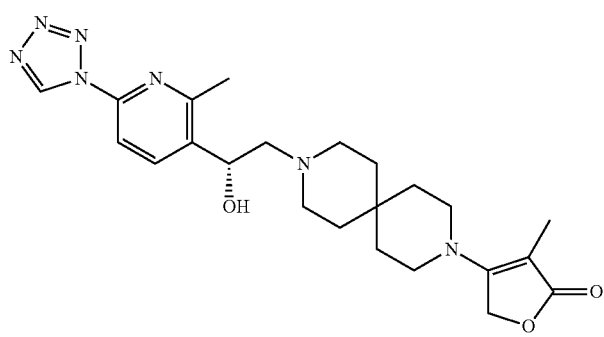<br>(R)-4-(9-(2-hydroxy-2-(2-methyl-6-(1H-tetrazol-1-yl)pyridin-3-yl)ethyl)-3,9-diazaspiro[5.5]undecan-3-yl)-3-methylfuran-2(5H)-one | [M + 1]$^+$: 454.22 |

| EXAMPLE | INTERMEDIATES | EXAMPLE STRUCTURE/NAME | Characterization, LC/MS |
|---|---|---|---|
| 46 | 10B, 52 | 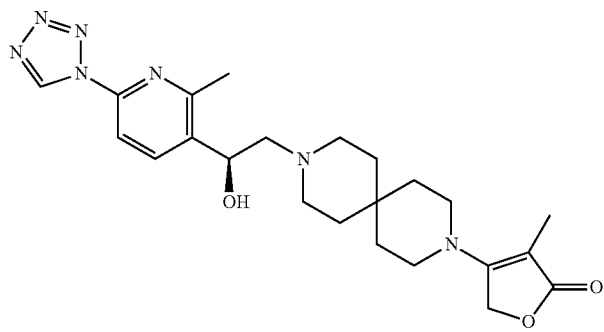 [SMILES: CC1=C(N2CCC3(CCN(C[C@@H](O)c4ccc(-n5cnnn5)nc4C)CC3)CC2)COC1=O]<br>(S)-4-(9-(2-hydroxy-2-(2-methyl-6-(1H-tetrazol-1-yl)pyridin-3-yl)ethyl)-3,9-diazaspiro[5.5]undecan-3-yl)-3-methylfuran-2(5H)-one | [M + 1]$^+$: 454.21 |
| 47 | 7A, 52 | 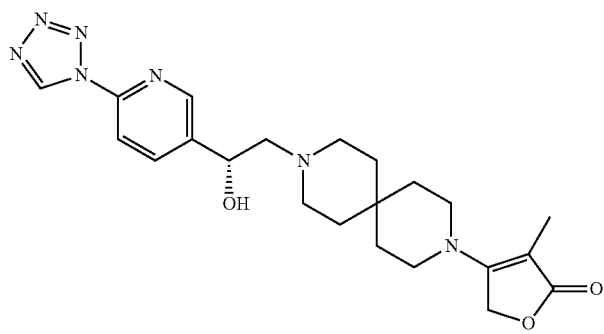 [SMILES: CC1=C(N2CCC3(CCN(C[C@H](O)c4ccc(-n5cnnn5)nc4)CC3)CC2)COC1=O]<br>(R)-4-(9-(2-(6-(1H-tetrazol-1-yl)pyridin-3-yl)-2-hydroxyethyl)-3,9-diazaspiro[5.5]undecan-3-yl)-3-methylfuran-2(5H)-one | [M + 23]$^+$: 462.20 |
| 48 | 7B, 52 | 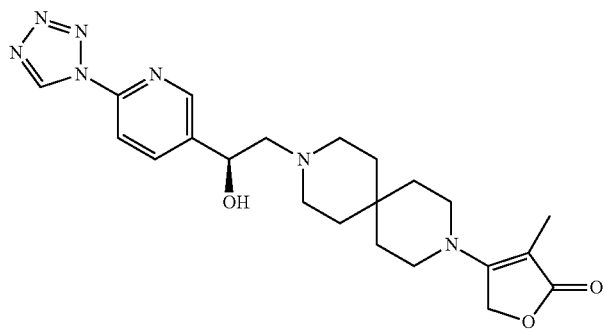 [SMILES: CC1=C(N2CCC3(CCN(C[C@@H](O)c4ccc(-n5cnnn5)nc4)CC3)CC2)COC1=O]<br>(S)-4-(9-(2-(6-(1H-tetrazol-1-yl)pyridin-3-yl)-2-hydroxyethyl)-3,9-diazaspiro[5.5]undecan-3-yl)-3-methylfuran-2(5H)-one | [M + 23]$^+$: 462.20 |

-continued
| EXAMPLE | INTERMEDIATES | EXAMPLE STRUCTURE/NAME | Characterization, LC/MS |
|---|---|---|---|
| 49 | 13A, 52 | 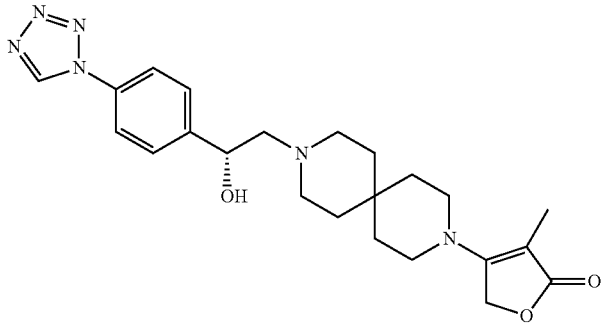 [SMILES: CC1=C(N2CCC3(CCN(C[C@H](O)c4ccc(-n5cnnn5)cc4)CC3)CC2)COC1=O](R)-4-(9-(2-(4-(1H-tetrazol-1-yl)phenyl)-2-hydroxyethyl)-3,9-diazaspiro[5.5]undecan-3-yl)-3-methylfuran-2(5H)-one | [M + 1]$^+$: 439.24 |
| 50 | 13B, 52 | 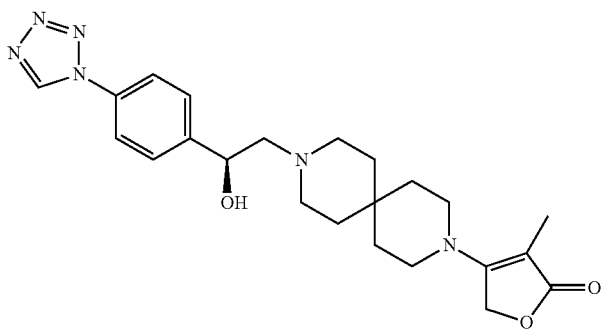 [SMILES: CC1=C(N2CCC3(CCN(C[C@@H](O)c4ccc(-n5cnnn5)cc4)CC3)CC2)COC1=O](S)-4-(9-(2-(4-(1H-tetrazol-1-yl)phenyl)-2-hydroxyethyl)-3,9-diazaspiro[5.5]undecan-3-yl)-3-methylfuran-2(5H)-one | [M + 1]$^+$: 439.26 |
| 51 | 9A, 52 | 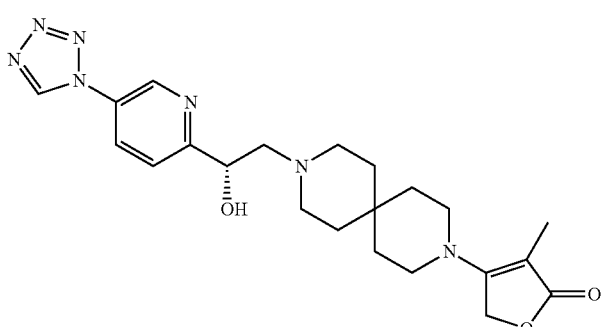(S)-4-(9-(2-(5-(1H-tetrazol-1-yl)pyridin-2-yl)-2-hydroxyethyl)-3,9-diazaspiro[5.5]undecan-3-yl)-3-methylfuran-2(5H)-one | [M + 1]$^+$: 440.19 |

| EXAMPLE | INTERMEDIATES | EXAMPLE STRUCTURE/NAME | Characterization, LC/MS |
|---|---|---|---|
| 52 | 9B, 52 | 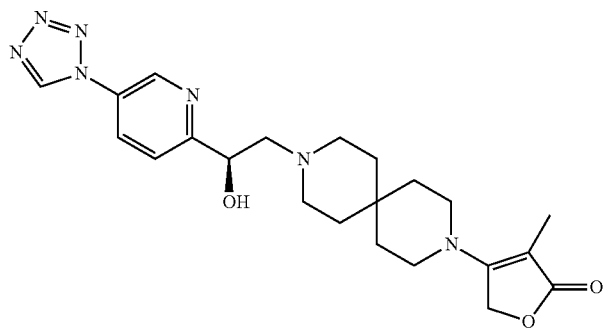 [SMILES: CC1=C(N2CCC3(CCN(C[C@@H](O)c4ccc(-n5cnnn5)cn4)CC3)CC2)COC1=O]<br>(R)-4-(9-(2-(5-(1H-tetrazol-1-yl)pyridin-2-yl)-2-hydroxyethyl)-3,9-diazaspiro[5.5]undecan-3-yl)-3-methylfuran-2(5H)-one | [M + 23]⁺: 462.19 |
| 53 | 16A, 52 | 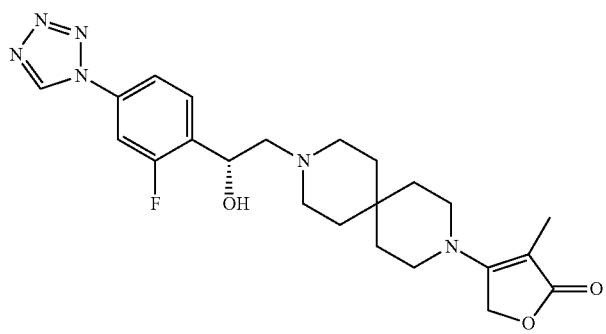 [SMILES: CC1=C(N2CCC3(CCN(C[C@H](O)c4ccc(-n5cnnn5)cc4F)CC3)CC2)COC1=O]<br>(R)-4-(9-(2-(2-fluoro-4-(1H-tetrazol-1-yl)phenyl)-2-hydroxyethyl)-3,9-diazaspiro[5.5]undecan-3-yl)-3-methylfuran-2(5H)-one | [M + 23]⁺: 479 |
| 54 | 16B, 52 | 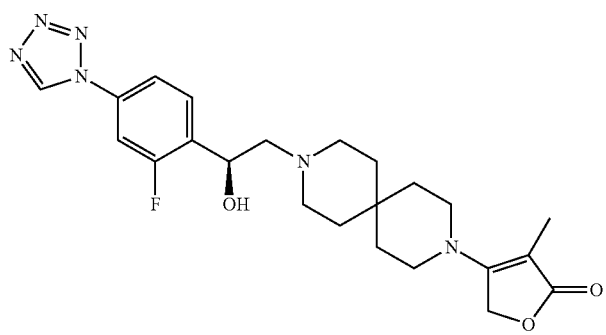 [SMILES: CC1=C(N2CCC3(CCN(C[C@@H](O)c4ccc(-n5cnnn5)cc4F)CC3)CC2)COC1=O]<br>(S)-4-(9-(2-(2-fluoro-4-(1H-tetrazol-1-yl)phenyl)-2-hydroxyethyl)-3,9-diazaspiro[5.5]undecan-3-yl)-3-methylfuran-2(5H)-one | [M + 1]⁺: 457 |

| EXAMPLE | INTERMEDIATES | EXAMPLE STRUCTURE/NAME | Characterization, LC/MS |
|---|---|---|---|
| 55 | 15A, 52 | 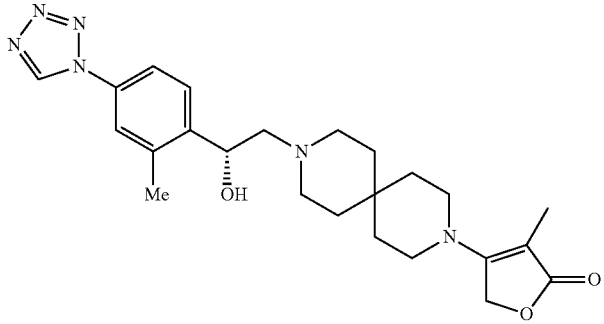 [SMILES: CC1=C(N2CCC3(CCN(C[C@H](O)c4ccc(-n5cnnn5)cc4C)CC3)CC2)COC1=O]<br>(R)-4-(9-(2-hydroxy-2-(2-methyl-4-(1H-tetrazol-1-yl)phenyl)ethyl)-3,9-diazaspiro[5.5]undecan-3-yl)-3-methylfuran-2(5H)-one | [M + 1]$^+$: 453 |
| 56 | 15B, 52 | 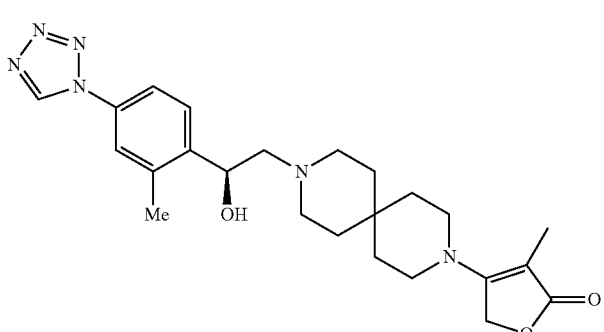<br>(S)-4-(9-(2-hydroxy-2-(2-methyl-4-(1H-tetrazol-1-yl)phenyl)ethyl)-3,9-diazaspiro[5.5]undecan-3-yl)-3-methylfuran-2(5H)-one | [M + 23]$^+$: 475 |
| 57 | 15A, 52 | 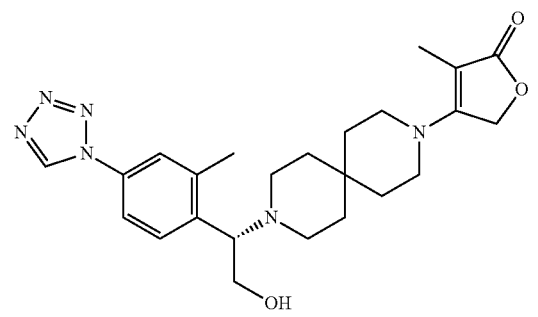 [SMILES: CC1=C(N2CCC3(CC2)CCN([C@H](CO)c2ccc(-n4cnnn4)cc2C)CC3)COC1=O]<br>(S)-4-(9-(2-hydroxy-1-(2-methyl-4-(1H-tetrazol-1-yl)phenyl)ethyl)-3,9-diazaspiro[5.5]undecan-3-yl)-3-methylfuran-2(5H)-one | [M + 1]$^+$: 453 |

| EXAMPLE | INTERMEDIATES | EXAMPLE STRUCTURE/NAME | Characterization, LC/MS |
|---|---|---|---|
| 58 | 15B, 52 | 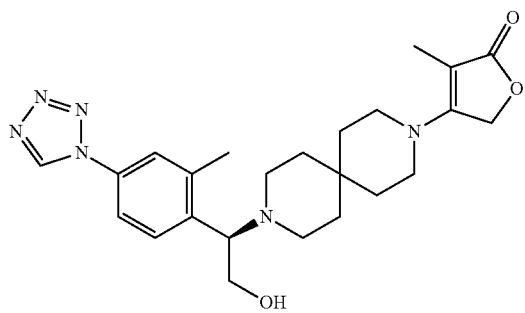 [SMILES: CC1=C(N2CCC3(CC2)CCN([C@@H](CO)c2ccc(-n4cnnn4)cc2C)CC3)COC1=O]<br>(R)-4-(9-(2-hydroxy-1-(2-methyl-4-(1H-tetrazol-1-yl)phenyl)ethyl)-3,9-diazaspiro[5.5]undecan-3-yl)-3-methylfuran-2(5H)-one | [M + 23]⁺: 475 |
| 59 | 22A, 52 | 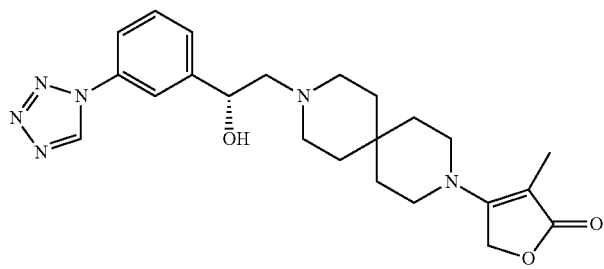 [SMILES: CC1=C(N2CCC3(CCN(C[C@H](O)c4cccc(-n5cnnn5)c4)CC3)CC2)COC1=O]<br>(R)-4-(9-(2-(3-(1H-tetrazol-1-yl)phenyl)-2-hydroxyethyl)-3,9-diazaspiro[5.5]undecan-3-yl)-3-methylfuran-2(5H)-one | [M + 1]⁺: 439 |
| 60 | 22B, 52 | 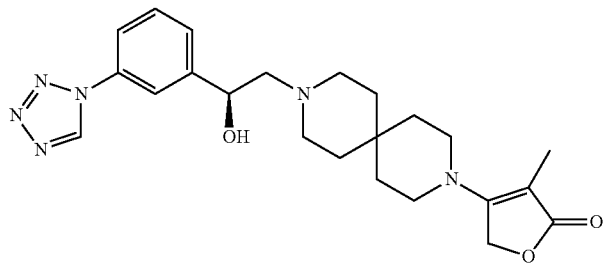 [SMILES: CC1=C(N2CCC3(CCN(C[C@@H](O)c4cccc(-n5cnnn5)c4)CC3)CC2)COC1=O]<br>(S)-4-(9-(2-(3-(1H-tetrazol-1-yl)phenyl)-2-hydroxyethyl)-3,9-diazaspiro[5.5]undecan-3-yl)-3-methylfuran-2(5H)-one | [M + 1]⁺: 439 |
| 61 | 23A, 52 | 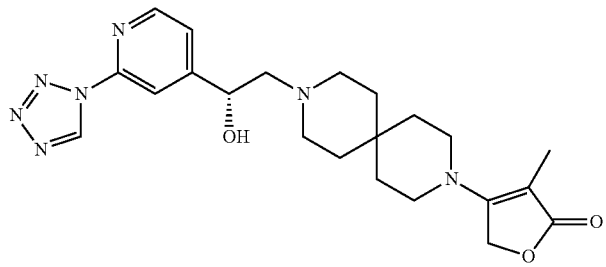 [SMILES: CC1=C(N2CCC3(CCN(C[C@H](O)c4ccnc(-n5cnnn5)c4)CC3)CC2)COC1=O]<br>(R)-4-(9-(2-(2-(1H-tetrazol-1-yl)pyridin-4-yl)-2-hydroxyethyl)-3,9-diazaspiro[5.5]undecan-3-yl)-3-methylfuran-2(5H)-one | [M + 1]⁺: 440 |

| EXAMPLE | INTERMEDIATES | EXAMPLE STRUCTURE/NAME | Characterization, LC/MS |
|---|---|---|---|
| 62 | 23B, 52 | 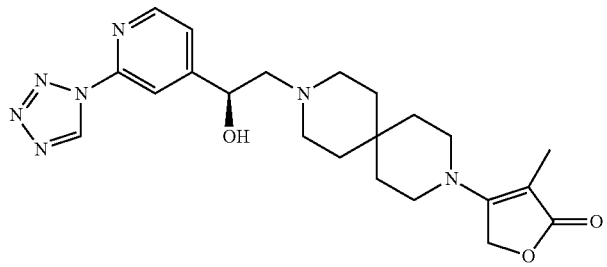 [SMILES: CC1=C(N2CCC3(CCN(C[C@@H](O)c4ccnc(-n5cnnn5)c4)CC3)CC2)COC1=O]<br>(S)-4-(9-(2-(2-(1H-tetrazol-1-yl)pyridin-4-yl)-2-hydroxyethyl)-3,9-diazaspiro[5.5]undecan-3-yl)-3-methylfuran-2(5H)-one | [M + 1]⁺: 440 |
| 63 | 20, 52 | 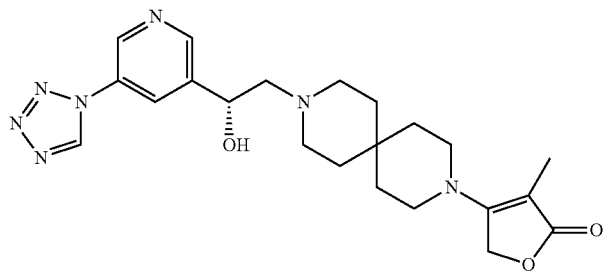 [SMILES: CC1=C(N2CCC3(CCN(C[C@H](O)c4cncc(-n5cnnn5)c4)CC3)CC2)COC1=O]<br>(R)-4-(9-(2-(5-(1H-tetrazol-1-yl)pyridin-3-yl)-2-hydroxyethyl)-3,9-diazaspiro[5.5]undecan-3-yl)-3-methylfuran-2(5H)-one; fast eluting isomer from chiral SFC separation using CHIRALCEL OJ-3 column | [M + 1]⁺: 440 |
| 64 | 20, 52 | 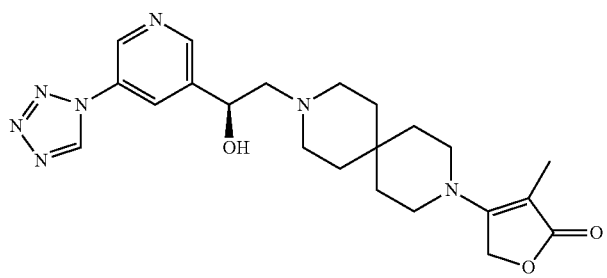 [SMILES: CC1=C(N2CCC3(CCN(C[C@@H](O)c4cncc(-n5cnnn5)c4)CC3)CC2)COC1=O]<br>(S)-4-(9-(2-(5-(1H-tetrazol-1-yl)pyridin-3-yl)-2-hydroxyethyl)-3,9-diazaspiro[5.5]undecan-3-yl)-3-methylfuran-2(5H)-one; slow eluting isomer from chiral SFC separation using CHIRALCEL OJ-3 column | [M + 1]⁺: 440 |
| 65 | 19, 52 | 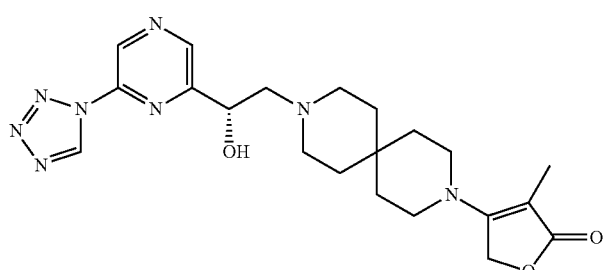<br>(S)-4-(9-(2-(6-(1H-tetrazol-1-yl)pyrazin-2-yl)-2-hydroxyethyl)-3,9-diazaspiro[5.5]undecan-3-yl)-3-methylfuran-2(5H)-one; fast eluting isomer from chiral SFC separation using CHIRALPAK AS-H column | [M + 1]⁺: 441 |

| EXAMPLE | INTERMEDIATES | EXAMPLE STRUCTURE/NAME | Characterization, LC/MS |
|---|---|---|---|
| 66 | 19, 52 | 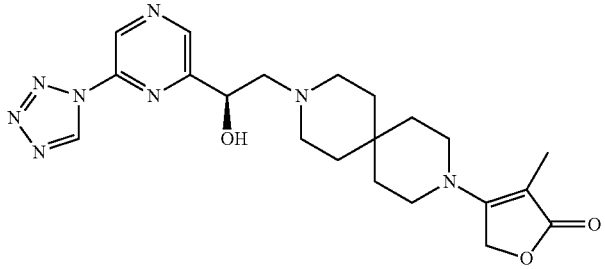 [SMILES: CC1=C(N2CCC3(CCN(C[C@@H](O)c4cncc(-n5cnnn5)n4)CC3)CC2)COC1=O]<br>(R)-4-(9-(2-(6-(1H-tetrazol-1-yl)pyrazin-2-yl)-2-hydroxyethyl)-3,9-diazaspiro[5.5]undecan-3-yl)-3-methylfuran-2(5H)-one; slow eluting isomer from chiral SFC separation using CHIRALPAK AS-H column | [M + 1]$^+$: 441 |
| 67 | 17, 52 | 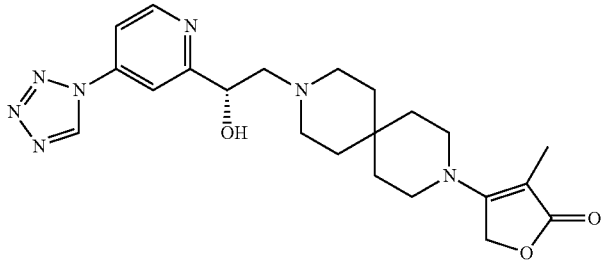 [SMILES: CC1=C(N2CCC3(CCN(C[C@H](O)c4cc(-n5cnnn5)ccn4)CC3)CC2)COC1=O]<br>(S)-4-(9-(2-(4-(1H-tetrazol-1-yl)pyridin-2-yl)-2-hydroxyethyl)-3,9-diazaspiro[5.5]undecan-3-yl)-3-methylfuran-2(5H)-one; fast eluting isomer from chiral SFC separation using CHIRALCEL OD-3 column | [M + 1]$^+$: 440 |
| 68 | 17, 52 | 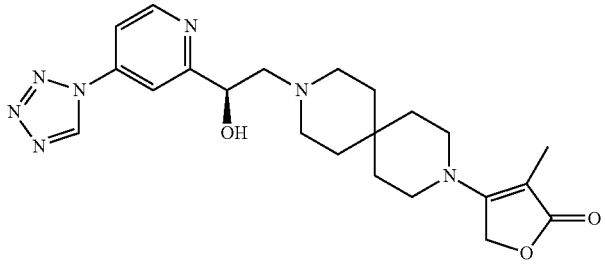 [SMILES: CC1=C(N2CCC3(CCN(C[C@@H](O)c4cc(-n5cnnn5)ccn4)CC3)CC2)COC1=O]<br>(R)-4-(9-(2-(4-(1H-tetrazol-1-yl)pyridin-2-yl)-2-hydroxyethyl)-3,9-diazaspiro[5.5]undecan-3-yl)-3-methylfuran-2(5H)-one; slow eluting isomer from chiral SFC separation using CHIRALCEL OD-3 column | [M + 1]$^+$: 440 |
| 69 | 21B, 52 | 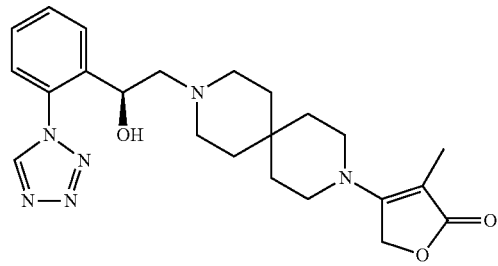 [SMILES: CC1=C(N2CCC3(CCN(C[C@@H](O)c4ccccc4-n4cnnn4)CC3)CC2)COC1=O]<br>(S)-4-(9-(2-(2-(1H-tetrazol-1-yl)phenyl)-2-hydroxyethyl)-3,9-diazaspiro[5.5]undecan-3-yl)-3-methylfuran-2(5H)-one; slow eluting isomer | [M + 1]$^+$: 439 |

| EXAMPLE | INTERMEDIATES | EXAMPLE STRUCTURE/NAME | Characterization, LC/MS |
|---|---|---|---|
| 70 | 10A, 63 | (R)-3-(9-(2-hydroxy-2-(2-methyl-6-(1H-tetrazol-1-yl)pyridin-3-yl)ethyl)-3,9-diazaspiro[5.5]undecan-3-yl)cyclopent-2-enone | [M + 1]⁺: 438 |
| 71 | 10B, 63 | (S)-3-(9-(2-hydroxy-2-(2-methyl-6-(1H-tetrazol-1-yl)pyridin-3-yl)ethyl)-3,9-diazaspiro[5.5]undecan-3-yl)cyclopent-2-enone | [M + 1]⁺: 438 |
| 72 | 4B, 63 | (R)-5-(1-hydroxy-2-(9-(3-oxocyclopent-1-en-1-yl)-3,9-diazaspiro[5.5]undecan-3-yl)ethyl)-4-methylisobenzofuran-1(3H)-one | [M + 1]⁺: 425 |
| 73 | 15A, 63 | (R)-3-(9-(2-hydroxy-2-(2-methyl-4-(1H-tetrazol-1-yl)phenyl)ethyl)-3,9-diazaspiro[5.5]undecan-3-yl)cyclopent-2-enone | [M + 1]⁺: 437 |

| EXAMPLE | INTERMEDIATES | EXAMPLE STRUCTURE/NAME | Characterization, LC/MS |
|---|---|---|---|
| 74 | 10A, 64 | 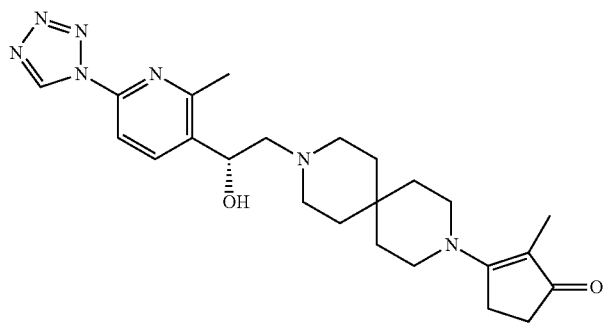 [SMILES: CC1=C(N2CCC3(CCN(C[C@H](O)c4ccc(-n5cnnn5)nc4C)CC3)CC2)CCC1=O]<br>(R)-3-(9-(2-hydroxy-2-(2-methyl-6-(1H-tetrazol-1-yl)pyridin-3-yl)ethyl)-3,9-diazaspiro[5.5]undecan-3-yl)-2-methylcyclopent-2-enone | [M + 1]$^+$: 452 |
| 75 | 10B, 64 | 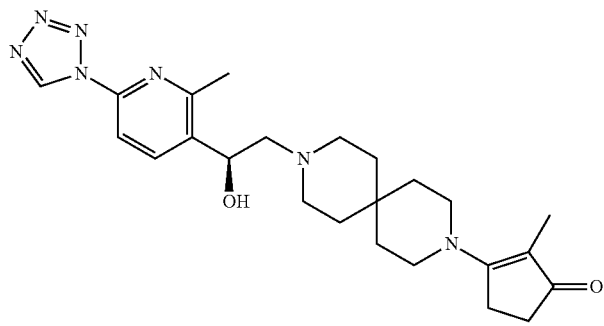 [SMILES: CC1=C(N2CCC3(CCN(C[C@@H](O)c4ccc(-n5cnnn5)nc4C)CC3)CC2)CCC1=O]<br>(S)-3-(9-(2-hydroxy-2-(2-methyl-6-(1H-tetrazol-1-yl)pyridin-3-yl)ethyl)-3,9-diazaspiro[5.5]undecan-3-yl)-2-methylcyclopent-2-enone | [M + 1]$^+$: 452 |
| 76 | 4B, 64 | 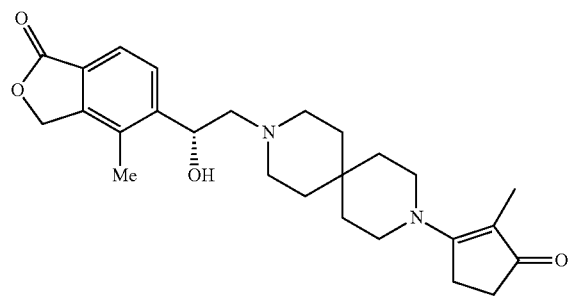 [SMILES: CC1=C(N2CCC3(CCN(C[C@H](O)c4ccc5c(c4C)COC5=O)CC3)CC2)CCC1=O]<br>(R)-5-(1-hydroxy-2-(9-(2-methyl-3-oxocyclopent-1-en-1-yl)-3,9-diazaspiro[5.5]undecan-3-yl)ethyl)-4-methylisobenzofuran-1(3H)-one | [M + 1]$^+$: 439 |

| EXAMPLE | INTERMEDIATES | EXAMPLE STRUCTURE/NAME | Characterization, LC/MS |
|---|---|---|---|
| 77 | 15A, 64 | 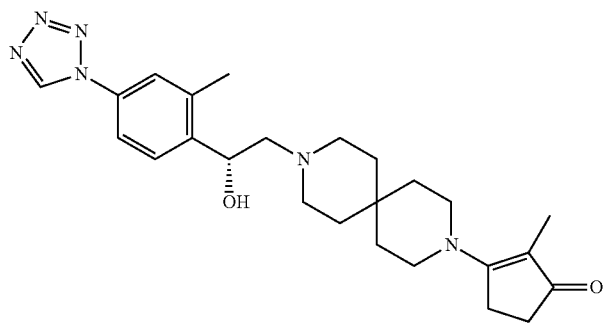 [SMILES: CC1=C(N2CCC3(CCN(C[C@H](O)c4ccc(-n5cnnn5)cc4C)CC3)CC2)CCC1=O]<br>(R)-3-(9-(2-hydroxy-2-(2-methyl-4-(1H-tetrazol-1-yl)phenyl)ethyl)-3,9-diazaspiro[5.5]undecan-3-yl)-2-methylcyclopent-2-enone | [M + 1]⁺: 451 |
| 78 | 4B, 65 | 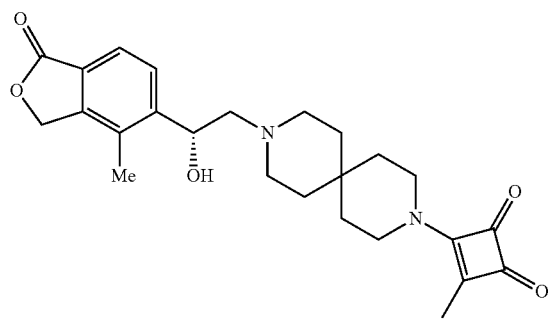 [SMILES: Cc1c([C@@H](O)CN2CCC3(CC2)CCN(c2c(C)c(=O)c2=O)CC3)ccc2c1COC2=O]<br>(R)-3-(9-(2-hydroxy-2-(4-methyl-1-oxo-1,3-dihydroisobenzofuran-5-yl)ethyl)-3,9-diazaspiro[5.5]undecan-3-yl)-4-methylcyclobut-3-ene-1,2-dione | [M + 1]⁺: 439 |
| 79 | 4B, 26, 34 | 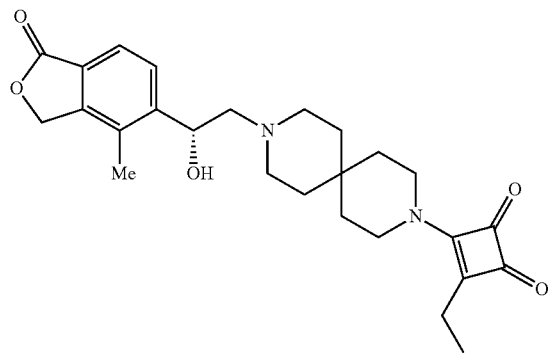 [SMILES: CCc1c(N2CCC3(CCN(C[C@H](O)c4ccc5c(c4C)COC5=O)CC3)CC2)c(=O)c1=O]<br>(R)-3-ethyl-4-(9-(2-hydroxy-2-(4-methyl-1-oxo-1,3-dihydroisobenzofuran-5-yl)ethyl)-3,9-diazaspiro[5.5]undecan-3-yl)cyclobut-3-ene-1,2-dione | [M + 1]⁺: 455 |

| EXAMPLE | INTERMEDIATES | EXAMPLE STRUCTURE/NAME | Characterization, LC/MS |
|---|---|---|---|
| 80 | 4B, 26, 35 | 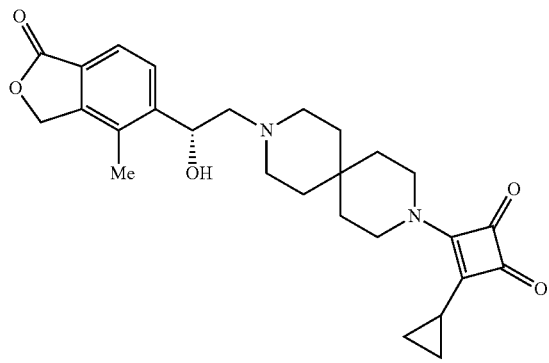 [SMILES: Cc1c([C@@H](O)CN2CCC3(CC2)CCN(c2c(C4CC4)c(=O)c2=O)CC3)ccc2c1COC2=O]<br>(R)-3-cyclopropyl-4-(9-(2-hydroxy-2-(4-methyl-1-oxo-1,3-dihydroisobenzofuran-5-yl)ethyl)-3,9-diazaspiro[5.5]undecan-3-yl)cyclobut-3-ene-1,2-dione | [M + 1]⁺: 465 |
| 81 | 7A, 65 | 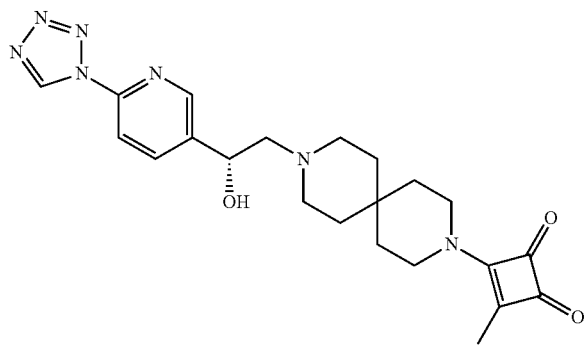 [SMILES: Cc1c(N2CCC3(CCN(C[C@H](O)c4ccc(-n5cnnn5)nc4)CC3)CC2)c(=O)c1=O]<br>(R)-3-(9-(2-(6-(1H-tetrazol-1-yl)pyridin-3-yl)-2-hydroxyethyl)-3,9-diazaspiro[5.5]undecan-3-yl)-4-methylcyclobut-3-ene-1,2-dione | [M + 1]⁺: 438 |
| 82 | 7B, 65 | 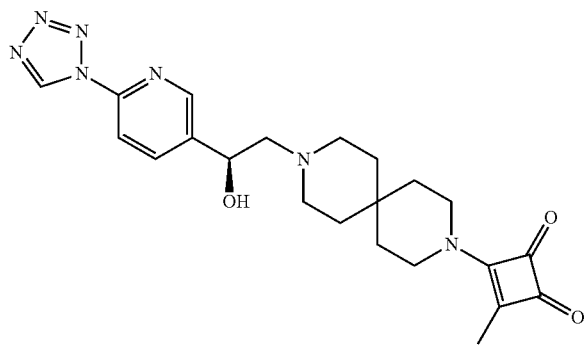 [SMILES: Cc1c(N2CCC3(CCN(C[C@@H](O)c4ccc(-n5cnnn5)nc4)CC3)CC2)c(=O)c1=O]<br>(S)-3-(9-(2-(6-(1H-tetrazol-1-yl)pyridin-3-yl)-2-hydroxyethyl)-3,9-diazaspiro[5.5]undecan-3-yl)-4-methylcyclobut-3-ene-1,2-dione | [M + 1]⁺: 438 |

| EXAMPLE | INTERMEDIATES | EXAMPLE STRUCTURE/NAME | Characterization, LC/MS |
|---|---|---|---|
| 83 | 11A, 65 | 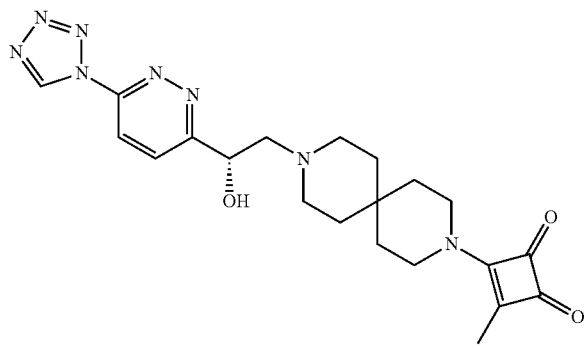 [SMILES: Cc1c(N2CCC3(CCN(C[C@H](O)c4ccc(-n5cnnn5)nn4)CC3)CC2)c(=O)c1=O]<br>(S)-3-(9-(2-(6-(1H-tetrazol-1-yl)pyridazin-3-yl)-2-hydroxyethyl)-3,9-diazaspiro[5.5]undecan-3-yl)-4-methylcyclobut-3-ene-1,2-dione | [M + 1]⁺: 439 |
| 84 | 11B, 65 | 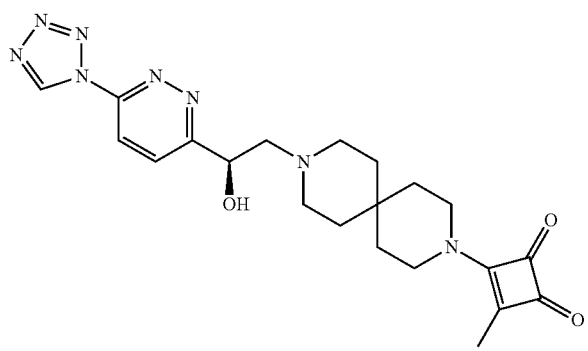 [SMILES: Cc1c(N2CCC3(CCN(C[C@@H](O)c4ccc(-n5cnnn5)nn4)CC3)CC2)c(=O)c1=O]<br>(R)-3-(9-(2-(6-(1H-tetrazol-1-yl)pyridazin-3-yl)-2-hydroxyethyl)-3,9-diazaspiro[5.5]undecan-3-yl)-4-methylcyclobut-3-ene-1,2-dione | [M + 1]⁺: 439 |
| 85 | 8A, 65 | 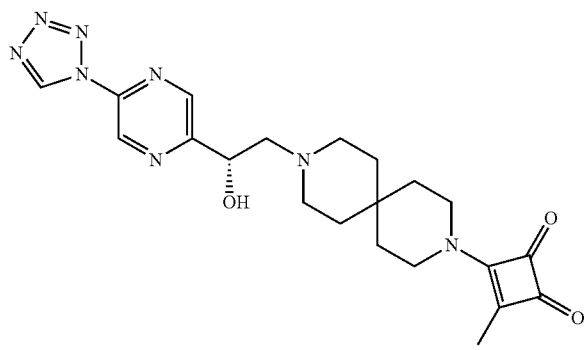 [SMILES: Cc1c(N2CCC3(CCN(C[C@H](O)c4cnc(-n5cnnn5)cn4)CC3)CC2)c(=O)c1=O]<br>(S)-3-(9-(2-(5-(1H-tetrazol-1-yl)pyrazin-2-yl)-2-hydroxyethyl)-3,9-diazaspiro[5.5]undecan-3-yl)-4-methylcyclobut-3-ene-1,2-dione | [M + 1]⁺: 439 |

| EXAMPLE | INTERMEDIATES | EXAMPLE STRUCTURE/NAME | Characterization, LC/MS |
|---|---|---|---|
| 86 | 8B, 65 | 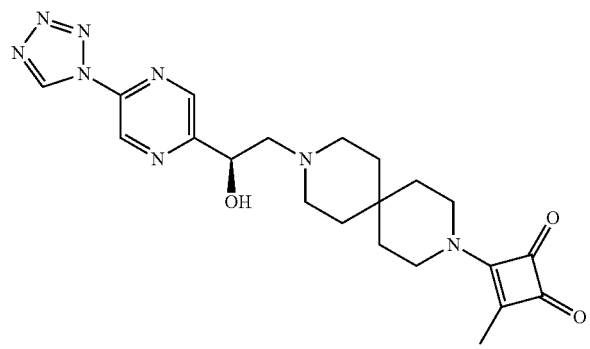 [SMILES: Cc1c(N2CCC3(CCN(C[C@@H](O)c4cnc(-n5cnnn5)cn4)CC3)CC2)c(=O)c1=O]<br>(R)-3-(9-(2-(5-(1H-tetrazol-1-yl)pyrazin-2-yl)-2-hydroxyethyl)-3,9-diazaspiro[5.5]undecan-3-yl)-4-methylcyclobut-3-ene-1,2-dione | [M + 1]$^+$: 439 |
| 87 | 9A, 65 | 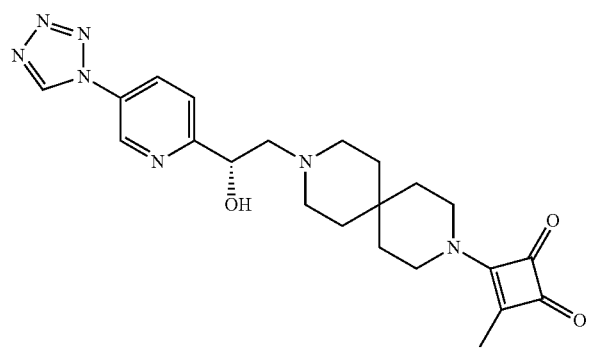 [SMILES: Cc1c(N2CCC3(CCN(C[C@H](O)c4ccc(-n5cnnn5)cn4)CC3)CC2)c(=O)c1=O]<br>(S)-3-(9-(2-(5-(1H-tetrazol-1-yl)pyridin-2-yl)-2-hydroxyethyl)-3,9-diazaspiro[5.5]undecan-3-yl)-4-methylcyclobut-3-ene-1,2-dione | [M + 1]$^+$: 438 |
| 88 | 24, 65 | 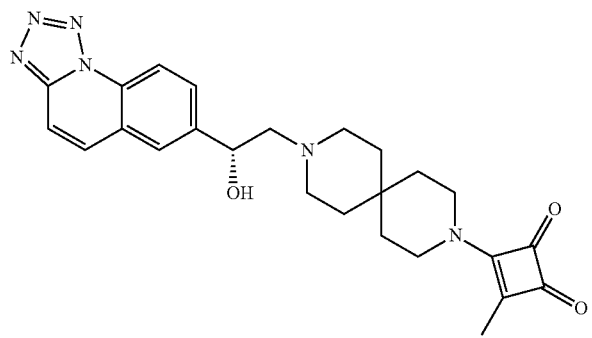 [SMILES: Cc1c(N2CCC3(CCN(C[C@H](O)c4ccc5c(ccc6nnnn65)c4)CC3)CC2)c(=O)c1=O]<br>(R)-3-(9-(2-hydroxy-2-(tetrazolo[1,5-a]quinolin-7-yl)ethyl)-3,9-diazaspiro[5.5]undecan-3-yl)-4-methylcyclobut-3-ene-1,2-dione; fast eluting isomer from chiral SFC separation using CHIRALPAK AS-H column | [M + 1]$^+$: 461 |

| EXAMPLE | INTERMEDIATES | EXAMPLE STRUCTURE/NAME | Characterization, LC/MS |
|---|---|---|---|
| 89 | 24, 65 | (S)-3-(9-(2-hydroxy-2-(tetrazolo[1,5-a]quinolin-7-yl)ethyl)-3,9-diazaspiro[5.5]undecan-3-yl)-4-methylcyclobut-3-ene-1,2-dione; slow eluting isomer from chiral SFC separation using CHIRALPAK AS-H column | [M + 1]+: 461 |

Example 90

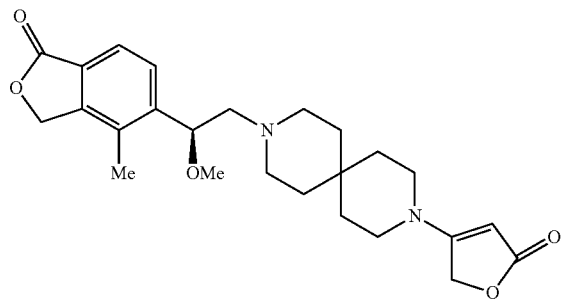 [SMILES: CO[C@H](CN1CCC2(CC1)CCN(C1=CC(=O)OC1)CC2)c1ccc2c(c1C)COC2=O]

(S)-5-(1-methoxy-2-(9-(5-oxo-2,5-dihydrofuran-3-yl)-3,9-diazaspiro[5.5]undecan-3-yl)ethyl)-4-methyl-isobenzofuran-1(3H)-one Step A: (R)-5-(1-chloro-2-(9-(5-oxo-2,5-dihydro-furan-3-yl)-3,9-diazaspiro[5.5]undecan-3-yl)ethyl)-4-methylisobenzofuran-1(3H)-one To a solution of (S)-5-(1-hydroxy-2-(9-(5-oxo-2,5-dihydrofuran-3-yl)-3,9-diazaspiro[5.5]undecan-3-yl)ethyl)-4-methylisobenzofuran-1(3H)-one (EXAMPLE 5, 0.41 g, 0.961 mmol) and methanesulfonyl chloride (0.090 ml, 1.154 mmol) in DCM (30 mL) was added TEA (0.161 ml, 1.154 mmol) and DMAP (0.012 g, 0.096 mmol) at −10 to −15° C. (ice-NaCl bath). The mixture was stirred at the same temperature for 20 min, and quenched with NH$_4$Cl aqueous. The organic layer was separated and the aqueous was extracted with DCM (30 ml). The combined organic layers were dried (MgSO$_4$) and concentrated. The residue was directly used in the next step. LC/MS: 445.17 [M+1]+.

Step B: (S)-5-(1-methoxy-2-(9-(5-oxo-2,5-dihydro-furan-3-yl)-3,9-diazaspiro[5.5]undecan-3-yl)ethyl)-4-methylisobenzofuran-1(3H)-one (R)-5-(1-Chloro-2-(9-(5-oxo-2,5-dihydrofuran-3-yl)-3,9-diazaspiro[5.5]undecan-3-yl)ethyl)-4-methylisobenzofuran-1(3H)-one (0.06 g, 0.135 mmol) and N,N-diisopropylethyl-amine (0.115 ml, 0.674 mmol) in methanol (5.46 µl, 0.135 mmol) were stirred overnight. LCMS showed a mixture of the desired compound and starting material. The desired compound was isolated by Reverse Phase (RP) chromatography GILSON (Middleton, Wis.) (5-65% water CH$_3$CN with 1% TFA). The TFA salt was converted to a free base by BOND ELUT SCX column eluted out with 1N NH$_3$ in methanol (~10 ml). The solution was concentrated to give the title compound as a free base. LC-MS: 441.15 [M+1]+.

Example 91

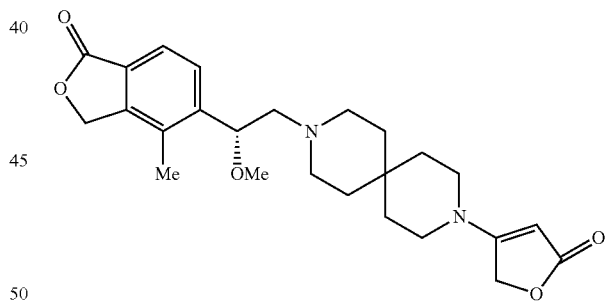

(R)-5-(1-methoxy-2-(9-(5-oxo-2,5-dihydrofuran-3-yl)-3,9-diazaspiro[5.5]undecan-3-yl)ethyl)-4-methyl-isobenzofuran-1(3H)-one (R)-5-(1-methoxy-2-(9-(5-oxo-2,5-dihydrofuran-3-yl)-3,9-diazaspiro[5.5]undecan-3-yl)ethyl)-4-methylisobenzofuran-1(3H)-one was prepared from (R)-5-(1-hydroxy-2-(9-(5-oxo-2,5-dihydrofuran-3-yl)-3,9-diazaspiro[5.5]undecan-3-yl)ethyl)-4-methylisobenzofuran-1(3H)-one (EXAMPLE 8) following the same procedure as described above. LC-MS: 441.18 [M+1]+.

Example 92

5-((1R)-2-(9-(2-ethoxy-5-oxo-2,5-dihydrofuran-3-yl)-3,9-diazaspiro[5.5]undecan-3-yl)-1-hydroxy-ethyl)-4-methylisobenzofuran-1(3H)-one

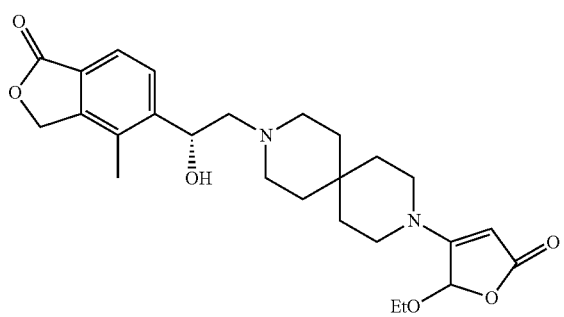 [SMILES: CCOC1OC(=O)C=C1N1CCC2(CCN(C[C@H](O)c3ccc4c(c3C)COC4=O)CC2)CC1]

To 4-bromo-5-ethoxyfuran-2(5H)-one (24.04 mg, 0.116 mmol) in THF (0.6 mL) was added Hunig's base (40.6 μL, 0.232 mmol) and (R)-5-(1-hydroxy-2-(3,9-diazaspiro[5.5]undecan-3-yl)ethyl)-4-methylisobenzofuran-1(3H)-one (INTERMEDIATE 45, 40 mg, 0.116 mmol). The reaction mixture was stirred at 76° C. overnight. The reaction mixture was concentrated, and purified by PTLC (5% MeOH/DCM) to give the title compound. LC/MS: [(M+1)]$^+$=471

The following compounds were prepared in an analogous fashion to EXAMPLE 92 starting from piperidine and other intermediates prepared as described above.

| EXAMPLE | INTERMEDIATES | EXAMPLE STRUCTURE/NAME | Characterization, LC/MS |
|---|---|---|---|
| 93 | 45, 32 | (R)-5-(1-hydroxy-2-(9-(6-oxo-3,6-dihydro-2H-pyran-4-yl)-3,9-diazaspiro[5.5]undecan-3-yl)ethyl)-4-methylisobenzofuran-1(3H)-one | [M + 1]$^+$: 441 |
| 94 | 47, 31 | 5-((R)-1-hydroxy-2-((R)-7-hydroxy-9-(4-methyl-5-oxo-2,5-dihydrofuran-3-yl)-3,9-diazaspiro[5.5]undecan-3-yl)ethyl)-4-methylisobenzofuran-1(3H)-one; fast eluting isomer from chiral SFC separation using CHIRALPAK AD-3 column | [M + 1]$^+$: 457 |

| EXAMPLE | INTERMEDIATES | EXAMPLE STRUCTURE/NAME | Characterization, LC/MS |
|---|---|---|---|
| 95 | 48, 31 | 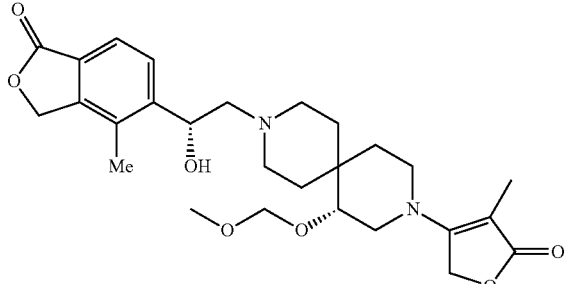
5-((R)-1-hydroxy-2-((R)-7-(methoxymethoxy)-9-(4-methyl-5-oxo-2,5-dihydrofuran-3-yl)-3,9-diazaspiro[5.5]undecan-3-yl)ethyl)-4-methylisobenzofuran-1(3H)-one; fast eluting isomer from chiral SFC separation using CHIRALPAK AS-H column | [M + 1]+: 501 |
| 96 | 48, 31 | 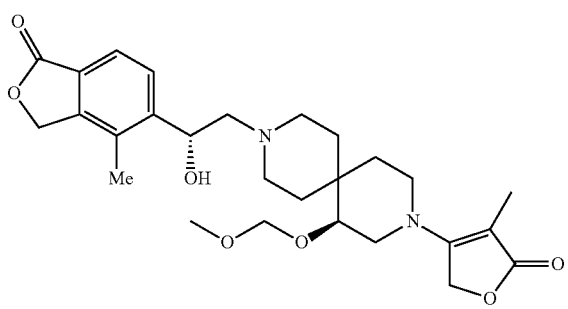
5-((R)-1-hydroxy-2-((S)-7-(methoxymethoxy)-9-(4-methyl-5-oxo-2,5-dihydrofuran-3-yl)-3,9-diazaspiro[5.5]undecan-3-yl)ethyl)-4-methylisobenzofuran-1(3H)-one; slow eluting isomer from chiral SFC separation using CHIRALPAK AS-H column | [M + 1]+: 501 |
| 97 | 49, 31 | 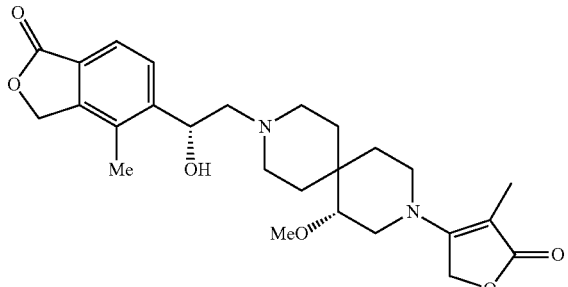
5-((R)-1-hydroxy-2-((R)-7-methoxy-9-(4-methyl-5-oxo-2,5-dihydrofuran-3-yl)-3,9-diazaspiro[5.5]undecan-3-yl)ethyl)-4-methylisobenzofuran-1(3H)-one; fast eluting isomer from chiral SFC separation using CHIRALPAK AD-H column | [M + 1]+: 471 |

| EXAMPLE | INTERMEDIATES | EXAMPLE STRUCTURE/NAME | Characterization, LC/MS |
|---------|---------------|------------------------|--------------------------|
| 98 | 49, 31 | 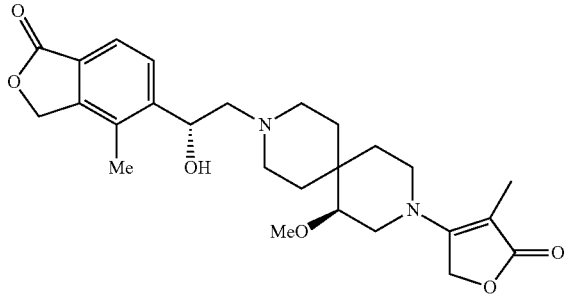 5-((R)-1-hydroxy-2-((S)-7-methoxy-9-(4-methyl-5-oxo-2,5-dihydrofuran-3-yl)-3,9-diazaspiro[5.5]undecan-3-yl)ethyl)-4-methylisobenzofuran-1(3H)-one; slow eluting isomer from chiral SFC separation using CHIRALPAK AD-H column | [M + 1]⁺: 471 |

Example 99

4-(9-(2-(6-(1H-tetrazol-1-yl)pyridin-3-yl)acetyl)-3,9-diazaspiro[5.5]undecan-3-yl)furan-2(5H)-one

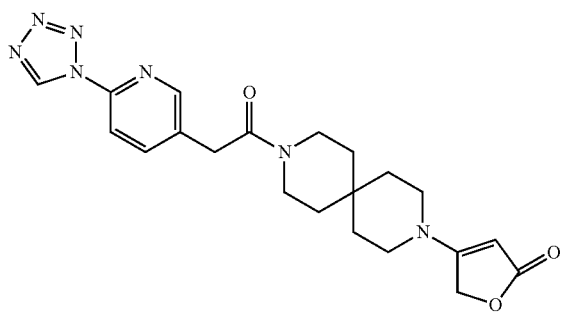 [SMILES: O=C1C=C(N2CCC3(CCN(C(=O)Cc4ccc(-n5cnnn5)nc4)CC3)CC2)CO1]

4-(3,9-Diazaspiro[5.5]undecan-3-yl)furan-2(5H)-one (INTERMEDIATE 50, 15 mg, 0.055 mmol), [6-(1H-tetrazol-1-yl)pyridin-3-yl]acetic acid (INTERMEDIATE 40, 12.4 mg, 0.060 mmol), HATU (25.09 mg, 0.066 mmol), and DIEA (0.029 ml, 0.165 mmol) were mixed in DMF. The mixture was stirred at rt for 2 h, and purified with reverse phase prep HPLC (10 to 100% ACN/Water, both containing 0.1% TFA) to afford the title compound. LC-MS (IE, m/z): 424.09 (M+1)⁺.

The following compounds were prepared in an analogous fashion to EXAMPLE 99 starting with 4-(3,9-Diazaspiro[5.5]undecan-3-yl)furan-2(5H)-one (INTERMEDIATE 50) and noted acid intermediates described above.

| EXAMPLE | INTERMEDIATES | EXAMPLE STRUCTURE/NAME | Characterization LC/MS [M + 1]⁺ |
|---------|---------------|------------------------|----------------------------------|
| 100 | 50, 39 | 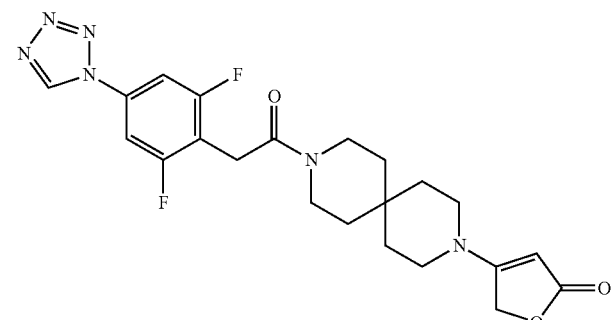 4-(9-(2-(2,6-difluoro-4-(1H-tetrazol-1-yl)phenyl)acetyl)-3,9-diazaspiro[5.5]undecan-3-yl)furan-2(5H)-one | 459.13 |

-continued

| EXAMPLE | INTERMEDIATES | EXAMPLE STRUCTURE/NAME | Characterization LC/MS [M + 1]+ |
|---|---|---|---|
| 101 | 50, 41 | 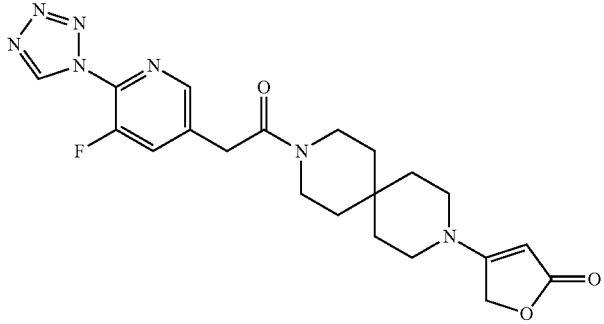<br>4-(9-(2-(5-fluoro-6-(1H-tetrazol-1-yl)pyridin-3-yl)acetyl)-3,9-diazaspiro[5.5]undecan-3-yl)furan-2(5H)-one | 442.09 |
| 102 | 50, 36 | 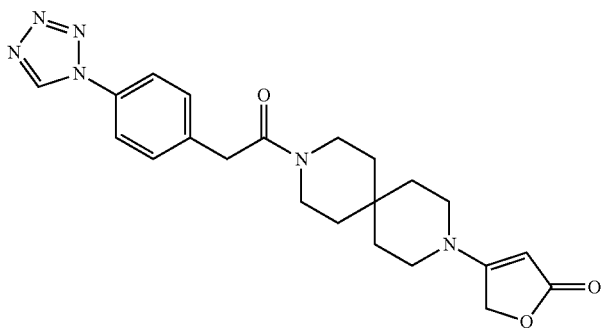<br>4-(9-(2-(4-(1H-tetrazol-1-yl)phenyl)acetyl)-3,9-diazaspiro[5.5]undecan-3-yl)furan-2(5H)-one | 423.16 |
| 103 | 50, 43 | 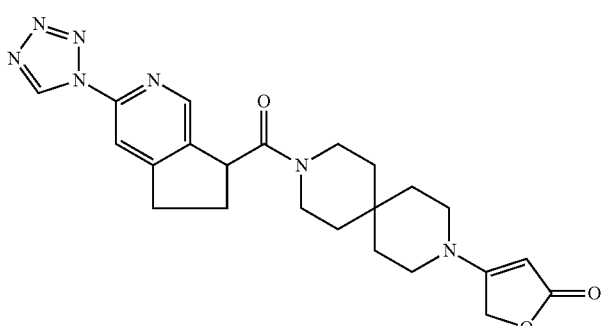<br>4-(9-(3-(1H-tetrazol-1-yl)-6,7-dihydro-5H-cyclopenta[c]pyridine-7-carbonyl)-3,9-diazaspiro[5.5]undecan-3-yl)furan-2(5H)-one | 450.13 |
| 104 | 50, 37 | 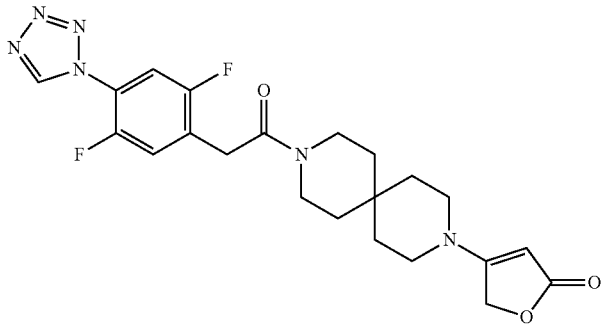<br>4-(9-(2-(2,5-difluoro-4-(1H-tetrazol-1-yl)phenyl)acetyl)-3,9-diazaspiro[5.5]undecan-3-yl)furan-2(5H)-one | 459.2 |

-continued

| EXAMPLE | INTERMEDIATES | EXAMPLE STRUCTURE/NAME | Characterization LC/MS [M + 1]+ |
|---|---|---|---|
| 105 | 50, 44 | 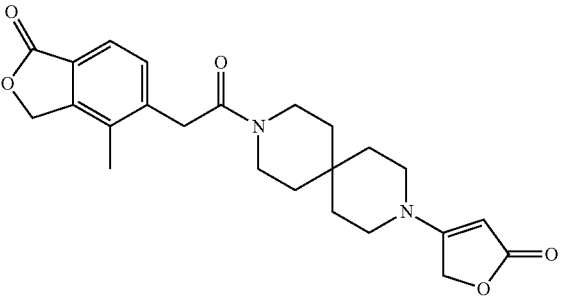<br>4-methyl-5-(2-oxo-2-(9-(5-oxo-2,5-dihydrofuran-3-yl)-3,9-diazaspiro[5.5]undecan-3-yl)ethyl)isobenzofuran-1(3H)-one | 425.17 |
| 106 | 50, 42 | 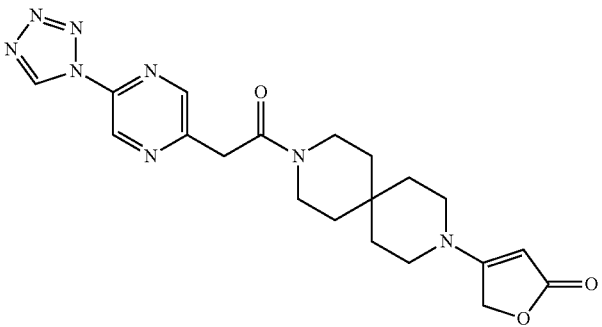<br>4-(9-(2-(5-(1H-tetrazol-1-yl)pyrazin-2-yl)acetyl)-3,9-diazaspiro[5.5]undecan-3-yl)furan-2(5H)-one | 425.16 |

Thallium Flux Assay

A Thallium Flux Assay was performed on each of the final product compounds in the Examples. When the final product of an Example was an HCl salt, the salt was run in the Assay. This assay has been described previously; see, e.g., PCT Published Application WO 2013/062900.

Data collected for compounds in the Examples of the present invention using the Thallium Flux Assay are shown in Table 10 below. All of the tested final product compounds in the Examples (diastereomeric mixtures and individual diastereomers) had $IC_{50}$ potencies less than 1 µM in the Thallium Flux Assay.

TABLE 10

| Example No. | Thallium Flux $IC_{50}$ (µM) |
|---|---|
| 1 | 0.017 |
| 2 | 0.031 |
| 3 | 0.093 |
| 4 | 0.23 |
| 5 | 0.063 |
| 6 | 0.022(6A) |
|   | 0.020(6B) |
| 7 | 0.013 |
| 8 | 0.049 |
| 9 | 0.220 |
| 10 | 0.596 |
| 11 | 0.180 |
| 12 | 0.685 |
| 13 | 0.014 |

TABLE 10-continued

| Example No. | Thallium Flux $IC_{50}$ (µM) |
|---|---|
| 14 | 0.024 |
| 15 | 0.443 |
| 16 | 0.041 |
| 17 | 0.091 |
| 18 | 0.016 |
| 19 | 0.074 |
| 20 | 0.098 |
| 21 | 0.181 |
| 22 | 0.017 |
| 23 | 0.028 |
| 24 | 0.040 |
| 25 | 0.022 |
| 26 | 0.048 |
| 27 | 0.433 |
| 28 | 0.552 |
| 29 | 0.33 |
| 30 | 0.171 |
| 31 | 0.065 |
| 32 | 0.049 |
| 33 | 0.042 |
| 34 | 0.275 |
| 35 | 0.236 |
| 36 | 0.115 |
| 37 | 0.140 |
| 38 | 0.007 |
| 39 | 0.011 |
| 40 | 0.005 |
| 41 | 0.168 |
| 42 | 0.352 |
| 43 | 0.016 |
| 44 | 0.017 |

TABLE 10-continued

| Example No. | Thallium Flux IC$_{50}$ (μM) |
|---|---|
| 45 | 0.016 |
| 46 | 0.038 |
| 47 | 0.013 |
| 48 | 0.019 |
| 49 | 0.016 |
| 50 | 0.016 |
| 51 | 0.070 |
| 52 | 0.037 |
| 53 | 0.014 |
| 54 | 0.008 |
| 55 | 0.011 |
| 56 | 0.011 |
| 57 | 0.232 |
| 58 | 0.256 |
| 59 | 0.022 |
| 60 | 0.032 |
| 61 | 0.033 |
| 62 | 0.039 |
| 63 | 0.196 |
| 64 | 0.117 |
| 65 | 0.109 |
| 66 | 0.110 |
| 67 | 0.305 |
| 68 | 0.185 |
| 69 | 0.634 |
| 70 | 0.049 |
| 71 | 0.243 |
| 72 | 0.439 |
| 73 | 0.179 |
| 74 | 0.069 |
| 75 | 0.279 |
| 76 | 0.109 |
| 77 | 0.140 |
| 78 | 0.030 |
| 79 | 0.11 |
| 80 | 0.141 |
| 81 | 0.015 |
| 82 | 0.034 |
| 83 | 0.317 |
| 84 | 0.765 |
| 85 | 0.08 |
| 86 | 0.336 |
| 87 | 0.688 |
| 88 | 0.223 |
| 89 | 0.257 |
| 90 | 0.165 |
| 91 | 0.198 |
| 92 | 0.539 |
| 93 | 0.146 |
| 94 | 0.639 |
| 95 | 0.114 |
| 96 | 0.132 |
| 97 | 0.042 |
| 98 | 0.053 |
| 99 | 0.109 |
| 100 | 0.408 |
| 101 | 0.246 |
| 102 | 0.116 |
| 103 | 0.132 |
| 104 | 0.115 |
| 105 | 0.483 |
| 106 | 0.379 |

While the invention has been described with reference to certain particular embodiments thereof, numerous alternative embodiments will be apparent to those skilled in the art from the teachings described herein. The scope of the claims should not be limited by the preferred embodiments set forth in the examples, but should be given the broadest interpretation consistent with the description as a whole. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

What is claimed is:

1. A compound of the formula I:

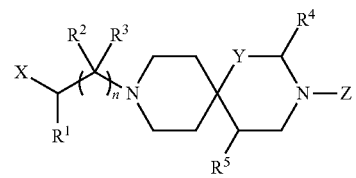

or a pharmaceutically acceptable salt thereof, wherein:

X is

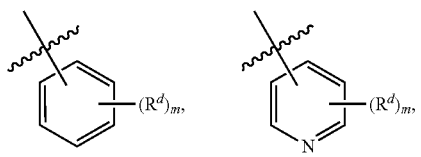

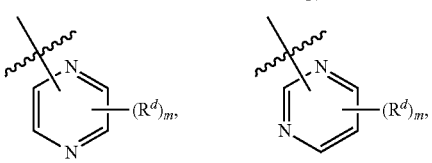

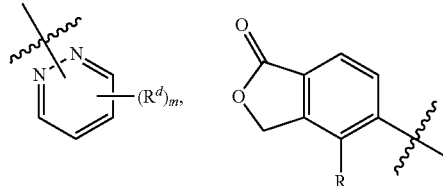

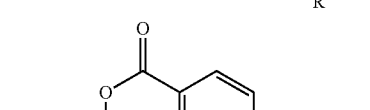

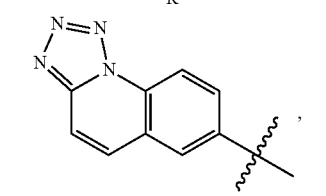

R is H, or $C_{1-6}$alkyl, wherein alkyl substituents are further optionally substituted with 1-4 halogen substituents, R' is H, or $C_{1-6}$alkyl, wherein alkyl substituents are further optionally substituted with 1-4 halogen substituents, R$^1$ is OH, H, $C_{1-6}$alkyl, $OC_{1-6}$alkyl, $CH_2OH$, or $C_{1-6}$alkylO$C_{1-6}$alkyl, wherein alkyl substituents are further optionally substituted with 1-4 halogen substituents, or

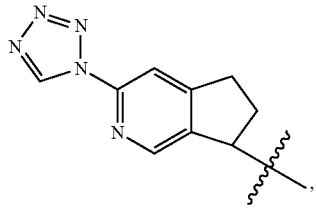 [SMILES: *C1CCc2cc(-n3cnnn3)ncc21]

X and R¹ together form
m is 0, 1, 2, 3, or 4,
n is 0, or 1,
R² and R³ are each independently H or $C_{1-6}$alkyl, wherein alkyl substituents are further optionally substituted with 1-4 halogen substituents, or R² and R³ together form oxo,
Y is $CH_2$ or O,
R⁴ is H, $C_{1-6}$alkyl, or oxo, wherein alkyl substituents are further optionally substituted with 1-4 halogen substituents,
R⁵ is H, OH, $C_{1-6}$alkyl, $OC_{1-6}$alkyl, $OC_{1-6}$alkyl $OC_{1-6}$alkyl, or halo, wherein alkyl substituents are further optionally substituted with 1-4 halogen substituents,
Z is

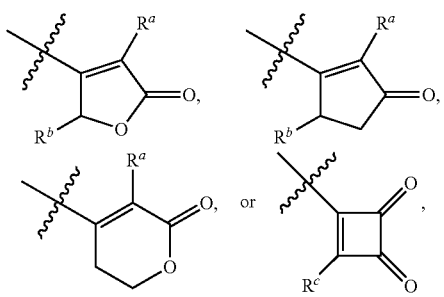

$R^a$ is H, F, Cl, $CH_3$, cyclopropyl, phenyl, or pyridyl, wherein $CH_3$, cyclopropyl, phenyl, or pyridyl substituents are further optionally substituted with 1-3 halogen substituents,
$R^b$ is H, $C_{1-6}$alkyl, or $OC_{1-6}$alkyl, wherein alkyl substituents are further optionally substituted with 1-4 halogen substituents,
$R^c$ is $C_{1-6}$alkyl, or 3-to 6-membered cycloalkyl, wherein alkyl or cycloalkyl substituents are further optionally substituted with 1-4 halogen substituents, and
each $R^d$ is independently halo, $C_{1-6}$alkyl, tetrazolyl, CN, or $OC_{1-6}$ alkyl, wherein alkyl substituents are further optionally substituted with 1-4 halogen substituents.

2. The compound of claim 1 or a pharmaceutically acceptable salt thereof, wherein:
X is

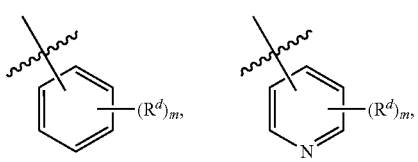

-continued

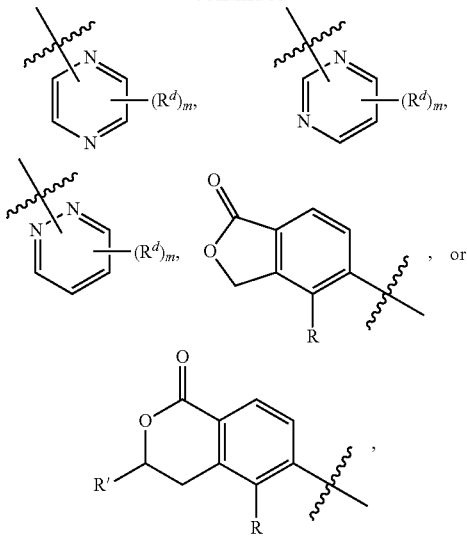

and
R¹ is OH, H, $C_{1-6}$alkyl, $OC_{1-6}$ alkyl, $CH_2OH$, or $C_{1-6}$alkyl$OC_{1-6}$alkyl, wherein alkyl substituents are further optionally substituted with 1-4 halogen substituents, and $R^d$, m, R and R' are as defined in claim 1.

3. The compound of claim 1, or a pharmaceutically acceptable salt thereof, wherein R and R' are independently H or $CH_3$.

4. The compound of claim 1, or a pharmaceutically acceptable salt thereof, wherein m is 1, or 2.

5. The compound of claim 1, or a pharmaceutically acceptable salt thereof, wherein n is 1.

6. The compound of claim 1, or a pharmaceutically acceptable salt thereof, wherein R² and R³ are each H, or R² and R³ together form oxo.

7. The compound of claim 1, or a pharmaceutically acceptable salt thereof, wherein Y is $CH_2$.

8. The compound of claim 1, or a pharmaceutically acceptable salt thereof, wherein $R^c$ is $CH_3$, $CH_2CH_3$, or cyclopropyl.

9. The compound of claim 1, or a pharmaceutically acceptable salt thereof, wherein:
Z is

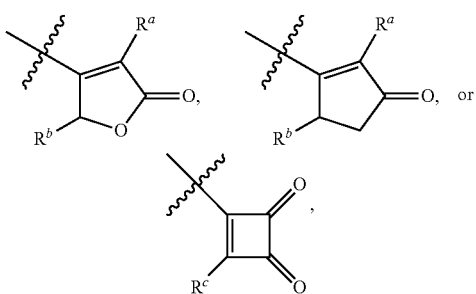

$R^a$, $R^b$ and $R^c$ are as defined in claim 1.

10. The compound of claim 1, or a pharmaceutically acceptable salt thereof, wherein $R^b$ is H, $CH_3$, or $OCH_2CH_3$.

11. The compound of claim 1, or a pharmaceutically acceptable salt thereof, wherein:
m is 1,
n is 1, R¹ is OH,
R², R³, R⁴, and R⁵ are each independently is H,
Rᵈ is tetrazolyl, and
Y is CH₂.

12. A compound which is:
5-{2-[9-(5-oxo-2,5-dihydrofuran-3-yl)-3,9-diazaspiro [5.5]undec-3-yl]ethyl}-2-benzofuran-1(3H)-one;
4-methyl-5-{2-[9-(5-oxo-2,5-dihydrofuran-3-yl)-3,9-diazaspiro[5.5]undec-3-yl]ethyl}-2-benzofuran-1(3H)-one;
3-methyl-4-(9-(2-(4-methyl-1-oxo-1,3-dihydroisobenzofuran-5-yl)ethyl)-3,9-diazaspiro[5.5]undecan-3-yl)cyclobut-3-ene-1,2-dione;
(R)-3-(9-(2-methoxy-2-(4-methyl-1-oxo-1,3-dihydroisobenzofuran-5-yl)ethyl)-3,9-diazaspiro[5.5]undecan-3-yl)-4-methylcyclobut-3-ene-1,2-dione;
5-{(1S)-1-hydroxy-2-[9-(5-oxo-2,5-dihydrofuran-3-yl)-3,9-diazaspiro[5.5]undec-3-yl]ethyl}-4-methyl-2-benzofuran-1(3H)-one;
4-(9-{(2S)-2-hydroxy-2-[6-(1H-tetrazol-1-yl)pyridin-2-yl]ethyl}-3,9-diazaspiro[5.5]undec-3-yl)-3-methylfuran-2(5H)-one;
4-(9-{(2R)-2-hydroxy-2-[6-(1H-tetrazol-1-yl)pyridin-2-yl]ethyl}-3,9-diazaspiro[5.5]undec-3-yl)-3-methylfuran-2(5H)-one;
5-{(1R)-1-hydroxy-2-[9-(4-methyl-5-oxo-2,5-dihydrofuran-3-yl)-3,9-diazaspiro[5.5]undec-3-yl]ethyl}-4-methyl-2-benzofuran-1(3H)-one;
5-{(1R)-1-hydroxy-2-[9-(5-oxo-2,5-dihydrofuran-3-yl)-3,9-diazaspiro[5.5]undec-3-yl]ethyl}-4-methyl-2-benzofuran-1(3H)-one;
6-{(1S)-1-hydroxy-2-[9-(5-oxo-2,5-dihydrofuran-3-yl)-3,9-diazaspiro[5.5]undec-3-yl]ethyl}-4-methoxypyridine-3-carbonitrile;
(3R)-6-{1-hydroxy-2-[9-(5-oxo-2,5-dihydrofuran-3-yl)-3,9-diazaspiro[5.5]undec-3-yl]ethyl}-3-methyl-3,4-dihydro-1H-isochromen-1-one;
(3S)-6-{(1R)-1-hydroxy-2-[9-(5-oxo-2,5-dihydrofuran-3-yl)-3,9-diazaspiro[5.5]undec-3-yl]ethyl}-3-methyl-3,4-dihydro-1H-isochromen-1-one;
(3S)-6-{(1S)-1-hydroxy-2-[9-(5-oxo-2,5-dihydrofuran-3-yl)-3,9-diazaspiro[5.5]undec-3-yl]ethyl}-3-methyl-3,4-dihydro-1H-isochromen-1-one;
4-(9-{(2R)-2-hydroxy-2-[2-methyl-6-(1H-tetrazol-1-yl)pyridin-3-yl]ethyl}-3,9-diazaspiro[5.5]undec-3-yl)furan-2(5H)-one;
4-(9-{(2S)-2-hydroxy-2-[2-methyl-6-(1H-tetrazol-1-yl)pyridin-3-yl]ethyl}-3,9-diazaspiro[5.5]undec-3-yl)furan-2(5H)-one;
4-(9-{2-hydroxy-2-[2-(1H-tetrazol-1-yl)pyrimidin-5-yl]ethyl}-3,9-diazaspiro[5.5]undec-3-yl)furan-2(5H)-one;
4-(9-{(2S)-2-hydroxy-2-[6-(1H-tetrazol-1-yl)pyridazin-3-yl]ethyl}-3,9-diazaspiro[5.5]undec-3-yl)furan-2 (5H)-one;
4-(9-{(2R)-2-hydroxy-2-[6-(1H-tetrazol-1-yl)pyridazin-3-yl]ethyl}-3,9-diazaspiro[5.5]undec-3-yl)furan-2 (5H)-one;
4-(9-{(2R)-2-hydroxy-2-[6-(1H-tetrazol-1-yl)pyridin-3-yl]ethyl}-3,9-diazaspiro[5.5]undec-3-yl)furan-2(5H)-one;
4-(9-{(2S)-2-hydroxy-2-[6-(1H-tetrazol-1-yl)pyridin-3-yl]ethyl}-3,9-diazaspiro[5.5]undec-3-yl)furan-2(5H)-one;
4-(9-{(2S)-2-hydroxy-2-[3-methyl-5-(1H-tetrazol-1-yl)pyridin-2-yl]ethyl}-3,9-diazaspiro[5.5]undec-3-yl)furan-2(5H)-one;
4-(9-{(2R)-2-hydroxy-2-[3-methyl-5-(1H-tetrazol-1-yl)pyridin-2-yl]ethyl}-3,9-diazaspiro[5.5]undec-3-yl)furan-2(5H)-one;
4-(9-{(2R)-2-[2-fluoro-4-(1H-tetrazol-1-yl)phenyl]-2-hydroxyethyl}-3,9-diazaspiro[5.5]undec-3-yl)furan-2(5H)-one;
4-(9-{(2S)-2-[2-fluoro-4-(1H-tetrazol-1-yl)phenyl]-2-hydroxyethyl}-3,9-diazaspiro[5.5]undec-3-yl)furan-2(5H)-one;
4-(9-{(2R)-2-hydroxy-2-[2-methyl-4-(1H-tetrazol-1-yl)phenyl]ethyl}-3,9-diazaspiro[5.5]undec-3-yl)furan-2(5H)-one;
4-(9-{(2S)-2-hydroxy-2-[2-methyl-4-(1H-tetrazol-1-yl)phenyl]ethyl}-3,9-diazaspiro[5.5]undec-3-yl)furan-2(5H)-one;
9-{(2R)-2-hydroxy-2-[2-methyl-6-(1H-tetrazol-1-yl)pyridin-3-yl]ethyl}-3-(5-oxo-2,5-dihydrofuran-3-yl)-3,9-diazaspiro[5.5]undecan-2-one;
9-[(2R)-2-hydroxy-2-(4-methyl-1-oxo-1,3-dihydro-2-benzofuran-5-yl)ethyl]-3-(5-oxo-2,5-dihydrofuran-3-yl)-3,9-diazaspiro[5.5]undecan-2-one;
9-[(2R)-2-hydroxy-2-(4-methyl-1-oxo-1,3-dihydro-2-benzofuran-5-yl)ethyl]-3-(4-methyl-5-oxo-2,5-dihydrofuran-3-yl)-3,9-diazaspiro[5.5]undecan-2-one;
9-{(2R)-2-hydroxy-2-[2-methyl-6-(1H-tetrazol-1-yl)pyridin-3-yl]ethyl}-3-(4-methyl-5-oxo-2,5-dihydrofuran-3-yl)-3,9-diazaspiro[5.5]undecan-2-one;
(R)-9-(2-(6-(1H-tetrazol-1-yl)pyridin-3-yl)-2-hydroxyethyl)-3-(5-oxo-2,5-dihydrofuran-3-yl)-1-oxa-3,9-diazaspiro[5.5]undecan-2-one;
(R)-9-(2-hydroxy-2-(2-methyl-6-(1H-tetrazol-1-yl)pyridin-3-yl)ethyl)-3-(5-oxo-2,5-dihydrofuran-3-yl)-1-oxa-3,9-diazaspiro[5.5]undecan-2-one;
5-{(1R)-1-hydroxy-2-[8-methyl-9-(5-oxo-2,5-dihydrofuran-3-yl)-3,9-diazaspiro[5.5]undec-3-yl]ethyl}-4-methyl-2-benzofuran-1(3H)-one;
5-{(1R)-1-hydroxy-2-[8-methyl-9-(5-oxo-2,5-dihydrofuran-3-yl)-3,9-diazaspiro[5.5]undec-3-yl]ethyl}-4-methyl-2-benzofuran-1(3H)-one;
5-{(1R)-2-[(7R)-7-fluoro-9-(4-methyl-5-oxo-2,5-dihydrofuran-3-yl)-3,9-diazaspiro[5.5]undec-3-yl]-1-hydroxyethyl}-4-methyl-2-benzofuran-1(3H)-one;
5-{(1R)-2-[(7S)-7-fluoro-9-(4-methyl-5-oxo-2,5-dihydrofuran-3-yl)-3,9-diazaspiro[5.5]undec-3-yl]-1-hydroxyethyl}-4-methyl-2-benzofuran-1(3H)-one;
4-{9-[2-(4-bromophenyl)-2-hydroxyethyl]-3,9-diazaspiro [5.5]undec-3-yl}-3-methylfuran-2(5H)-one;
5-{(1R)-1-hydroxy-2-[9-(2-methyl-5-oxo-2,5-dihydrofuran-3-yl)-3,9-diazaspiro[5.5]undec-3-yl]ethyl}-4-methyl-2-benzofuran-1(3H)-one;
5-{(1R)-2-[9-(4-fluoro-5-oxo-2,5-dihydrofuran-3-yl)-3,9-diazaspiro[5.5]undec-3-yl]-1-hydroxyethyl}-4-methyl-2-benzofuran-1(3H)-one;
3-fluoro-4-(9-{(2R)-2-hydroxy-2-[2-methyl-6-(1H-tetrazol-1-yl)pyridin-3-yl]ethyl}-3,9-diazaspiro[5.5]undec-3-yl)furan-2(5H)-one;
5-{(1R)-2-[9-(4-chloro-5-oxo-2,5-dihydrofuran-3-yl)-3,9-diazaspiro[5.5]undec-3-yl]-1-hydroxyethyl}-4-methyl-2-benzofuran-1(3H)-one;
5-{(1R)-1-hydroxy-2-[9-(5-oxo-4-phenyl-2,5-dihydrofuran-3-yl)-3,9-diazaspiro[5.5]undec-3-yl]ethyl}-4-methyl-2-benzofuran-1(3H)-one;
5-{(1R)-1-hydroxy-2-[9-(5-oxo-4-pyridin-4-yl-2,5-dihydrofuran-3-yl)-3,9-diazaspiro[5.5]undec-3-yl]ethyl}-4-methyl-2-benzofuran-1(3H)-one;

3-cyclopropyl-4-(9-{2-hydroxy-2-[2-methyl-6-(1H-tetrazol-1-yl)pyridin-3-yl]ethyl}-3,9-diazaspiro[5.5]undec-3-yl)furan-2(5H)-one;

5-{(1R)-2-[9-(4-cyclopropyl-5-oxo-2,5-dihydrofuran-3-yl)-3,9-diazaspiro[5.5]undec-3-yl]-1-hydroxyethyl}-4-methyl-2-benzofuran-1(3H)-one;

4-(9-{(2R)-2-hydroxy-2-[2-methyl-6-(1H-tetrazol-1-yl)pyridin-3-yl]ethyl}-3,9-diazaspiro[5.5]undec-3-yl)-3-methylfuran-2(5H)-one;

4-(9-{(2S)-2-hydroxy-2-[2-methyl-6-(1H-tetrazol-1-yl)pyridin-3-yl]ethyl}-3,9-diazaspiro[5.5]undec-3-yl)-3-methylfuran-2(5H)-one;

4-(9-{(2R)-2-hydroxy-2-[6-(1H-tetrazol-1-yl)pyridin-3-yl]ethyl}-3,9-diazaspiro[5.5]undec-3-yl)-3-methylfuran-2(5H)-one;

4-(9-{(2S)-2-hydroxy-2-[6-(1H-tetrazol-1-yl)pyridin-3-yl]ethyl}-3,9-diazaspiro[5.5]undec-3-yl)-3-methylfuran-2(5H)-one;

4-(9-{(2R)-2-hydroxy-2-[4-(1H-tetrazol-1-yl)phenyl]ethyl}-3,9-diazaspiro[5.5]undec-3-yl)-3-methylfuran-2(5H)-one;

4-(9-{(2S)-2-hydroxy-2-[4-(1H-tetrazol-1-yl)phenyl]ethyl}-3,9-diazaspiro[5.5]undec-3-yl)-3-methylfuran-2(5H)-one;

4-(9-{(2S)-2-hydroxy-2-[5-(1H-tetrazol-1-yl)pyridin-2-yl]ethyl}-3,9-diazaspiro[5.5]undec-3-yl)-3-methylfuran-2(5H)-one;

4-(9-{(2R)-2-hydroxy-2-[5-(1H-tetrazol-1-yl)pyridin-2-yl]ethyl}-3,9-diazaspiro[5.5]undec-3-yl)-3-methylfuran-2(5H)-one;

4-(9-{2-[2-fluoro-4-(1H-tetrazol-1-yl)phenyl]-2-hydroxyethyl}-3,9-diazaspiro[5.5]undec-3-yl)-3-methylfuran-2(5H)-one;

4-(9-{2-[2-fluoro-4-(1H-tetrazol-1-yl)phenyl]-2-hydroxyethyl}-3,9-diazaspiro[5.5]undec-3-yl)-3-methylfuran-2(5H)-one;

4-(9-{2-hydroxy-2-[2-methyl-4-(1H-tetrazol-1-yl)phenyl]ethyl}-3,9-diazaspiro[5.5]undec-3-yl)-3-methylfuran-2(5H)-one;

4-(9-{2-hydroxy-2-[2-methyl-4-(1H-tetrazol-1-yl)phenyl]ethyl}-3,9-diazaspiro[5.5]undec-3-yl)-3-methylfuran-2(5H)-one;

4-(9-{2-hydroxy-1-[2-methyl-4-(1H-tetrazol-1-yl)phenyl]ethyl}-3,9-diazaspiro[5.5]undec-3-yl)-3-methylfuran-2(5H)-one;

4-(9-{2-hydroxy-1-[2-methyl-4-(1H-tetrazol-1-yl)phenyl]ethyl}-3,9-diazaspiro[5.5]undec-3-yl)-3-methylfuran-2(5H)-one;

4-(9-{(2R)-2-hydroxy-2-[3-(1H-tetrazol-1-yl)phenyl]ethyl}-3,9-diazaspiro[5.5]undec-3-yl)-3-methylfuran-2(5H)-one;

4-(9-{(2S)-2-hydroxy-2-[3-(1H-tetrazol-1-yl)phenyl]ethyl}-3,9-diazaspiro[5.5]undec-3-yl)-3-methylfuran-2(5H)-one;

4-(9-{(2R)-2-hydroxy-2-[2-(1H-tetrazol-1-yl)pyridin-4-yl]ethyl}-3,9-diazaspiro[5.5]undec-3-yl)-3-methylfuran-2(5H)-one;

4-(9-{(2S)-2-hydroxy-2-[2-(1H-tetrazol-1-yl)pyridin-4-yl]ethyl}-3,9-diazaspiro[5.5]undec-3-yl)-3-methylfuran-2(5H)-one;

4-(9-{(2R)-2-hydroxy-2-[5-(1H-tetrazol-1-yl)pyridin-3-yl]ethyl}-3,9-diazaspiro[5.5]undec-3-yl)-3-methylfuran-2(5H)-one;

4-(9-{(2S)-2-hydroxy-2-[5-(1H-tetrazol-1-yl)pyridin-3-yl]ethyl}-3,9-diazaspiro[5.5]undec-3-yl)-3-methylfuran-2(5H)-one;

4-(9-{(2S)-2-hydroxy-2-[6-(1H-tetrazol-1-yl)pyrazin-2-yl]ethyl}-3,9-diazaspiro[5.5]undec-3-yl)-3-methylfuran-2(5H)-one;

4-(9-{(2R)-2-hydroxy-2-[6-(1H-tetrazol-1-yl)pyrazin-2-yl]ethyl}-3,9-diazaspiro[5.5]undec-3-yl)-3-methylfuran-2(5H)-one;

4-(9-{(2S)-2-hydroxy-2-[4-(1H-tetrazol-1-yl)pyridin-2-yl]ethyl}-3,9-diazaspiro[5.5]undec-3-yl)-3-methylfuran-2(5H)-one;

4-(9-{(2R)-2-hydroxy-2-[4-(1H-tetrazol-1-yl)pyridin-2-yl]ethyl}-3,9-diazaspiro[5.5]undec-3-yl)-3-methylfuran-2(5H)-one;

4-(9-{(2S)-2-hydroxy-2-[2-(1H-tetrazol-1-yl)phenyl]ethyl}-3,9-diazaspiro[5.5]undec-3-yl)-3-methylfuran-2(5H)-one;

3-(9-{(2R)-2-hydroxy-2-[2-methyl-6-(1H-tetrazol-1-yl)pyridin-3-yl]ethyl}-3,9-diazaspiro[5.5]undec-3-yl)cyclopent-2-en-1-one;

3-(9-{(2S)-2-hydroxy-2-[2-methyl-6-(1H-tetrazol-1-yl)pyridin-3-yl]ethyl}-3,9-diazaspiro[5.5]undec-3-yl)cyclopent-2-en-1-one;

5-{(1R)-1-hydroxy-2-[9-(3-oxocyclopent-1-en-1-yl)-3,9-diazaspiro[5.5]undec-3-yl]ethyl}-4-methyl-2-benzofuran-1(3H)-one;

3-(9-{2-hydroxy-2-[2-methyl-4-(1H-tetrazol-1-yl)phenyl]ethyl}-3,9-diazaspiro[5.5]undec-3-yl)cyclopent-2-en-1-one;

3-(9-{(2R)-2-hydroxy-2-[2-methyl-6-(1H-tetrazol-1-yl)pyridin-3-yl]ethyl}-3,9-diazaspiro[5.5]undec-3-yl)-2-methylcyclopent-2-en-1-one;

3-(9-{(2S)-2-hydroxy-2-[2-methyl-6-(1H-tetrazol-1-yl)pyridin-3-yl]ethyl}-3,9-diazaspiro[5.5]undec-3-yl)-2-methylcyclopent-2-en-1-one;

5-{(1R)-1-hydroxy-2-[9-(2-methyl-3-oxocyclopent-1-en-1-yl)-3,9-diazaspiro[5.5]undec-3-yl]ethyl}-4-methyl-2-benzofuran-1(3H)-one;

3-(9-{(2R)-2-hydroxy-2-[2-methyl-4-(1H-tetrazol-1-yl)phenyl]ethyl}-3,9-diazaspiro[5.5]undec-3-yl)-2-methylcyclopent-2-en-1-one;

3-{9-[(2R)-2-hydroxy-2-(4-methyl-1-oxo-1,3-dihydro-2-benzofuran-5-yl)ethyl]-3,9-diazaspiro[5.5]undec-3-yl}-4-methylcyclobut-3-ene-1,2-dione;

(R)-3-ethyl-4-(9-(2-hydroxy-2-(4-methyl-1-oxo-1,3-dihydroisobenzofuran-5-yl)ethyl)-3,9-diazaspiro[5.5]undecan-3-yl)cyclobut-3-ene-1,2-dione;

(R)-3-cyclopropyl-4-(9-(2-hydroxy-2-(4-methyl-1-oxo-1,3-dihydroisobenzofuran-5-yl)ethyl)-3,9-diazaspiro[5.5]undecan-3-yl)cyclobut-3-ene-1,2-dione;

(R)-3-(9-(2-(6-(1H-tetrazol-1-yl)pyridin-3-yl)-2-hydroxyethyl)-3,9-diazaspiro[5.5]undecan-3-yl)-4-methylcyclobut-3-ene-1,2-dione;

(S)-3-(9-(2-(6-(1H-tetrazol-1-yl)pyridin-3-yl)-2-hydroxyethyl)-3,9-diazaspiro[5.5]undecan-3-yl)-4-methylcyclobut-3-ene-1,2-dione;

(S)-3-(9-(2-(6-(1H-tetrazol-1-yl)pyridazin-3-yl)-2-hydroxyethyl)-3,9-diazaspiro[5.5]undecan-3-yl)-4-methylcyclobut-3-ene-1,2-dione;

(R)-3-(9-(2-(6-(1H-tetrazol-1-yl)pyridazin-3-yl)-2-hydroxyethyl)-3,9-diazaspiro[5.5]undecan-3-yl)-4-methylcyclobut-3-ene-1,2-dione;

(S)-3-(9-(2-(5-(1H-tetrazol-1-yl)pyrazin-2-yl)-2-hydroxyethyl)-3,9-diazaspiro[5.5]undecan-3-yl)-4-methylcyclobut-3-ene-1,2-dione;

(R)-3-(9-(2-(5-(1H-tetrazol-1-yl)pyrazin-2-yl)-2-hydroxyethyl)-3,9-diazaspiro[5.5]undecan-3-yl)-4-methylcyclobut-3-ene-1,2-dione;

(S)-3-(9-(2-(5-(1H-tetrazol-1-yl)pyridin-2-yl)-2-hydroxyethyl)-3,9-diazaspiro[5.5]undecan-3-yl)-4-methylcyclobut-3-ene-1,2-dione;

(R)-3-(9-(2-hydroxy-2-(tetrazolo[1,5-a]quinolin-7-yl)ethyl)-3,9-diazaspiro[5.5]undecan-3-yl)-4-methylcyclobut-3-ene-1,2-dione;

(S)-3-(9-(2-hydroxy-2-(tetrazolo[1,5-a]quinolin-7-yl)ethyl)-3,9-diazaspiro[5.5]undecan-3-yl)-4-methylcyclobut-3-ene-1,2-dione;

5-{(1S)-1-methoxy-2-[9-(5-oxo-2,5-dihydrofuran-3-yl)-3,9-diazaspiro[5.5]undec-3-yl]ethyl}-4-methyl-2-benzofuran-1(3H)-one;

5-{(1R)-1-methoxy-2-[9-(5-oxo-2,5-dihydrofuran-3-yl)-3,9-diazaspiro[5.5]undec-3-yl]ethyl}-4-methyl-2-benzofuran-1(3H)-one;

5-{(1R)-2-[9-(2-ethoxy-5-oxo-2,5-dihydrofuran-3-yl)-3,9-diazaspiro[5.5]undec-3-yl]-1-hydroxyethyl}-4-methyl-2-benzofuran-1(3H)-one;

5-{(1R)-1-hydroxy-2-[9-(6-oxo-3,6-dihydro-2H-pyran-4-yl)-3,9-diazaspiro[5.5]undec-3-yl]ethyl}-4-methyl-2-benzofuran-1(3H)-one;

5-{(1R)-1-hydroxy-2-[(7R)-7-hydroxy-9-(4-methyl-5-oxo-2,5-dihydrofuran-3-yl)-3,9-diazaspiro[5.5]undec-3-yl]ethyl}-4-methyl-2-benzofuran-1(3H)-one;

5-{(1R)-1-hydroxy-2-[(7R)-7-(methoxymethoxy)-9-(4-methyl-5-oxo-2,5-dihydrofuran-3-yl)-3,9-diazaspiro[5.5]undec-3-yl]ethyl}-4-methyl-2-benzofuran-1(3H)-one;

5-{(1R)-1-hydroxy-2-[(7S)-7-(methoxymethoxy)-9-(4-methyl-5-oxo-2,5-dihydrofuran-3-yl)-3,9-diazaspiro[5.5]undec-3-yl]ethyl}-4-methyl-2-benzofuran-1(3H)-one;

5-{(1R)-1-hydroxy-2-[(7R)-7-methoxy-9-(4-methyl-5-oxo-2,5-dihydrofuran-3-yl)-3,9-diazaspiro[5.5]undec-3-yl]ethyl}-4-methyl-2-benzofuran-1(3H)-one;

5-{(1R)-1-hydroxy-2-[(7S)-7-methoxy-9-(4-methyl-5-oxo-2,5-dihydrofuran-3-yl)-3,9-diazaspiro[5.5]undec-3-yl]ethyl}-4-methyl-2-benzofuran-1(3H)-one;

4-(9-{[6-(1H-tetrazol-1-yl)pyridin-3-yl]acetyl}-3,9-diazaspiro[5.5]undec-3-yl)furan-2(5H)-one;

4-(9-{[2,6-difluoro-4-(1H-tetrazol-1-yl)phenyl]acetyl}-3,9-diazaspiro[5.5]undec-3-yl)furan-2(5H)-one;

4-(9-{[5-fluoro-6-(1H-tetrazol-1-yl)pyridin-3-yl]acetyl}-3,9-diazaspiro[5.5]undec-3-yl)furan-2(5H)-one;

4-(9-{[4-(1H-tetrazol-1-yl)phenyl]acetyl}-3,9-diazaspiro[5.5]undec-3-yl)furan-2(5H)-one;

4-(9-{[3-(1H-tetrazol-1-yl)-6,7-dihydro-5H-cyclopenta[c]pyridin-7-yl]carbonyl}-3,9-diazaspiro[5.5]undec-3-yl)furan-2(5H)-one;

4-(9-{[2,5-difluoro-4-(1H-tetrazol-1-yl)phenyl]acetyl}-3,9-diazaspiro[5.5]undec-3-yl)furan-2(5H)-one;

4-methyl-5-{2-oxo-2-[9-(5-oxo-2,5-dihydrofuran-3-yl)-3,9-diazaspiro[5.5]undec-3-yl]ethyl}-2-benzofuran-1(3H)-one;

4-(9-{[5-(1H-tetrazol-1-yl)pyrazin-2-yl]acetyl}-3,9-diazaspiro[5.5]undec-3-yl)furan-2(5H)-one; or a pharmaceutically acceptable salt thereof.

13. A pharmaceutical composition comprised of a compound of claim 1 or a pharmaceutically acceptable salt thereof and a pharmaceutically acceptable carrier.

14. The pharmaceutical composition of claim 13 further comprising an additional active agent selected from losartan, valsartan, candesartan, olmesartan, telmesartan, eprosartan, irbesartan, amlodipine, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril, amiloride, spironolactone, epleranone or triamterene, or a pharmaceutically acceptable salt of any of the foregoing.

15. A method for causing diueresis, natriuresis or both, comprising administering a compound of claim 1 or a pharmaceutically acceptable salt thereof in a therapeutically effective amount to a patient in need thereof.

16. A method for the treatment of one or more disorders selected from hypertension, acute heart failure, chronic heart failure, or pulmonary arterial hypertension comprising administering a compound of claim 1 or a pharmaceutically acceptable salt thereof in a therapeutically effective amount to a patient in need thereof.

* * * * *